US011318120B2

(12) United States Patent
Sandanayaka et al.

(10) Patent No.: US 11,318,120 B2
(45) Date of Patent: May 3, 2022

(54) NUCLEAR TRANSPORT MODULATORS AND USES THEREOF

(71) Applicant: Biogen MA Inc., Cambridge, MA (US)

(72) Inventors: Vincent P. Sandanayaka, Northboro, MA (US); Sharon Shechter, Andover, MA (US); Sharon Shacham, Newton, MA (US); Dilara McCauley, Arlington, MA (US); Erkan Baloglu, Stoneham, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 17/179,512

(22) Filed: Feb. 19, 2021

(65) Prior Publication Data

US 2021/0251968 A1  Aug. 19, 2021

Related U.S. Application Data

(63) Continuation of application No. 16/840,841, filed on Apr. 6, 2020, now Pat. No. 10,925,859, which is a continuation of application No. 16/037,798, filed on Jul. 17, 2018, now Pat. No. 10,617,677, which is a continuation of application No. 15/413,889, filed on Jan. 24, 2017, now Pat. No. 10,058,535, which is a continuation of application No. 14/989,377, filed on Jan. 6, 2016, now Pat. No. 9,585,874, which is a continuation of application No. 14/399,868, filed as application No. PCT/US2013/040404 on May 9, 2013, now Pat. No. 9,266,843.

(60) Provisional application No. 61/798,188, filed on Mar. 15, 2013, provisional application No. 61/644,802, filed on May 9, 2012.

(51) Int. Cl.
| | |
|---|---|
| *C07D 249/08* | (2006.01) |
| *C07D 401/10* | (2006.01) |
| *C07D 401/12* | (2006.01) |
| *C07D 403/12* | (2006.01) |
| *C07D 413/12* | (2006.01) |
| *A61K 31/4196* | (2006.01) |
| *A61K 31/454* | (2006.01) |
| *A61K 31/497* | (2006.01) |
| *A61K 31/5377* | (2006.01) |
| *A61K 45/06* | (2006.01) |

(52) U.S. Cl.
CPC ........ *A61K 31/4196* (2013.01); *A61K 31/454* (2013.01); *A61K 31/497* (2013.01); *A61K 31/5377* (2013.01); *A61K 45/06* (2013.01); *C07D 249/08* (2013.01); *C07D 401/10* (2013.01); *C07D 401/12* (2013.01); *C07D 403/12* (2013.01); *C07D 413/12* (2013.01); *Y02A 50/30* (2018.01)

(58) Field of Classification Search
CPC .. C07D 249/08; C07D 401/10; C07D 401/12; C07D 403/12; C07D 413/12
See application file for complete search history.

(56) References Cited

U.S. PATENT DOCUMENTS

| | | | |
|---|---|---|---|
| 5,153,201 | A | 10/1992 | Aono et al. |
| 5,817,677 | A | 10/1998 | Linz et al. |
| 6,462,049 | B1 | 10/2002 | Ogura et al. |
| 7,342,115 | B2 | 3/2008 | Hutchison et al. |
| 7,667,041 | B2 | 2/2010 | Kimura et al. |
| 7,795,457 | B2 | 9/2010 | Fu et al. |
| 7,858,621 | B2 | 12/2010 | Kim et al. |
| 7,902,367 | B2 | 3/2011 | Nomura et al. |
| 8,273,738 | B2 | 9/2012 | Osakada et al. |
| 8,299,102 | B2 | 10/2012 | Strobel et al. |
| 8,304,438 | B2 | 11/2012 | Strobel et al. |
| 8,513,230 | B2 | 8/2013 | Shacham et al. |
| 8,598,168 | B2 | 12/2013 | Moradei et al. |
| 8,999,996 | B2 | 4/2015 | Sandanayaka et al. |
| 9,079,865 | B2 | 7/2015 | Sandanayaka et al. |
| 9,096,543 | B2 | 8/2015 | Sandanayaka |

(Continued)

FOREIGN PATENT DOCUMENTS

| | | |
|---|---|---|
| CN | 101309912 A | 11/2008 |
| CN | 101466687 A | 6/2009 |

(Continued)

OTHER PUBLICATIONS

Final Office Action dated Feb. 27, 2015 for U.S. Appl. No. 13/350,864, "Olefin Containing Nuclear Transport Modulators And Uses Thereof".

(Continued)

*Primary Examiner* — Rebecca L Anderson
(74) *Attorney, Agent, or Firm* — Rothwell, Figg, Ernst & Manbeck, P.C.

(57) ABSTRACT

Compounds of formula I:

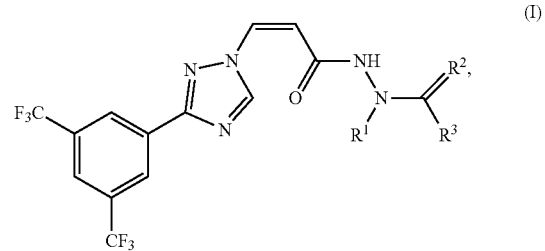

and pharmaceutically acceptable salts, solvates, or hydrates thereof, pharmaceutical compositions comprising the compounds of formula I, and methods of making and using the compounds, salts, solvates, or hydrates and the compositions in the treatment of various disorders associated with CRM1 activity.

6 Claims, 38 Drawing Sheets

(56) References Cited

U.S. PATENT DOCUMENTS

| | | |
|---|---|---|
| 9,206,158 B2 | 12/2015 | Sandanayaka et al. |
| 9,266,843 B2 | 2/2016 | Sandanayaka |
| 9,303,000 B2 | 4/2016 | Sandanayaka et al. |
| 9,428,490 B2 | 8/2016 | Sandanayaka et al. |
| 9,550,757 B2 | 1/2017 | Shacham et al. |
| 9,585,874 B2 | 3/2017 | Sandanayaka |
| 9,714,226 B2 | 7/2017 | Sandanayaka et al. |
| 9,738,624 B2 | 8/2017 | Baloglu et al. |
| 9,828,373 B2 | 11/2017 | Liu et al. |
| 9,861,614 B2 | 1/2018 | Sandanayaka |
| 10,058,535 B2 | 8/2018 | Sandanayaka |
| 10,173,987 B2 | 1/2019 | Sandanayaka et al. |
| 10,202,366 B2 | 2/2019 | Rashal et al. |
| 10,335,393 B2 | 7/2019 | Sandanayaka |
| 10,407,405 B2 | 9/2019 | Shechter et al. |
| 10,617,677 B2 | 4/2020 | Sandanayaka |
| 2003/0018025 A1 | 1/2003 | Thurkauf et al. |
| 2009/0221586 A1 | 9/2009 | Okada et al. |
| 2009/0298896 A1 | 12/2009 | Sakuma et al. |
| 2010/0016272 A1 | 1/2010 | Strobel et al. |
| 2010/0056569 A1 | 3/2010 | Nan et al. |
| 2011/0009374 A1 | 1/2011 | Keller |
| 2011/0275607 A1 | 11/2011 | Shacham et al. |
| 2012/0258986 A1 | 10/2012 | Sandanayaka et al. |
| 2013/0317031 A1 | 11/2013 | Sandanayaka et al. |
| 2014/0155370 A1 | 6/2014 | Shacham et al. |
| 2014/0235653 A1 | 8/2014 | Sandanayaka et al. |
| 2014/0364408 A1 | 12/2014 | Sandanayaka et al. |
| 2015/0018332 A1 | 1/2015 | Sandanayaka et al. |
| 2015/0111893 A1 | 4/2015 | Sandanayaka et al. |
| 2015/0274698 A1 | 10/2015 | Sandanayaka et al. |
| 2016/0145246 A1 | 5/2016 | Sandanayaka et al. |
| 2016/0152596 A1 | 6/2016 | Baloglu et al. |
| 2016/0258931 A1 | 9/2016 | Silva et al. |
| 2016/0304500 A1 | 10/2016 | Rashal et al. |
| 2017/0137430 A1 | 5/2017 | Sandanayaka et al. |
| 2017/0319551 A1 | 11/2017 | Sandanayaka et al. |
| 2018/0155317 A1 | 6/2018 | Baloglu et al. |
| 2019/0016690 A1 | 1/2019 | Baloglu |
| 2019/0023693 A1 | 1/2019 | Chennuru et al. |
| 2019/0160063 A1 | 5/2019 | Baloglu |

FOREIGN PATENT DOCUMENTS

| | | |
|---|---|---|
| CN | 103002742 A | 3/2013 |
| CN | 103874690 B | 7/2016 |
| EP | 0069513 A2 | 1/1983 |
| EP | 1 939 180 A1 | 7/2008 |
| EP | 1992618 A1 | 11/2008 |
| EP | 2003118 A1 | 12/2008 |
| EP | 2 090 570 A1 | 8/2009 |
| JP | S5841875 A | 3/1983 |
| JP | S62103065 A | 5/1987 |
| JP | H04211089 A | 8/1992 |
| JP | H07118237 A | 5/1995 |
| JP | H11263764 A | 9/1999 |
| JP | 2003/342262 A | 12/2003 |
| JP | 2004509941 A | 4/2004 |
| JP | 2004168768 A | 6/2004 |
| JP | 2005-508905 A | 4/2005 |
| JP | 2005-255683 A | 9/2005 |
| JP | 2006/504761 A | 2/2006 |
| JP | 2007210929 A | 8/2007 |
| JP | 2009-203238 A | 9/2009 |
| JP | 2009-536615 A | 10/2009 |
| JP | 2009-544696 A | 12/2009 |
| JP | 2010-513341 A | 4/2010 |
| JP | 2010-519337 A | 6/2010 |
| JP | 2015-516434 A | 6/2015 |
| JP | 2018-012715 A | 1/2018 |
| KR | 20050062645 A | 6/2005 |
| WO | WO-96/16040 A1 | 5/1996 |
| WO | WO-97/15567 A1 | 5/1997 |
| WO | WO-97/37996 A1 | 10/1997 |
| WO | WO-97/48696 A1 | 12/1997 |
| WO | WO-98/25893 A1 | 6/1998 |
| WO | WO-99/50264 A1 | 10/1999 |
| WO | WO-01/62756 A1 | 8/2001 |
| WO | WO-02/26696 A1 | 4/2002 |
| WO | WO-2003/024448 A2 | 3/2003 |
| WO | WO-2004/039365 A1 | 5/2004 |
| WO | WO-2004/039764 A1 | 5/2004 |
| WO | WO-2004/043925 A2 | 5/2004 |
| WO | WO-2004/043951 A1 | 5/2004 |
| WO | WO-2004/076418 A1 | 9/2004 |
| WO | WO-2005/115990 A1 | 12/2005 |
| WO | WO-2006/016637 A1 | 2/2006 |
| WO | WO-2006/019020 A1 | 2/2006 |
| WO | WO-2006/088246 A1 | 8/2006 |
| WO | WO-2007/102580 A1 | 9/2007 |
| WO | WO-2007/147336 A1 | 12/2007 |
| WO | WO-2008/029825 A1 | 3/2008 |
| WO | WO-2008/074413 A2 | 6/2008 |
| WO | WO-2011/069039 A1 | 6/2011 |
| WO | WO-2011/109799 A1 | 9/2011 |
| WO | WO-2012/099807 A1 | 7/2012 |
| WO | WO-2013/019548 A1 | 2/2013 |
| WO | WO-2013/019561 A1 | 2/2013 |
| WO | WO-2013/020024 A2 | 2/2013 |
| WO | WO-2013/170068 A2 | 11/2013 |
| WO | WO-2014/144772 A1 | 9/2014 |
| WO | WO-2014/152263 A1 | 9/2014 |
| WO | WO-2014/205389 A1 | 12/2014 |
| WO | WO-2014/205393 A1 | 12/2014 |
| WO | WO-2016/025904 A1 | 2/2016 |
| WO | WO-2017/117529 A1 | 7/2017 |
| WO | WO-2017/117535 A1 | 7/2017 |
| WO | WO-2018/098472 A1 | 5/2018 |
| WO | WO-2018/129227 A1 | 7/2018 |

OTHER PUBLICATIONS

Final Rejection for U.S. Appl. No. 13/931,372, "Nuclear Transport Modulators and Uses Thereof," dated Oct. 16, 2015 (our reference KTQ-003.02).
Final Rejection for U.S. Appl. No. 14/747,394, "Nuclear Transport Modulators and Uses Thereof," dated Feb. 1, 2017 (our reference KTQ-100.03).
Final Rejection for U.S. Appl. No. 14/777,302, "Methods of Promoting Wound Healing Usind CRM1 Inhibitors," dated Nov. 15, 2017 (our reference KTQ-009.01).
Non-Final Office Action dated Jul. 3, 2014 for U.S. Appl. No. 14/219,638 "Hydrazide Containing Nuclear Transport Modulators And Uses Thereof" (4823.1002-025).
Non-Final Office Action dated May 27, 2014 for U.S. Appl. No. 13/350,864 "Olefin Containing Nuclear Transport Modulators And Uses Thereof" (4823.1005-001).
Non-Final Office Action dated Sep. 21, 2012 for U.S. Appl. No. 13/041,377 "Nuclear Transport Modulators and Uses Thereof" (4823.1003-003).
Non-Final Office Action for U.S. Appl. No. 13/891,044 "Nuclear Transport Modulators And Uses Thereof" dated Oct. 21, 2014.
Non-Final Office Action for U.S. Appl. No. 13/931,372 "Nuclear Transport Modulators And Uses Thereof" dated Feb. 9, 2015.
Non-Final Office Action for U.S. Appl. No. 14/399,868 "Nuclear Transport Modulators and Uses Thereof" dated Feb. 13, 2015.
Non-Final Office Action for U.S. Appl. No. 14/747,394 "Nuclear Transport Modulators and Uses Thereof" dated Apr. 20, 2016.
Non-Final Office Action for U.S. Appl. No. 15/831,048 "Nuclear Transport Modulators and Uses Thereof" dated Aug. 2, 2018.
Non-Final Rejection for U.S. Appl. No. 14/235,342, "Nuclear Transport Modulators and Uses Thereof," dated Aug. 28, 2015 (our reference KTQ-O01.01).
Non-Final Rejection for Non-Final Rejection for U.S. Appl. No. 14/777,302, "Methods of Promoting Wound Healing Using CRM1 Inhibitors," dated Mar. 9, 2017 (our reference KTQ-009.01).
Non-Final Rejection for U.S. Appl. No. 14/900,469, "Nuclear Transport Modulators and Uses Thereof," dated Nov. 14, 2016 (our reference KTQ-011.01).

(56) References Cited

OTHER PUBLICATIONS

Non-Final Rejection for U.S. Appl. No. 14/940,310, "Hydrazide Containing Nuclear Transport Modulators and Uses Thereof," dated Aug. 11, 2016 (our reference KTQ-002.04).
Non-Final Rejection for U.S. Appl. No. 15/217,514 "Nuclear Transport Modulators and Uses Thereof" dated Mar. 9, 2018.
Non-Final Rejection for U.S. Appl. No. 15/413,889, "Nuclear Transport Modulators and Uses Thereof," dated Sep. 14, 2017 (our reference KTQ-100.05).
Non-Final Rejection for U.S. Appl. No. 15/629,307, "Hydrazide Containing Nuclear Transport Modulators and Uses Thereof," dated Feb. 14, 2018 (our reference KTQ-002.05).
Notice of Allowability for U.S. Appl. No. 13/041,377 "Nuclear Transpott Modulators and Uses Thereof", dated May 2, 2013.
Notice of Allowability for U.S. Appl. No. 14/219,638 "Hydrazide Containing Nuclear Transport Modulators And Uses Thereof", dated Oct. 10, 2014.
Notice of Allowability for U.S. Appl. No. 14/235,306 "Hydrazide Containing Nuclear Transport Modulators And Uses Thereof", dated Apr. 6, 2015.
Notice of Allowability for U.S. Appl. No. 14/399,868 "Nuclear Transport Modulators and Uses Thereof", dated Sep. 18, 2015.
Notice of Allowance for U.S. Appl. No. 15/629,307 dated Aug. 29, 2018 (Our reference KTQ-00205).
Notice of Allowance for U.S. Appl. No. 13/350,864, "Olefin Containing Nuclear Transport Modulators and Uses Thereof," dated Dec. 1, 2015 (our reference KTQ-005.01).
Notice of Allowance for U.S. Appl. No. 13/891,044 "Nuclear Transport Modulators and Uses Thereof", dated Apr. 7, 2015.
Notice of Allowance for U.S. Appl. No. 13/931,372, "Nuclear Transport Modulators and Uses Thereof," dated Sep. 7, 2016 (our reference KTQ-003.02).
Notice of Allowance for U.S. Appl. No. 14/235,342, "Nuclear Transport Modulators and Uses Thereof," dated Apr. 25, 2016 (our reference KTQ-001.01).
Notice of Allowance for U.S. Appl. No. 14/735,853 "Nuclear Transport Modulators and Uses Thereof", dated Aug. 4, 2015.
Notice of Allowance for U.S. Appl. No. 14/900,469, "Nuclear Transport Modulators and Uses Thereof,"dated Apr. 18, 2017 (our reference KTQ-01101).
Notice of Allowance for U.S. Appl. No. 14/940,310, "Hydrazide Containing Nuclear Transport Modulators and Uses Thereof," dated Mar. 14, 2017 (our reference KTQ-00204).
Notice of Allowance for U.S. Appl. No. 14/989,377, "Nuclear Transport Modulators and Uses Thereof," dated Oct. 28, 2016 (our reference KTQ-100.04).
Notice of Allowance for U.S. Appl. No. 15/651,856, "Nuclear Transport Modulators and Uses Therof" dated Apr. 24, 2019
Notice of Allowance for U.S. Appl. No. 14/777,302 dated Sep. 21, 2018 (Our reference KTQ-00901).
Notice of Allowance for U.S. Appl. No. 15/413,889, "Nuclear Transport Modulators and Uses Thereof," dated Apr. 10, 2018 (our reference KTQ-10005).
Notice of Allowance for U.S. Appl. No. 14/747,394, "Nuclear Transport Modulators and Uses Thereof," dated Aug. 30, 2017 (our reference KTQ-10003).
Requirement for Restriction/Election for U.S. Appl. No. 13/041,377, "Nuclear Transport Modulators and Uses Thereof," dated Jul. 5, 2012 (our reference KTQ-003.01).
Requirement for Restriction/Election for U.S. Appl. No. 13/350,864, "Olefin Containing Nuclear Transport Modulators And Uses Thereof," dated Dec. 19, 2013 (our reference KTQ-005.01).
Requirement for Restriction/Election for U.S. Appl. No. 13/931,372, "Nuclear Transport Modulators and Uses Thereof," dated May 22, 2014 (our reference KTQ-003.02).
Requirement for Restriction/Election for U.S. Appl. No. 14/235,342, "Nuclear Transport Modulators and Uses Thereof," dated Jun. 9, 2015 (our reference KTQ-001.01).

Requirement for Restriction/Election for U.S. Appl. No. 14/777,302, "Methods of Promoting Wound Healing Using CRM1 Inhibitors," dated Sep. 22, 2016 (our reference KTQ-009.01).
Requirement for Restriction/Election for U.S. Appl. No. 15/217,514, "Nuclear Transport Modulators and Uses Thereof," dated Aug. 8, 2017 (our reference KTQ-001.02).
Balsamini, "(E)-3-(2-(N-Phenylcarbamoyl)vinyl)pyrrole-2-carboxylic Acid Derivatives. A Novel Class of Glycine Site Antagonists", Journal of Medicinal Chemistry, 41(6):808-820 (Jan. 1, 1998).
Brekhov, Y. et al., "Cyanomethyltetrazoles II reactions of the methylene Fragment", Zhurnal organicheskoi Khimii, 2892: 1921-1925 (1922).
Brittain, "Drugs in Pharmaceutical Sciences, v. 192. Polymorphism in Pharmaceutical Solids," CRC Press (2009).
Buckler, R.T. et al., "Synthesis and Antiinflammatory Activity of Some 1,2,3- and 1,2,4-Triazolepropionic Acids", Journal of Medicinal Chemistry, 21(12): 1254-1260 (1978).
Burdeska et al., "Anil-Synthese. 23. Mitteilung. Ueber die Herstellung von Styryl- und Stilbenyl-Derivaten des Pyrimidins // Anil synthesis. Part 23. Preparation of styryl and stilbenyl derivatives of pyrimidines," Helv Chim Acta, 64(1): 113-152 (1981).
Cai, X., et al., "Inhibition of Thr-55 phosphorylation restores p53 nuclear localization and sensitizes cancer cells to DNA damage", Proc Nat Acad Sci, 105(44):16958-16963 (2008).
Cancer [online], [retrieved on Jul. 6, 2007] Retrieved from the Internet, URL: http://www.nlm.nih.gov/medlineplus/cancer.html (Year: 2007).
Cantu et al., "Using the Selective Inhibitor of Nuclear Export (SINE) Compound KPT-350 to Reduce Critical Circuit Hyperexcitability an Interneuron Cell Loss in the Controlled Cortical Impact (CCI) Model of Traumatic Brain Injury (TBI) (I11.001)," Neurology, 86(16 Supplement): I11.001 (2016).
CHEMCATS RN# 1035122-02-1; Publicly available on Jul. 12, 2009.
CHEMCATS RN# 1134927-58-4; Publicly available on Apr. 15, 2009.
CHEMCATS RN# 930886-49-0; Publicly available on Apr. 29, 2007.
Cheng et al., "XPO1 (CRM1) Inhibition Represses STAT3 Activation to Drive a Survivin-Dependent Oncogenic Switch in Triple-Negative Breast Cancer," Cancer Biology and Signal Transduction, 13(3):OF1-OF12 (2014).
Cooper et al., "Synthesis of Some 1,2,4-Triazoles and 1,2,4-Triazolines by Reaction of Oxamidrazone Condensation Products with Acetic Anhydride," Journal of Chemical Society Perkin Transactions 1, 15: 1433-1437 (1975).
Cronshaw, J.M. et al., "The nuclear pore complex: disease associations and functional correlations", TRENDS Endocrin Metab. 15:34-39 (2004).
Daelemans, D. et al., "A synthetic HIV-1 Rev inhibitor interfering with the CRM1-mediated nuclear export", PNAS, 99(22):14440-14445 (2002).
Database PubChem Compound, Database Accession No. 33777540 (May 29, 2009), 3 pages.
Database PubChem Compound, Database Accession No. 33777561 (May 29, 2009), 3 pages.
Database PubChem Compound, Database Accession No. 33777585 (May 29, 2009), 3 pages.
Database PubChem Compound, Database Accession No. 66525271 (Oct. 24, 2012), 3 pages.
Database PubChem Compound, Database Accession No. 66525276 (Oct. 24, 2012), 3 pages.
Database PubChem Compound, Database Accession No. 72062355 (2007), 11 pages.
Database PubChem Compound, Database Accession No. 940775133 (Jul. 7, 2017), 1 page.
Davis, J.R. et al., "Controlling protein compartmentalization to overcome disease" Pharmaceut Res., 24:17-27 (2007).
Dorwald, "Side Reactions in Organic Synthesis: A Guide to Successful Synthesis Design," Wiley-VCH Verlag GmbH & Co. KGaA, Weinheim (2005).

(56) References Cited

OTHER PUBLICATIONS

Etchin et al., "KPT-330 inhibitor of CRM1 (XPO1)-mediated nuclear export has selective anti-leukaemic activity in preclinical models of T-cell acute lymphoblastic leukaemia and acute myeloid leukaemia," British Journal of Haematology, 161:117-127 (2013).
Extended European Search Report for EP Application No. 17189480.1 dated May 16, 2018 (our reference KTQ-002.97).
Extended European Search Report for EP Application No. EP 18202641 dated Feb. 15, 2019 (Our reference KTQ-01197).
Extended European Search Report issued by the European Patent Office in corresponding European Application No. 181647570 dated Aug. 8, 2018 (our references KTQ-10097).
Extended Search Report for EP Application No. 11751491.9, "Nuclear Transport Modulators And Uses Thereof", Date of Completion of the Search: Dec. 17, 2013. (4823.1003-007), 6 pages.
Extended Search Report for EP Application No. 12736172.3, "Olefin Containing Nuclear Transport Modulators And Uses Thereof", Date of Completion of the Search: May 8, 2014. (4823.1005-006), 3 pages.
Falini, B. et al., "Both carboxy-terminus NES motif and mutated tryptophan(S) are crucial for aberrant nuclear export of nucleophosmin leukemic mutants in NPMc+ AML", Blood Journal, 107(11):4514-4523 (2013).
Freundt, E.C. et al., "Molecular Determinants for Subcellular Localization of the Severe Acute Respiratory Syndrome Coronavirus Open Reading Frame 3b Protein", Journal of Virology, 83(13):6631-6640 (Jul. 2009)
Ghildyal, R. et al., "The Respiratory Syncytial Virus Matrix Protein Possesses a Crm1-Mediated Nuclear Export Mechanism", Journal of Virology, 83(11):5353-5362 (2009).
Ghosh, C.C. et al., "Analysis of nucleocytoplasmic shuttling of NF kappa B proteins in human leukocytes", Methods Mol. Biol. 457:279-92 (2008).
Golub, T.R. et al., "Molecular Classification of Cancer: Class Discovery and Class Prediction by Gene Expression Monitoring", Science, 286: 531-537 (1999).
Gravina et al., "XPO1/CRM1-Selective inhibitors of nuclear export (SINE) reduce tumor spreading and improve overall survival in preclinical models of prostate cancer (PCa)," Journal of Hematology & Oncology, 7(46):1-17 (2014).
Gupta, N. et. al., "Retinal tau pathology in human glaucomas" Can J Ophthalmol. 43(1):53-60 (2008).
Haines et al., "Selective Inhibitors of Nuclear Export Avert Progression in Preclinical Models of Inflammatom Demyelination," Nature Neuroscience, 18(4): 511-520 (2015).
Hilliard et al., "The anti-inflammatory prostaglandin 15-Deoxy-Δ12,14 PGJ2 inhibits CRM1-dependent nuclear protein export," Journal of Biological Chemistry, 1-12 (2010).
Hoffman et al., "Synthesis of Vinyl-Functionalized Oxazoles by Olefin Cross-Metathesis", J. Org. Chem. 73: 2400-2403 (2008).
Hoshino, I. et al., "Combined effects of p53 gene therapy and leptomycin B in human esophageal squamous cell carcinoma", Oncology, 75:113-119 (2008).
Huff, J., "HIV Protease: A Novel Chemotherapeutic Target for AIDS", Journal of Medicinal Chemistry, 34(8): 2305-2314 (1991).
International Preliminary Report on Patentability for International Application No. PCT/US2011/027328, "Nuclear Transport Modulators and Uses Thereof" dated Sep. 11, 2012.
International Preliminary Report on Patentability for International Application No. PCT/US2012/021406, "Olefin Containing Nuclear Transport Modulators and Uses Thereof"dated Jul. 17, 2013.
International Preliminary Report on Patentability for International Application No. PCT/US2014/029322 dated Sep. 15, 2015 (our reference KTQ-009.25).
International Preliminary Report on Patentability for International Application No. PCT/US2014/043479, dated Dec. 22, 2015.
International Preliminary Report on Patentability for International Application No. PCT/US2014/043484, dated Dec. 22, 2015.
International Preliminary Report on Patentability for International Application No. PCT/US2015/045395 dated Feb. 21, 2017 (our reference KTQ-017.25).
International Preliminary Report on Patentability for International Application No. PCT/US2016/069492 dated Jul. 3, 2018 (our reference KTQ-025.25).
International Preliminary Report on Patentability for International Application No. PCT/US2016/069508 dated Jul. 3, 2018 (our reference KTQ-026.25).
International Preliminary Report on Patentability for International Application No. PCT/US2012/048319, "Hydrazide Containing Nuclear Transport Modulators And Uses Thereof"; dated Feb. 4, 2014 (4823.1002-006).
International Preliminary Report on Patentability for International Application No. PCT/US2012/048368, "Nuclear Transport Modulators And Uses Thereof"; dated Feb. 4, 2014 (4823.1001-002).
International Preliminary Report on Patentability for International Application No. PCT/US2013/040404, "Nuclear Transport Modulators And Uses Thereof"; dated Nov. 11, 2014 (4823.1000-003).
International Search Report and The Written Opinion of the International Searching Authority for International Application No. PCT/US2012/021406, "Olefin Containing Nuclear Transport Modulators And Uses Thereof" dated Apr. 30, 2012. (4823.1005-002).
International Search Report and The Written Opinion of the International Searching Authority for International Application No. PCT/US2012/049470, "Maleimide Compounds and Methods of Treatment," dated Feb. 13, 2013. (4823.1004-003).
International Search Report and The Written Opinion of the International Searching Authority for International Application No. PCT/US2013/040404, "Nuclear Transport Modulators And Uses Thereof" ; dated Nov. 18, 2013.
International Search Report and the Written Opinion of the International Searching Authority, or the Declaration for International Application No.: PCT/US2014/027136 "Exo Olefin—Containing Nuclear Transport Modulators And Uses Thereof"; dated Jul. 11, 2014.
International Search Report and the Written Opinion of the International Searching Authority, or the Declaration for International Application No.: PCT/US2014/029322 "Methods Of Promoting Wound Healing Using CRM1 Inhibitors"; dated May 28, 2014.
International Search Report and the Written Opinion of the International Searching Authority, or the Declaration for International Application No.: PCT/US2014/043479 "Nuclear Transport Modulators And Uses Thereof"; dated Sep. 17, 2014.
International Search Report and the Written Opinion of the International Searching Authority, or the Declaration for International Application No.: PCT/US2014/043484 "Nuclear Transport Modulators And Uses Thereof"; dated Sep. 2, 2014.
International Search Report and Written Opinion for International Application No. PCT/US2015/045395 dated Jan. 12, 2016 (our reference KTQ-017.252.
International Search Report and Written Opinion for International Application No. PCT/US2016/069492 dated Feb. 16, 2017 (our reference KTQ-025252).
International Search Report and Written Opinion for International Application No. PCT/US2016/069508 dated May 23, 2017 (our reference KTQ-026.25).
International Search Report and Written Opinion for International Application No. PCT/US2017/063439 dated Feb. 2, 2018 (our reference KTQ-029.25).
International Search Report for International Application No. PCT/US2011/027328, "Nuclear Transport Modulators And Uses Thereof" dated Apr. 29, 2011 (4823.1003-002).
International Search Report for International Application No. PCT/US2012/048319, "Hydrazide Containing Nuclear Transport Modulators And Uses Thereof" dated Nov. 9, 2012 (4823.1002-006).
International Search Report for International Application No. PCT/US2012/048368, "Nuclear Transport Modulators And Uses Thereof" dated Sep. 21, 2012 (4823.1001-002).
Jiang et al., "Palladium-Catalyzed Alkenylation of 1,2,3-Trizoles with Terminal Conjugated Alkenes by Direct C-H Bond Functionalization," Eur J Org Chem, 7:1227-30 (2010).

(56) References Cited

OTHER PUBLICATIONS

Karyagin, A. Yu., Reagents for addressed modification of biopolymers, Russian Chemical Bulletin, 2000, 49(3):540-5.

Karypoharm Therapeutics, "Karyopharm Presents Date Demonstrating the Potential of Nuclear Export Protein Exportin 1 (XP01) Inhibition in the Treatment of Traumatic Brain Injury," Apr. 20, 2016, Retrieved from the Internet: http://investors.karyopharm.com/static-files/577eb861-4183-463a-9a5b-d0f1def1629d [retrieved on Jan. 25, 2018].

Kau, T.R. et al., "A chemical genetic screen identifies inhibitors of regulated nuclear export of a Forkhead transcription factor in PTEN-deficient tumor cells", Cancer Cell, pp. 463-476 (2003).

Kaur et al., "Tyrphostin Induced Growth Inhibition: Correlation with Effect on p210bcr-abl Autokinase Activity in K562 Chronic Myelogenous Leukemia," Anti-Cancer Drugs, 5(2): 213-222 (1994).

Lain, S. et al., "Accumulating active p53 in the nucleus by inhibition of nuclear export: a novel strategy to promote the p53 tumor suppressor function", Exp Cell Res. 253: 315-324 (1999).

Lain, S. et al., "An inhibitor of nuclear export activates the p53 response and induces the localization of HDM2 and p53 to U1A-positive nuclear bodies associated with the PODs", Exp Cell Res. 248:457-472 (1999).

Lala, P.K. et al., "Role of nitric oxide in tumor progression: Lessons from experimental tumors", Cancer and Metastasis Reviews, 17: 91-106 (1998).

Lapalombella, R. et al., "Selective Inhibitors of nuclear exports show that CRM1/XPO1 is a target in chronic lymphocytic leukemia", Blood, 120(23): 4621-4634 (Nov. 29, 2012).

Li, A. et al., "Upregulation of CRM1 Relates to Neuronal Apoptosis after Traumatic Brain Injury in Adult Rats", J Mol Neurosci, 51(1):208-218 (2013).

Maekawa et al., "Efficient Formation of a Triazole Ring Via Novel Ring-Opening Reaction of (z)-2-Methyl-4-arylmethylene-5(4H)-Oxazolones with Hydrazides," Heterocycles, 75(12): 2959-2971 (2008).

Maga et al., "Pharmacophore modeling and molecular docking led to the discovery of inhibitors of human immunodeficiency virus-1 replication targeting the human cellular aspartic acid-glutamic acid-alanine-aspartic acid box polypeptide 3," J Med Chem, 51(21):6635-8 (2008).

Marelli et al., "Tumor targeting via integrin ligands," Frontiers in Oncology, 3(222):1-12 (2013).

Miskolci et al., "TNFα release from peripheral blood leukocytes depends on a CRM1-mediated nuclear export," Biochemical and Biophysical Research Communications, 351:354-360 (2006).

Modzelewska-Banachiewicz, B. et al., "Synthesis and biological activity of (Z) and (E) isomers of 3-(3,4-diaryl-1,2,4-triazole-5-yl)prop-2-enoic acid" Monatsh Chem. 140:439-444 (2009).

Modzelewska-Banachiewicz, B. et al., "Synthesis and biological activity of new derivatives of 3-(3,4-diaryl-1,2,4-triazole-5-yl)propenoic acid" European Journal of Medicinal Chemistry, 39:873-877 (2004).

Monecke, T. et al., "Crystal Structure of the Nuclear Export Receptor CRM1 in Complex with Snurportin1 and RanGTP", Science, 324:1087-1091 (2009).

Morales et al., "Mechanical Particle-Size Reduction Techniques, Formulating Poorly Water Soluble Dugs," AAPS Advances in Pharmaceutical Sciences Series, 133-170 (2012).

Morissette et al., "High-throughput crystallization: polymorphs, salts, co-crystals and solvate of pharmaceutical solids," Adv Drug Deliv Rev, 56(3):275-300 (2004).

Muller, P.A.J. et al., "Nuclear-Cytosolic Transport of COMMD1 Regulates NF-κB and HIF-1 Activity", Traffic, 10:514-527 (2009).

Mutka et al., "Identification of Nuclear Export Inhibitors with Potent Anticancer Activity in Vivo," Cancer Research, 69(2): 510-517 (2009).

Mutka, S. et al., "Nuclear export inhibitors (NEIs) as novel cancer therapeutics", 98th AACr Ann. Mtg., 2 pgs (Apr. 14-18, 2007) (Poster).

Nagase, The Practice of Medicinal Chemistry, Chapter 13. Conversion of Molecules Based on Eguivalent Substitution, vol. 1, Technomics Inc., 1998, 253.

Nair, V., "Thermally induced skeletal rearrangement in a triazepine," J Heterocyclic Chem, 12(1):183-4 (1975).

Nakahara, J. et al., "Abnormal expression of TIP30 and arrested nucleocytoplasmic transport within oligodendrocyte precursor cells in multiple sclerosis", Journal of Clinical Investigation, 119(1):169-181 (2009).

Nautiyal et al., "Distinct functions for RIP140 in development, inflammation, and metabolism," Trends in Endocrinology and Metabolism, 24(9):451-459 (2013).

Noske, A., et al., "Expression of the Nuclear Export Protein Chromosomal Region Maintenance/Exportin 1/Xpo1 Is a Prognostic Factor in Human Ovarian Cancer", Cancer, 112(8):1733-1743 (2008).

Orsted et al., "Basic principles of wound healing," Wound Care Canada, 9(2): 4-12 (2011).

Patani, G.A., et al., "Bioisosterism: A Rational Approach in Drug Design", Chem Rev, 96:3147-3176 (1996).

Procopiou et al., "Inhibitors of Cholesterol Biosynthesis. 2. 3,5-Dihydroxy-7-(N-pyrrolyl)-6-heptenoates, a Novel Series of HMG-CoA Reductase Inhibitors," J Med Chem, 36(23): 3658-3662 (1993).

Quan, M.L. et al., "Design and Synthesis of Isoxazoline Derivatives as Factor Xa Inhibitors", J. Med. Chem. 42: 2760-2773 (1999).

Rawlinson, S.M. et al., "CRM1-mediated Nuclear Export of Dengue Virus RNA Polymerase NS5 Modulates Interleukin-8 Induction and Virus Production", Journal of Biological Chemistry, 284(23):15589-15597 (2009).

Registry(STN)[online], Jan. 23, 2008, CAS registered number 1000508-38-2, 1 page.

Sakamoto et al., "Studies on Pyrimidine Derivatives. XXV. Reaction of Pyrimidinyl Aldehydes and Ketones with Wittig Reagents," Chem Pharm Bull, 30(2): 610-614 (1982).

Sanchez, V. et al., "Nuclear Export of the Human Cytomegalovirus Tegument Protein pp65 Requires Cyclin-Dependent Kinase Activity and the Crm1 Exporter", Journal of Virology, 81 (21):11730-11736 (2007).

Shaoyong, Ke. et al., "Research Advance of Acylhydrazine Derivatives with Biological Activities", Chinese Journal of Organic Chemistry 30(12):1820-1830 (2010).

Shasheva, "Reactions of Hydroxyphenyl-Substituted 1,2,4-Triazoles with Electrophylic Reagents", Russian Journal of General Chemistry, 79(10): 2234-2243 (2009).

Sorokin, A.V. et al., "Nucleocytoplasmic Transport of Proteins", Biochemistry Moscow, 72(13):1439-1457 (2007).

Storey et al., "Solid State Characterization of Pharmaceuticals," Blackwell Publishing, (2011).

Sun Q., et al., "Nuclear export inhibition through covalent conjugation and hydrolysis of Leptomycin B by CRM1", Proc Nat Acad Sci, 110(4): 1303-1308 (2013).

Tai et al., "CRM1 inhibition induces tumor cell cytotoxicity and impairs osteoclastogenesis in multiple myeloma: molecular mechanisms and therapeutic implications," Leukemia, 28:155-165 (2014).

Tamir et al., "KPT-350, a Selective Inhibitor of Nuclear Export (SINE) Compound, Shows Efficacy in the Mouse Pilocapine Model of Temporal Lobe Epilepsy," Journal of Neurological Sciences, 381: 87-88 (2017).

Terry, L.J. et al., "Crossing the Nuclear Envelope: Hierarchical Regulation of Nucleocytoplasmic Transport", Science, 318:1412-1416 (2007).

Van der Watt, P.J. et al., "The Karyopherin proteins, Crm1 and Karyopherin β1, are overexpressed in cervical cancer and are critical for cancer cell survival and proliferation", Int. J. Cancer, 124:1829-1840 (2009).

Van Neck, T., et al., "Inhibition of the CRM1-mediated nucleocytoplasmic transport by N-azolylacrylates: Structure-activity relationship and mechanism of action", Bioorganic & Medicinal Chemistry 16:9487-9497 (2008).

Walsh, Jr., M.D., et al., Exportin 1 Inhibition Attenuates Nuclear Factor-κB-Dependent Gene Expression, Shock, 29(2):160-166 (2008).

Wang et al., "Mathematical modeling in cancer drug discovery," Drug Discovery Today, 19(2):145-150 (2014).

(56) References Cited

OTHER PUBLICATIONS

Williams, P., et al., "Characterization of a CRM1-Dependent Nuclear Export Signal in the C Terminus of Herpes Simplex Virus Type 1 Tegument Protein UL47", Journal of Virology, 82(21):10946-10952 (2008).

Written Opinion of the International Searching Authority for International Application No. PCT/US2011/027328, "Nuclear Transport Modulators And Uses Thereof"(4823.1003-002) dated Apr. 29, 2011, 8 pages.

Written Opinion of the International Searching Authority for International Application No. PCT/US2012/048319, "Hydrazide Containing Nuclear Transport Modulators And Uses Thereof" (4823.1002-006) dated Nov. 9, 2012, 9 pages.

Written Opinion of the International Searching Authority for International Application No. PCT/US2012/048368, "Nuclear Transport Modulators And Uses Thereof" (4823.1001-002) dated Sep. 21, 2012, 11 pages.

Yao, Y., et al., "The expression of CRM1 is associated with prognosis in human osteosarcoma", Oncology Reports, 21:229-235 (2009).

Zheng et al., "KPT-330 inhibitor of XPO1-mediated nuclear export has anti-proliferative activity in hepatocellular carcinoma," Cancer Chemother Pharmacol, 74:487-495 (2014).

Zimmerman, T.L. et al., "Nuclear Export of Retinoid X Receptor α in Response to Interleukin-1β-mediated Cell Signaling Roles for JNK and Ser260", The Journal of Biological Chemistry, 281(22):15434-15440 (2006).

Bryn, "Pharmaceutical Solids: A Strategic Approach To Regulatory Considerations," Pharma Res 12(7):945-954 (1995).

International Preliminary Report on Patentability for International Application No. PCT/US2017/063439 dated May 28, 2019 (Our reference KTQ-02925).

Lala et al., "Role of nitric oxide in tumor progression: lessons from experimental tumors", Cancer and Metastasis Reviews (1998), 17 (1), 91-106.

Golub et al., "Molecular Classification of Cancer: Class Discover and Class Prediction by Gene Expression Monitoring", Science (1999), vol. 286, 531-537.

A) Naive

B) Model

C) Positive Control

D) Compound 2

NUCLEAR TRANSPORT MODULATORS AND USES THEREOF

CROSS-REFERENCE TO RELATED APPLICATIONS

This application is a Continuation of U.S. application Ser. No. 16/840,841 filed Apr. 6, 2020, now U.S. Pat. No. 10,925,859, which is a Continuation of U.S. application Ser. No. 16/037,798 filed Jul. 17, 2018, now U.S. Pat. No. 10,617,677, which is a Continuation of U.S. application Ser. No. 15/413,889, filed Jan. 24, 2017, now U.S. Pat. No. 10,058,535, which is a Continuation of U.S. application Ser. No. 14/989,377, filed Jan. 6, 2016, now U.S. Pat. No. 9,585,874, which is a Continuation of U.S. application Ser. No. 14/399,868, filed Nov. 7, 2014, now U.S. Pat. No. 9,266,843, which is the U.S. National Stage of International Application No. PCT/US2013/040404, filed May 9, 2013, which designates the U.S., published in English, and claims the benefit of U.S. Provisional Application No. 61/798,188, filed Mar. 15, 2013 and U.S. Provisional Application No. 61/644,802, filed May 9, 2012. The entire disclosures of the above applications are incorporated herein by reference.

BACKGROUND OF THE INVENTION

Cells from most major human solid and hematologic malignancies exhibit abnormal cellular localization of a variety of oncogenic proteins, tumor suppressor proteins, and cell cycle regulators (Cronshaw et al, 2004, Falini et al 2006). For example, certain p53 mutations lead to localization in the cytoplasm rather than in the nucleus. This results in the loss of normal growth regulation, despite intact tumor suppressor function. In other tumors, wild-type p53 is sequestered in the cytoplasm or rapidly degraded, again leading to loss of its suppressor function. Restoration of appropriate nuclear localization of functional p53 protein can normalize some properties of neoplastic cells (Cai et al, 2008; Hoshino et al 2008; Lain et al 1999a; Lain et al 1999b; Smart et al 1999), can restore sensitivity of cancer cells to DNA damaging agents (Cai et al, 2008), and can lead to regression of established tumors (Sharpless & DePinho 2007, Xue et al, 2007). Similar data have been obtained for other tumor suppressor proteins such as forkhead (Turner and Sullivan 2008) and c-Abl (Vignari and Wang 2001). In addition, abnormal localization of several tumor suppressor and growth regulatory proteins may be involved in the pathogenesis of autoimmune diseases (Davis 2007, Nakahara 2009). CRM1 inhibition may provide particularly interesting utility in familial cancer syndromes (e.g., Li-Fraumeni Syndrome due to loss of one p53 allele, BRCA1 or 2 cancer syndromes), where specific tumor suppressor proteins (TSP) are deleted or dysfunctional and where increasing TSP levels by systemic (or local) administration of CRM1 inhibitors could help restore normal tumor suppressor function.

Specific proteins and RNAs are carried into and out of the nucleus by specialized transport molecules, which are classified as importins if they transport molecules into the nucleus, and exportins if they transport molecules out of the nucleus (Terry et al, 2007; Sorokin et al 2007). Proteins that are transported into or out of the nucleus contain nuclear import/localization (NLS) or export (NES) sequences that allow them to interact with the relevant transporters. Chromosomal Region Maintenance 1 (Crm1), which is also called exportin-1 or Xpo1, is a major exportin.

Overexpression of Crm1 has been reported in several tumors, including human ovarian cancer (Noske et al, 2008), cervical cancer (van der Watt et al, 2009), pancreatic cancer (Huang et al, 2009), hepatocellular carcinoma (Pascale et al, 2005) and osteosarcoma (Yao et al, 2009) and is independently correlated with poor clinical outcomes in these tumor types.

Inhibition of Crm1 blocks the exodus of tumor suppressor proteins and/or growth regulators such as p53, c-Abl, p21, p27, pRB, BRCA1, IkB, ICp27, E2F4, KLF5, YAP1, ZAP, KLF5, HDAC4, HDAC5 or forkhead proteins (e.g. FOXO3a) from the nucleus that are associated with gene expression, cell proliferation, angiogenesis and epigenetics. Crm1 inhibitors have been shown to induce apoptosis in cancer cells even in the presence of activating oncogenic or growth stimulating signals, while sparing normal (untransformed) cells. Most studies of Crm1 inhibition have utilized the natural product Crm1 inhibitor Leptomycin B (LMB). LMB itself is highly toxic to neoplastic cells, but poorly tolerated with marked gastrointestinal toxicity in animals (Roberts et al, 1986) and humans (Newlands et al, 1996). Derivatization of LMB to improve drug-like properties leads to compounds that retain antitumor activity and are better tolerated in animal tumor models (Yang et al, 2007, Yang et al, 2008, Mutka et al, 2009). Therefore, nuclear export inhibitors could have beneficial effects in neoplastic and other proliferative disorders. To date, however, small-molecule, drug-like Crm1 inhibitors for use in vitro and in vivo are uncommon.

In addition to tumor suppressor proteins, Crm1 also exports several key proteins that are involved in many inflammatory processes. These include IkB, NF-kB, Cox-2, RXRα, Commd1, HIF1, HMGB1, FOXO, FOXP and others. The nuclear factor kappa B (NF-kB/rel) family of transcriptional activators, named for the discovery that it drives immunoglobulin kappa gene expression, regulate the mRNA expression of variety of genes involved in inflammation, proliferation, immunity and cell survival. Under basal conditions, a protein inhibitor of NF-kB, called IkB, binds to NF-kB in the nucleus and the complex IkB-NF-kB renders the NF-kB transcriptional function inactive. In response to inflammatory stimuli, IkB dissociates from the IkB-NF-kB complex, which releases NF-kB and unmasks its potent transcriptional activity. Many signals that activate NF-kB do so by targeting IkB for proteolysis (Phosphorylation of IkB renders it "marked" for ubiquitination and then proteolysis). The nuclear IkBa-NF-kB complex can be exported to the cytoplasm by Crm1 where it dissociates and NF-kB can be reactivated. Ubiquitinated IkB may also dissociate from the NF-kB complex, restoring NF-kB transcriptional activity. Inhibition of Crm1 induced export in human neutrophils and macrophage like cells (U937) by LMB not only results in accumulation of transcriptionally inactive, nuclear IkBa-NF-kB complex but also prevents the initial activation of NF-kB even upon cell stimulation (Ghosh 2008, Huang 2000). In a different study, treatment with LMB inhibited IL-1β induced NF-kB DNA binding (the first step in NF-kB transcriptional activation), IL-8 expression and intercellular adhesion molecule expression in pulmonary microvascular endothelial cells (Walsh 2008). COMMD1 is another nuclear inhibitor of both NF-kB and hypoxia-inducible factor 1 (HIF1) transcriptional activity. Blocking the nuclear export of COMMD1 by inhibiting Crm1 results in increased inhibition of NF-kB and HIF1 transcriptional activity (Muller 2009).

Crm1 also mediates Retinoid X receptor α (RXRα) transport. RXRα is highly expressed in the liver and plays a central role in regulating bile acid, cholesterol, fatty acid, steroid and xenobiotic metabolism and homeostasis. During liver inflammation, nuclear RXRα levels are significantly reduced, mainly due to inflammation-mediated nuclear export of RXRα by Crm1. Lep B is able to prevent IL-1β induced cytoplasmic increase in RXRα levels in human liver derived cells (Zimmerman 2006).

The role of Crm1-mediated nuclear export in NF-kB, HIF-1 and RXRα signalling suggests that blocking nuclear export can be potentially beneficial in many inflammatory processes across multiple tissues and organs including the vasculature (vasculitis, arteritis, polymyalgia rheumatic, atherosclerosis), dermatologic (see above), rheumatologic (rheumatoid and related arthritis, psoriatic arthritis, spondyloarthropathies, crystal arthropathies, systemic lupus erythematosus, mixed connective tissue disease, myositis syndromes, dermatomyositis, inclusion body myositis, undifferentiated connective tissue disease, Sjogren's syndrome, scleroderma and overlap syndromes, etc.).

CRM1 Inhibition affects gene expression by inhibiting/activating a series of transcription factors like ICp27, E2F4, KLF5, YAP1, ZAP Crm1 inhibition has potential therapeutic effects across many dermatologic syndromes including inflammatory dermatoses (atopy, allergic dermatitis, chemical dermatitis, psoriasis), sun-damage (Ultraviolet/UV damage), and infections. CRM1 inhibition, best studied with LMB, showed minimal effects on normal keratinocytes, and exerted anti-inflammatory activity on keratinocytes subjected to UV, TNFa, or other inflammatory stimuli (Kobayashi & Shinkai 2005, Kannan & Jaiswal 2006). Crm1 inhibition also upregulates NRF2 (nuclear factor erythroid-related factor 2) activity, which protects keratinocytes (Schafer et al, 2010, Kannan & Jaiswal 2006) and other cell types (Wang et al, 2009) from oxidative damage. LMB induces apoptosis in keratinocytes infected with oncogenic human papillomavirus (HPV) strains such as HPV16, but not in uninfected keratinocytes (Jolly et al, 2009).

Crm1 also mediates the transport of key neuroprotectant proteins that may be useful in neurodegenerative diseases including Parkinson's Disease (PD), Alzheimer's Disease, and Amyotrophic Lateral Sclerosis. For example, (1) forcing nuclear retention of key neuroprotective regulators such as NRF2 (Wang 2009), FOXA2 (Kittappa et al, 2007), parking in neuronal cells and/or by (2) inhibiting NFκB transcriptional activity by sequestering IκB to the nucleus in glial cells, Crm1 inhibition could slow or prevent neuronal cell death found in these disorders. There is also evidence linking abnormal glial cell proliferation to abnormalities in CRM1 levels or CR1 function (Shen 2008).

Intact nuclear export, primarily mediated through CRM1, is also required for the intact maturation of many viruses. Viruses where nuclear export, and/or CRM1 itself, has been implicated in their lifecycle include human immunodeficiency virus (HIV), adenovirus, simian retrovirus type 1, Borna disease virus, influenza (usual strains as well as H1N1 and avian H5N1 strains), hepatitis B (HBV) and C (HCV) viruses, human papillomavirus (HPV), respiratory syncytial virus (RSV), Dungee, Severe Acute Respiratory Syndrome coronavirus, yellow fever virus, West Nile Virus, herpes simplex virus (HSV), cytomegalovirus (CMV), and Merkel cell polyomavirus (MCV). (Bhuvanakantham 2010, Cohen 2010, Whittaker 1998). It is anticipated that additional viral infections reliant on intact nuclear export will be uncovered in the near future.

The HIV-1 Rev protein, which traffics through nucleolus and shuttles between the nucleus and cytoplasm, facilitates export of unspliced and singly spliced HIV transcripts containing Rev Response Elements (RRE) RNA by the CRM1 export pathway. Inhibition of Rev-mediated RNA transport using CRM1 inhibitors such as LepB or PKF050-638 can arrest the HIV-1 transcriptional process, inhibit the production of new HIV-1 virions, and thereby reduce HIV-1 levels (Pollard 1998, Daelemans 2002).

Dengue virus (DENV) is the causative agent of the common arthropod-borne viral disease, dengue fever (DF), and its more severe and potentially deadly dengue hemorrhagic fever (DHF). DHF appears to be the result of an over exuberant inflammatory response to DENV. NS5 is the largest and most conserved protein of DENV. CRM1 regulates the transport of NS5 from the nucleus to the cytoplasm, where most of the NS5 functions are mediated. Inhibition of CRM1 mediated export of NS5 results in altered kinetics of virus production and reduces induction of the inflammatory chemokine interleukin-8 (IL-8), presenting a new avenue for the treatment of diseases caused by DENV and other medically important flaviviruses including Hepatitis C virus (Rawlinson 2009).

Other virus-encoded RNA-binding proteins that use CRM1 to exit the nucleus include the HSV type 1 tegument protein (VP13/14, or hUL47), human CMV protein pp65, the SARS Coronavirus ORF 3b Protein, and the RSV matrix (M) protein (Williams 2008, Sanchez 2007, Freundt 2009, Ghildyal 2009).

Interestingly, many of these viruses are associated with specific types of human cancer including hepatocellular carcinoma (HCC) due to chronic HBV or HCV infection, cervical cancer due to HPV, and Merkel cell carcinoma associated with MCV. CRM1 inhibitors could therefore have beneficial effects on both the viral infectious process as well as on the process of neoplastic transformation due to these viruses.

CRM1 controls the nuclear localization and therefore activity of multiple DNA metabolizing enzymes including histone deacetylases (HDAC), histone acetyltransferases (HAT), and histone methyltransferases (HMT). Suppression of cardiomyocyte hypertrophy with irreversible CRM1 inhibitors has been demonstrated and is believed to be linked to nuclear retention (and activation) of HDAC 5, an enzyme known to suppress a hypertrophic genetic program (Monovich et al, 2009). Thus, CRM1 inhibition may have beneficial effects in hypertrophic syndromes, including certain forms of congestive heart failure and hypertrophic cardiomyopathies.

CRM1 has also been linked to other disorders. Leber's disorder, a hereditary disorder characterized by degeneration of retinal ganglion cells and visual loss, is associated with inaction of the CRM1 switch (Gupta N 2008). There is also evidence linking neurodegenerative disorders to abnormalities in nuclear transport.

In view of the above, the discovery of compounds that modulate nuclear transport is desirable.

SUMMARY OF THE INVENTION

The present invention relates to compounds, and pharmaceutically acceptable salts thereof, useful as nuclear transport modulators, pharmaceutically acceptable compositions comprising compounds of the present invention and methods of using said compositions in the treatment of various disorders. It has now been found that nuclear transport modulators of the present invention, and pharmaceutically acceptable salts and/or compositions thereof, provide desirable in vivo exposure as measured by AUC in mouse while exhibiting lower levels of brain penetration as compared to other modulators. The compounds of the invention have the general formula I:

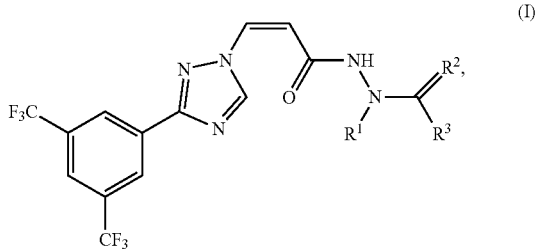

or a pharmaceutically acceptable salt thereof, wherein each variable is as defined and described herein.

Compounds of the present invention and pharmaceutically acceptable compositions thereof are useful for treating a variety of diseases, disorders or conditions, associated with abnormal cellular responses triggered by improper nuclear transport. Such diseases, disorders, or conditions include those described herein.

Compounds provided by this invention are also useful for the study of nuclear transport modulation in biological and pathological phenomena; the study of intracellular signal transduction pathways mediated by such kinases; and the comparative evaluation of new nuclear transport modulators.

BRIEF DESCRIPTION OF THE FIGURES

The foregoing will be apparent from the following more particular description of example embodiments of the invention.

DETAILED DESCRIPTION OF THE INVENTION

Compounds of the Invention

Figure 1:
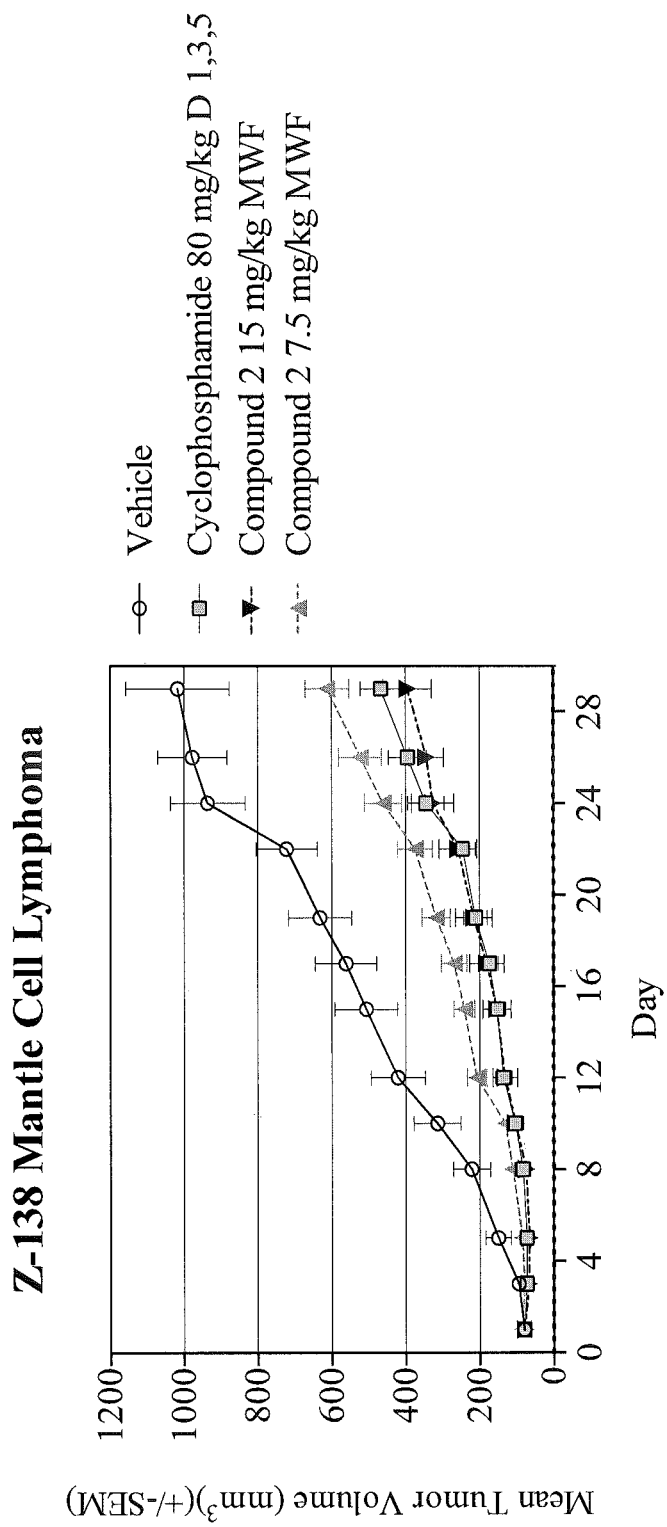
FIG. 1 is a graph of mean tumor volume versus time, and shows the group mean volume of Z-138 xenograft tumors on mice treated with vehicle, 80 mg/kg cyclophosphamide, 15 mg/kg Compound 2 or 7.5 mg/kg Compound 2 (error bars represent SEM for each group).

A first embodiment provides a compound of formula I:

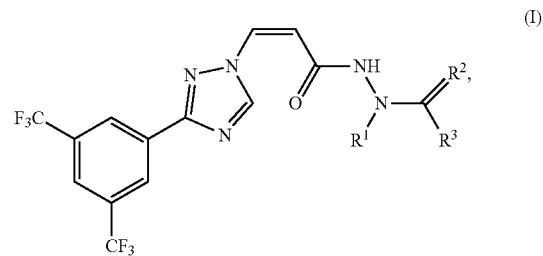

or a pharmaceutically acceptable salt thereof, wherein:
$R^1$ is selected from hydrogen and $C_1$-$C_4$ alkyl;
$R^2$ is selected from O and S; and
$R^3$ is selected from —N($R^4$)—($C_3$-$C_6$ cycloalkyl), —$C_1$-$C_6$ alkyl, —($C_0$-$C_4$ alkylene)-heterocyclyl, and —($C_0$-$C_4$ alkylene)-heteroaryl, wherein any alkyl, alkylene, heterocyclyl, or heteroaryl portion of $R^3$ is optionally and independently substituted; and $R^4$ is selected from hydrogen and $C_1$-$C_4$ alkyl.

In a first aspect of the first embodiment, $R^1$ is selected from hydrogen and methyl. The values for the remaining variables are as described in the first embodiment.

In a second aspect of the first embodiment, $R^1$ is hydrogen. The values for the remaining variables are as described in the first embodiment.

In a third aspect of the first embodiment, $R^2$ is O. The values for the remaining variables are as described in the first embodiment, or first or second aspect thereof.

In a fourth aspect of the first embodiment, $R^2$ is S. The values for the remaining variables are as described in the first embodiment, or first through third aspects thereof.

In a fifth aspect of the first embodiment, $R^4$ is hydrogen.

In a sixth aspect of the first embodiment, $R^3$ is selected from —N($R^4$)—($C_3$-$C_6$ cycloalkyl), —$C_3$-$C_6$ alkyl, —($C_0$-$C_1$ alkylene)-heterocyclyl, and —($C_0$-$C_1$ alkylene)-heteroaryl, wherein any alkyl or alkylene portion of $R^3$ is optionally substituted with —N($R^5$)$_2$, wherein each $R^5$ is independently selected from hydrogen and $C_1$-$C_4$ alkyl; any heterocyclyl, and heteroaryl portion of $R^3$ comprises at least one nitrogen atom in a ring; and any heterocyclyl, and heteroaryl portion of $R^3$ is optionally substituted with $C_1$-$C_4$ alkyl. The values for the remaining variables are as described in the first embodiment, or first through fifth aspects thereof.

In a seventh aspect of the first embodiment, $R^3$ is selected from —C(CH$_3$)$_3$, —CH(NH$_2$)—CH(CH$_3$)$_2$, —NH-cyclopropyl, —(CH$_2$)$_{0-1}$-pyrazinyl, piperidinyl, hydroxypiperidinyl, N-methylpiperidinyl, —CH$_2$-morpholin-4-yl, and methylpyrazolyl. The values for the remaining variables are as described in the first embodiment, or first through fifth aspects thereof.

In an eighth aspect of the first embodiment, $R^3$ is selected from —C(CH$_3$)$_3$, —CH(NH$_2$)—CH(CH$_3$)$_2$, —NH-cyclopropyl, —(CH$_2$)$_{0-1}$-pyrazin-2-yl, piperidin-3-yl, —CH$_2$-morpholin-4-yl, and 5-methyl-1-H-pyrazol-4-yl. The values for the remaining variables are as described in the first embodiment, or first through fifth aspects thereof.

In a ninth aspect of the first embodiment, $R^3$ is selected from —C(CH$_3$)$_3$, —NH-cyclopropyl, —CH$_2$-pyrazin-2-yl, -pyrazin-2-yl, —CH$_2$-morpholin-4-yl, and 5-methyl-1-H-pyrazol-4-yl. The values for the remaining variables are as described in the first embodiment, or first through fifth aspects thereof.

A second embodiment is a compound of formula (I), or a pharmaceutically acceptable salt thereof, wherein $R^3$ is selected from —N($R^4$)—($C_3$-$C_6$ cycloalkyl), —$C_3$-$C_6$ alkyl, —($C_0$-$C_1$ alkylene)-heterocyclyl, and —($C_0$-$C_1$ alkylene)-heteroaryl, wherein:

any alkyl or alkylene portion of $R^3$ is optionally substituted with —N($R^5$)$_2$, wherein each $R^5$ is independently selected from hydrogen and $C_1$-$C_4$ alkyl;

any heterocyclyl, and heteroaryl portion of $R^3$ comprises at least one nitrogen atom in a ring; and any heterocyclyl, and heteroaryl portion of $R^3$ is optionally substituted with $C_1$-$C_4$ alkyl.

In a first aspect of the second embodiment, $R^3$ is selected from —C(CH$_3$)$_3$, —CH(NH$_2$)—CH(CH$_3$)$_2$, —NH-cyclopropyl, —(CH$_2$)$_{0-1}$-pyrazinyl, piperidinyl, hydroxypiperidinyl, N-methylpiperidinyl, —CH$_2$-morpholin-4-yl, and methylpyrazolyl.

In a second aspect of the second embodiment, $R^3$ is selected from —C(CH$_3$)$_3$, —CH(NH$_2$)—CH(CH$_3$)$_2$, —NH-cyclopropyl, —(CH$_2$)$_{0-1}$-pyrazin-2-yl, piperidin-3-yl, —CH$_2$-morpholin-4-yl, and 5-methyl-1-H-pyrazol-4-yl.

In a third aspect of the second embodiment, $R^3$ is selected from —C(CH$_3$)$_3$, —NH-cyclopropyl, —CH$_2$-pyrazin-2-yl, -pyrazin-2-yl, —CH$_2$-morpholin-4-yl, and 5-methyl-1-H-pyrazol-4-yl.

A third embodiment provides a compound of formula I, or a pharmaceutically acceptable salt thereof, wherein $R^3$ is selected from —N($R^4$)—($C_3$-$C_6$ cycloalkyl), —$C_3$-$C_6$ alkyl, —($C_0$-$C_1$ alkylene)-heterocyclyl, and —($C_0$-$C_1$ alkylene)-heteroaryl, wherein:

any alkyl or alkylene portion of any $R^3$ is optionally and independently substituted with one or more substituents selected from the group consisting of oxo and —N($R^5$)$_2$, wherein each $R^5$ is independently selected from hydrogen and $C_1$-$C_4$ alkyl;

any heterocyclyl portion of $R^3$ comprises at least one nitrogen atom in a ring, and is optionally substituted with one or more substituents selected from the group consisting of $C_1$-$C_4$ alkyl and oxo; and any heteroaryl portion of $R^3$ comprises at least one nitrogen atom in a ring and is optionally substituted with one or more $C_1$-$C_4$ alkyl. The values for the remaining variables are as described in the first embodiment, or first through fifth aspects thereof.

In a first aspect of the third embodiment, $R^3$ is —($C_0$-$C_1$ alkylene)-heterocyclyl. The values for the remaining variables are as described in the first embodiment, or first through fifth aspects thereof.

In a second aspect of the third embodiment, $R^3$ is —($C_0$-$C_1$ alkylene)-heterocyclyl, wherein the heterocyclyl is selected from pyrazinyl, piperidinyl, morpholinyl, and pyrazolyl. The values for the remaining variables are as described in the first embodiment, or first through fifth aspects thereof.

In a third aspect of the third embodiment, $R^3$ is —($C_0$-$C_1$ alkylene)-heterocyclyl, wherein the heterocyclyl is morpholinyl. The values for the remaining variables are as described in the first embodiment, or first through fifth aspects thereof.

In a fourth aspect of the third embodiment, $R^3$ is —($C_1$ alkylene)-heterocyclyl. The values for the remaining variables are as described in the first embodiment, or first through fifth aspects thereof.

In a fifth aspect of the third embodiment, $R^3$ is —($C_1$ alkylene)-morpholinyl. The values for the remaining variables are as described in the first embodiment, or first through fifth aspects thereof.

Exemplary compounds of formula I are set forth in Table 1.

TABLE 1

Exemplary compounds of formula I.

| Cmpd No. | Compound Structure | Physical Data (¹H NMR and LCMS (M + H)⁺) |
|---|---|---|
| 1 | 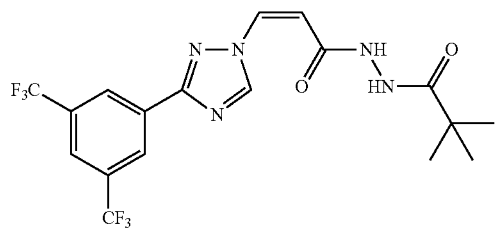 [SMILES: CC(C)(C)C(=O)NNC(=O)/C=C\n1cnc(-c2cc(C(F)(F)F)cc(C(F)(F)F)c2)n1] | ¹H NMR (400 MHz, DMSO-d6, ppm) δ = 10.35 (s, 1H), 9.66 (s, 1H), 9.64 (s, 1H), 8.57 (s, 2H), 8.28 (s, 2H), 7.48-7.50 (d, J = 8 Hz, 1H), 6.00-6.03 (d, J = 12 Hz, 1H), 1.15 (s, 9H). LCMS calcd: 450.36, found: 450.19 (retention time 2.89 min, purity: 94.5%). |
| 2 | 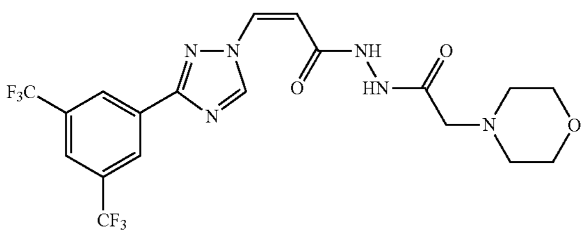 [SMILES: O=C(/C=C\n1cnc(-c2cc(C(F)(F)F)cc(C(F)(F)F)c2)n1)NNC(=O)CN1CCOCC1] | ¹H NMR (400 MHz, DMSO-d6, ppm) δ = 10.56 (s, 1H), 9.94 (s, 1H), 9.61 (s, 1H), 8.55 (s, 2H), 8.28 (s, 2H), 7.48-7.51 (d, J = 10.8 Hz, 1H), 6.01-6.03 (d, J = 10.4 Hz, 1H), 3.60-3.62 (t, 4H), 3.08 (s, 2H). LCMS calcd: 493.38, found: 493.24 (retention time 2.29 min, purity: 99.48%) |
| 3 | 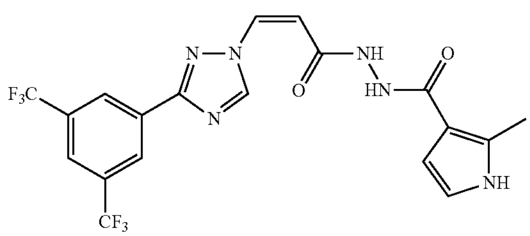 [SMILES: Cc1[nH]ccc1C(=O)NNC(=O)/C=C\n1cnc(-c2cc(C(F)(F)F)cc(C(F)(F)F)c2)n1] | ¹H NMR (400 MHz, DMSO-d6, ppm) δ = 13.01 (bs, 1H), 10.47 (bs, 1H), 10.03 (s, 1H), 9.70 (s, 1H), 8.56 (s, 2H), 8.28 (s, 1H), 7.97 (bs, 1H), 7.51-7.54 (d, J = 10.8 Hz, 1H), 6.06-6.08 (d, J = 10.4 Hz, 1H), 2.41 (s, 3H). LCMS calcd: 474.34, found: 474.14 (retention time 2.51 min, purity: 99.88%) |
| 4 | 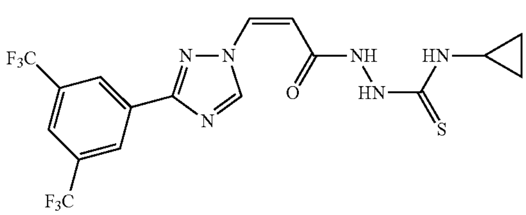 [SMILES: O=C(/C=C\n1cnc(-c2cc(C(F)(F)F)cc(C(F)(F)F)c2)n1)NNC(=S)NC1CC1] | ¹H NMR (400 MHz, MeOD, ppm) δ = 9.67 (s, 1H), 8.66 (s, 2H), 8.09 (s, 1H), 7.44-7.47 (d, J = 10.8 Hz, 1H), 6.02 (m, 1H), 4.64 (s, 1H), 3.33 (m, 1H), 2.88 (m, 1H), 0.91 (m, 2H), 0.79 (m, 2H). LCMS calcd for: C₁₇H₁₅F₆N₆OS [M + H]⁺: 465.40, found: 465.19 (retention time 2.78 min, purity: 99.63%) |
| 5 | 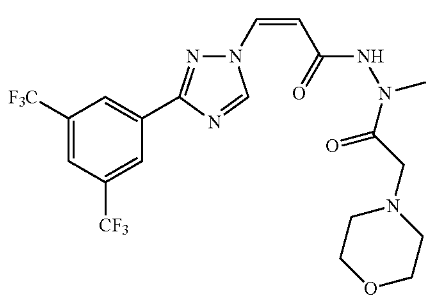 [SMILES: CN(NC(=O)/C=C\n1cnc(-c2cc(C(F)(F)F)cc(C(F)(F)F)c2)n1)C(=O)CN1CCOCC1] | ¹H NMR (400 MHz, DMSO-d6, ppm) δ = 10.36 (s, 1H), 9.10 (s, 1H), 8.53 (s, 2H), 8.29 (s, 1H), 7.32-7.34 (d, J = 10.0 Hz, 1H), 6.05-6.07 (d, J = 10.0 Hz, 1H), 3.56 (s, 4H), 3.10 (s, 3H), 3.05 (s, 2H), 2.51 (s, 4H). LCMS calcd for: C₂₀H₂₁F₆N₆O₃ [M + H]⁺: 507.41, found: 507.24 (retention time 2.40 min, purity: 99.61%) |
| 6 | 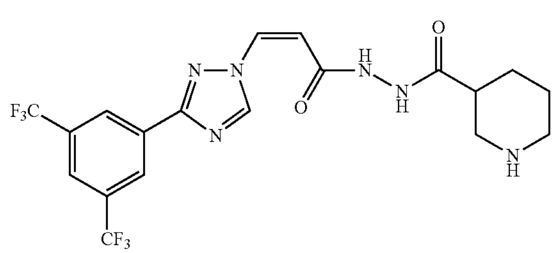 [SMILES: O=C(/C=C\n1cnc(-c2cc(C(F)(F)F)cc(C(F)(F)F)c2)n1)NNC(=O)C1CCCNC1] | ¹H NMR (400 MHz, DMSO-d6, ppm) δ = 9.73 (s, 1H), 8.56 (s, 2H), 8.29 (s, 1H), 7.41-7.44 (d, J = 10.4 Hz, 1H), 5.98-6.00 (d, J = 10.4 Hz, 1H), 2.91 (d, 1H), 2.81 (d, 1H), 2.34-2.58 (m, 4H), 1.77 (m, 1H), 1.54 (m, 2H), 1.34 (m, 1H), 1.23 (s, 2H). LCMS calcd: 477.38, found: 477.24 (retention time 2.38 min, purity: 95.46%). |

TABLE 1-continued

Exemplary compounds of formula I.

| Cmpd No. | Compound Structure | Physical Data (¹H NMR and LCMS (M + H)⁺) |
|---|---|---|
| 7 | 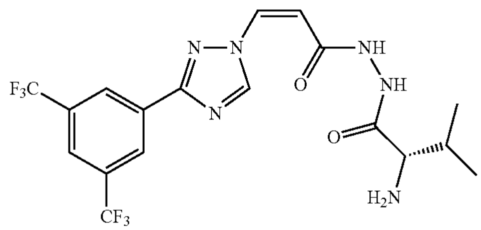 [SMILES: CC(C)[C@H](N)C(=O)NNC(=O)/C=C\n1cnc(-c2cc(C(F)(F)F)cc(C(F)(F)F)c2)n1] | ¹H NMR (400 MHz, DMSO-d6, ppm) δ = 10.88 (s, 1H), 10.76 (s, 1H), 9.58 (s, 1H), 8.55 (s, 2H), 8.31 (s, 1H), 8.24 (s, 2H), 7.53-7.56 (d, J = 10.4 Hz, 1H), 6.06-6.09 (d, J = 10.4 Hz, 1H), 3.69 (s, 1H), 2.13 (m, 1H), 1.01 (d, 6H). LCMS calcd: 465.37, found: 465.24 (retention time 2.45 min, purity: 95.19%) |
| 8 | 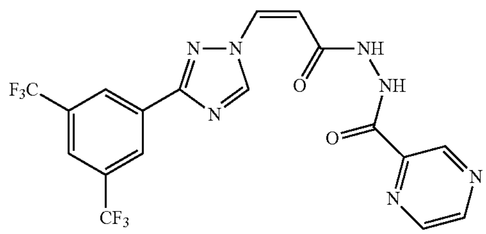 [SMILES: O=C(/C=C\n1cnc(-c2cc(C(F)(F)F)cc(C(F)(F)F)c2)n1)NNC(=O)c1cnccn1] | ¹H NMR (400 MHz, DMSO-d6, ppm) δ = 10.95 (s, 1H), 10.82 (s, 1H), 9.62 (s, 1H), 9.22 (s, 1H), 8.95 (s, 1H), 8.81 (s, 1H), 8.55 (s, 2H), 8.29 (s, 1H), 7.56-7.53 (d, J = 10.4 Hz, 1H), 6.10-6.08 (d, J = 10.4 Hz, 1H). LCMS calcd: 472.32, found: 472.14 (retention time 2.68 min, purity: 93.5%) |
| 9 | 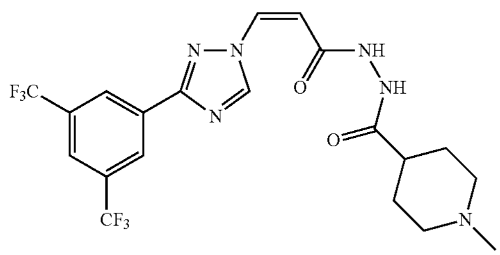 [SMILES: CN1CCC(C(=O)NNC(=O)/C=C\n2cnc(-c3cc(C(F)(F)F)cc(C(F)(F)F)c3)n2)CC1] | ¹H NMR (400 MHz, DMSO-d6, ppm) δ = 10.61 (s, 1H), 10.26 (s, 1H), 9.62 (s, 1H), 8.57 (s, 2H), 8.30 (s, 1H), 7.52-7.49 (d, J = 10.4 Hz, 1H), 6.02-6.05 (d, J = 10.4 Hz, 1H), 3.38 (m, 3H), 2.91 (m, 2H), 2.70 (s, 3H), 1.80 (m, 2H), 1.76 (m, 2H). LCMS calcd: 491.41, found: 491.24 (retention time 2.28 min, purity: 99.97%) |
| 10 | 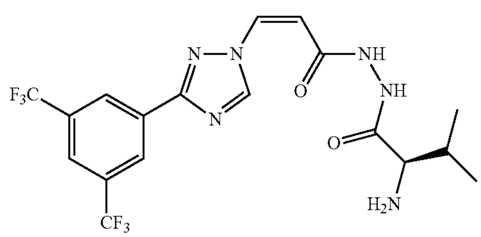 [SMILES: CC(C)[C@@H](N)C(=O)NNC(=O)/C=C\n1cnc(-c2cc(C(F)(F)F)cc(C(F)(F)F)c2)n1] | ¹H NMR (400 MHz, DMSO-d6, ppm) δ = 10.88 (s, 1H), 10.76 (s, 1H), 9.58 (s, 1H), 8.55 (s, 2H), 8.31 (s, 1H), 8.24 (s, 2H), 7.53-7.56 (d, J = 10.4 Hz, 1H), 6.06-6.09 (d, J = 10.4 Hz, 1H), 3.69 (s, 1H), 2.13 (m, 1H), 1.01 (d, 6H). LCMS calcd: 465.37, found: 465.24 (retention time 2.45 min, purity: 95.19%) |
| 11 | 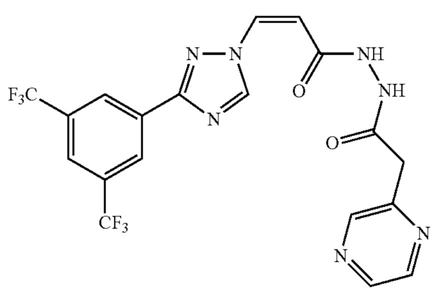 [SMILES: O=C(/C=C\n1cnc(-c2cc(C(F)(F)F)cc(C(F)(F)F)c2)n1)NNC(=O)Cc1cnccn1] | ¹H NMR (400 MHz, DMSO-d6, ppm) δ = 10.69 (s, 1H), 10.54 (s, 1H), 9.62 (s, 1H), 8.67 (s, 1H), 8.58 (m, 2H), 8.56 (s, 2H), 8.28 (s, 1H), 7.49-7.51 (d, J = 10.8 Hz, 1H), 6.01-6.04 (d, J = 10.4 Hz, 1H), 3.84 (s, 2H). LCMS calcd: 486.35, found: 486.29 (retention time 2.49 min, purity: 99.96%) |
| 12 | 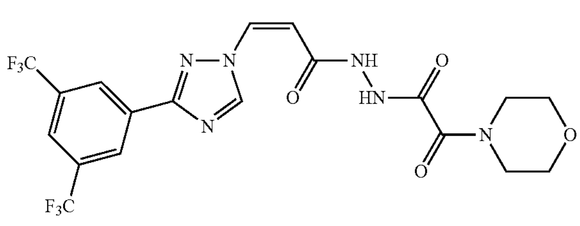 [SMILES: O=C(/C=C\n1cnc(-c2cc(C(F)(F)F)cc(C(F)(F)F)c2)n1)NNC(=O)C(=O)N1CCOCC1] | ¹H NMR (400 MHz, DMSO-d₆) δ 10.70-10.88 (m, 2H), 9.56 (s, 1H), 8.57 (s, 2H), 8.29 (s, 1H), 7.52-7.55 (d, J = 10.4 Hz, 1H), 6.0-6.03 (d, J = 10.4 Hz, 1H), 3.51-3.64 (m, 8H). LCMS m/z 507.25 [M + H]⁺, $t_R$ = 2.012 min |

TABLE 1-continued

Exemplary compounds of formula I.

| Cmpd No. | Compound Structure | Physical Data ($^1$H NMR and LCMS (M + H)$^+$) |
|---|---|---|
| 13 | 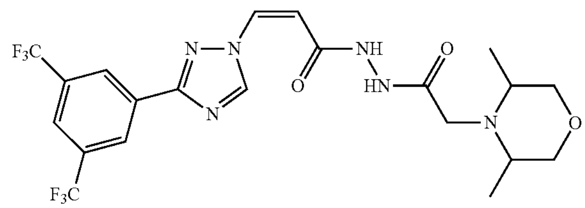 [SMILES: CC1COCC(C)N1CC(=O)NNC(=O)/C=C\n1cnc(-c2cc(C(F)(F)F)cc(C(F)(F)F)c2)n1] | $^1$H NMR (400 MHz, DMSO-d$_6$) δ 10.58 (s, 1H), 9.83 (s, 1H), 9.56 (s, 1H), 8.54-8.56 (m, 2H), 8.25-8.30 (m, 1H), 7.49-7.51 (d, J = 10.4 Hz, 1H) ), 6.01-6.04 (d, J = 10.4 Hz, 1H), 3.44-3.57 (m, 2H), 3.28-3.34 (m, 2H), 3.21 (s, 1H), 3.15 (s, 1H), 2.84-2.88 (m, 2H), 0.93-1.04 (m, 6H): LCMS m/z 521.18 [M + H]$^+$, t$_R$ 1.898 min |
| 14 | 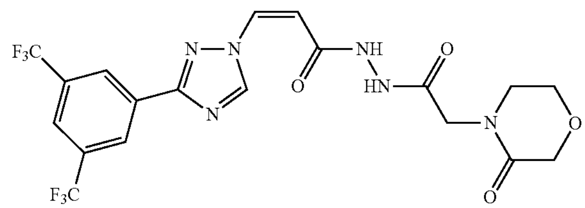 [SMILES: O=C(/C=C\n1cnc(-c2cc(C(F)(F)F)cc(C(F)(F)F)c2)n1)NNC(=O)CN1CCOCC1=O] | $^1$H NMR (400 MHz, DMSO-d$_6$) δ 10.33 (bs, 2H), 9.63 (s, 1H), 8.57 (s, 2H), 8.30 (s, 1H), 7.50-7.52 (d, J = 8 Hz, 1H) ), 6.01-6.03 (d, J = 8 Hz, 1H), 4.08-4.12 (m, 4H), 3.85-3.87 (m, 2H), 3.41-3.44 (m, 2H). LCMS m/z 507.13 [M + H]$^+$, t$_R$ 1.950 min |
| 15 | 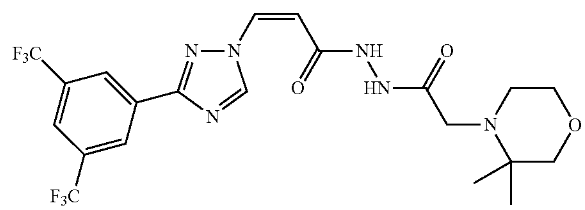 [SMILES: CC1(C)COCCN1CC(=O)NNC(=O)/C=C\n1cnc(-c2cc(C(F)(F)F)cc(C(F)(F)F)c2)n1] | $^1$H NMR (400 MHz, DMSO-d$_6$) δ 10.55 (s, 1H), 9.81 (s, 1H), 9.62 (s, 1H), 8.56 (s, 2H), 8.29 (s, 1H), 7.49-7.51 (d, J = 10.4 Hz, 1H) ), 6.01-6.03 (d, J = 10.4 Hz, 1H), 3.65-3.67 (m, 2H), 3.30-3.34 (m, 2H), 3.08 (bs, 2H), 2.55-2.58 (m, 2H), 0.96 (s, 6H). LCMS m/z 521.18 [M + H]$^+$, t$_R$ 1.937 min |

In some embodiments, the compound of the invention is selected from any one of compounds 1 to 11. In one aspect of these embodiments, the compound is selected from any one of compounds 1, 2, 3, 4, 8 and 11.

Pharmacokinetics (PK) play an increasing role in drug discovery and development. Pharmacokinetics is the quantitative study of the time course of drug absorption, distribution, metabolism and/or excretion. When a drug is administered, it distributes rapidly from its administration site into the systemic blood circulation. One measure of the extent of a therapeutic agent's distribution is the area under the plasma concentration-time curve (AUC), calculated to the last measured concentration (AUC$_t$) and extrapolated to infinity (AUC$_{Inf}$). AUC is thus a frequently used metric to quantitate drug exposure.

In general, the higher the exposure of a therapeutic agent, the greater the effects of the agent. However, high exposure of a therapeutic agent may have deleterious effects on certain tissues such as the brain. While the blood-brain barrier (BBB), a protective network consisting of tight junctions between endothelial cells, restricts the diffusion of hydrophilic and/or large molecules, drugs with high AUC are still capable of penetrating the BBB and/or cerebrospinal fluid. Such penetration is often undesirable and can lead to unwanted side effects. Current drug discovery efforts are aimed, in part, at striking a balance between maximizing drug exposure (i.e. AUC) while minimizing brain penetration.

The brain to plasma (B:P) ratio is once such method of quantifying the relative distribution of a therapeutic agent in brain tissue to that in circulation. Such a ratio provides one indication of the brain penetration of a given therapeutic agent. A high brain to plasma ratio is preferred when targeting diseases localized in the central nervous system (CNS), including the brain and the cerebrospinal fluid. However, a lower brain to plasma ratio is generally preferable for non-CNS therapeutic agents to minimize brain penetration to avoid potential side effects. Thus, a low brain to plasma ratio is preferable to avoid unwanted accumulation of therapeutic agents in the brain and CNS tissue.

As set forth in more detail in the Example section, the compounds of the present invention display a higher AUC and/or a lower B:P as compared to other nuclear transport inhibitors, such as those disclosed in co-owned U.S. patent application Ser. No. 13/041,377, filed Mar. 5, 2011 and published as US 2009/0275607 on Nov. 10, 2011. In some embodiments, the present invention provides a compound of formula I, wherein the compound has <1 µM (less than 1 µM) nuclear export activity, an AUC$_{Inf}$ greater than about 3500; and a B:P of less than about 2.5 when dosed in a mouse at 10 mg/kg po.

The novel features of the present invention will become apparent to those of skill in the art upon examination of the following detailed description of the invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

Compounds of the present invention may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers or enantiomers, with all possible isomers and mixtures thereof, including optical isomers, being included in the present invention.

The term "halo" or "halogen" as used herein means halogen and includes, for example, and without being limited thereto, fluoro, chloro, bromo, iodo and the like, in both radioactive and non-radioactive forms.

The term "alkyl," as used herein, unless otherwise indicated, means straight or branched saturated monovalent hydrocarbon radicals, typically $C_1$-$C_{12}$, preferably $C_1$-$C_6$. As such, "$C_1$-$C_6$ alkyl" means a straight or branched saturated monovalent hydrocarbon radical having from one to six carbon atoms (e.g., 1, 2, 3, 4, 5 or 6). Examples of alkyl groups include, but are not limited to, methyl, ethyl, propyl, isopropyl, and t-butyl.

It is understood that substituents and substitution patterns on the compounds of the invention can be selected by one of ordinary skill in the art to provide compounds that are chemically stable and that can be readily synthesized by techniques known in the art, as well as those methods set forth below. In general, the term "substituted," whether preceded by the term "optionally" or not, means that one or more hydrogens of the designated moiety are replaced with a suitable substituent. Unless otherwise indicated, an "optionally substituted group" can have a suitable substituent at each substitutable position of the group and, when more than one position in any given structure may be substituted with more than one substituent selected from a specified group, the substituent can be either the same or different at every position. Alternatively, an "optionally substituted group" can be unsubstituted.

Combinations of substituents envisioned by this invention are preferably those that result in the formation of stable or chemically feasible compounds. If a substituent is itself substituted with more than one group, it is understood that these multiple groups can be on the same carbon atom or on different carbon atoms, as long as a stable structure results. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted group" are independently halogen; —$(CH_2)_{0-4}R°$; —$(CH_2)_{0-40}R°$; —O$(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}$-Ph which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR—$, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-40}S(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O—$N(R°)_2$, wherein each R° may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, and sulfur, or, notwithstanding the definition above, two independent occurrences of R°, taken together with their intervening atom(s), form a 3-12-membered saturated, partially unsaturated, or aryl monocyclic or bicyclic ring having 0-4 heteroatoms independently selected from nitrogen, oxygen, and sulfur, which may be substituted as defined below.

Suitable monovalent substituents on R° (or the ring formed by taking two independent occurrences of R° together with their intervening atoms), are independently halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR^{\bullet}$, —$(C_{1-4}$ straight or branched alkylene)C(O)O$R^{\bullet}$, or —SS$R^{\bullet}$ wherein each $R^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents on a saturated carbon atom of an "optionally substituted group" include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, and —$S(C(R^*_2))_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —$O(CR^*_2)_{2-3}O$—, wherein each independent occurrence of R* is selected from hydrogen, $C_1$-6 aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —R●, -(haloR●), —OH, —OR●, —O(haloR●), —CN, —C(O)OH, —C(O)OR●, —NH₂, —NHR●, —NR●₂, and —NO₂, wherein each R● is unsubstituted or where preceded by "halo" is substituted only with one or more halogens, and is independently $C_{1-4}$ aliphatic, —CH₂Ph, —O(CH₂)₀₋₁-Ph, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted group" include —R†, —NR†₂, —C(O)R†, —C(O)OR†, —C(O)C(O)R†, —C(O)CH₂C(O)R†, —S(O)₂R†, —S(O)₂NR†₂, —C(S)NR†₂, —C(NH)NR†₂, and —N(R†)S(O)₂R†; wherein each R† is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of RY, taken together with their intervening atom(s) form an unsubstituted 3-12-membered saturated, partially unsaturated, or aryl monocyclic or bicyclic ring having 0-4 heteroatoms independently selected from nitrogen, oxygen, and sulfur.

Suitable substituents on the aliphatic group of R† are independently halogen, —R●, -(haloR●), —OH, —OR●, —O(haloR●), —CN, —C(O)OH, —C(O)OR●, —NH₂, —NHR●, —NR●₂, or —NO₂, wherein each R● is unsubstituted or where preceded by "halo" is substituted only with one or more halogens, and is independently $C_{1-4}$ aliphatic, —CH₂Ph, —O(CH₂)₀₋₁-Ph, or a 5-6-membered saturated, partially unsaturated, or aryl ring having 0-4 heteroatoms independently selected from nitrogen, oxygen, and sulfur.

Preferred substituents on heteroaryl can be selected from the group consisting of —OH, —SH, nitro, halogen, amino, cyano, $C_1$-$C_{12}$ alkyl, $C_2$-$C_{12}$ alkenyl, $C_2$-$C_{12}$ alkynyl, $C_1$-$C_{12}$ alkoxy, $C_1$-$C_{12}$ haloalkyl, $C_1$-$C_{12}$ haloalkoxy and $C_1$-$C_{12}$ alkyl sulfanyl. Preferred substituents on alkyl, alkylene and heterocyclyl include the preferred substituents on heteroaryl and oxo. In one embodiment, the substituent on an alkyl, alkylene, heterocyclyl or heteroaryl is an amino group having the formula —N($R^5$)₂, wherein each $R^5$ is independently selected from hydrogen and $C_1$-$C_4$ alkyl.

Substituents on alkyl, aklylene, heterocyclyl and heteroaryl can be selected from —OH, —SH, nitro, halogen, amino, cyano, $C_1$-$C_{12}$ alkyl, $C_2$-$C_{12}$ alkenyl, $C_2$-$C_{12}$ alkynyl group, $C_1$-$C_{12}$ alkoxy, $C_1$-$C_{12}$ haloalkyl, $C_1$-$C_{12}$ haloalkoxy and $C_1$-$C_{12}$ alkyl sulfanyl. In one embodiment, the substituent is an amino group having the formula —N($R^5$)₂, wherein each $R^5$ is independently selected from hydrogen and $C_1$-$C_4$ alkyl.

The term "cycloalkyl", as used herein, means saturated cyclic hydrocarbons, i.e. compounds where all ring atoms are carbons. Examples of cycloalkyl include, but are not limited to, cyclopropyl, cyclobutyl, cyclopentyl, cyclohexyl, and cycloheptyl. In some embodiments, cycloalkyl can optionally be substituted with one or more substituents selected from —OH, —SH, halogen, amino, nitro, cyano, $C_1$-$C_{12}$ alkyl, $C_2$-$C_{12}$ alkenyl or $C_2$-$C_{12}$ alkynyl group, $C_1$-$C_{12}$ alkoxy, $C_1$-$C_{12}$ haloalkyl, and $C_1$-$C_{12}$ haloalkoxy.

The term "heteroaryl", as used herein, refers to aromatic groups containing one or more heteroatoms (O, S, or N). A heteroaryl group can be monocyclic or polycyclic, e.g. a monocyclic heteroaryl ring fused to one or more carbocyclic aromatic groups or other monocyclic heteroaryl groups. The heteroaryl groups of this invention can also include ring systems substituted with one or more oxo moieties. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

The foregoing heteroaryl groups may be C-attached or N-attached (where such is possible). For instance, a group derived from pyrrole may be pyrrol-1-yl (N-attached) or pyrrol-3-yl (C-attached).

"Heterocyclyl" means a cyclic 4-13 membered saturated or unsaturated aliphatic ring containing 1, 2, 3, 4 or 5 heteroatoms independently selected from N, O or S. When one heteroatom is S, it can be optionally mono- or di-oxygenated (i.e. —S(O)— or —S(O)₂—). The heterocyclyl can be monocyclic, fused bicyclic, bridged bicyclic, spiro bicyclic or polycyclic.

"Oxo" means =O.

As used herein, the term "alkenyl" means a saturated straight chain or branched non-cyclic hydrocarbon having from 2 to 12 carbon atoms and having at least one carbon-carbon double bond. Alkenyl groups may be optionally substituted with one or more substituents.

As used herein, the term "alkynyl" means a saturated straight chain or branched non-cyclic hydrocarbon having from 2 to 12 carbon atoms and having at least one carbon-carbon triple bond. Alkynyl groups may be optionally substituted with one or more substituents.

As used herein, the term "alkylene" refers to an alkyl group that has two points of attachment to the rest of the compound. Non-limiting examples of alkylene groups include methylene (—CH2-), ethylene (—CH2CH2-), n-propylene (—CH2CH2CH2-), isopropylene (—CH2CH (CH3)-), and the like. Alkylene groups may be optionally substituted with one or more substituents.

The term "haloalkyl", as used herein, includes an alkyl substituted with one or more F, Cl, Br, or I, wherein alkyl is defined above.

The terms "alkoxy", as used herein, means an "alkyl-O—" group, wherein alkyl is defined above. Examples of alkoxy group include methoxy or ethoxy groups.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid (2,2,2-trifluoroacetic acid), oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, trifluoroacetate (2,2,2-trifluoroacetate), undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

The term "pharmaceutically acceptable salt" means either an acid addition salt or a basic addition salt which is compatible with the treatment of patients.

In some embodiments, exemplary inorganic acids which form suitable salts include, but are not limited thereto, hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, trifluoroacetic acid (2,2,2-trifluoroacetic acid), glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms. Other non-pharmaceutically acceptable salts e.g. oxalates may be used for example in the isolation of compounds of Formula I for laboratory use, or for subsequent conversion to a pharmaceutically acceptable acid addition salt.

A "pharmaceutically acceptable basic addition salt" is any non-toxic organic or inorganic base addition salt of the acid compounds represented by Formula I or any of its intermediates. Illustrative inorganic bases which form suitable salts include, but are not limited thereto, lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

Acid addition salts of the compounds of Formula I are most suitably formed from pharmaceutically acceptable acids, and include for example those formed with inorganic acids e.g. hydrochloric, sulphuric or phosphoric acids and organic acids e.g. succinic, maleic, acetic, trifluoroacetic or fumaric acid. Other non-pharmaceutically acceptable salts e.g. oxalates may be used for example in the isolation of compounds of Formula I for laboratory use, or for subsequent conversion to a pharmaceutically acceptable acid addition salt. Also included within the scope of the invention are base addition salts (such as sodium, potassium and ammonium salts), solvates and hydrates of compounds of the invention. The conversion of a given compound salt to a desired compound salt is achieved by applying standard techniques, well known to one skilled in the art.

The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating or lessening the severity of one or more symptoms of a disorder or condition.

When introducing elements disclosed herein, the articles "a", "an", "the", and "said" are intended to mean that there are one or more of the elements. The terms "comprising", "having", "including" are intended to be open-ended and mean that there may be additional elements other than the listed elements.

Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit CRM1, in a biological sample or in a patient. In certain embodiments, a composition of this invention is formulated for administration to a patient in need of such composition. The term "patient", as used herein, means an animal. In some embodiments, the animal is a mammal. In certain embodiments, the patient is a veterinary patient (i.e., a non-human mammal patient). In some embodiments, the patient is a dog. In other embodiments, the patient is a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or intraperitoneally.

The term "parenteral" as used herein includes subcutaneous, intravenous, intramuscular, intraocular, intravitreal, intra-articular, intra-synovial, intrasternal, intrathecal, intra-hepatic, intraperitoneal intralesional and intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A provided compound can also be in micro-encapsulated form.

Alternatively, pharmaceutically acceptable compositions of this invention may be administered in the form of suppositories for rectal administration. Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For ophthalmic use, provided pharmaceutically acceptable compositions may be formulated as micronized suspensions or in an ointment such as petrolatum.

Pharmaceutically acceptable compositions of this invention may also be administered by nasal aerosol or inhalation.

In some embodiments, pharmaceutically acceptable compositions of this invention are formulated for intra-peritoneal administration.

The amount of compounds of the present invention that may be combined with the carrier materials to produce a composition in a single dosage form will vary depending upon the host treated, the particular mode of administration. In one embodiment, provided compositions should be formulated so that a dosage of between 0.01-100 mg/kg body weight/day of the inhibitor can be administered to a patient receiving these compositions. In another embodiment, the dosage is from about 0.5 to about 100 mg/kg of body weight, or between 1 mg and 1000 mg/dose, every 4 to 120 hours, or according to the requirements of the particular drug. Typically, the pharmaceutical compositions of this invention will be administered from about 1 to about 6 times per day.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Uses of Compounds and Pharmaceutically Acceptable Compositions

Compounds and compositions described herein are generally useful for the inhibition of CRM1 and are therefore useful for treating one or more disorders associated with activity of CRM1. Thus, in certain embodiments, the present invention provides a method for treating a CRM1-mediated disorder comprising the step of administering to a patient in need thereof a compound of the present invention, or pharmaceutically acceptable composition thereof. The compounds and compositions described herein can also be administered to cells in culture, e.g. in vitro or ex vivo, or to a subject, e.g., in vivo, to treat, prevent, and/or diagnose a variety of disorders, including those described herein below.

The activity of a compound utilized in this invention as an inhibitor of CRM1 may be assayed in vitro, in vivo or in a cell line. Detailed conditions for assaying a compound utilized in this invention as an inhibitor of CRM1 are set forth in the Examples below.

As used herein, the term "CRM1-mediated" disorder or condition, as used herein, means any disease or other deleterious condition in which CRM1 is known to play a role. Accordingly, another embodiment of the present invention relates to treating or lessening the severity of one or more diseases in which CRM1 is known to play a role. In some embodiments, the present invention provides methods of treating a disease associated with expression or activity of p53, p73, p21, pRB, p27, IκB, NFκB, c-Abl, FOXO proteins, COX-2, or an HDAC (histone deacetylases) in a subject comprising administering to the patient a therapeutically effective amount of a compound described herein. In another embodiment, the present invention relates to a method of treating or lessening the severity of a disease or condition selected from a proliferative disorder (e.g., cancer), an inflammatory disorder, an autoimmune disorder, a viral infection, an ophthalmological disorder or a neurodegenerative disorder wherein said method comprises administering to a patient in need thereof a compound or composition according to the present invention. In a more specific embodiment, the present invention relates to a method of treating or lessening the severity of cancer. Specific examples of the above disorders are set forth in detail below.

Cancers treatable by the compounds of this invention include, but are not limited to, hematologic malignancies (leukemias, lymphomas, myelomas including multiple myeloma, myelodysplastic and myeloproliferative syndromes) and solid tumors (carcinomas such as prostate, breast, lung, colon, pancreatic, renal, ovarian as well as soft tissue and osteosarcomas, and stromal tumors). Breast cancer (BC) can include basal-like breast cancer (BLBC), triple negative breast cancer (TNBC) and breast cancer that is both BLBC and TNBC. In addition, breast cancer can include invasive or non-invasive ductal or lobular carcinoma, tubular, medullary, mucinous, papillary, cribriform carcinoma of the breast, male breast cancer, recurrent or metastatic breast cancer, phyllodes tumor of the breast and Paget's disease of the nipple.

Inflammatory disorders treatable by the compounds of this invention include, but are not limited to, multiple sclerosis, rheumatoid arthritis, degenerative joint disease, systemic lupus, systemic sclerosis, vasculitis syndromes (small, medium and large vessel), atherosclerosis, inflammatory bowel disease, irritable bowel syndrome, Crohn's disease, mucous colitis, ulcerative colitis, gastritis, sepsis, psoriasis and other dermatological inflammatory disorders (such as eczema, atopic dermatitis, contact dermatitis, urticaria, scleroderma, and dermatosis with acute inflammatory components, pemphigus, pemphigoid, allergic dermatitis), and urticarial syndromes.

Viral diseases treatable by the compounds of this invention include, but are not limited to, acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster. Viral diseases treatable by the compounds of this invention also include chronic viral infections, including hepatitis B and hepatitis C.

Exemplary ophthalmology disorders include, but are not limited to, macular edema (diabetic and nondiabetic macular edema), aged related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epitheliitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency or cataract.

Neurodegenerative diseases treatable by a compound of Formula I include, but are not limited to, Parkinson's, Alzheimer's, and Huntington's, and Amyotrophic lateral sclerosis (ALS/Lou Gehrig's Disease).

Compounds and compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, polycystic kidney disorder (PKD) and other renal disorders.

Compounds and compositions described herein may also be used to treat disorders related to food intake such as obesity and hyperphagia.

In another embodiment, a compound or composition described herein may be used to treat or prevent allergies and respiratory disorders, including asthma, bronchitis, pulmonary fibrosis, allergic rhinitis, oxygen toxicity, emphysema, chronic bronchitis, acute respiratory distress syndrome, and any chronic obstructive pulmonary disease (COPD).

In some embodiments, the disorder or condition associated with CRM1 activity is muscular dystrophy, arthritis, for example, osteoarthritis and rheumatoid arthritis, ankylosing spondilitis, traumatic brain injury, spinal cord injury, sepsis, rheumatic disease, cancer atherosclerosis, type 1 diabetes, type 2 diabetes, leptospiriosis renal disease, glaucoma, retinal disease, ageing, headache, pain, complex regional pain syndrome, cardiac hypertrophy, musclewasting, catabolic disorders, obesity, fetal growth retardation, hypercholesterolemia, heart disease, chronic heart failure, ischemia/reperfusion, stroke, cerebral aneurysm, angina pectoris, pulmonary disease, cystic fibrosis, acid-induced lung injury, pulmonary hypertension, asthma, chronic obstructive pulmonary disease, Sjogren's syndrome, hyaline membrane disease, kidney disease, glomerular disease, alcoholic liver disease, gut diseases, peritoneal endometriosis, skin diseases, nasal sinusitis, mesothelioma, anhidrotic ecodermal dysplasia-ID, behcet's disease, incontinentia pigmenti, tuberculosis, asthma, crohn's disease, colitis, ocular allergy, appendicitis, paget's disease, pancreatitis, periodonitis, endometriosis, inflammatory bowel disease, inflammatory lung disease, silica-induced diseases, sleep apnea, AIDS, HIV-1, autoimmune diseases, antiphospholipid syndrome, lupus, lupus nephritis, familial mediterranean fever, hereditary periodic fever syndrome, psychosocial stress diseases, neuropathological diseases, familial amyloidotic polyneuropathy, inflammatory neuropathy, parkinson's disease, multiple sclerosis, alzheimer's disease, amyotropic lateral sclerosis, huntington's disease, cataracts, or hearing loss.

In other embodiments, the disorder or condition associated with CRM1 activity is head injury, uveitis, inflammatory pain, allergen induced asthma, non-allergen induced asthma, glomerular nephritis, ulcerative colitis, necrotizing enterocolitis, hyperimmunoglobulinemia D with recurrent fever (HIDS), TNF receptor associated periodic syndrome (TRAPS), cryopyrin-associated periodic syndromes, Muckle-Wells syndrome (urticaria deafness amyloidosis), familial cold urticaria, neonatal onset multisystem inflammatory disease (NOMID), periodic fever, aphthous stomatitis, pharyngitis and adenitis (PFAPA syndrome), Blau syndrome, pyogenic sterile arthritis, pyoderma gangrenosum, acne (PAPA), deficiency of the interleukin-1-receptor antagonist (DIRA), subarachnoid hemorrhage, polycystic kidney disease, transplant, organ transplant, tissue transplant, myelodysplastic syndrome, irritant-induced inflammation, plant irritant-induced inflammation, poison ivy/urushiol oil-induced inflammation, chemical irritant-induced inflammation, bee sting-induced inflammation, insect bite-induced inflammation, sunburn, burns, dermatitis, endotoxemia, lung injury, acute respiratory distress syndrome, alcoholic hepatitis, or kidney injury caused by parasitic infections.

In further aspects, the present invention provides a use of a compound of formula I for the manufacture of a medicament for the treatment of a disease associated with expression or activity of p53, p73, p21, pRB, p27, IκB, NFκB, c-Abl, FOXO proteins, COX-2 or an HDAC in a subject. In some embodiments, the present invention provides a use of a compound of formula I in the manufacture of a medicament for the treatment of any of cancer and/or neoplastic disorders, angiogenesis, autoimmune disorders, inflammatory disorders and/or diseases, epigenetics, hormonal disorders and/or diseases, viral diseases, neurodegenerative disorders and/or diseases, wounds, and ophthalmologic disorders.

In some embodiments, the present invention provides a method for inhibiting CRM1 in a biological sample comprising contacting the biological sample with, or administering to the patient, a pharmaceutically acceptable salt of a compound of Formula I, or pharmaceutically acceptable composition thereof.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders, e.g., tumors arising from prostate, brain, bone, colon, lung, breast, ovarian, and liver origin, hematopoietic neoplastic disorders, e.g., leukemias, lymphomas, myeloma and other malignant plasma cell disorders, and metastatic tumors. Prevalent cancers include: breast, prostate, colon, lung, liver, and pancreatic cancers. Treatment with the compound can be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof, as well as in familial cancer syndromes such as Li Fraumeni Syndrome, Familial Breast-Ovarian Cancer (BRCA1 or BRAC2 mutations) Syndromes, and others. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Exemplary cancers described by the National Cancer Institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

Further exemplary cancers include diffuse large B-cell lymphoma (DLBCL) and mantle cell lymphoma (MCL).

Metastases of the aforementioned cancers can also be treated or prevented in accordance with the methods described herein.

Combination Therapies

In some embodiments, a compound described herein is administered together with an additional "second" therapeutic agent or treatment. The choice of second therapeutic agent may be made from any agent that is typically used in a monotherapy to treat the indicated disease or condition. As used herein, the term "administered together" and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art. The additional agents may be administered separately, as part of a multiple dose regimen, from the compounds of this invention. Alternatively, those agents may be part of a single dosage form, mixed together with the compounds of this invention in a single composition.

Cancer Combination Therapies

In some embodiments, a compound described herein is administered together with an additional cancer treatment. Exemplary additional cancer treatments include, for example: chemotherapy, targeted therapies such as antibody therapies, kinase inhibitors, immunotherapy, and hormonal therapy, epigenetic therapy, proteosome inhibitors, and anti-angiogenic therapies. Examples of each of these treatments are provided below. As used herein, the term "combination," "combined," and related terms refer to the simultaneous or sequential administration of therapeutic agents in accordance with this invention. For example, a compound of the present invention can be administered with another therapeutic agent simultaneously or sequentially in separate unit dosage forms or together in a single unit dosage form. Accordingly, the present invention provides a single unit dosage form comprising a compound of the invention, an additional therapeutic agent, and a pharmaceutically acceptable carrier, adjuvant, or vehicle.

The amount of both a compound of the invention and additional therapeutic agent (in those compositions which comprise an additional therapeutic agent as described above) that can be combined with the carrier materials to produce a single dosage form will vary depending upon the host treated and the particular mode of administration. Preferably, compositions of this invention should be formulated so that a dosage of between 0.01-100 mg/kg body weight/day of a compound of the invention can be administered.

Chemotherapy

In some embodiments, a compound described herein is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, topoisomerase inhibitors and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, Bendamustin, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafururacil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erolotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (Herceptin®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g., Gleevec (Vignari and Wang 2001).

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Angiogenesis

Compounds and methods described herein may be used to treat or prevent a disease or disorder associated with angiogenesis. Diseases associated with angiogenesis include cancer, cardiovascular disease and macular degeneration.

Angiogenesis is the physiological process involving the growth of new blood vessels from pre-existing vessels. Angiogenesis is a normal and vital process in growth and development, as well as in wound healing and in granulation tissue. However, it is also a fundamental step in the transition of tumors from a dormant state to a malignant one. Angiogenesis may be a target for combating diseases characterized by either poor vascularisation or abnormal vasculature.

Application of specific compounds that may inhibit or induce the creation of new blood vessels in the body may help combat such diseases. The presence of blood vessels where there should be none may affect the mechanical properties of a tissue, increasing the likelihood of failure. The absence of blood vessels in a repairing or otherwise metabolically active tissue may inhibit repair or other essential functions. Several diseases, such as ischemic chronic wounds, are the result of failure or insufficient blood vessel formation and may be treated by a local expansion of blood vessels, thus bringing new nutrients to the site, facilitating repair. Other diseases, such as age-related macular degeneration, may be created by a local expansion of blood vessels, interfering with normal physiological processes.

Vascular endothelial growth factor (VEGF) has been demonstrated to be a major contributor to angiogenesis, increasing the number of capillaries in a given network. Upregulation of VEGF is a major component of the physiological response to exercise and its role in angiogenesis is suspected to be a possible treatment in vascular injuries. In vitro studies clearly demonstrate that VEGF is a potent stimulator of angiogenesis because, in the presence of this growth factor, plated endothelial cells will proliferate and migrate, eventually forming tube structures resembling capillaries.

Tumors induce blood vessel growth (angiogenesis) by secreting various growth factors (e.g., VEGF). Growth factors such as bFGF and VEGF can induce capillary growth into the tumor, which some researchers suspect supply required nutrients, allowing for tumor expansion.

Angiogenesis represents an excellent therapeutic target for the treatment of cardiovascular disease. It is a potent, physiological process that underlies the natural manner in which our bodies respond to a diminution of blood supply to vital organs, namely the production of new collateral vessels to overcome the ischemic insult.

Overexpression of VEGF causes increased permeability in blood vessels in addition to stimulating angiogenesis. In wet macular degeneration, VEGF causes proliferation of capillaries into the retina. Since the increase in angiogenesis also causes edema, blood and other retinal fluids leak into the retina, causing loss of vision.

Anti-angiogenic therapy can include kinase inhibitors targeting vascular endothelial growth factor (VEGF) such as sunitinib, sorafenib, or monoclonal antibodies or receptor "decoys" to VEGF or VEGF receptor including bevacizumab or VEGF-Trap, or thalidomide or its analogs (lenalidomide, pomalidomide), or agents targeting non-VEGF angiogenic targets such as fibroblast growth factor (FGF), angiopoietins, or angiostatin or endostatin.

Epigenetics

Compounds and methods described herein may be used to treat or prevent a disease or disorder associated with epigenetics. Epigenetics is the study of heritable changes in phenotype or gene expression caused by mechanisms other than changes in the underlying DNA sequence. One example of epigenetic changes in eukaryotic biology is the process of cellular differentiation. During morphogenesis, stem cells become the various cell lines of the embryo which in turn become fully differentiated cells. In other words, a single fertilized egg cell changes into the many cell types including neurons, muscle cells, epithelium, blood vessels etc. as it continues to divide. It does so by activating some genes while inhibiting others.

Epigenetic changes are preserved when cells divide. Most epigenetic changes only occur within the course of one individual organism's lifetime, but, if a mutation in the DNA has been caused in sperm or egg cell that results in fertilization, then some epigenetic changes are inherited from one generation to the next. Specific epigenetic processes include paramutation, bookmarking, imprinting, gene silencing, X chromosome inactivation, position effect, reprogramming, transvection, maternal effects, the progress of carcinogenesis, many effects of teratogens, regulation of histone modifications and heterochromatin, and technical limitations affecting parthenogenesis and cloning.

Exemplary diseases associated with epigenetics include ATR-syndrome, fragile X-syndrome, ICF syndrome, Angelman's syndrome, Prader-Wills syndrome, BWS, Rett syndrome, α-thalassaemia, cancer, leukemia, Rubinstein-Taybi syndrome and Coffin-Lowry syndrome.

The first human disease to be linked to epigenetics was cancer. Researchers found that diseased tissue from patients with colorectal cancer had less DNA methylation than normal tissue from the same patients. Because methylated genes are typically turned off, loss of DNA methylation can cause abnormally high gene activation by altering the arrangement of chromatin. On the other hand, too much methylation can undo the work of protective tumor suppressor genes.

DNA methylation occurs at CpG sites, and a majority of CpG cytosines are methylated in mammals. However, there are stretches of DNA near promoter regions that have higher concentrations of CpG sites (known as CpG islands) that are free of methylation in normal cells. These CpG islands become excessively methylated in cancer cells, thereby causing genes that should not be silenced to turn off. This abnormality is the trademark epigenetic change that occurs in tumors and happens early in the development of cancer. Hypermethylation of CpG islands can cause tumors by shutting off tumor-suppressor genes. In fact, these types of changes may be more common in human cancer than DNA sequence mutations.

Furthermore, although epigenetic changes do not alter the sequence of DNA, they can cause mutations. About half of the genes that cause familial or inherited forms of cancer are turned off by methylation. Most of these genes normally suppress tumor formation and help repair DNA, including 06-methylguanine-DNA methyltransferase (MGMT), MLH1 cyclin-dependent kinase inhibitor 2B (CDKN2B), and RASSF1A. For example, hypermethylation of the promoter of MGMT causes the number of G-to-A mutations to increase.

Hypermethylation can also lead to instability of microsatellites, which are repeated sequences of DNA. Microsatellites are common in normal individuals, and they usually consist of repeats of the dinucleotide CA. Too much methylation of the promoter of the DNA repair gene MLH1 can make a microsatellite unstable and lengthen or shorten it. Microsatellite instability has been linked to many cancers, including colorectal, endometrial, ovarian, and gastric cancers.

Fragile X syndrome is the most frequently inherited mental disability, particularly in males. Both sexes can be affected by this condition, but because males only have one X chromosome, one fragile X will impact them more severely. Indeed, fragile X syndrome occurs in approximately 1 in 4,000 males and 1 in 8,000 females. People with this syndrome have severe intellectual disabilities, delayed verbal development, and "autistic-like" behavior.

Fragile X syndrome gets its name from the way the part of the X chromosome that contains the gene abnormality looks under a microscope; it usually appears as if it is hanging by a thread and easily breakable. The syndrome is caused by an abnormality in the FMR1 (fragile X mental retardation 1) gene. People who do not have fragile X syndrome have 6 to 50 repeats of the trinucleotide CGG in their FMR1 gene. However, individuals with over 200 repeats have a full mutation, and they usually show symptoms of the syndrome. Too many CGGs cause the CpG islands at the promoter region of the FMR1 gene to become methylated; normally, they are not. This methylation turns the gene off, stopping the FMR1 gene from producing an important protein called fragile X mental retardation protein. Loss of this specific protein causes fragile X syndrome. Although a lot of attention has been given to the CGG expansion mutation as the cause of fragile X, the epigenetic change associated with FMR1 methylation is the real syndrome culprit.

Fragile X syndrome is not the only disorder associated with mental retardation that involves epigenetic changes. Other such conditions include Rubenstein-Taybi, Coffin-Lowry, Prader-Willi, Angelman, Beckwith-Wiedemann, ATR-X, and Rett syndromes.

Epigenetic therapies include inhibitors of enzymes controlling epigenetic modifications, specifically DNA methyltransferases and histone deacetylases, which have shown promising anti-tumorigenic effects for some malignancies, as well as antisense oligonucleotides and siRNA.

Immunotherapy

In some embodiments, a compound described herein is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, prostate cancer vaccine Provenge, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with a hormonal therapy. The growth of some cancers can be inhibited by providing or blocking certain hormones. Common examples of hormone-sensitive tumors include certain types of breast and prostate cancers, as well as certain types of leukemia which respond to certain retinoids/retinoic acids. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Hormonal therapy agents include the administration of hormone agonists or hormone antagonists and include retinoids/retinoic acid, compounds that inhibit estrogen or testosterone, as well as administration of progestogens.

Inflammation and Autoimmune Disease

The compounds and methods described herein may be used to treat or prevent a disease or disorder associated with inflammation, particularly in humans and other mammals. A compound described herein may be administered prior to the onset of, at, or after the initiation of inflammation. When used prophylactically, the compounds are preferably provided in advance of any inflammatory response or symptom. Administration of the compounds can prevent or attenuate inflammatory responses or symptoms. Exemplary inflammatory conditions include, for example, multiple sclerosis, rheumatoid arthritis, psoriatic arthritis, degenerative joint disease, spondouloarthropathies, other seronegative inflammatory arthridities, polymyalgia rheumatica, various vasculidities (e.g., giant cell arteritis, ANCA+ vasculitis), gouty arthritis, systemic lupus erythematosus, juvenile arthritis, juvenile rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, schleroderma, psoriasis, and dermatosis with acute inflammatory components.

In another embodiment, a compound or method described herein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, a compound or method described herein may be used to treat autoimmune diseases and/or inflammation associated with autoimmune diseases, such as organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

In a particular embodiment, the compounds described herein can be used to treat multiple sclerosis. In a specific aspect, the compound used to treat multiple sclerosis is Compound 1: (Z)-3-(3-(3,5-bis(trifluoromethyl)phenyl)-1H-1,2,4-triazol-1-yl)-1-(3,3-difluoroazetidin-1-yl)prop-2-en-1-one).

Combination Therapy

In certain embodiments, a compound described herein may be administered alone or in combination with other compounds useful for treating or preventing inflammation. Exemplary anti-inflammatory agents include, for example, steroids (e.g., Cortisol, cortisone, fludrocortisone, prednisone, 6[alpha]-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other compound is drotrecogin alfa.

Further examples of anti-inflammatory agents include, for example, aceclofenac, acemetacin, e-acetamidocaproic acid, acetaminophen, acetaminosalol, acetanilide, acetylsalicylic acid, S-adenosylmethionine, alclofenac, alclometasone, alfentanil, algestone, allylprodine, alminoprofen, aloxiprin, alphaprodine, aluminum bis(acetylsalicylate), amcinonide, amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antrafenine, apazone, beclomethasone, bendazac, benorylate, benoxaprofen, benzpiperylon, benzydamine, benzylmorphine, bermoprofen, betamethasone, betamethasone-17-valerate, bezitramide, [alpha]-bisabolol, bromfenac, p-bromoacetanilide, 5-bromosalicylic acid acetate, bromosaligenin, bucetin, bucloxic acid, bucolome, budesonide, bufexamac, bumadizon, buprenorphine, butacetin, butibufen, butorphanol, carbamazepine, carbiphene, caiprofen, carsalam, chlorobutanol, chloroprednisone, chlorthenoxazin, choline salicylate, cinchophen, cinmetacin, ciramadol, clidanac, clobetasol, clocortolone, clometacin, clonitazene, clonixin, clopirac, cloprednol, clove, codeine, codeine methyl bromide, codeine phosphate, codeine sulfate, cortisone, cortivazol, cropropamide, crotethamide, cyclazocine, deflazacort, dehydrotestosterone, desomorphine, desonide, desoximetasone, dexamethasone, dexamethasone-21-isonicotinate, dexoxadrol, dextromoramide, dextropropoxyphene, deoxycorticosterone, dezocine, diampromide, diamorphone, diclofenac, difenamizole, difenpiramide, diflorasone, diflucortolone, diflunisal, difluprednate, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, enoxolone, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, fluazacort, flucloronide, flufenamic acid, flumethasone, flunisolide, flunixin, flunoxaprofen, fluocinolone acetonide, fluocinonide, fluocinolone acetonide, fluocortin butyl, fluocoitolone, fluoresone, fluorometholone, fluperolone, flupirtine, fluprednidene, fluprednisolone, fluproquazone, flurandrenolide, flurbiprofen, fluticasone, formocortal, fosfosal, gentisic acid, glafenine, glucametacin, glycol salicylate, guaiazulene, halcinonide, halobetasol, halometasone, haloprednone, heroin, hydrocodone, hydro cortamate, hydrocortisone, hydrocortisone acetate, hydrocortisone succinate, hydrocortisone hemisuccinate, hydrocortisone 21-lysinate, hydrocortisone cypionate, hydromorphone, hydroxypethidine, ibufenac, ibuprofen, ibuproxam, imidazole salicylate, indomethacin, indoprofen, isofezolac, isoflupredone, isoflupredone acetate, isoladol, isomethadone, isonixin, isoxepac, isoxicam, ketobemidone, ketoprofen, ketorolac, p-lactophenetide, lefetamine, levallorphan, levorphanol, levophenacylmorphan, lofentanil, lonazolac, lornoxicam, loxoprofen, lysine acetylsalicylate, mazipredone, meclofenamic acid, medrysone, mefenamic acid, meloxicam, meperidine, meprednisone, meptazinol, mesalamine, metazocine, methadone, methotrimeprazine, methylprednisolone, methylprednisolone acetate, methylprednisolone sodium succinate, methylprednisolone suleptnate, metiazinic acid, metofoline, metopon, mofebutazone, mofezolac, mometasone, morazone, morphine, morphine hydrochloride, morphine sulfate, morpholine salicylate, myrophine, nabumetone, nalbuphine, nalorphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paramethasone, paranyline, parsalmide, pentazocine, perisoxal, phenacetin, phenadoxone, phenazocine, phenazopyridine hydrochloride, phenocoll, phenoperidine, phenopyrazone, phenomorphan, phenyl acetylsalicylate, phenylbutazone, phenyl salicylate, phenyramidol, piketoprofen, piminodine, pipebuzone, piperylone, pirazolac, piritramide, piroxicam, pirprofen, pranoprofen, prednicarbate, prednisolone, prednisone, prednival, prednylidene, proglumetacin, proheptazine, promedol, propacetamol, properidine, propiram, propoxyphene, propyphenazone, proquazone, protizinic acid, proxazole, ramifenazone, remifentanil, rimazolium metilsulfate, salacetamide, salicin, salicylamide, salicylamide o-acetic acid, salicylic acid, salicylsulfuric acid, salsalate, salverine, simetride, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tixocortol, tolfenamic acid, tolmetin, tramadol, triamcinolone, triamcinolone acetonide, tropesin, viminol, xenbucin, ximoprofen, zaltoprofen and zomepirac.

In one embodiment, a compound described herein may be administered with a selective COX-2 inhibitor for treating or preventing inflammation. Exemplary selective COX-2 inhibitors include, for example, deracoxib, parecoxib, celecoxib, valdecoxib, rofecoxib, etoricoxib, and lumiracoxib.

In some embodiments, a provided compound is administered in combination with an anthracycline or a Topo II inhibitor. In certain embodiments, a provided compound is administered in combination with Doxorubicin (Dox). In certain embodiments, a provided compound is administered in combination with bortezomib (and more broadly including carfilzomib). It was surprisingly found that a provided compound in combination with Dox or bortezomib resulted in a synergystic effect (i.e., more than additive).

Viral Infections

Compounds and methods described herein may be used to treat or prevent a disease or disorder associated with a viral infection, particularly in humans and other mammals. A compound described herein may be administered prior to the onset of, at, or after the initiation of viral infection. When used prophylactically, the compounds are preferably provided in advance of any viral infection or symptom thereof.

Exemplary viral diseases include acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster.

Exemplary viral pathogens include Adenovirus, Coxsackievirus, Dengue virus, Encephalitis Virus, Epstein-Barr virus, Hepatitis A virus, Hepatitis B virus, Hepatitis C virus, Herpes simplex virus type 1, Herpes simplex virus type 2, cytomegalovirus, Human herpesvirus type 8, Human immunodeficiency virus, Influenza virus, measles virus, Mumps virus, Human papillomavirus, Parainfluenza virus, Poliovirus, Rabies virus, Respiratory syncytial virus, Rubella virus, Varicella-zoster virus, West Nile virus, Dungee, and Yellow fever virus. Viral pathogens may also include viruses that cause resistant viral infections.

Antiviral drugs are a class of medications used specifically for treating viral infections. Antiviral action generally falls into one of three mechanisms: interference with the ability of a virus to infiltrate a target cell (e.g., amantadine, rimantadine and pleconaril), inhibition of the synthesis of virus (e.g., nucleoside analogues, e.g., acyclovir and zidovudine (AZT), and inhibition of the release of virus (e.g., zanamivir and oseltamivir).

Ophthalmology

Compounds and methods described herein may be used to treat or prevent an ophthamology disorder. Exemplary ophthamology disorders include macular edema (diabetic and nondiabetic macular edema), age related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency and cataract.

Other ophthalmology disorders treatable using the compounds and methods described herein include proliferative vitreoretinopathy and chronic retinal detachment.

Inflammatory eye diseases are also treatable using the compounds and methods described herein.

Neurodegenerative Disease

Neurodegeneration is the umbrella term for the progressive loss of structure or function of neurons, including death of neurons. Many neurodegenerative diseases including Parkinson's, Alzheimer's, and Huntington's occur as a result of neurodegenerative processes. As research progresses, many similarities appear which relate these diseases to one another on a sub-cellular level. Discovering these similarities offers hope for therapeutic advances that could ameliorate many diseases simultaneously. There are many parallels between different neurodegenerative disorders including atypical protein assemblies as well as induced cell death.

Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus.

Huntington's disease causes astrogliosis and loss of medium spiny neurons. Areas of the brain are affected according to their structure and the types of neurons they contain, reducing in size as they cumulatively lose cells. The areas affected are mainly in the striatum, but also the frontal and temporal cortices. The striatum's subthalamic nuclei send control signals to the globus pallidus, which initiates and modulates motion. The weaker signals from subthalamic nuclei thus cause reduced initiation and modulation of movement, resulting in the characteristic movements of the disorder. Exemplary treatments for Huntington's disease include tetrabenazine, neuroleptics, benzodiazepines, amantadine, remacemide, valproic acid, selective serotonin reuptake inhibitors (SSRIs), mirtazapine and antipsychotics.

The mechanism by which the brain cells in Parkinson's are lost may consist of an abnormal accumulation of the protein alpha-synuclein bound to ubiquitin in the damaged cells. The alpha-synuclein-ubiquitin complex cannot be directed to the proteosome. This protein accumulation forms proteinaceous cytoplasmic inclusions called Lewy bodies. The latest research on pathogenesis of disease has shown that the death of dopaminergic neurons by alpha-synuclein is due to a defect in the machinery that transports proteins between two major cellular organelles the endoplasmic reticulum (ER) and the Golgi apparatus. Certain proteins like Rabl may reverse this defect caused by alpha-synuclein in animal models. Exemplary Parkinson's disease therapies include levodopa, dopamine agonists such as include bromocriptine, pergolide, pramipexole, ropinirole, piribedil, cabergoline, apomorphine and lisuride, dopa decarboxylate inhibitors, MAO-B inhibitors such as selegilene and rasagilene, anticholinergics and amantadine.

Amyotrophic lateral sclerosis (ALS/Lou Gehrig's Disease) is a disease in which motor neurons are selectively targeted for degeneration. Exemplary ALS therapies include riluzole, baclofen, diazepam, trihexyphenidyl and amitriptyline.

Other exemplary neurodegenerative therapeutics include antisense oligonucleotides and stem cells.

Wound Healing

Wounds are a type of condition characterized by cell or tissue damage. Wound healing is a dynamic pathway that optimally leads to restoration of tissue integrity and function. The wound healing process consists of three overlapping phases. The first phase is an inflammatory phase, which is characterized by homeostasis, platelet aggregation and degranulation. Platelets as the first response, release multiple growth factors to recruit immune cells, epithelial cells, and endothelial cells. The inflammatory phase typically occurs over days 0-5. The second stage of wound healing is the proliferative phase during which macrophages and granulocytes invade the wound. Infiltrating fibroblasts begin to produce collagen. The principle characteristics of this phase are epithelialization, angiogenesis, granulation tissue formation and collagen production. The proliferative phase typically occurs over days 3-14. The third phase is the remodeling phase where matrix formation occurs. The fibroblasts, epithelial cells, and endothelial cells continue to produce collagen and collagenase as well as matrix metalloproteases (MMPs) for remodeling. Collagen crosslinking takes place and the wound undergoes contraction. The remodeling phase typically occurs from day 7 to one year.

Compounds and compositions described herein can be used for promoting wound healing (e.g., promoting or accelerating wound closure and/or wound healing, mitigating scar fibrosis of the tissue of and/or around the wound, inhibiting apoptosis of cells surrounding or proximate to the wound). Thus, in certain embodiments, the present invention provides a method for promoting wound healing in a subject, comprising administering to the subject a compound (e.g., a CRM1 inhibitor), or pharmaceutically acceptable salt or composition thereof. The method need not achieve complete healing or closure of the wound; it is sufficient for the method to promote any degree of wound closure. In this respect, the method can be employed alone or as an adjunct to other methods for healing wounded tissue.

The compounds and compositions described herein can be used to treat wounds during the inflammatory (or early) phase, during the proliferative (or middle) wound healing phase, and/or during the remodeling (or late) wound healing phase.

In some embodiments, the subject in need of wound healing is a human or an animal, for example, a horse, a pig, or a rodent, such as a mouse.

In some embodiments, the compounds and compositions described herein useful for wound healing are administered topically, for example, proximate to the wound site, or systemically.

More specifically, the compound or composition described herein can be administered (optionally in combination with other agents) to the wound site by coating the wound or applying a bandage, packing material, stitches, etc., that are coated or treated with the compound or composition described herein. As such, the compounds and compositions described herein can be formulated for topical administration to treat surface wounds. Topical formulations include those for delivery via the mouth (buccal) and to the skin such that a layer of skin (i.e., the epidermis, dermis, and/or subcutaneous layer) is contacted with the compound or composition described herein. Topical delivery systems may be used to administer topical formulations of the compounds and compositions described herein.

Alternatively, the compounds and compositions described herein can be administered at or near the wound site by, for example, injection of a solution, injection of an extended release formulation, or introduction of a biodegradable implant comprising the compound or composition described herein.

The compounds and compositions described herein can be used to treat acute wounds or chronic wounds. A chronic wound results when the normal reparative process is interrupted. Chronic wounds can develop from acute injuries as a result of unrecognized persistent infections or inadequate primary treatment. In most cases however, chronic lesions are the end stage of progressive tissue breakdown owing to venous, arterial, or metabolic vascular disease, pressure sores, radiation damage, or tumors.

In chronic wounds, healing does not occur for a variety of reasons, including improper circulation in diabetic ulcers, significant necrosis, such as in burns, and infections. In these chronic wounds, viability or the recovery phase is often the rate-limiting step. The cells are no longer viable and thus initial recovery phase is prolonged by unfavorable wound bed environment.

Chronic wounds include, but are not limited to the following: chronic ischemic skin lesions; scleroderma ulcers; arterial ulcers; diabetic foot ulcers; pressure ulcers; venous ulcers; non-healing lower extremity wounds; ulcers due to inflammatory conditions; and/or long-standing wounds.

In a particular embodiment, the compounds and compositions described herein can be used for diabetic wound healing or accelerating healing of leg and foot ulcers secondary to diabetes or ischemia in a subject.

In one embodiment, the wound is a surface wound. In another embodiment, the wound is a surgical wound (e.g., abdominal or gastrointestinal surgical wound). In a further embodiment, the wound is a burn. In yet another embodiment, the wound is the result of radiation exposure.

The compounds and compositions described herein can also be used for diabetic wound healing, gastrointestinal wound healing, or healing of an adhesion due, for example, to an operation.

The compounds and compositions described herein can also be used to heal wounds that are secondary to another disease. For example, in inflammatory skin diseases, such as psoriasis and dermatitis, there are numerous incidents of skin lesions that are secondary to the disease, and are caused by deep cracking of the skin, or scratching of the skin. The compounds and compositions described herein can be used to heal wounds that are secondary to these diseases, for example, inflammatory skin diseases, such as psoriasis and dermatitis.

In a further embodiment, the wound is an internal wound. In a specific aspect, the internal wound is a chronic wound. In another specific aspect, the wound is a vascular wound. In yet another specific aspect, the internal wound is an ulcer.

Examples of wounds include, but are not limited to, abrasions, avulsions, blowing wounds (i.e., open pneumothorax), burn wounds, contusions, gunshot wounds, incised wounds, open wounds, penetrating wounds, perforating wounds, puncture wounds, séton wounds, stab wounds, surgical wounds, subcutaneous wounds, diabetic lesions, or tangential wounds. Additional examples of wounds that can be treated by the compounds and compositions described herein include acute conditions or wounds, such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies; trauma-induced injuries including cuts, incisions, excoriations; injuries sustained from accidents; post-surgical injuries, as well as chronic conditions, such as pressure sores, bedsores, conditions related to diabetes and poor circulation, and all types of acne. In addition, the wound can include dermatitis, such as impetigo, intertrigo, folliculitis and eczema, wounds following dental surgery; periodontal disease; wounds following trauma; and tumor-associated wounds. Yet other examples of wounds include animal bites, arterial disease, insect stings and bites, bone infections, compromised skin/muscle grafts, gangrene, skin tears or lacerations, skin aging, surgical incisions, including slow or non-healing surgical wounds, intracerebral hemorrhage, aneurysm, dermal asthenia, and post-operation infections.

In preferred embodiments, the wound is selected from the group consisting of a burn wound, an incised wound, an open wound, a surgical or post surgical wound, a diabetic lesion, a thermal burn, a chemical burn, a radiation burn, a pressure sore, a bedsore, and a condition related to diabetes or poor circulation.

The present disclosure also relates to methods and compositions of reducing scar formation during wound healing in a subject. The compounds and compositions described herein can be administered directly to the wound or to cells proximate the wound at an amount effective to reduce scar formation in and/or around the wound.

The wound can include any injury to any portion of the body of a subject. According to embodiments, methods are provided to ameliorate, reduce, or decrease the formation of scars in a subject that has suffered a burn injury. According to preferred embodiments, methods are provided to treat, reduce the occurrence of, or reduce the probability of developing hypertrophic scars in a subject that has suffered an acute or chronic wound or injury.

Other Disorders

Compounds and compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, and other renal disorders.

Combination Radiation Therapy

Compounds and compositions described herein are useful as radiosensitizers. Therefore, compounds and compositions described herein can be administered in combination with radiation therapy. Radiation therapy is the medical use of high-energy radiation (e.g., x-rays, gamma rays, charged particles) to shrink tumors and kill malignant cells, and is generally used as part of cancer treatment. Radiation therapy kills malignant cells by damaging their DNA.

Radiation therapy can be delivered to a patient in several ways. For example, radiation can be delivered from an external source, such as a machine outside the patient's body, as in external beam radiation therapy. External beam radiation therapy for the treatment of cancer uses a radiation source that is external to the patient, typically either a radioisotope, such as $^{60}$Co, $^{137}$Cs, or a high energy x-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiating of healthy tissue can be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The irradiation of healthy tissue also can be reduced by tightly collimating the radiation beam to the general cross section of the tumor taken perpendicular to the axis of the radiation beam. Numerous systems exist for producing such a circumferential collimation, some of which use multiple sliding shutters which, piecewise, can generate a radio-opaque mask of arbitrary outline.

For administration of external beam radiation, the amount can be at least about 1 Gray (Gy) fractions at least once every other day to a treatment volume. In a particular embodiment, the radiation is administered in at least about 2 Gray (Gy) fractions at least once per day to a treatment volume. In another particular embodiment, the radiation is administered in at least about 2 Gray (Gy) fractions at least once per day to a treatment volume for five consecutive days per week. In another particular embodiment, radiation is administered in 10 Gy fractions every other day, three times per week to a treatment volume. In another particular embodiment, a total of at least about 20 Gy is administered to a patient in need thereof. In another particular embodiment, at least about 30 Gy is administered to a patient in need thereof. In another particular embodiment, at least about 40 Gy is administered to a patient in need thereof.

Typically, the patient receives external beam therapy four or five times a week. An entire course of treatment usually lasts from one to seven weeks depending on the type of cancer and the goal of treatment. For example, a patient can receive a dose of 2 Gy/day over 30 days.

Internal radiation therapy is localized radiation therapy, meaning the radiation source is placed at the site of the tumor or affected area. Internal radiation therapy can be delivered by placing a radiation source inside or next to the area requiring treatment. Internal radiation therapy is also called brachytherapy. Brachytherapy includes intercavitary treatment and interstitial treatment. In intracavitary treatment, containers that hold radioactive sources are put in or near the tumor. The sources are put into the body cavities. In interstitial treatment, the radioactive sources alone are put into the tumor. These radioactive sources can stay in the patient permanently. Typically, the radioactive sources are removed from the patient after several days. The radioactive sources are in containers.

There are a number of methods for administration of a radiopharmaceutical agent. For example, the radiopharmaceutical agent can be administered by targeted delivery or by systemic delivery of targeted radioactive conjugates, such as a radiolabeled antibody, a radiolabeled peptide and a liposome delivery system. In one particular embodiment of targeted delivery, the radiolabelled pharmaceutical agent can be a radiolabelled antibody. See, for example, Ballangrud A. M., et al. *Cancer Res.,* 2001; 61:2008-2014 and Goldenber, D. M. *J. Nucl. Med.,* 2002; 43(5):693-713, the contents of which are incorporated by reference herein.

In another particular embodiment of targeted delivery, the radiopharmaceutical agent can be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. See, for example, Emfietzoglou D, Kostarelos K, Sgouros G. An analytical dosimetry study for the use of radionuclide-liposome conjugates in internal radiotherapy. J Nucl Med 2001; 42:499-504, the contents of which are incorporated by reference herein.

In yet another particular embodiment of targeted delivery, the radiolabeled pharmaceutical agent can be a radiolabeled peptide. See, for example, Weiner R E, Thakur M L. Radiolabeled peptides in the diagnosis and therapy of oncological diseases. Appl Radiat Isot 2002 November; 57(5): 749-63, the contents of which are incorporated by reference herein.

In addition to targeted delivery, bracytherapy can be used to deliver the radiopharmaceutical agent to the target site. Brachytherapy is a technique that puts the radiation sources as close as possible to the tumor site. Often the source is inserted directly into the tumor. The radioactive sources can be in the form of wires, seeds or rods. Generally, cesium, iridium or iodine are used.

Systemic radiation therapy is another type of radiation therapy and involves the use of radioactive substances in the blood. Systemic radiation therapy is a form of targeted therapy. In systemic radiation therapy, a patient typically ingests or receives an injection of a radioactive substance, such as radioactive iodine or a radioactive substance bound to a monoclonal antibody.

A "radiopharmaceutical agent," as defined herein, refers to a pharmaceutical agent which contains at least one radiation-emitting radioisotope. Radiopharmaceutical agents are routinely used in nuclear medicine for the diagnosis and/or therapy of various diseases. The radiolabelled pharmaceutical agent, for example, a radiolabelled antibody, contains a radioisotope (RI) which serves as the radiation source. As contemplated herein, the term "radioisotope" includes metallic and non-metallic radioisotopes. The radioisotope is chosen based on the medical application of the radiolabeled pharmaceutical agents. When the radioisotope is a metallic radioisotope, a chelator is typically employed to bind the metallic radioisotope to the rest of the molecule. When the radioisotope is a non-metallic radioisotope, the non-metallic radioisotope is typically linked directly, or via a linker, to the rest of the molecule.

As used herein, a "metallic radioisotope" is any suitable metallic radioisotope useful in a therapeutic or diagnostic procedure in vivo or in vitro. Suitable metallic radioisotopes include, but are not limited to: Actinium-225, Antimony-124, Antimony-125, Arsenic-74, Barium-103, Barium-140, Beryllium-7, Bismuth-206, Bismuth-207, Bismuth212, Bismuth213, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-60, Copper-62, Copper-64, Copper-67, Erbium-169, Europium-152, Gallium-64, Gallium-67, Gallium-68, Gadolinium153, Gadolinium-157 Gold-195, Gold-199, Hafnium-175, Hafnium-175-181, Holmium-166, Indium-110, Indium-111, Iridium-192, Iron 55, Iron-59, Krypton85, Lead-203, Lead-210, Lutetium-177, Manganese-54, Mercury-197, Mercury203, Molybdenum-99, Neodymium-147, Neptunium-237, Nickel-63, Niobium95, Osmium-185+191, Palladium-103, Palladium-109, Platinum-195m, Praseodymium-143, Promethium-147, Promethium-149, Protactinium-233, Radium-226, Rhenium-186, Rhenium-188, Rubidium-86, Ruthenium-97, Ruthenium-103, Ruthenium-105, Ruthenium-106, Samarium-153, Scandium-44, Scandium-46, Scandium-47, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, Zirconium-89, and Zirconium-95.

As used herein, a "non-metallic radioisotope" is any suitable nonmetallic radioisotope (non-metallic radioisotope) useful in a therapeutic or diagnostic procedure in vivo or in vitro. Suitable non-metallic radioisotopes include, but are not limited to: Iodine-131, Iodine-125, Iodine-123, Phosphorus-32, Astatine-211, Fluorine-18, Carbon-11, Oxygen-15, Bromine-76, and Nitrogen-13.

Identifying the most appropriate isotope for radiotherapy requires weighing a variety of factors. These include tumor uptake and retention, blood clearance, rate of radiation delivery, half-life and specific activity of the radioisotope, and the feasibility of large-scale production of the radioisotope in an economical fashion. The key point for a therapeutic radiopharmaceutical is to deliver the requisite amount of radiation dose to the tumor cells and to achieve a cytotoxic or tumoricidal effect while not causing unmanageable side-effects.

It is preferred that the physical half-life of the therapeutic radioisotope be similar to the biological half-life of the radiopharmaceutical at the tumor site. For example, if the half-life of the radioisotope is too short, much of the decay will have occurred before the radiopharmaceutical has reached maximum target/background ratio. On the other hand, too long a half-life could cause unnecessary radiation dose to normal tissues. Ideally, the radioisotope should have a long enough half-life to attain a minimum dose rate and to irradiate all the cells during the most radiation sensitive phases of the cell cycle. In addition, the half-life of a radioisotope has to be long enough to allow adequate time for manufacturing, release, and transportation.

Other practical considerations in selecting a radioisotope for a given application in tumor therapy are availability and quality. The purity has to be sufficient and reproducible, as trace amounts of impurities can affect the radiolabeling and radiochemical purity of the radiopharmaceutical.

The target receptor sites in tumors are typically limited in number. As such, it is preferred that the radioisotope have high specific activity. The specific activity depends primarily on the production method. Trace metal contaminants must be minimized as they often compete with the radioisotope for the chelator and their metal complexes compete for receptor binding with the radiolabeled chelated agent.

The type of radiation that is suitable for use in the methods of the present invention can vary. For example, radiation can be electromagnetic or particulate in nature. Electromagnetic radiation useful in the practice of this invention includes, but is not limited to, x-rays and gamma rays. Particulate radiation useful in the practice of this invention includes, but is not limited to, electron beams (beta particles), protons beams, neutron beams, alpha particles, and negative pi mesons. The radiation can be delivered using conventional radiological treatment apparatus and methods, and by intraoperative and stereotactic methods. Additional discussion regarding radiation treatments suitable for use in the practice of this invention can be found throughout Steven A. Leibel et al., Textbook of Radiation Oncology (1998) (publ. W. B. Saunders Company), and particularly in Chapters 13 and 14. Radiation can also be delivered by other methods such as targeted delivery, for example by radioactive "seeds," or by systemic delivery of targeted radioactive conjugates. J. Padawer et al., Combined Treatment with Radioestradiol lucanthone in Mouse C3HBA Mammary Adenocarcinoma and with Estradiol lucanthone in an Estrogen Bioassay, Int. J. Radiat. Oncol. Biol. Phys. 7:347-357 (1981). Other radiation delivery methods can be used in the practice of this invention.

For tumor therapy, both a and β-particle emitters have been investigated. Alpha particles are particularly good cytotoxic agents because they dissipate a large amount of energy within one or two cell diameters. The β-particle emitters have relatively long penetration range (2-12 mm in the tissue) depending on the energy level. The long-range penetration is particularly important for solid tumors that have heterogeneous blood flow and/or receptor expression. The β-particle emitters yield a more homogeneous dose distribution even when they are heterogeneously distributed within the target tissue.

In a particular embodiment, therapeutically effective amounts of the compounds and compositions described herein are administered in combination with a therapeutically effective amount of radiation therapy to treat cancer (e.g., lung cancer, such as non-small cell lung cancer). The amount of radiation necessary can be determined by one of skill in the art based on known doses for a particular type of cancer. See, for example, Cancer Medicine $5^{th}$ ed., Edited by R. C. Bast et al., July 2000, BC Decker.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXEMPLIFICATION

Abbreviations aq. Aqueous
Boc tert-butoxycarbonyl
$CH_2Cl_2$ Dichloromethane
DABCO 1,4-diazabicyclo[2.2.2]octane
DIPEA N,N-Diisopropylethylamine
DMF N,N-Dimethylformamide DMSO Dimethylsulfoxide
eq. equivalent(s)
EtOAc Ethyl acetate
EtOH Ethanol
h hour(s)
HPLC High performance liquid chromatography
LCMS Liquid Chromatography Mass Spectrometry
LiOH Lithium hydroxide
NMR Nuclear magnetic resonance
RT Room Temperature or Retention Time
T3P Propylphosphonic anhydride
TFA Trifluoroacetic acid
THF Tetrahydrofuran Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). Techniques for purification of intermediates and final products include for example, straight and reversed phase chromatography on column or rotating plate, recrystallization, distillation and liquid-liquid or solid-liquid extraction, which will be readily understood by the one skilled in the art. The definitions of substituents and groups are as in formula I except where defined differently. The term "room temperature" and "ambient temperature" shall mean, unless otherwise specified, a temperature between 16 and 25° C. The term "reflux" shall mean, unless otherwise stated, in reference to an employed solvent a temperature at or above the boiling point of named solvent.

Example 1. Synthesis of (Z)-3-(3-(3,5-bis(trifluoromethyl)phenyl)-1H-1,2,4-triazol-1-yl)-N'-pivaloylacrylohydrazide (Compound 1). Compound 1 was Synthesized According to the Following Scheme

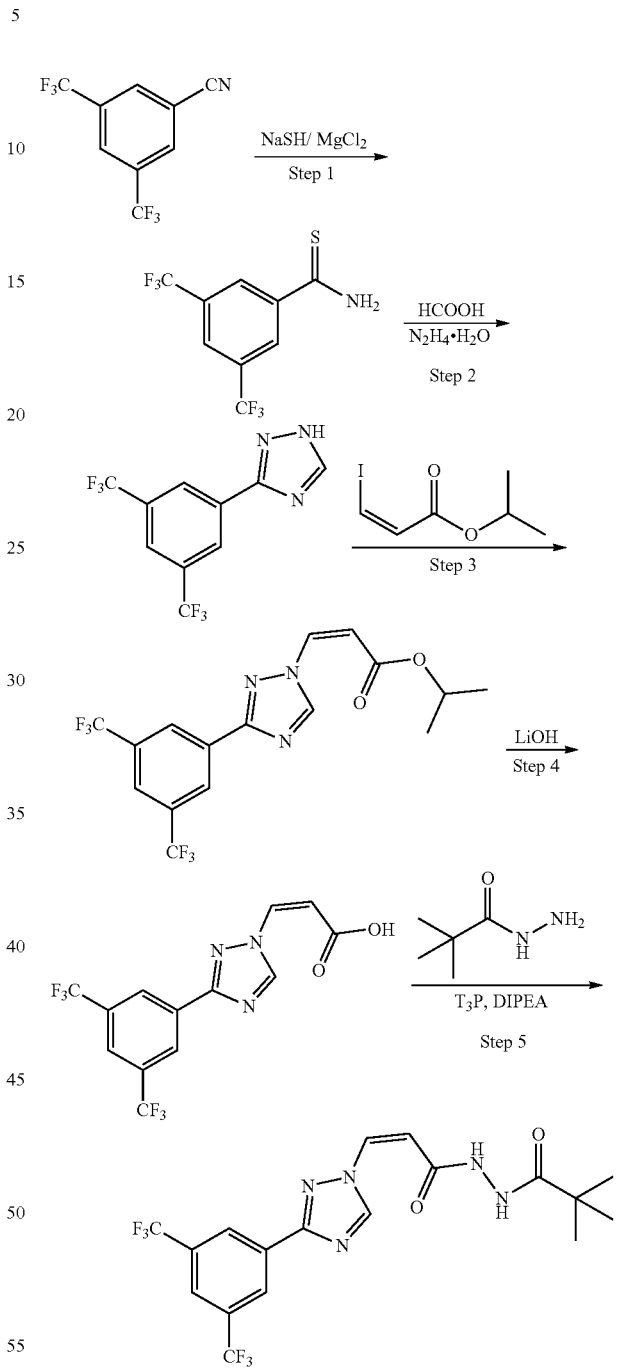

3,5-bis(trifluoromethyl)benzothioamide (Step 1). A 2 L 3-neck round-bottom flask was charged with a solution of 3,5-bis(trifluoromethyl)benzonitrile (200 g) in DMF (1 L). The solution was then treated with NaSH (123.7 g, 2.0 eq.) and MgCl$_2$ (186.7 g, 1.0 eq.) and the reaction mixture was stirred at RT for 3 h. The mixture was poured into an ice-water slurry (10 L) and the compound was extracted with EtOAc (3×1 L). The combined organic layers were washed with aqueous saturated sodium chloride solution (3×100 mL), dried over anhydrous Na$_2$SO$_4$, filtered, and concentrated under reduced pressure to afford 205 g of the desired crude 3,5-bis(trifluoromethyl)benzothioamide (yield: 90%), which was used without further purification in the following step.

3-(3,5-bis(trifluoromethyl)phenyl)-1H-1,2,4-triazole (Step 2). A 5 L 3-neck round-bottom flask was charged with a solution of 3,5-bis(trifluoromethyl)benzothioamide (205.65 g) in DMF (1.03 L). Hydrazine hydrate (73.2 mL, 2.0 eq.) was added dropwise and the reaction mixture was stirred at RT for 1 h. HCOOH (1.03 L) was added dropwise and the reaction mixture was refluxed at 90° C. for 3 h. After being allowed to cool down to RT, the reaction mixture was poured into saturated aqueous sodium bicarbonate solution (7 L) and extracted with EtOAc (3×1 L). The combined organic layers were washed with aqueous saturated sodium chloride solution (3×500 mL), dried over anhydrous $Na_2SO_4$, filtered, and concentrated under reduced pressure (35° C., 20 mmHg) to afford 180 g of the crude product. The crude material was stirred with petroleum ether (3×500 mL), filtered, and dried to obtain 160 g of the desired 3-(3,5-bis(trifluoromethyl)phenyl)-1H-1,2,4-triazole obtained as a pale yellow solid (yield: 75%).

(Z)-isopropyl 3-(3-(3,5-bis(trifluoromethyl)phenyl)-1H-1,2,4-triazol-1-yl)acrylate (Step 3). A 2 L 3-neck round-bottom flask was charged with a solution of 3-(3,5-bis(trifluoromethyl)phenyl)-1H-1,2,4-triazole (160 g) in DMF (960 mL). The solution was treated with DABCO (127.74 g, 2 eq.) and stirred for 30 min before adding (Z)-isopropyl 3-iodoacrylate (150.32 g, 1.1 eq.) dropwise. After 1 h, the reaction mixture was poured into an ice-water slurry (5 L) and extracted with EtOAc (3×1 L). The combined organic layers were washed with aqueous saturated sodium chloride solution (3×100 mL), dried over anhydrous $Na_2SO_4$, filtered, and concentrated under reduced pressure (35° C., 20 mmHg) to afford 250 g of the crude product that was purified by column chromatography (60/120 silica gel) using ethyl acetate/n-hexane gradient (the column was packed in hexane and the desired compound started eluting from 2% EtOAC/n-hexane). Fractions containing the desired compounds were combined to afford (Z)-isopropyl 3-(3-(3,5-bis(trifluoromethyl)phenyl)-1H-1,2,4-triazol-1-yl)acrylate (138 g, yield: 61%).

(Z)-3-(3-(3,5-bis(trifluoromethyl)phenyl)-1H-1,2,4-triazol-1-yl)acrylic acid (Step 4). In a 5 L, 3-neck round-bottom flask, (Z)-isopropyl 3-(3-(3,5-bis(trifluoromethyl) phenyl)-1H-1,2,4-triazol-1-yl)acrylate (130 g, 1.0 eq.) was dissolved in THF (1.3 L). A solution of LiOH (69.3 g, 5.0 eq.) in water (1.3 L) was added dropwise to the solution and the reaction mixture was stirred at RT for 4 h before being quenched with 400 mL ice-water slurry and made acidic (pH=2-3) with dilute aqueous HCl. The mixture was extracted with EtOAc (3×1 L) and the combined organic layers were washed with aqueous saturated sodium chloride solution, dried over anhydrous $Na_2SO_4$, and concentrated under reduced pressure to afford 110 g of (Z)-3-(3-(3,5-bis(trifluoromethyl)phenyl)-1H-1,2,4-triazol-1-yl)acrylic acid (yield: 94%), (cis content=90.0%, trans content=8.2% by LCMS).

(Z)-3-(3-(3,5-bis(trifluoromethyl)phenyl)-1H-1,2,4-triazol-1-yl)-N'-pivaloylacrylohydrazide (Compound 1). In a 50 mL, 3-neck round-bottom flask, (Z)-3-(3-(3,5-bis(trifluoromethyl)phenyl)-1H-1,2,4-triazol-1-yl)acrylic acid (0.2 g, 1.0 eq.) was dissolved in EtOAc (20 mL) and cooled to −60° C. where pivalohydrazide (0.08 g, 1.2 eq.) was introduced dropwise. T3P (50% in EtOAc) (0.4 mL, 4 eq.) was added dropwise followed by DIPEA (0.4 mL, 4 eq.) and the reaction mixture was stirred for 1 h at −60° C. The reaction mixture was concentrated under reduced pressure (25° C., 20 mm Hg) to afford the crude product that was purified by column chromatography (60/120 silica gel) using methanol/dichloromethane gradient (the column was packed in dichloromethane and the desired compound started eluting from 3% methanol/dichloromethane). Fractions containing the desired compounds were combined to afford (Z)-3-(3-(3,5-bis(trifluoromethyl)phenyl)-1H-1,2,4-triazol-1-yl)-N'-pivaloylacrylohydrazide (0.11 g, yield: 43%);

Example 2. Synthesis of (Z)-3-(3-(3,5-bis(trifluoromethyl)phenyl)-1H-1,2,4-triazol-1-yl)-N'-(2-morpholinoacetyl)acrylohydrazide (Compound 2)

2-morpholinoacetohydrazide. In a 25 mL, 3-neck round-bottom flask, methyl 2-morpholinoacetate (0.25 g, 1.0 eq.) was dissolved in ethanol (5 mL) at RT. Hydrazine hydrate (0.087 g, 1.1 eq.) was introduced dropwise at RT and the reaction mixture was refluxed at 95° C. for 20 h. The reaction mixture was concentrated under reduced pressure (40° C., 20 mm Hg) to afford the crude 2-morpholinoacetohydrazide (0.23 g) which was used without further purification in the following step.

(Z)-3-(3-(3,5-bis(trifluoromethyl)phenyl)-1H-1,2,4-triazol-1-yl)-N'-(2-morpholinoacetyl)acrylohydrazide (Compound 2). In a 50 mL, 3-neck round-bottom flask, (Z)-3-(3-(3,5-bis(trifluoromethyl)phenyl)-1H-1,2,4-triazol-1-yl) acrylic acid (Example 1, Step 4; 0.5 g, 1.0 eq.) was dissolved in $CH_2Cl_2$:EtOAc (20 mL, 2:1) and cooled to −60° C. where 2-morpholinoacetohydrazide (0.23 g, 1.0 eq.) was introduced dropwise. T3P (50% in EtOAc) (1.27 mL, 1.5 eq.) was added dropwise followed by DIPEA (0.96 mL, 2 eq.) and the reaction mixture was stirred for 1 h at −60° C. The reaction mixture was concentrated under reduced pressure (25° C., 20 mm Hg) to afford the crude product that was purified by column chromatography (60/120 silica gel) using methanol/dichloromethane gradient (the column was packed in dichloromethane and the desired compound started eluting from 3% methanol/dichloromethane). Fractions containing the desired compounds were combined to afford (Z)-3-(3-(3,5-bis(trifluoromethyl)phenyl)-1H-1,2,4-triazol-1-yl)-N'-(2-morpholinoacetyl)acrylohydrazide (0.1 g, yield: 14%).

Example 3. Synthesis of (Z)-N'-(3-(3-(3,5-bis(trifluoromethyl)phenyl)-1H-1,2,4-triazol-1-yl)acryloyl)-5-methyl-1H-pyrazole-4-carbohydrazide (Compound 3)

5-methyl-1H-pyrazole-4-carbohydrazide. In a 25 mL sealed tube, ethyl 5-methyl-1H-pyrazole-4-carboxylate (0.25 g, 1.0 eq.) was dissolved in ethanol (5 mL) at RT. Hydrazine hydrate (1 mL, 5 eq.) was introduced dropwise at RT and the reaction mixture was heated at 120° C. for 20 h. The reaction mixture was concentrated under reduced pressure (40° C., 20 mm Hg) to afford the crude 5-methyl-1H-pyrazole-4-carbohydrazide (0.24 g) which was used without further purification in the following step.

(Z)-N'-(3-(3-(3,5-bis(trifluoromethyl)phenyl)-1H-1,2,4-triazol-1-yl)acryloyl)-5-methyl-1H-pyrazole-4-carbohydrazide (Compound 3). In a 50 mL, 3-neck round-bottom flask, (Z)-3-(3-(3,5-bis(trifluoromethyl)phenyl)-1H-1,2,4-triazol-1-yl)acrylic acid (Example 1, Step 4; 0.5 g, 1.0 eq.) was dissolved in EtOAc:EtOH (15 mL, 2:1) and cooled to −60° C. where 5-methyl-1H-pyrazole-4-carbohydrazide (0.24 g, 1.0 eq.) was introduced dropwise. T3P (50% in EtOAc) (1.69 mL, 1.5 eq.) was added dropwise followed by DIPEA (2 mL, 8 eq.) and the reaction mixture was stirred for 1 h at −60° C. The reaction mixture was concentrated under reduced pressure (25° C., 20 mm Hg) to afford the crude product that was purified by column chromatography (60/120 silica gel) using methanol/dichloromethane gradient (the column was packed in dichloromethane and the desired compound started eluting from 3% methanol/dichloromethane). Fractions containing the desired compounds were combined to afford (Z)-N'-(3-(3-(3,5-bis(trifluoromethyl)phenyl)-1H-1,2,4-triazol-1-yl)acryloyl)-5-methyl-1H-pyrazole-4-carbohydrazide (0.2 g, yield: 42%).

Example 4. Synthesis of (Z)-2-(3-(3-(3,5-bis(trifluoromethyl)phenyl)-1H-1,2,4-triazol-1-yl)acryloyl)-N-cyclopropylhydrazinecarbothioamide (Compound 4)

In a 50 mL, 3-neck round-bottom flask, (Z)-3-(3-(3,5-bis(trifluoromethyl)phenyl)-1H-1,2,4-triazol-1-yl)acrylic acid (Example 1, Step 4; 0.5 g, 1.0 eq.) was dissolved in EtOAc:EtOH (15 mL, 2:1) and cooled to −60° C. where N-cyclopropylhydrazinecarbothioamide (0.22 g, 1.2 eq.) was introduced dropwise. T3P (50% in EtOAc) (1.69 mL, 2 eq.) was added dropwise followed by DIPEA (1 mL, 4 eq.) and the reaction mixture was stirred for 1 h at −60° C. The reaction mixture was concentrated under reduced pressure (25° C., 20 mm Hg) to afford the crude product that was purified by column chromatography (60/120 silica gel) using methanol/dichloromethane gradient (the column was packed in dichloromethane and the desired compound started eluting from 3% methanol/dichloromethane). Fractions containing the desired compounds were combined to afford (Z)-2-(3-(3-(3,5-bis(trifluoromethyl)phenyl)-1H-1,2,4-triazol-1-yl)acryloyl)-N-cyclopropylhydrazinecarbothioamide (0.06 g, yield: 9%).

Example 5. Synthesis of (Z)-3-(3-(3,5-bis(trifluoromethyl)phenyl)-1H-1,2,4-triazol-1-yl)-N'-methyl-N'-(2-morpholinoacetyl)acrylohydrazide (Compound 5)

N-methyl-2-morpholinoacetohydrazide. In a 25 mL, sealed tube, methyl 2-morpholinoacetate (0.5 g, 1.0 eq.) was dissolved in ethanol (5 mL) at RT. Methylhydrazine (0.16 g, 1.1 eq.) was introduced dropwise at RT and the reaction mixture was refluxed at 95° C. for 48 h. The reaction mixture was concentrated under reduced pressure (40° C., 20 mm Hg) to afford the crude N-methyl-2-morpholinoacetohydrazide (0.27 g) which was used without further purification in the following step.

(Z)-3-(3-(3,5-bis(trifluoromethyl)phenyl)-1H-1,2,4-triazol-1-yl)-N'-methyl-N'-(2-morpholinoacetyl)acrylohydrazide (Compound 5). In a 50 mL, 3-neck round-bottom flask, (Z)-3-(3-(3,5-bis(trifluoromethyl)phenyl)-1H-1,2,4-triazol-1-yl)acrylic acid (Example 1, Step 4; 0.3 g, 1.0 eq.) was dissolved in THF:EtOAc (15 mL, 2:1) and cooled to −60° C. where N-methyl-2-morpholinoacetohydrazide (0.23 g, 1.5 eq.) was introduced dropwise. T3P (50% in EtOAc) (1.27 mL, 2.5 eq.) was added dropwise followed by DIPEA (0.45 mL, 3 eq.) and the reaction mixture was stirred for 1 h at −60° C. The reaction mixture was concentrated under reduced pressure (25° C., 20 mm Hg) to afford the crude product that was purified by column chromatography (60/120 silica gel) using methanol/dichloromethane gradient (the column was packed in dichloromethane and the desired compound started eluting from 3% methanol/dichloromethane). Fractions containing the desired compounds were combined to afford (Z)-3-(3-(3,5-bis(trifluoromethyl)phenyl)-1H-1,2,4-triazol-1-yl)-N'-methyl-N'-(2-morpholinoacetyl)acrylohydrazide (0.052 g, yield: 12%).

Example 6. Synthesis of (Z)-N'-(3-(3-(3,5-bis(trifluoromethyl)phenyl)-1H-1,2,4-triazol-1-yl)acryloyl)piperidine-3-carbohydrazide (Compound 6)

Piperidine-3-carbohydrazide. In a 30 mL sealed tube, ethyl methyl piperidine-3-carboxylate (1 g, 1.0 eq.) was dissolved in ethanol (5 mL) at RT. Hydrazine hydrate (1.05 g, 3 eq.) was introduced dropwise at RT and the reaction mixture was heated at 120° C. for 20 h. The reaction mixture was concentrated under reduced pressure (40° C., 20 mm Hg) to afford the crude piperidine-3-carbohydrazide (0.8 g) which was used without further purification in the following step.

(Z)-N'-(3-(3-(3,5-bis(trifluoromethyl)phenyl)-1H-1,2,4-triazol-1-yl)acryloyl)piperidine-3-carbohydrazide (Compound 6). In a 50 mL, 3-neck round-bottom flask, (Z)-3-(3-(3,5-bis(trifluoromethyl)phenyl)-1H-1,2,4-triazol-1-yl)acrylic acid (Example 1, Step 4; 0.25 g, 1.0 eq.) was dissolved in THF:EtOAc (15 mL, 2:1) and cooled to −60° C. where piperidine-3-carbohydrazide (0.113 g, 1.1 eq.) was introduced dropwise. T3P (50% in EtOAc) (1.69 mL, 4 eq.) was added dropwise followed by DIPEA (0.25 mL, 2 eq.) and the reaction mixture was stirred for 1 h at −60° C. The reaction mixture was concentrated under reduced pressure (25° C., 20 mm Hg) to afford the crude product that was purified by column chromatography (60/120 silica gel) using methanol/dichloromethane gradient (the column was packed in dichloromethane and the desired compound started eluting from 3% methanol/dichloromethane). Fractions containing the desired compounds were combined to afford (Z)-N'-(3-(3-(3,5-bis(trifluoromethyl)phenyl)-1H-1,2,4-triazol-1-yl)acryloyl)piperidine-3-carbohydrazide (0.01 g, yield: 2.4%).

Example 7. Synthesis of (S,Z)-2-amino-N'-(3-(3-(3,5-bis(trifluoromethyl)phenyl)-1H-1,2,4-triazol-1-yl)acryloyl)-3-methylbutanehydrazide 2,2,2-trifluoroacetate (Compound 7)

Compound 7 was synthesized by the following scheme:

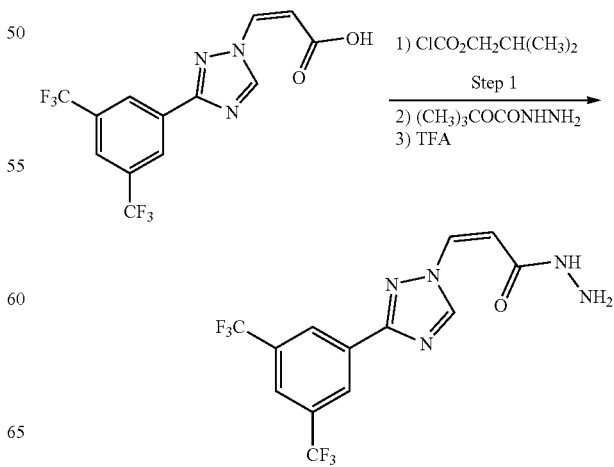

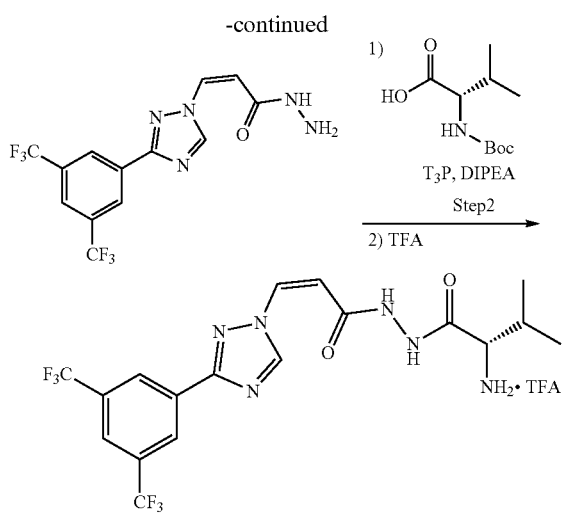

(Z)-3-(3-(3,5-bis(trifluoromethyl)phenyl)-1H-1,2,4-triazol-1-yl)acrylohydrazide (Step 1). In a 50 mL, 3-neck round-bottom flask, (Z)-3-(3-(3,5-bis(trifluoromethyl)phenyl)-1H-1,2,4-triazol-1-yl)acrylic acid (Example 1, Step 4; 0.5 g, 1.0 eq.) was dissolved in THF (10 mL) and cooled to −10° C. where NMP (0.3 g, 2.1 eq.) was added and the reaction mixture was stirred for 5 min. Isobutyl chloroformate (0.465 g, 2.4 eq.) was then added and the reaction mixture was stirred for 1 h. The solid formed was removed by filtration. The filtrate was cooled to 0° C. and tert-butoxycarbonyl hydrazide (0.21 g, 1.1 eq.) was introduced. The reaction mixture was allowed to warm to RT where it was stirred for 1 h. The reaction mixture was poured into an iced-water slurry and extracted with EtOAc (3×50 mL). The combined organic layers were washed with aqueous saturated sodium chloride solution (25 mL), dried over anhydrous $Na_2SO_4$, filtered, and concentrated under reduced pressure (25° C., 20 mmHg) to afford 0.5 g of the crude product. The crude product was then dissolved in THF (10 mL) and TFA (2 mL) was added dropwise at RT and the reaction mixture was stirred for 2 h. The reaction mixture was concentrated under reduced pressure (25° C., 20 mmHg) and the solid formed was triturated with pentane to afford (Z)-3-(3-(3,5-bis(trifluoromethyl)phenyl)-1H-1,2,4-triazol-1-yl)acrylohydrazide (0.25 g, yield: 48.5%).

(S)-2-((tert-butoxycarbonyl)amino)-3-methylbutanoic acid. In a 25 mL, 3-neck round-bottom flask, (S)-2-amino-3-methylbutanoic acid (0.8 g, 1.0 eq.) was dissolved in water (4 mL). Sodium bicarbonate (0.63 g, 1.1 eq.), followed by di-tert-butyl dicarbonate (2.97 g, 2.0 eq.) was added and the reaction mixture was stirred for 2 h at RT. The reaction mixture was extracted with EtOAc (3×10 mL). The combined organic layers were washed with aqueous saturated sodium chloride solution (25 mL), dried over anhydrous $Na_2SO_4$, filtered, and concentrated under reduced pressure (25° C., 20 mmHg) to afford 1.2 g of the crude product that was purified by column chromatography (60/120 silica gel) using methanol/dichloromethane gradient (the column was packed in dichloromethane and the desired compound started eluting from 3% methanol/dichloromethane). Fractions containing the desired compounds were combined to afford (S)-2-((tert-butoxycarbonyl)amino)-3-methylbutanoic acid (0.7 g, yield: 47.3%).

(S,Z)-2-amino-N'-(3-(3-(3,5-bis(trifluoromethyl)phenyl)-1H-1,2,4-triazol-1-yl)acryloyl)-3-methylbutanehydrazide 2,2,2-trifluoroacetate (Compound 7). In a 10 mL round-bottom flask, (Z)-3-(3-(3,5-bis(trifluoromethyl)phenyl)-1H-1,2,4-triazol-1-yl)acrylohydrazide (0.25 g, 1.0 eq.) was dissolved in THF (5 mL) and cooled to −60° C. where (S)-2-((tert-butoxycarbonyl)amino)-3-methylbutanoic acid (0.19 g, 1.3 eq.) was introduced dropwise. T3P (50% in EtOAc) (0.81 mL, 2 eq.) was added dropwise followed by DIPEA (0.48 mL, 4 eq.) and the reaction mixture was stirred for 1 h at −60° C. The reaction mixture was concentrated under reduced pressure (25° C., 20 mm Hg) to afford the crude product that was purified by column chromatography (60/120 silica gel) using methanol/dichloromethane gradient (the column was packed in dichloromethane and the desired compound started eluting from 3% methanol/dichloromethane). Fractions containing the desired compounds were combined to afford (S,Z)-tert-butyl (1-(2-(3-(3-(3,5-bis(trifluoromethyl)phenyl)-1H-1,2,4-triazol-1-yl)acryloyl)hydrazinyl)-3-methyl-1-oxobutan-2-yl)carbamate (0.07 g, yield: 18%). In a 10 mL round-bottom flask, (S,Z)-tert-butyl (1-(2-(3-(3-(3,5-bis(trifluoromethyl)phenyl)-1H-1,2,4-triazol-1-yl)acryloyl)hydrazinyl)-3-methyl-1-oxobutan-2-yl)carbamate was then dissolved in dichloromethane (2 mL). TFA (0.05 mL) was added and the reaction mixture was stirred at RT for 5 h. The reaction mixture was concentrated under reduced pressure (25° C., 20 mm Hg) to afford the crude product (0.01 g), which was triturated with petroleum ether and dried under reduced pressure to yield (S,Z)-2-amino-N'-(3-(3-(3,5-bis(trifluoromethyl)phenyl)-1H-1,2,4-triazol-1-yl)acryloyl)-3-methylbutanehydrazide 2,2,2-trifluoroacetate (0.006 g, yield: 2%).

Example 8. Synthesis of (Z)-N'-(3-(3-(3,5-bis(trifluoromethyl)phenyl)-1H-1,2,4-triazol-1-yl)acryloyl) pyrazine-2-carbohydrazide (Compound 8)

In a 25 mL, 3-neck round-bottom flask, (Z)-3-(3-(3,5-bis(trifluoromethyl)phenyl)-1H-1,2,4-triazol-1-yl)acrylic acid (Example 1, Step 4; 0.5 g, 1.0 eq.) was dissolved in dichloromethane (5 mL) and cooled to −60° C. where pyrazine-2-carbohydrazide (0.216 g, 1.1 eq.) was introduced. T3P (50% in EtOAc) (3.39 mL, 4 eq.) was added dropwise followed by DIPEA (0.5 mL, 2 eq.) and the reaction mixture was stirred for 1 h at −60° C. The reaction mixture was concentrated under reduced pressure (25° C., 20 mm Hg) to afford the crude product that was purified by column chromatography (60/120 silica gel) using methanol/dichloromethane gradient (the column was packed in dichloromethane and the desired compound started eluting from 3% methanol/dichloromethane). Fractions containing the desired compounds were combined to afford (Z)-N'-(3-(3-(3,5-bis(trifluoromethyl)phenyl)-1H-1,2,4-triazol-1-yl)acryloyl)pyrazine-2-carbohydrazide (0.13 g, yield: 19.4%).

Example 9. Synthesis of (Z)-N'-(3-(3-(3,5-bis(trifluoromethyl)phenyl)-1H-1,2,4-triazol-1-yl)acryloyl)-1-methylpiperidine-4-carbohydrazide (Compound 9)

1-methylpiperidine-4-carbohydrazide. In a 25 mL sealed tube, methyl 1-methylpiperidine-4-carboxylate (0.2 g, 1.0 eq.) was dissolved in ethanol (5 mL) at RT. Hydrazine hydrate (0.127 g, 2 eq.) was introduced dropwise at RT and the reaction mixture was heated at 120° C. for 20 h. The reaction mixture was concentrated under reduced pressure (40° C., 20 mm Hg) to afford the crude 1-methylpiperidine-4-carbohydrazide (0.145 g) which was used without further purification in the following step.

(Z)-N'-(3-(3-(3,5-bis(trifluoromethyl)phenyl)-1H-1,2,4-triazol-1-yl)acryloyl)-1-methylpiperidine-4-carbohydrazide (Compound 9). In a 50 mL, 3-neck round-bottom flask, (Z)-3-(3-(3,5-bis(trifluoromethyl)phenyl)-1H-1,2,4-triazol-1-yl)acrylic acid (0.25 g, 1.0 eq.) was dissolved in EtOAc:THF (15 mL; 2:1) and cooled to −60° C. where 1-methylpiperidine-4-carbohydrazide (0.123 g, 1.1 eq.) was introduced. T3P (50% in EtOAc) (0.85 mL, 2 eq.) was added dropwise followed by DIPEA (0.31 mL, 2.5 eq.) and the reaction mixture was stirred for 1 h at −60° C. The reaction mixture was concentrated under reduced pressure (35° C., 20 mm Hg) to afford the crude product that was purified by column chromatography (60/120 silica gel) using methanol/dichloromethane gradient (the column was packed in dichloromethane and the desired compound started eluting from 3% methanol/dichloromethane). Fractions containing the desired compounds were combined to afford (Z)-N'-(3-(3-(3,5-bis(trifluoromethyl)phenyl)-1H-1,2,4-triazol-1-yl)acryloyl)-1-methylpiperidine-4-carbohydrazide (0.016 g, yield: 4.5%).

Example 10. Synthesis of (R,Z)-2-amino-N'-(3-(3-(3,5-bis(trifluoromethyl)phenyl)-1H-1,2,4-triazol-1-yl)acryloyl)-3-methylbutanehydrazide 2,2,2-trifluoroacetate (Compound 10)

(R)-2-((tert-butoxycarbonyl)amino)-3-methylbutanoic acid. In a 25 mL, 3-neck round-bottom flask, (R)-2-amino-3-methylbutanoic acid (0.8 g, 1.0 eq.) was dissolved in water (4 mL). Sodium bicarbonate (0.394 g, 1.1 eq.), followed by di-tert-butyl dicarbonate (1.86 g, 2.0 eq.) was added and the reaction mixture was stirred for 2 h at RT. The reaction mixture was extracted with EtOAc (3×10 mL). The combined organic layers were washed with aqueous saturated sodium chloride solution (25 mL), dried over anhydrous Na$_2$SO$_4$, filtered, and concentrated under reduced pressure (25° C., 20 mmHg) to afford 0.75 g of the crude product that was purified by column chromatography (60/120 silica gel) using methanol/dichloromethane gradient (the column was packed in dichloromethane and the desired compound started eluting from 3% methanol/dichloromethane). Fractions containing the desired compounds were combined to afford (R)-2-((tert-butoxycarbonyl)amino)-3-methylbutanoic acid (0.44 g, yield: 47.3%).

(R,Z)-2-amino-N'-(3-(3-(3,5-bis(trifluoromethyl)phenyl)-1H-1,2,4-triazol-1-yl)acryloyl)-3-methylbutanehydrazide 2,2,2-trifluoroacetate (Compound 10). In a 10 mL round-bottom flask, (Z)-3-(3-(3,5-bis(trifluoromethyl)phenyl)-1H-1,2,4-triazol-1-yl)acrylohydrazide (0.05 g, 1.0 eq.) was dissolved in THF (5 mL) and cooled to −60° C. where (R)-2-((tert-butoxycarbonyl)amino)-3-methylbutanoic acid (0.038 g, 1.3 eq.) was introduced dropwise. T3P (50% in EtOAc) (0.16 mL, 2 eq.) was added dropwise followed by DIPEA (0.095 mL, 4 eq.) and the reaction mixture was stirred for 1 h at −60° C. The reaction mixture was concentrated under reduced pressure (25° C., 20 mm Hg) to afford the crude product that was purified by column chromatography (60/120 silica gel) using methanol/dichloromethane gradient (the column was packed in dichloromethane and the desired compound started eluting from 3% methanol/dichloromethane). Fractions containing the desired compounds were combined to afford (R,Z)-tert-butyl (1-(2-(3-(3-(3,5-bis(trifluoromethyl)phenyl)-1H-1,2,4-triazol-1-yl)acryloyl)hydrazinyl)-3-methyl-1-oxobutan-2-yl)carbamate (0.017 g, yield: 26%). In a 10 mL round-bottom flask, (R,Z)-tert-butyl (1-(2-(3-(3-(3,5-bis(trifluoromethyl)phenyl)-1H-1,2,4-triazol-1-yl)acryloyl)hydrazinyl)-3-methyl-1-oxobutan-2-yl)carbamate was then dissolved in dichloromethane (2 mL). TFA (0.2 mL) was added and the reaction mixture was stirred at RT for 5 h. The reaction mixture was concentrated under reduced pressure (25° C., 20 mm Hg) to afford the crude product (0.02 g), which was triturated with petroleum ether and dried under reduced pressure to yield (R,Z)-2-amino-N'-(3-(3-(3,5-bis(trifluoromethyl)phenyl)-1H-1,2,4-triazol-1-yl)acryloyl)-3-methylbutanehydrazide 2,2,2-trifluoroacetate (0.007 g, yield: 35%).

Example 11. Synthesis of (Z)-3-(3-(3,5-bis(trifluoromethyl)phenyl)-1H-1,2,4-triazol-1-yl)-N'-(2-(pyrazin-2-yl)acetyl)acrylohydrazide (Compound 11)

2-(pyrazin-2-yl)acetohydrazide. In a 25 mL sealed tube, methyl 2-(pyrazin-2-yl)acetate (0.25 g, 1.0 eq.) was dissolved in ethanol (5 mL) at RT. Hydrazine hydrate (0.33 g, 4 eq.) was introduced dropwise at RT and the reaction mixture was heated at 120° C. for 20 h. The reaction mixture was concentrated under reduced pressure (40° C., 20 mm Hg) to afford the crude 2-(pyrazin-2-yl)acetohydrazide (0.2 g) which was used without further purification in the following step.

(Z)-3-(3-(3,5-bis(trifluoromethyl)phenyl)-1H-1,2,4-triazol-1-yl)-N'-(2-(pyrazin-2-yl)acetyl)acrylohydrazide (Compound 11). In a 50 mL, 3-neck round-bottom flask, (Z)-3-(3-(3,5-bis(trifluoromethyl)phenyl)-1H-1,2,4-triazol-1-yl)acrylic acid (0.3 g, 1.0 eq.) was dissolved in EtOAc:THF (15 mL; 2:1) and cooled to −60° C. where 2-(pyrazin-2-yl)acetohydrazide (0.129 g, 1.1 eq.) was introduced. T3P (50% in EtOAc) (1.01 mL, 2 eq.) was added dropwise followed by DIPEA (0.35 mL, 2.5 eq.) and the reaction mixture was stirred for 1 h at −60° C. The reaction mixture was concentrated under reduced pressure (25° C., 20 mm Hg) to afford the crude product that was purified by column chromatography (60/120 silica gel) using methanol/dichloromethane gradient (the column was packed in dichloromethane and the desired compound started eluting from 3% methanol/dichloromethane). Fractions containing the desired compounds were combined to afford (Z)-3-(3-(3,5-bis(trifluoromethyl)phenyl)-1H-1,2,4-triazol-1-yl)-N'-(2-(pyrazin-2-yl)acetyl)acrylohydrazide (0.025 g, yield: 5%).

Example 12. Synthesis of (Z)-3-(3-(3,5-bis(trifluoromethyl)phenyl)-1H-1,2,4-triazol-1-yl)-N'-(2-morpholino-2-oxoacetyl)acrylohydrazide (Compound 12)

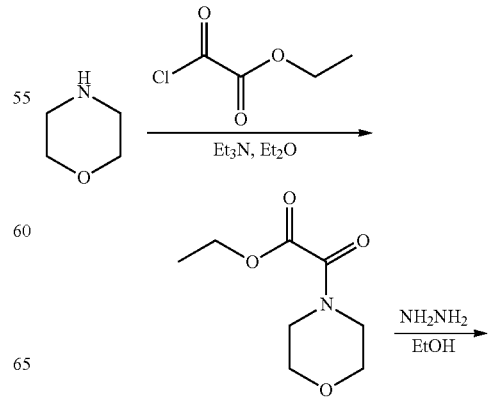

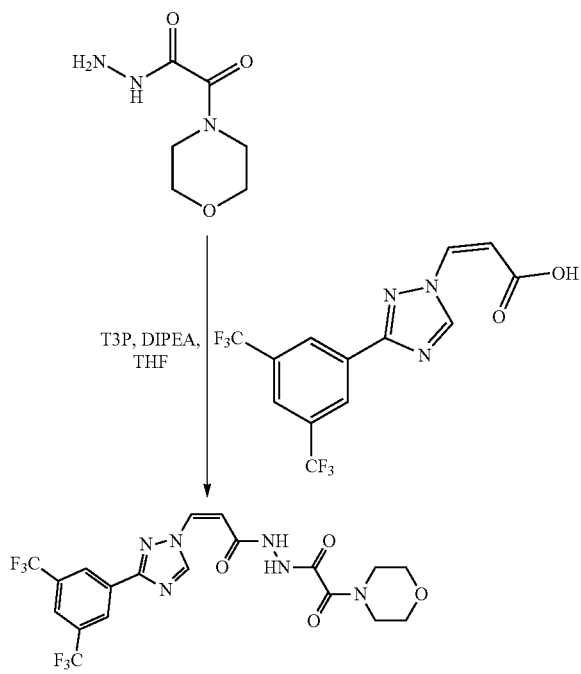

Synthesis of ethyl 2-morpholino-2-oxoacetate

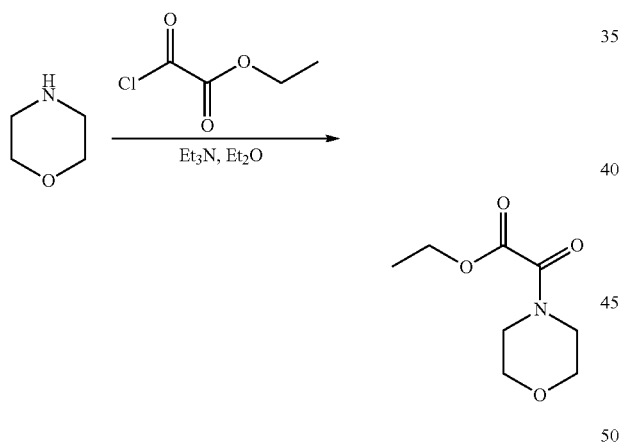

A solution of ethyl 2-chloro-2-oxoacetate (1.25 g, 9.18 mmol) in diethyl ether (5 mL) was added dropwise to a solution of morpholine (1.0 g, 11.48 mmol) in diethyl ether (20 mL) and triethylamine (1.16 g, 11.48 mmol) at 0° C. The reaction mixture was allowed to warm to room temperature and stirred for 2 h. The reaction mixture was filtered and the filtrate was concentrated under reduced pressure. The yellow-colored oil was transferred into 25 mL iced water and extracted with ethyl acetate (3×20 mL). Combined organic layers were washed with brine, dried over anhydrous sodium sulphate, and concentrated under reduced pressure to give 1 g of the crude product, which was used further without any purification. Crude yield 47%. $^1$H NMR (400 MHz, CDCl$_3$) δ 4.33-4.38 (q, 2H), 3.72-3.76 (m, 4H), 3.65-3.68 (m, 2H), 3.47-3.50 (m, 2H), 1.37-1.40 (t, 3H). LCMS m/z 187.93 [M+H]$^+$, $t_R$=0.525 min.

Synthesis of 2-morpholino-2-oxoacetohydrazide

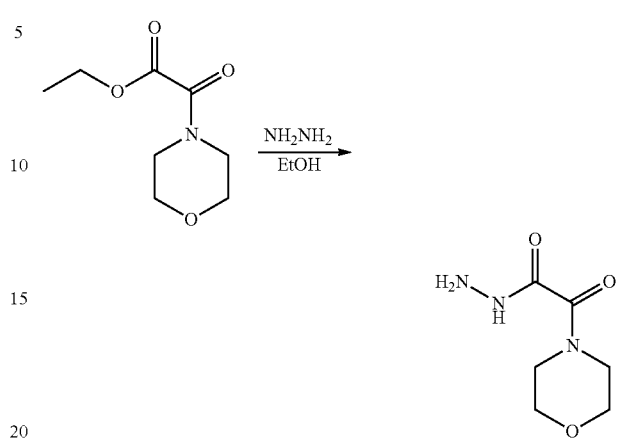

Ethyl 2-morpholino-2-oxoacetate (1.0 g, 5.34 mmol) was dissolved in ethanol (7 mL) and hydrazine hydrate (0.267 g, 5.34 mmol) was added dropwise at 0° C. The reaction mixture was stirred at room temperature for 1.5 h. The reaction mixture was concentrated under reduced pressure to give 0.9 g of the crude product, which was used without further purification in the following step. Crude yield 90%. $^1$H NMR (400 MHz, CDCl$_3$) δ 9.79 (s, 1H), 4.43-4.48 (m, 2H), 3.56-3.61 (m, 4H), 3.40-3.48 (m, 4H). LCMS m/z 174.16 [M+H]$^+$, $t_R$=2.031 min.

Synthesis of (Z)-3-(3-(3,5-bis(trifluoromethyl)phenyl)-1H-1,2,4-triazol-1-yl)-N'-(2-morpholino-2-oxoacetyl)acrylohydrazide

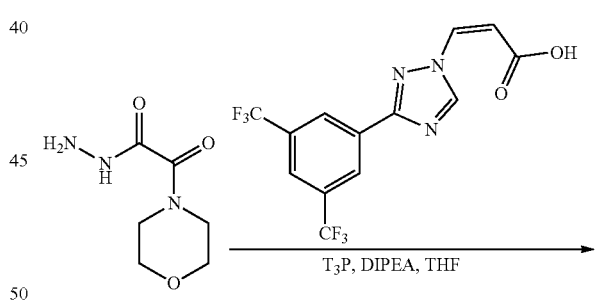

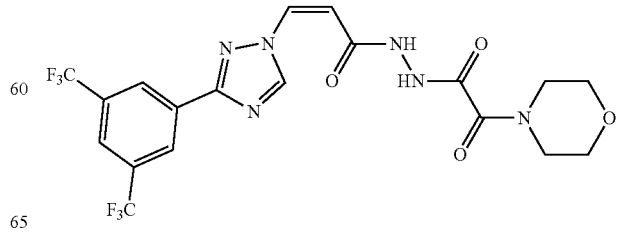

A solution of (Z)-3-(3-(3,5-bis(trifluoromethyl)phenyl)-1H-1,2,4-triazol-1-yl)acrylic acid (0.2 g, 0.569 mmol) and 2-morpholino-2-oxoacetohydrazide (0.02 g, 0.175 mmol) in THF (3 mL) was cooled to −60° C. T₃P (0.098 g, 0.569 mmol) (0.50 mL) was added dropwise followed by DIPEA (0.11 g, 0.854 mmol) and stirred at −60° C. for 1 h. The reaction mixture was transferred into 25 mL of iced water and extracted with ethyl acetate (2×25 mL). Combined organic layers were washed with brine, dried over anhydrous sodium sulphate, and concentrated under reduced pressure to give 0.3 g of crude product, which was purified by chromatography (0-4% MeOH/CH₂Cl₂) to give 0.15 g of (Z)-3-(3-(3,5-bis(trifluoromethyl)phenyl)-1H-1,2,4-triazol-1-yl)-N'-(2-morpholino-2-oxoacetyl) acrylohydrazide (Yield 50%). ¹H NMR (400 MHz, DMSO-d₆) δ 10.70-10.88 (m, 2H), 9.56 (s, 1H), 8.57 (s, 2H), 8.29 (s, 1H), 7.52-7.55 (d, J=10.4 Hz, 1H), 6.0-6.03 (d, J=10.4 Hz, 1H), 3.51-3.64 (m, 8H). LCMS m/z 507.25 [M+H]⁺, t_R=2.012 min.

Example 13. Synthesis of (Z)-3-(3-(3,5-bis(trifluoromethyl)phenyl)-1H-1,2,4-triazol-1-yl)-N'-(2-(3,5-dimethylmorpholino)acetyl)acrylohydrazide (Compound 13)

-continued

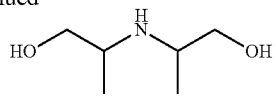

2-Aminopropan-1-ol (5 g, 66.57 mmol) and 1-hydroxypropan-2-one (5.77 g, 77.89 mmol) were dissolved in ethanol (115 mL) and 50 mg of PtO₂ was added. The reaction mixture was stirred at 50 psi H₂ pressure at room temperature for 24 h. The reaction mixture was filtered and the filtrate was concentrated under reduced pressure to give the crude product, which was used without further purification in the following step. Crude yield: 79%. ¹H NMR (400 MHz, CDCl₃) δ 4.45 (bs, 2H), 3.42-3.43 (m, 1H), 3.16-3.22 (m, 4H), 2.65-2.69 (m, 2H) 0.87-0.91 (m, 6H): LCMS m/z 133.99 [M+H]⁺, t_R: 4.077 min.

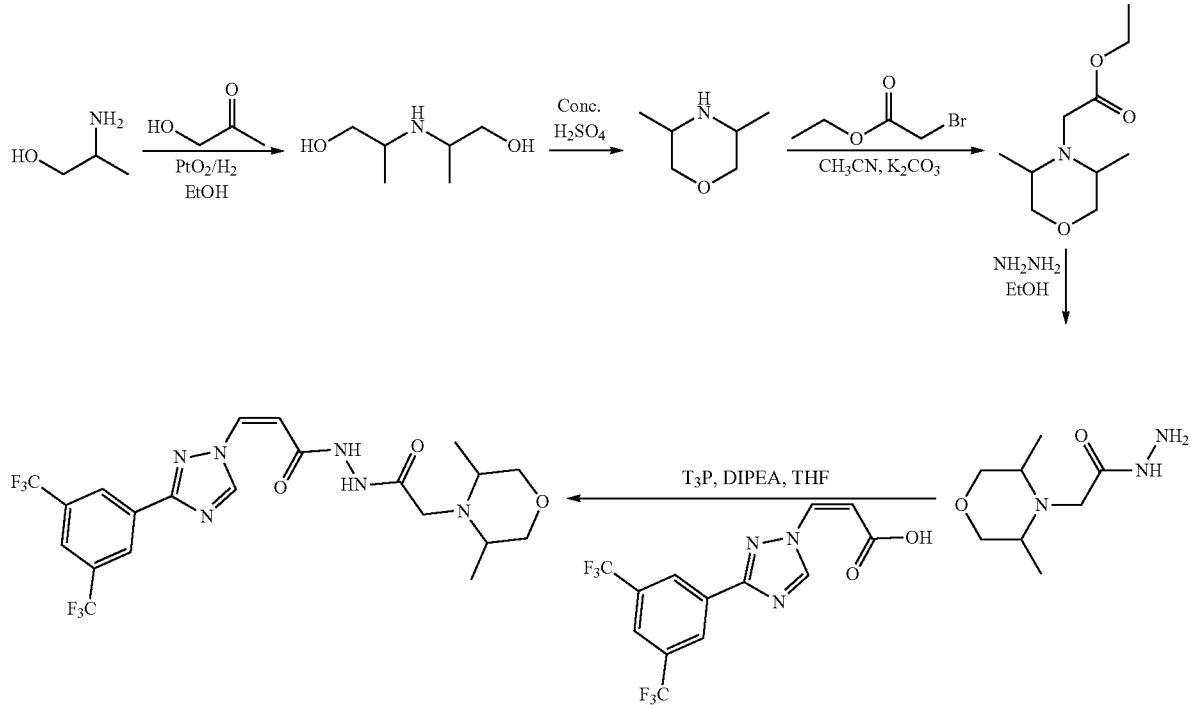

Synthesis of 2,2'-azanediyldipropan-1-ol

Synthesis of 3,5-dimethylmorpholine

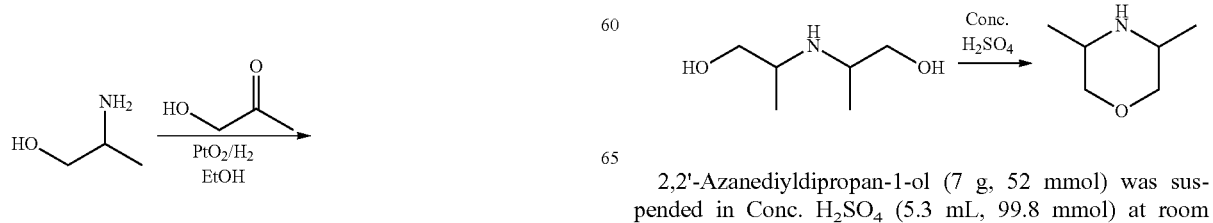

2,2'-Azanediyldipropan-1-ol (7 g, 52 mmol) was suspended in Conc. H₂SO₄ (5.3 mL, 99.8 mmol) at room temperature and heated at 180° C. for 8 h. The reaction mixture was cooled at 0° C. and solution of KOH (11.79 g, 21.02 mmol) in 60 mL water was added dropwise. The reaction mixture was stirred at room temperature for 12 h. The reaction mixture was filtered and filtrate was extracted with CHCl$_3$:MeOH (85:15; 5×50 mL). The combined organic layers were dried over anhydrous sodium sulphate and concentrated under reduced pressure to give 3.5 g of crude product, which was used without further purification in the following step (Crude Yield: 58%).

Synthesis of ethyl 2-(3,5-dimethylmorpholino)acetate

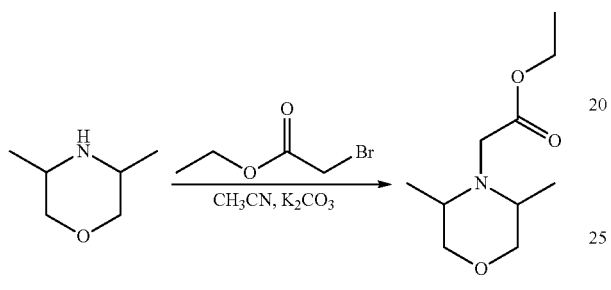

Potassium carbonate (0.311 g, 2.25 mmol) and ethyl bromoacetate (0.319 g, 1.91 mmol) was added to the solution of 3,5-dimethylmorpholine (0.2 g, 1.73 mmol) in acetonitrile (4 mL) at room temperature. The reaction mixture was stirred at 60° C. for 12 h. The reaction mixture was transferred into iced-water and extracted with ethyl acetate (20 mL×3). The combined organic layers was washed with brine, dried over anhydrous Na$_2$SO$_4$, and concentrated under reduced pressure to give the crude product, which was used in the next step without further purification (Crude Yield: 54%).

Synthesis of ethyl 2-(3,5-dimethylmorpholino)acetohydrazide

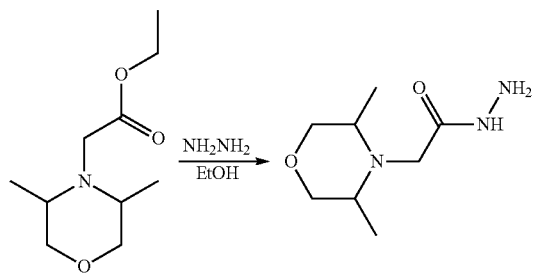

Ethyl-2-(3,5-dimethylmorpholino)acetate (0.19 g, 0.944 mmol) was dissolved in ethanol (4 mL) and hydrazine hydrate (0.047 g, 0.944 mmol) was added dropwise. The reaction mixture was stirred at 80° C. for 20 h and the reaction mixture was concentrated under reduced pressure to give the crude product, which was used without further purification in the subsequent step. (Crude yield: 97%). $^1$H NMR (400 MHz, DMSO-d$_6$) δ 8.95 (s, 2H), 8.84 (s, 1H), 3.60-3.63 (m, 2H), 3.25-3.29 (m, 2H), 3.14 (s, 2H), 3.05 (s, 2H), 0.86-0.88 (m, 6H): LCMS m/z 188.12 [M+H]$^+$, t$_R$ 4.716 min.

Synthesis of (Z)-3-(3-(3,5-bis(trifluoromethyl)phenyl)-1H-1,2,4-triazol-1-yl)-N'-(2-(3,5-dimethylmorpholino)acetyl)acrylohydrazide

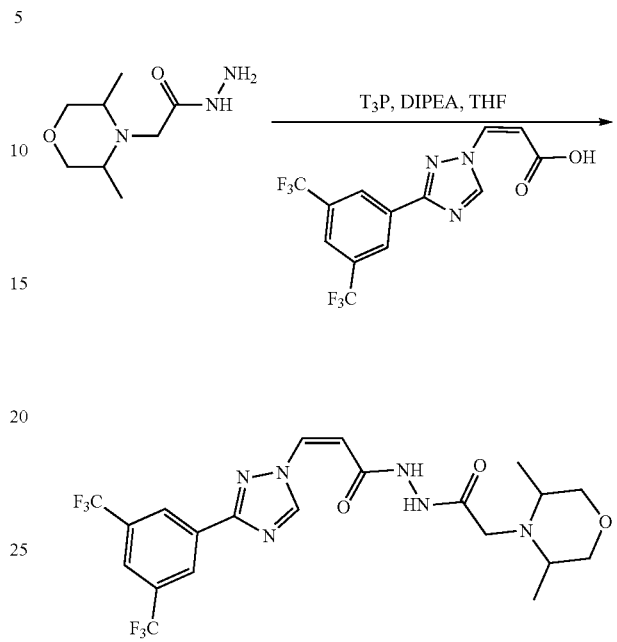

To the solution of (Z)-3-(3-(3,5-bis(trifluoromethyl)phenyl)-1H-1,2,4-triazol-1-yl)acrylic acid (0.2 g, 0.569 mmol) and 2-(3,5-dimethylmorpholino)acetohydrazide (0.106 g, 0.569 mmol) in THF (10 mL) were added T3P (0.543 g, 0.854 mmol) followed by DIPEA (0.110 g, 0.854 mmol) at −60° C. and stirred for 2 h. The reaction mixture was transferred into 25 mL iced-water and extracted with ethyl acetate (2×25 mL) and the combined organic layers was washed with brine, dried over anhydrous sodium sulphate, and concentrated under reduced pressure to afford the crude product, which was purified by chromatography (0-3% MeOH/CH$_2$Cl$_2$) to give 0.02 g of (Z)-3-(3-(3,5-bis(trifluoromethyl)phenyl)-1H-1,2,4-triazol-1-yl)-N'-(2-(3,5-dimethylmorpholino)acetyl)acrylohydrazide (Yield: 7%). $^1$H NMR (400 MHz, DMSO-d$_6$) δ 10.58 (s, 1H), 9.83 (s, 1H), 9.56 (s, 1H), 8.54-8.56 (m, 2H), 8.25-8.30 (m, 1H), 7.49-7.51 (d, J=10.4 Hz, 1H)), 6.01-6.04 (d, J=10.4 Hz, 1H), 3.44-3.57 (m, 2H), 3.28-3.34 (m, 2H), 3.21 (s, 1H), 3.15 (s, 1H), 2.84-2.88 (m, 2H), 0.93-1.04 (m, 6H): LCMS m/z 521.18 [M+H]$^+$, t$_R$ 1.898 min.

Example 14. Synthesis of (Z)-3-(3-(3,5-bis(trifluoromethyl)phenyl)-1H-1,2,4-triazol-1-yl)-N'-(2-(3-oxomorpholino)acetyl)acrylohydrazide (Compound 14)

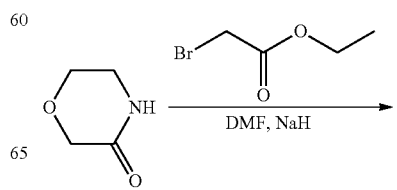

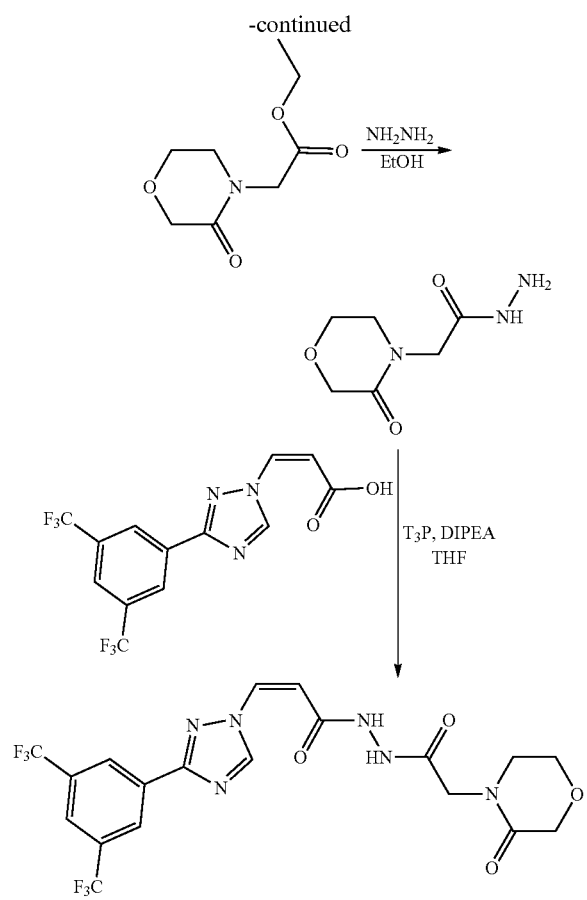

Synthesis of Ethyl 2-(3-oxomorpholino) acetate

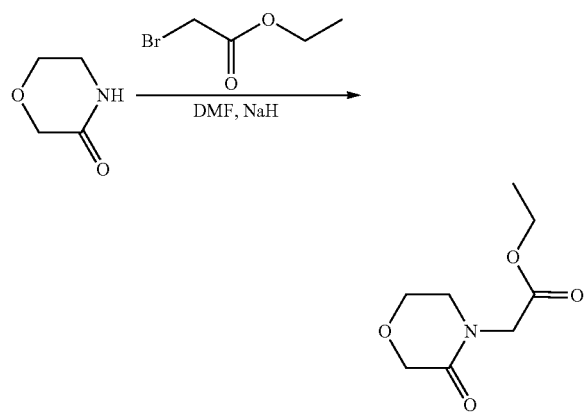

Morpholin-3-one (3 g, 29.67 mmol) was dissolved in DMF (15 mL, 29.67 mmol) and NaH (1.78 g, 44.51 mmol) was added at 0° C. The reaction mixture was stirred at room temperature for 30 min and ethylbromo acetate (3.76 mL, 32.64 mmol) was added dropwise. The reaction mixture was further stirred at room temperature for 3 h and transferred into 50 mL water and extracted with EtOAc (3×50 mL). The combined organic layers was washed with brine solution (2×50 mL), dried over anhydrous sodium sulphate and concentrated under reduced pressure to give the crude product, which was purified by chromatography (0-100% ethyl acetate/hexane) to give 600 mg of ethyl-2-(3-oxomorpholino)acetate (Yield: 10%). LCMS m/z 187 [M+H]$^+$, $t_R$ 2.505 min.

Synthesis of 2-(3-oxomorpholino)acetohydrazide

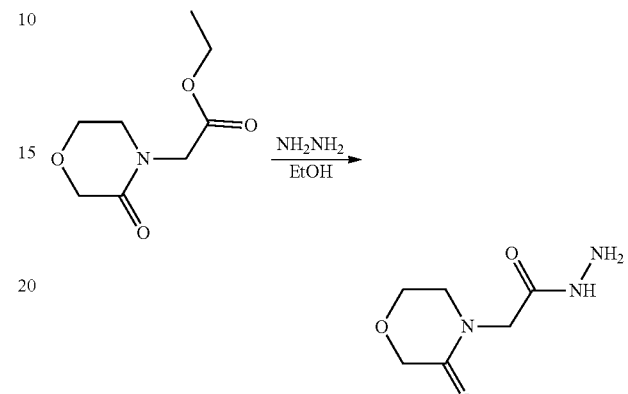

Ethyl-2-(3-oxomorpholino)acetate (600 mg, 3.21 mmol) was dissolved in ethanol (3 mL) and hydrazine hydrate (160.46 mg, 3.21 mmol) was added at room temperature. The reaction mixture was heated at 80° C. for 1 h. The reaction mixture was transferred into 50 mL water and extracted with EtOAc (3×50 mL). The combined organic layers was washed with brine, dried over anhydrous sodium sulphate, and concentrated under reduced pressure to give the crude product, which was used without further purification in the subsequent step (Crude yield: 54%). LCMS m/z 174.05 [M+H]$^+$ $t_R$ 2.489 min.

Synthesis of (Z)-3-(3-(3,5-bis(trifluoromethyl)phenyl)-1H-1,2,4-triazol-1-yl)-N'-(2-(3-oxomorpholino)acetyl)acrylohydrazide

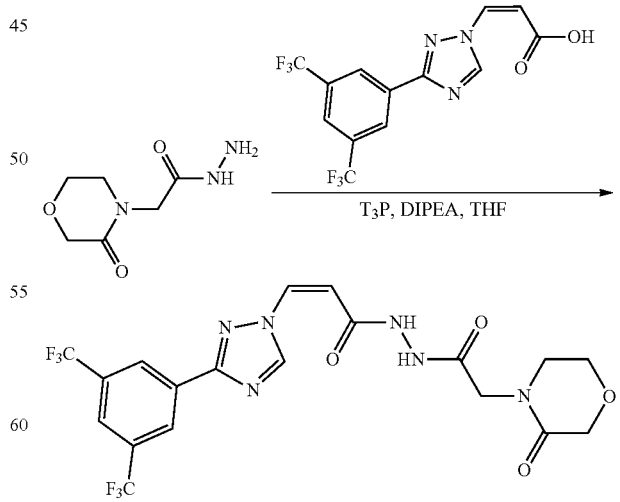

(Z)-3-(3-(3,5-bis(trifluoromethyl)phenyl)-1H-1,2,4-triazol-1-yl)acrylic acid (0.400 g, 1.14 mmol) was dissolved in THF (4 mL) and 2-(3-oxomorpholino)acetohydrazide (0.295 g, 1.71 mmol) was added. T₃P (1.09 g, 1.71 mmol) was added dropwise followed by DIPEA (220.80 mg, 1.71 mmol) at −60° C. and the reaction mixture was stirred for 1 h. The reaction mixture was transferred into 25 mL iced-water and extracted with EtOAc (2×25 mL). Combined organic layers was washed with brine, dried over anhydrous sodium sulphate, and concentrated under reduced pressure to give the crude product which was purified by chromatography (0-4% MeOH/CH₂Cl₂) to give 0.05 g of (Z)-3-(3-(3,5-bis(trifluoromethyl)phenyl)-1H-1,2,4-triazol-1-yl)-N'-(2-(3-oxomorpholino)acetyl) acrylohydrazide (Yield: 8%). ¹H NMR (400 MHz, DMSO-d₆) δ 10.33 (bs, 2H), 9.63 (s, 1H), 8.57 (s, 2H), 8.30 (s, 1H), 7.50-7.52 (d, J=8 Hz, 1H)), 6.01-6.03 (d, J=8 Hz, 1H), 4.08-4.12 (m, 4H), 3.85-3.87 (m, 2H), 3.41-3.44 (m, 2H). LCMS m/z 507.13 [M+H]⁺, $t_R$ 1.950 min.

Example 15. Synthesis of (Z)-3-(3-(3,5-bis(trifluoromethyl)phenyl)-1H-1,2,4-triazol-1-yl)-N'-(2-(3,3-dimethylmorpholino)acetyl)acrylohydrazide (Compound 15)

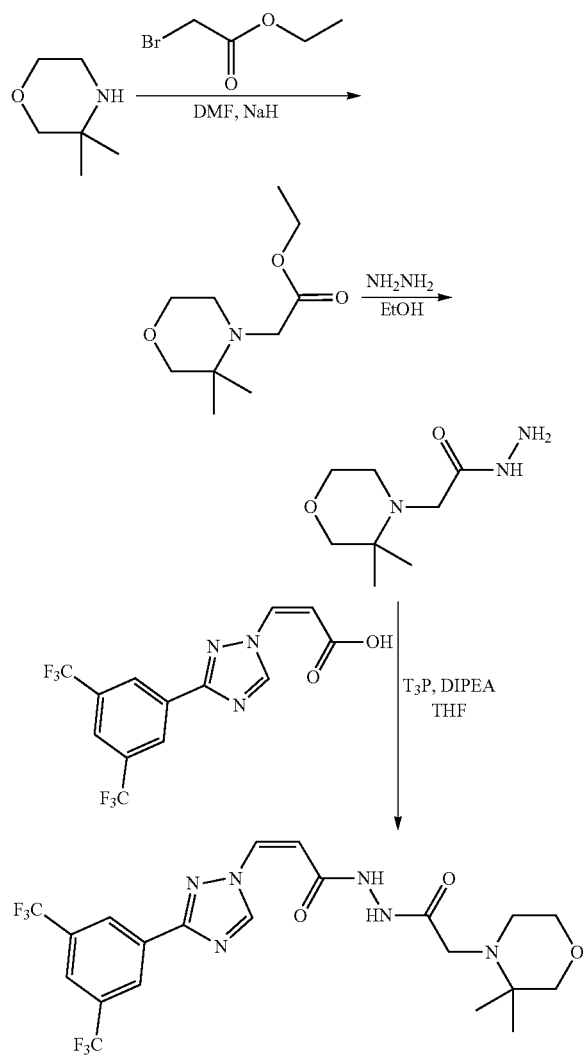

Synthesis of Ethyl 2-(3,3-dimethylmorpholino)acetate

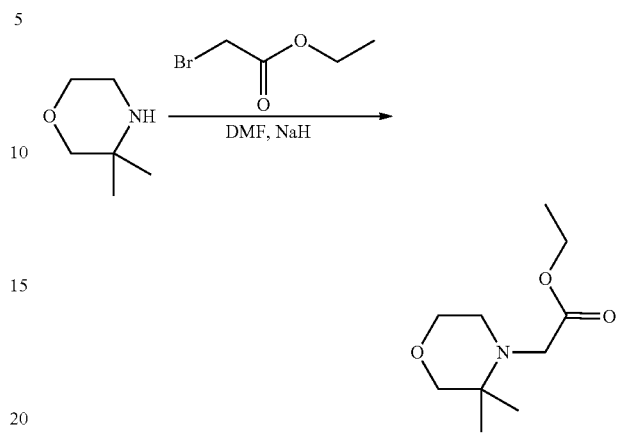

3,3-Dimethylmorpholin (1 g, 8.68 mmol) was dissolved in acetonitrile (5 mL) and potassium carbonate (1.8 g, 13 mmol) was added. The reaction mixture was stirred at room temperature for 30 min and ethylbromo acetate (1.1 mL, 9.55 mmol) was added. The reaction mixture was heated at 60° C. for 1 h. Then reaction mixture was transferred into 50 mL water and extracted with ethyl acetate (3×50 mL). The combined organic layers was washed with brine, dried over anhydrous sodium sulphate, and concentrated under reduced pressure to give the crude product, which was used without further purification in the next step (Crude yield: 91%). LCMS m/z 202.9 [M+H]⁺, $t_R$ 2.33 min.

Synthesis of 2-(3,3-dimethylmorpholino)acetohydrazide

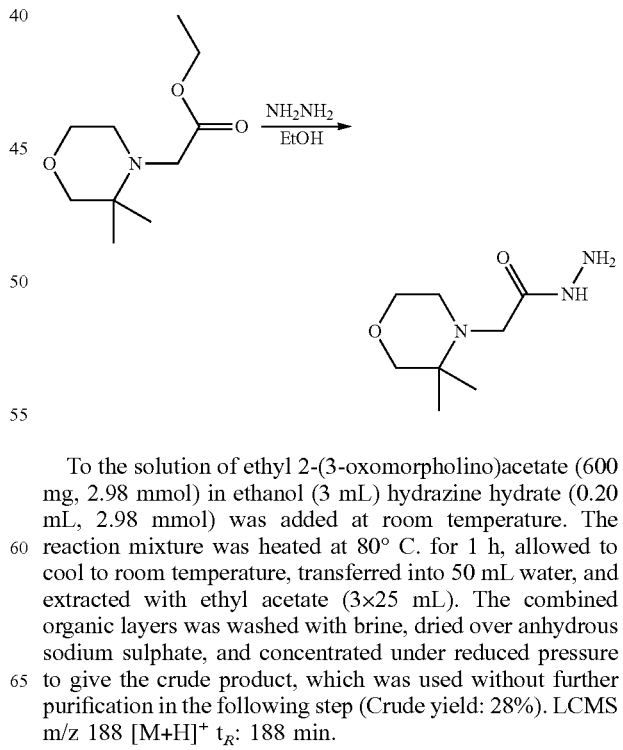

To the solution of ethyl 2-(3-oxomorpholino)acetate (600 mg, 2.98 mmol) in ethanol (3 mL) hydrazine hydrate (0.20 mL, 2.98 mmol) was added at room temperature. The reaction mixture was heated at 80° C. for 1 h, allowed to cool to room temperature, transferred into 50 mL water, and extracted with ethyl acetate (3×25 mL). The combined organic layers was washed with brine, dried over anhydrous sodium sulphate, and concentrated under reduced pressure to give the crude product, which was used without further purification in the following step (Crude yield: 28%). LCMS m/z 188 [M+H]⁺ $t_R$: 188 min.

Synthesis of (Z)-3-(3-(3,5-bis(trifluoromethyl)phenyl)-1H-1,2,4-triazol-1-yl)-N'-(2-(3,3-dimethylmorpholino)acetyl)acrylohydrazide

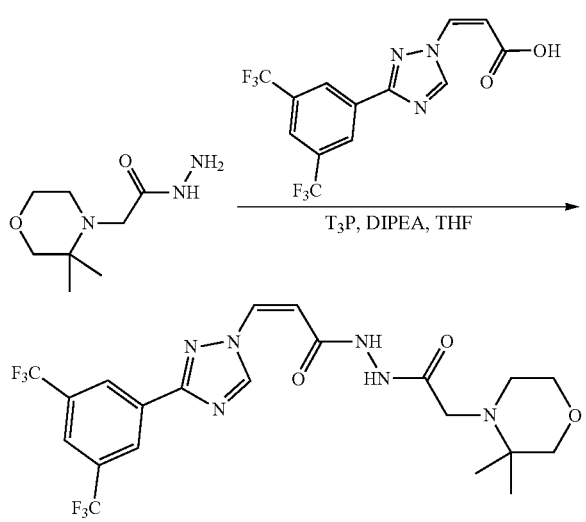

To the solution of (Z)-3-(3-(3,5-bis(trifluoromethyl)phenyl)-1H-1,2,4-triazol-1-yl)acrylic acid (0.250 g, 0.7 mmol) and 2-(3,3-dimethylmorpholino)acetohydrazide (0.160 g, 0.85 mmol) in THF (2.5 mL) T$_3$P (0.63 mL, 1.06 mmol) was added dropwise followed by DIPEA (0.18 mL, 1.06 mmol) at −60° C. The reaction mixture was stirred for 1 h, transferred into 25 mL iced-water, and extracted with ethyl acetate (2×25 mL). The combined organic layers was washed with brine, dried over anhydrous sodium sulphate, and concentrated under reduced pressure to give the crude product, which was purified by chromatography (0-4% MeOH:CH$_2$Cl$_2$) to give 0.05 g of (Z)-3-(3-(3,5-bis(trifluoromethyl)phenyl)-1H-1,2,4-triazol-1-yl)-N'-(2-(3,3-dimethylmorpholino) acetyl)acrylohydrazide (Yield: 13%). $^1$H NMR (400 MHz, DMSO-d$_6$) δ 10.55 (s, 1H), 9.81 (s, 1H), 9.62 (s, 1H), 8.56 (s, 2H), 8.29 (s, 1H), 7.49-7.51 (d, J=10.4 Hz, 1H)), 6.01-6.03 (d, J=10.4 Hz, 1H), 3.65-3.67 (m, 2H), 3.30-3.34 (m, 2H), 3.08 (bs, 2H), 2.55-2.58 (m, 2H), 0.96 (s, 6H). LCMS m/z 521.18 [M+H]$^+$, t$_R$ 1.937 min.

Example 16. Assays

Certain compounds of the invention, along with Compounds X-1, X-2 and X-3 (shown below) were tested in various assays.

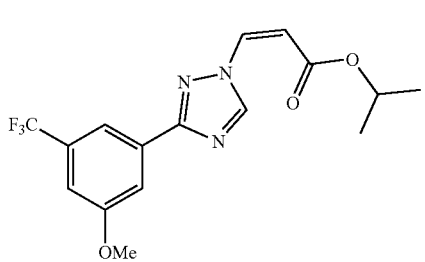

(X-1)

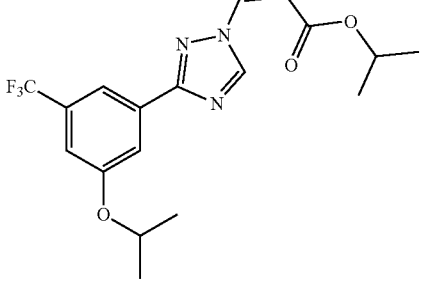

(X-2)

(X-3)

Inhibition of Nuclear Export

The inhibition of CRM1 mediated nuclear export by compounds of the invention was determined. The results are shown in Table 2. The inhibitory activity of compounds for the CRM1 protein was determined in the RevGFP assay. Compounds of the invention are active in Rev-GFP assay with IC$_{50}$<10 μM with the most preferred compounds having activities with IC$_{50}$ values of 1 μM.

Experimental protocol: Rev is a protein from human immunodeficiency virus type 1 (HIV-1) and contains a nuclear export signal (NES) in its C-terminal domain and a nuclear localization signal (NLS) in its N-terminal domain. Nuclear export of Rev protein is dependent on the classical NES/CRM1 pathway (Neville et al, 1997, Kau et al, 2003). Nuclear accumulation of Rev is observed in cells treated with specific inhibitors of CRM1, such as LMB (Kau et al, 2003). In this assay, U2OS-RevGFP cells are seeded onto clear-bottom, black, 384-well plates the day before the experiment. Compounds are serially diluted 1:2 starting from 40 M in a separate 384-well plate in DMEM, and then transferred onto cells. Cells are incubated with compound for ~1 hr before fixation with 3.7% formaldehyde and nuclei staining with Hoechst 33258. The amount of GFP in cell nuclei was measured and compound IC$_{50}$s were determined (Kau et al, 2003).

MTT Cell Proliferation Assay

The CellTiter 96® AQueous One Solution cell proliferation assay (Promega) was used on MM1.S, Jurkat and HCT-116 cells to study the cytotoxic and cytostatic properties of the compounds. The assay is based on the cleavage of the tetrazolium salt, MTS, in the presence of an electron-coupling reagent PES (phenazine ethosulfate). The MTS tetrazolium compound is bioreduced by cells into a colored formazan product that is soluble in tissue culture medium. This conversion is presumably accomplished by NADPH or NADH produced by dehydrogenase enzymes in metabolically active cells. Assays are performed by adding a small amount of the CellTiter 96® AQueous One solution reagent directly to culture wells, incubating for 1-4 hours and then recording the absorbance at 490 nm with a 96-well plate reader. The absorbance revealed directly correlates to the cell number and their metabolic activity. The cells were seeded at $5\times10^3$ to $1.5\times10^4$ cells (depending on cell type) in each well of 96-well plate in 100 μL of fresh culture medium and adherent cells were allowed to attach for overnight. The stock solutions of the compounds were diluted in cell culture medium to obtain eight concentrations of each drug, ranging from 1 nM to 30 μM and DMSO at less than 1% v/v was used as a negative control. After 72 h of treatment 20 μl of CellTiter 96® AQueous reagent was added into each well of the 96-well assay plates and the plate was incubate at 37° C. for 1-4 hours in a humidified, 5% CO2 atmosphere. Then the absorbance of each well was recorded at 490 nm by using a 96-well plate reader. In most cases the assay was performed in triplicates and the results were presented as half maximal inhibitory concentration ($IC_{50}$) described below. Optical density versus compound concentration was plotted and analyzed using non linear regression equations (Excel Fit) and the $IC_{50}$ for each compound was calculated. The results are shown in Table 2.

Determination of Pharmacokinetics (PK) and Brain: Plasma Ratio Blood was collected from mice (N=3) to contribute to the total of 10 time points (pre-dose, 5 min, 15 min, 30 min, 1 hour, 2 hours, 4 hours, 8 hours, 12 hours and 24 hours post dose). Mice were bled on a rotating basis, each mouse contributing 3 time points to the blood collection. At the designated time points, animals were anaesthetized under isoflurane, and approximately 110 μL of blood per time point was collected via retro-orbital puncture into pre-cooled $K_2$EDTA (anti-coagulant) tubes. Blood samples were put on wet ice and centrifuged (2000 g, 5 min at 4° C.) to obtain plasma within 30 minutes of sample collection. All samples were stored frozen at approximately −80° C. until analysis. Prior to analysis, samples were mixed with internal standard (dexamethasone) in acetonitrile, vortexed, centrifuged, and supernatant was injected for analysis. Concentration of compounds in plasma was determined using LC-MS-MS instrumentation (API 4000, Triple Quadruple with electrospray ionization; Acuity Ultra Performance Liquid Chromatography column C18, with MeOH and formic acid as organic solvents). PK parameters including but not limited to Tmax, Cmax, $t_{1/2}$, $AUC_{last}$, $AUC_{inf}$ were calculated using WinNonlin Professional 6.2 software package, non-compartmental pharmacokinetic model NCA200.

Brain to Plasma Ratio (B:P). A separate group of mice (N=3) were dosed (PO at 10 mg/kg unless otherwise indicated) and then sacrificed at the time of maximal plasma concentration (estimated $T_{max}$ at 2 hours post-dose) where terminal plasma and brain were collected. Brain tissue following collection was rinsed with cold saline, dried on filter paper, weighed and snap-frozen by placing on dry ice. All samples were stored frozen at approximately −80° C. until analysis. At the time of analysis, brain tissue was homogenized (homogenizing solution PBS, pH 7.4), mixed with internal standard (dexamethasone) in acetonitrile, vortexed, centrifuged, and supernatant was injected for analysis of compound concentration using LC-MS-MS methodology (API 4000, Triple Quadruple with electrospray ionization; Acuity Ultra Performance Liquid Chromatography column C18, with MeOH and formic acid as organic solvents). Plasma samples were treated with the identical method (except homogenization step) and concentration of compound in either matrix was calculated based on the generated standard curves. The results are shown in Table 2.

TABLE 2

Assay Results for Compounds of Formula I and Comparators Thereto.

| Compound | Rev Export [$IC_{50}$] | Cytotoxicity [$IC_{50}$] | $AUC_{Inf}$ (hr · ng/mL)* | B:P* |
|---|---|---|---|---|
| X-1** | <1 μM | <1 μM | 209‡ | NT |
| X-2*** | <1 μM | <1 μM | 68.3† | 1.27† |
| X-3 | <1 μM | <1 μM | 12300 | 5.0 |
| 1 | NT | <1 μM | 33100 | 2.25 |
| 2 | <1 μM | <1 μM | 28900 | 0.16 |
| 3 | <1 μM | <1 μM | 15200 | 0.03 |
| 4 | NT | <1 μM | 20929 | 0.028 |
| 5 | NT | <1 μM | NT | NT |
| 6 | NT | <1 μM | NT | NT |
| 7 | NT | <1 μM | NT | NT |
| 8 | NT | <1 μM | 9150 | 0.41 |
| 19 | NT | <1 μM | 671**** | N/A |
| 10 | NT | <1 μM | NT | NT |
| 11 | NT | <1 μM | 8340 | 0.095 |
| 12 | <1 μM | <1 μM | 19600 | 0.06 |
| 13 | NT | <1 μM | 1103 | 1.5 |
| 14 | NT | <1 μM | 1419 | 0 |
| 15 | NT | <1 μM | 588 | 0 |

*Dosed in mice at 10 mg/kg po.
**Compound 26 from U.S. 2009/0275607.
***Compound 44 from U.S. 2009/0275607.
****Dosed in mice at 5 mg/kg po
‡$AUC_{Inf}$ values for compound X-1 dosed in mice at 10 mg/kg po were below limit of quantitation. Data reported for 5 mg/kg iv.
†Dosed in rats at 10 mg/kg po.
NT = not tested
N/A = below quantifiable limit The $AUC_{Inf}$ for compound X-1 was below the limit of detection when dosed in mice at 10 mg/kg po. When dosed at 5 mg/kg iv, compound X-1 showed minimal exposure, as indicated by the low $AUC_{Inf}$ of 209 hr·ng/mL. The brain to plasma ratio for compound X-1 was not determined due to its negligible levels (below the quantitation limit) in the brain when dosed po.

The $AUC_{Inf}$ for compound X-2 was calculated to be 68.3 hr·ng/mL when dosed in rats at 10 mg/kg po. Such exposure levels are exceedingly low when compared to compound X-3 and compounds of Formula I of the present invention. However, compound X-2 exhibits a moderate brain to plasma ratio. The low $AUC_{hf}$ coupled with a non-negligible brain to plasma ratio suggests that compound X-2 can crosses the BBB despite the low exposure levels. Applicants believe that Compound X-2 would have a significantly higher brain to plasma ratio if its $AUC_{Inf}$ were increased.

The $AUC_{Inf}$ for compound X-3 was calculated to be 12300 hr·ng/mL when dosed in rats at 10 mg/kg po, indicated good exposure. However, X-3 demonstrated a high B:P ratio of 5.0.

The compounds of Formula I, all show a high $AUC_{Inf}$ (>3500 hr·ng/mL) and a relatively low B:P (<2.5). Generally, greater exposure levels of a therapeutic agent often increase the likelihood of brain penetration. It is therefore surprising and unexpected that compounds of formula I exhibit high $AUC_{Inf}$ levels while relatively low brain to plasma ratios.

Example 17. Models

Evaluation of the Effects of Compound 2 on Tumor Growth in the Z-138 Lymphoma Cell Line Grown as a Xenograft in SCID Mice Z-138 (ATCC #CRL-3001) mantle cell lymphoma cells were obtained from ATCC. These cells were grown in IMEM medium supplemented with 10% horse serum, 1% penicillin and streptomycin, and 2 mM L-glutamine. Cells were sub-cultured by dilution at a ratio of 1:5 to 1:10. Twenty-four (24) female CB-17 SCID mice (Charles River Labs strain code 236), aged 5 to 6 weeks were used. The SCID mice were inoculated in the left flank with Z-138 cells in a volume of 0.2 mL, equivalent to $4 \times 10^7$ cells per mouse.

Treatment was initiated when the tumors reached a mean volume of 84.3 mm$^3$. Mice were allocated to four (4) groups of eight (8) prior to the initiation of treatment based on tumor volume such that mean tumor volume in each group was within the range of 77 to 92 mm$^3$. Mice were treated with vehicle, standard of care drug/positive control drug (cyclophosphamide) or Compound 2, as shown in Table 3.

TABLE 3

Initial Study Groups

| Group | Number of animals | Test Article | Dose | Route of Administration | Schedule |
|---|---|---|---|---|---|
| 1 | 8 | Vehicle | 10 ml/kg | PO | MWF |
| 2 | 8 | Cyclophosphamide | 80 mg/kg | IP | Days 1, 3, 5 |
| 3 | 8 | Compound 2 | 15 mg/kg | PO | MWF |
| 4 | 8 | Compound 2 | 7.5 mg/kg | PO | MWF |

Animals were fed with Labdiet® 5001 rodent chow and sterile water ad libitum. Tumors were measured once every two days with micro-calipers, and tumor volume was calculated as (length×width×width)/2. All animals were weighed every day in order to assess possible differences in animal weight among treatment groups as an indication of possible toxicity resulting from the treatments. Animals with weight loss of more than 20% of their starting weight were euthanized. Mice with weight loss of more than 15% of their starting weight were not treated again until weight loss recovered to less than 5% of their starting weight. Any animals with a tumor volume of more than 1500 mm$^3$ were euthanized.

Dosing solutions were prepared fresh on each day of dosing. Compound 2 was supplied as a lyophilized powder containing 69.61% Compound 2 with the balance made up of Pluronic F-68 and PVP K29/32. This was prepared by dissolving the lyophilized powder in sterile water. Cyclophosphamide was dissolved at 8 mg/mL in sterile water for injection. All test articles were administered in a volume of 10 mL/kg body weight.

Statistical differences between treatment groups were determined using Mann-Whitney Rank Sum or ANOVA tests with a critical value of 0.05.

FIG. 1 shows that all treatment groups showed statistically significant reductions in tumor growth relative to vehicle when evaluated by comparing the area under the growth curves using an ANOVA test for both tumor volume and percent tumor volume. These treatment groups showed significant tumor growth reductions at p<0.0001. Some weight loss was observed in the group treated with Compound 2 at 15 mg/kg and, although statistically significant, when compared to vehicle controls, severe weight loss was limited to a few animals.

Compound 2, administered orally, had antitumor effect at both 7.5 mg/kg and 15 mg/kg doses in a dose dependent manner.

Anti-Tumor Activity of Compound 2 in the A549 Small Cell Lung Carcinoma Model

The A549 cell line was derived from explant culture of alveolar carcinoma tissue from a 58-year-old Caucasian male. The cells were grown in Ham's F12-K tissue culture media with 10% fetal calf serum and 1% penicillin/streptomycin. Cells were routinely trypsinized and passaged 1:10. Thirty-two (32) female CB-17 SCID mice (Charles River Labs strain code 236), aged 5 to 6 weeks were used with a mean pre-treatment body weight of 16.3 grams. Mice were divided into four (4) groups of eight (8) prior to the initiation of treatment based on tumor volume. On the day of implantation, cells were washed in PBS, trypsinized and resuspended in complete media to a density of $2 \times 10^7$ cells/mL prior to being mixed with an equal volume of Matrigel. This mixture was then inoculated subcutaneously into mice in a volume of 0.1 mL using a 23G needle.

Mice were treated with vehicle, standard of care drug/positive control drug (cisplatin) or Compound 2, as shown in Table 4. Animal weights and condition were recorded daily, and tumors were measured on Mondays, Wednesdays and Fridays with micro-calipers, and tumor volume was calculated as (length×width×width)/2.

TABLE 4

Initial Study Groups

| Group | Number of animals | Test Article | Dose | Route of Administration | Schedule |
|---|---|---|---|---|---|
| 1 | 8 | Vehicle | 10 ml/kg | PO | MWF |
| 2 | 8 | Cisplatin | 5 mg/kg | IP | Days 1, 15 |
| 3 | 8 | Compound 2 | 10 mg/kg | PO | MWF |
| 4 | 8 | Compound 2 | 5 mg/kg | PO | MWF |

Animals with weight loss of more than 20% of their starting weight were euthanized. Mice with weight loss of more than 15% of their starting weight were not treated again until weight loss recovered to less than 5% of their starting weight. Any animals with a tumor volume of more than 1500 mm$^3$ were euthanized.

Dosing solutions were prepared fresh on each day of dosing. Compound 2 was supplied as a lyophilized powder containing 69.61% Compound 2 with the balance made up of Pluronic F-68 and PVP K29/32. This was prepared by dissolving the lyophilized powder in sterile water. Cisplatin was dissolved at 5 mg/mL in DMSO and diluted 1:10 in sterile water for injection. All test articles were administered in a volume of 0.1 mL/10 g body weight.

Statistical differences between treatment groups were determined using Mann-Whitney Rank Sum or ANOVA tests with a critical value of 0.05.

Figure 2:
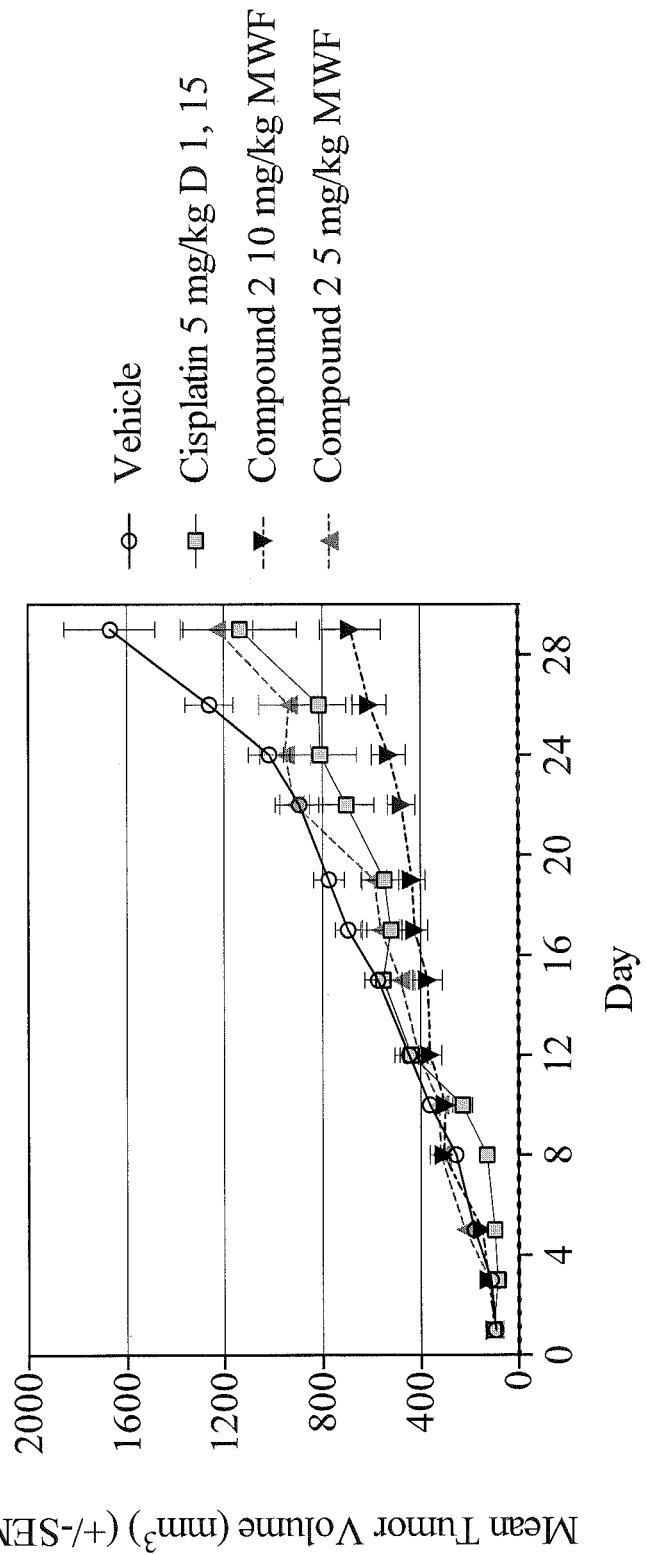
FIG. 2 is a graph of mean tumor volume versus time, and shows the group mean volume of A549 xenograft tumors on mice treated with vehicle, 5 mg/kg cisplatin, 10 mg/kg Compound 2 or 5 mg/kg Compound 2 (error bars represent SEM for each group).

The data for tumor volume change during the study are shown in FIG. 2. The mean tumor volume for the vehicle control group increased from 95 mm$^3$ on Day 1 to 1669 mm$^3$ on Day 29. The group treated with cisplatin had a mean tumor volume of 104 mm$^3$ on Day 1, increasing to 1136 mm$^3$ on Day 29. Mice treated with Compound 2 at 10 mg/kg PO (Group 3) had a mean tumor volume of 101 mm$^3$ on Day 1, which increased to 686 mm$^3$ by Day 29. Mice treated with Compound 2 at 5 mg/kg PO (Group 6) had a mean tumor volume of 101 mm$^3$ on Day 1, which increased to 1231 mm$^3$ by Day 29.

Additional analyses of the tumor volume data were performed by calculating the mean area under the curve (AUC) for each tumor and comparing the groups using a one-way ANOVA test. This analysis indicated that there were statistically significant differences between the vehicle control group and the group treated with Compound 2 at 10 mg/kg (p=0.0005). It should be noted that there was that there was no statistically significant reduction in tumor growth in the positive control group (cisplatin).

Compound 2, administered orally, had an antitumor effect at both 5 mg/kg and 10 mg/kg doses in a dose dependent manner. However, it was only the 10 mg/kg group that showed a statistically significant difference when compared to the vehicle treated group.

Evaluation of Compound 2 in the Anti-Collagen Antibody Induced Mouse Model of Rheumatorid Arthritis (CAIA)

Twenty-four (24) male Balb/c mice, aged 6 to 8 weeks were used. The weight variation of animals at the time of treatment initiation did not exceed ±20% of the mean weight. Animals were randomly assigned to 3 groups that would receive vehicle, dexamethasone or Compound 2. On study Day 0 (study commencement), all mice were subjected to a 2 mg intravenous injection of ArthritoMAb™ antibody cocktail (MD Biosciences #S1203001) followed by an intraperitoneal injection of LPS (100 g/mouse) on study Day 3. Study animals were treated with 7.5 mg/kg Compound 2 or 4 mg/kg Compound 2 orally; 1 mg/kg dexamethasone intraperitoneally; or vehicle orally. Treatments were administered once daily on days 4, 6, 8 and 10 for all groups, except where dosing vacations applied. If an animal's weight dropped below 87% of its day 0 starting weight, the animal was not dosed until it gained weight equivalent to 90% or more of day 0 weight.

Arthritis development, clinical signs and body weights were monitored in all mice on study days 0, 3-8, 10 and 12. Observations included changes in skin, fur, eyes, mucous membranes, occurrence of secretions and excretions (e.g., diarrhea) and autonomic activity (e.g., lacrimation, salivation, piloerection, pupil size, unusual respiratory pattern). All paws (front left and right, and rear left and right) of each animal were examined for signs of arthritogenic responses prior to arthritis induction and test item or control item administration on study Day 0 and subsequently on study Days 3-8, 10 and 12 (study termination). Arthritis reactions were scored and recorded according to a 0-4 scale in ascending order of severity, as shown Table 5 below. Paw thickness was also measured using a dial caliper (Kroeplin, Munich, Germany).

TABLE 5

Arthritis clinical score

| Arthritis Score | Grade |
| --- | --- |
| No reaction, normal | 0 |
| Mild, but definite redness and swelling of the ankle/wrist or apparent redness and swelling limited to individual digits, regardless of the number of affected digits | 1 |
| Moderate to severe redness and swelling of the ankle/wrist | 2 |
| Redness and swelling of the entire paw including digits | 3 |
| Maximally inflamed limb with involvement of multiple joints | 4 |

The dose administered was calculated based on the assumption that the animals weighed, on average, 20 g. A stock solution of dexamethasone was prepared in 100% ethanol and diluted to the appropriate concentration in PBS prior to use. Vehicle for the vehicle control group was prepared by dissolving 0.6 g Pluronic and 0.6 g PVP in 100 mL distilled deionised water. The MAb stock solution (10 mg/mL) was supplied by MD Biosciences, Division of Morwell Diagnostics GmbH. LPS was diluted with PBS to achieve the appropriate concentration. Thorough vortexing was required just prior to its injection. Compound 2 was supplied as a lyophilized drug powder containing 70.71% Compound 2 with the balance made up of Pluronic F-68 and PVP K29/32. A fixed volume of 200 L was administered to each mouse.

Evaluation was primarily based on the mean values for arthritis scoring and paw thickness measurements. Where appropriate, analysis of the data by ANOVA with Tukey post hoc analysis was applied to determine significance of treatment effects.

Figure 3A:
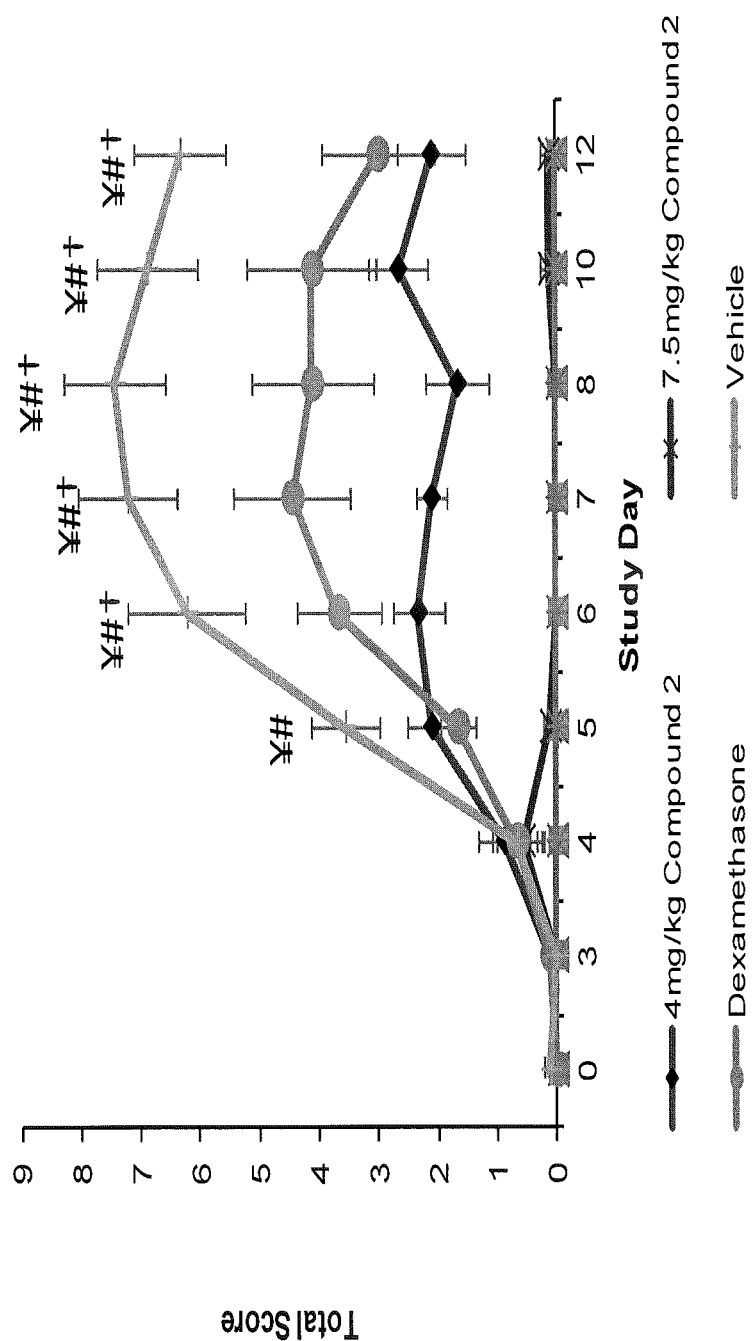
FIG. 3A is a graph of total arthritis score versus time, and shows the clinical arthritis score anti-collagen antibody induced male BALB/c arthritis mice treated with vehicle, dexamethasone, 4 mg/kg Compound 2 or 7.5 mg/kg Compound 2 over a 12-day observation period (Y=dexamethasone-treated group significantly different from vehicle-treated group; #=7.5 mg/kg Compound 2-treated group significantly different from vehicle-treated group; †=4 mg/kg Compound 2-treated group significantly different from vehicle-treated group).
Figure 3B:
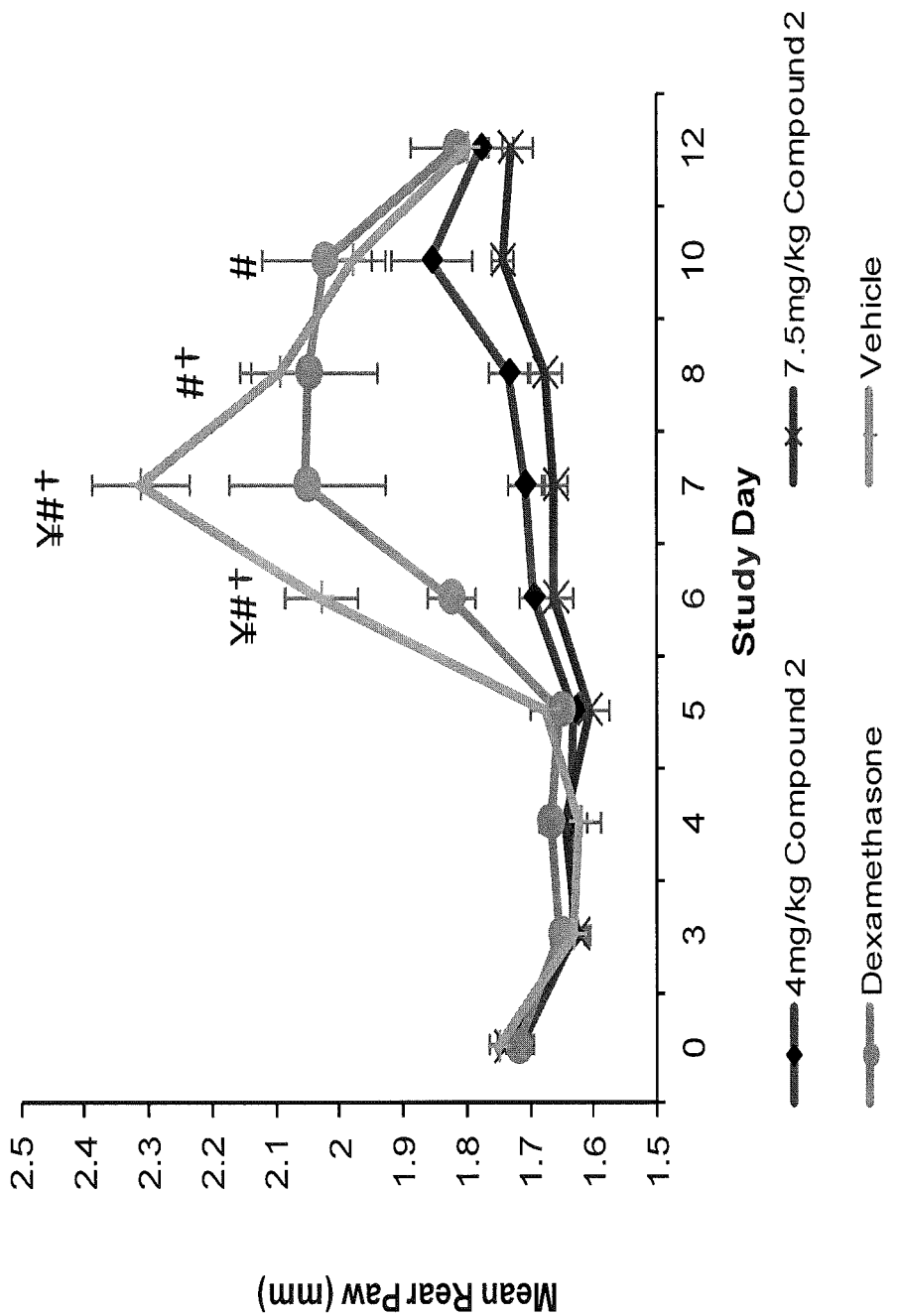
FIG. 3B is a graph of mean rear paw versus time, and shows the group mean rear paw thickness for anti-collagen antibody induced male BALB/c arthritis mice treated with vehicle, dexamethasone, 4 mg/kg Compound 2 or 7.5 mg/kg Compound 2 over a 12-day observation period (Y=dexamethasone-treated group significantly different from vehicle-treated group; #=7.5 mg/kg Compound 2-treated group significantly different from vehicle-treated group; †=4 mg/kg Compound 2-treated group significantly different from vehicle-treated group).

FIGS. 3A and 3B show the results of the CAIA mouse model experiments. Clinical signs associated with LPS-administration developed in all groups following the LPS boost on day 3. Compared to vehicle treated mice, mice treated with 7.5 mg/kg or 4 mg/kg Compound 2 had significantly reduced total arthritis scores on days 5-12 and 6-12, respectively. Dexamethasone treatment significantly reduced total arthritis score compared to the vehicle group on days 6-12. Compared to vehicle treated mice, mice treated with 7.5 mg/kg or 4 mg/kg Compound 2 had significantly reduced rear paw arthritis scores on days 5-12. Dexamethasone treatment significantly reduced rear paw arthritis score compared to the vehicle group on days 5 and 12. There were no significant differences in body weight between the vehicle-treated group and test item-treated groups.

In view of the findings in the present study, Compound 2 at 7.5 mg/kg or 4 mg/kg delivered orally exhibited significant anti-arthritic activity in the anti-collagen antibody induced model of rheumatoid arthritis, with sustained reductions in mean arthritis scores and reductions in paw thickness.

Efficacy Study of Compound 2 in Collagen-Induced Arthritis (CIA) in Lewis Rats

Forty (40) female Lewis rats (BK), aged 6 to 8 weeks with a pre-treatment body weight range of 180 to 200 g were divided randomly into four (4) groups (Groups A-D) of ten (10) rats each. The rats in Groups B to D were immunized intradermally with bovine CII in IFA at three sites near the base of the tail and over the back with 500 μL of the emulsion on day 0 (200 μL, 200 μL, 100 μL for each site). On day 7, the rats in Groups B-D were given booster injections with the same amount of the emulsion intradermally near the former injection sites. In the therapeutic treatment model (Groups C and D), dexamethasone or Compound 2 was orally administered to rats with CIA after the onset of arthritis, as shown in Table 6. Rats were weighed daily and a drug holiday was given to an animal when a weight loss of greater than 13%.

TABLE 6

Initial study groups

| Group | Immunization | Treatment | | Administration | n |
| --- | --- | --- | --- | --- | --- |
| A | Naive | PBS | vehicle | PO. QD, from onset to day 28 | 10 |
| B | Model | Col II in IFA | vehicle | PO. QD, from onset to day 28 | 10 |
| C | DEX (1MPK) | Col II in IFA | DEX (1MPK) | PO. QD, from onset to day 28 | 10 |
| D | Compound 2 (4MPK) | Col II in IFA | Compound 2 (4MPK) | PO. QoD, from onset to day 28 | 10 |

CIA development was evaluated via macroscopic scoring and measurements of paw swelling. This was assessed every day for the first 5 days after sensitization (day 7) and then twice per week (Monday and Thursday) for the remaining time with the clinical scoring system for each paw shown in Table 7.

TABLE 7

Arthritis clinical scores

| Arthritis score | Grade |
| --- | --- |
| No evidence of erythema and swelling | 0 |
| Erythema and swelling confined to the mid-foot (tarsals) or ankle joint | 1 |
| Erythema and mild swelling extending from the ankle to the mid-foot | 2 |
| Erythema and moderate swelling extending from the ankle to the metatarsal | 3 |
| Erythema and severe swelling encompass the ankle, foot, and digits | 4 |

Foot volume was measured by plethysmometry on the same day of the arthritic measurement throughout the study period. The cubage of each hind paw and swelling rate were measured and using the following equation:

Swelling Rate=$(C_N-C_0)/C_0 \times 100\%$.

Figure 4A:
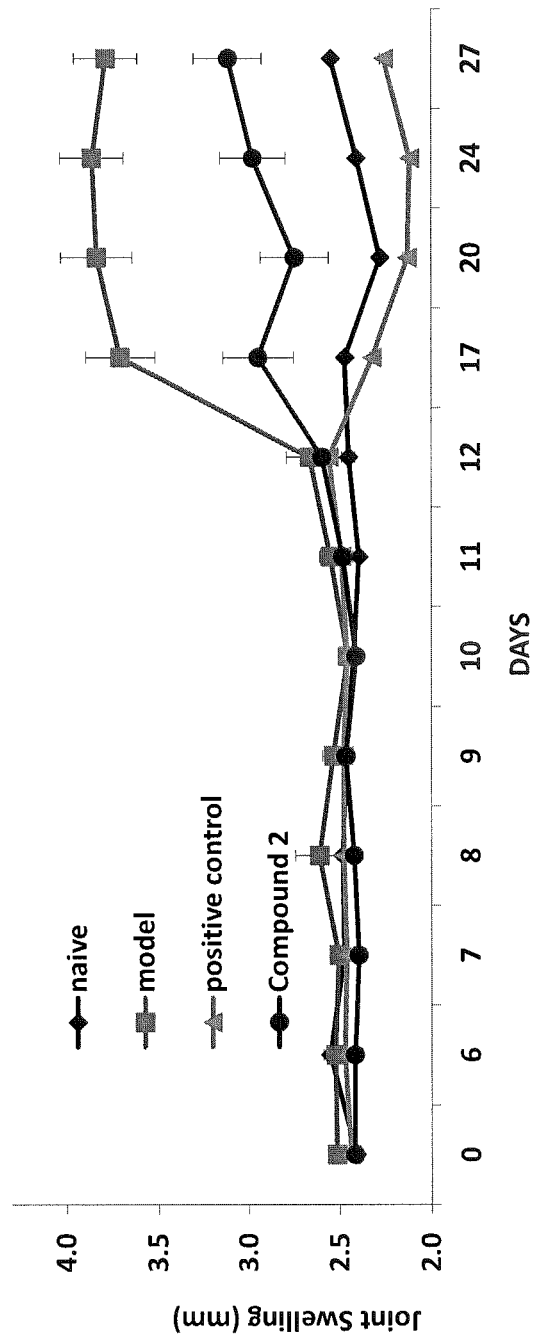
FIG. 4A is a graph of joint swelling versus time, and shows the joint swelling measured on a scale of 0-4 in naïve rats and rats treated according to the CIA model, with positive control, or with Compound 2.

FIG. 4A is a graph of joint swelling versus time, and shows the joint swelling measured on a scale of 0-4 in naïve rats and rats treated according to the model, with positive control, or with Compound 2.

Bovine CII (in 10 mM acetic acid) at 4 mg/mL was emulsified with an equal volume of IFA.

Figure 4B:
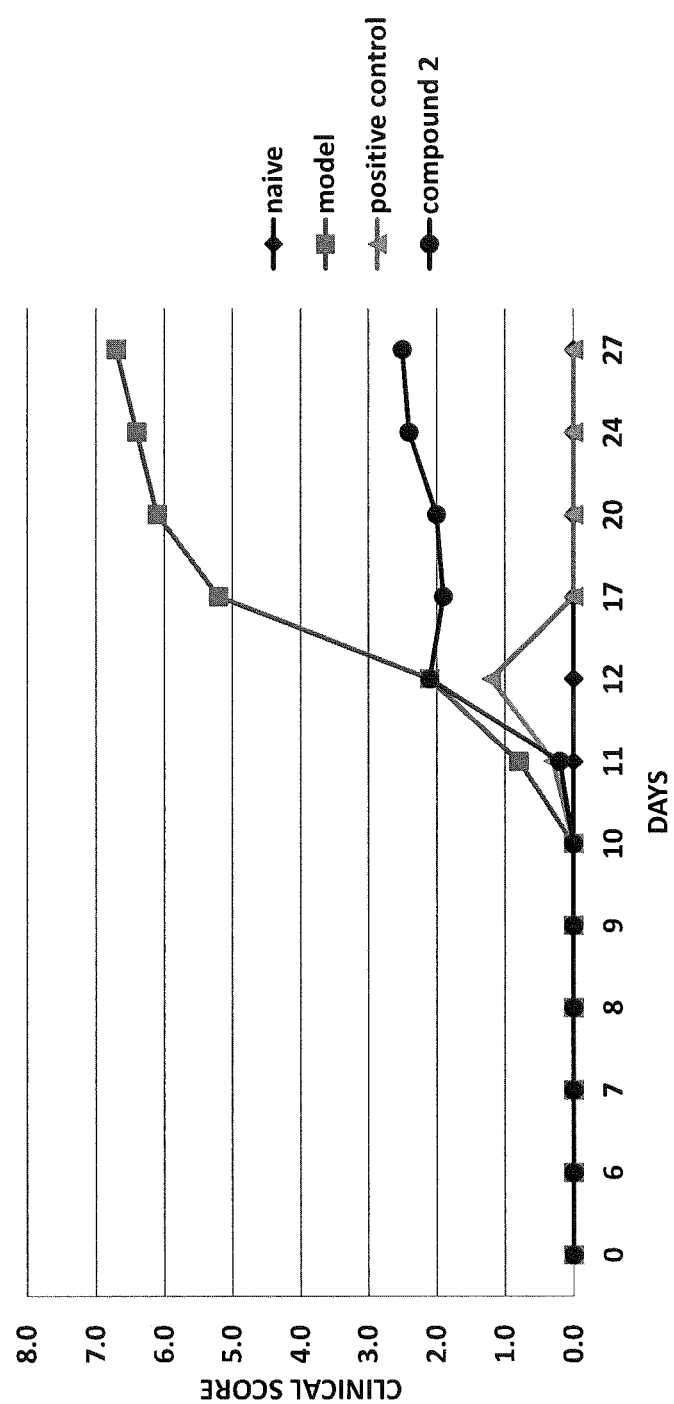
FIG. 4B is a graph of clinical scores as a function of time, and shows the clinical arthritis scores of naïve rats and rats treated according to the CIA model, with positive control, or with Compound 2.

The clinical scores were summed for each animal, and the total average of all animals in each group was expressed as the mean arthritic score. FIG. 4B is a graph of clinical scores as a function of time, and shows the clinical arthritis scores of naïve rats and rats treated according to the model, with positive control, or with Compound 2.

On day 28 of the study, three representatives from each treatment group were euthanized and hind paws were harvested and stored in 4% neutral buffered formalin. Prepared sections of hind paws were subjected to hematoxylin and eosin (H&E) staining.

Figure 5:
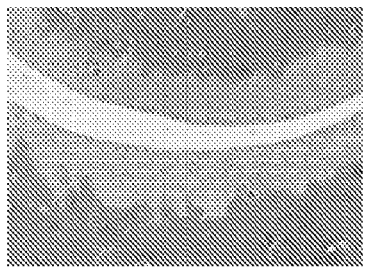
FIG. 5 is representative images from each treatment group in the CIA model, and shows the histopathology of hind paws of naïve rats and rats treated according to the model, with positive control, or with Compound 2.
Figure 5:
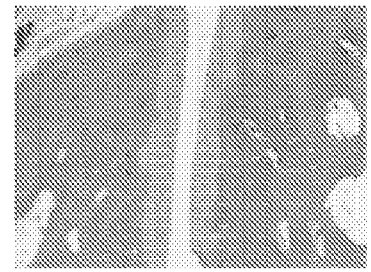
Figure 5:
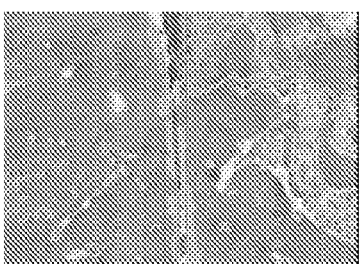
Figure 5:
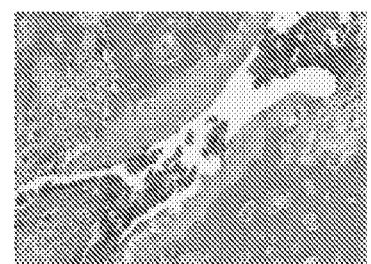
Figure 5:
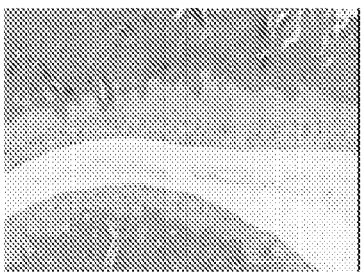
Figure 5:
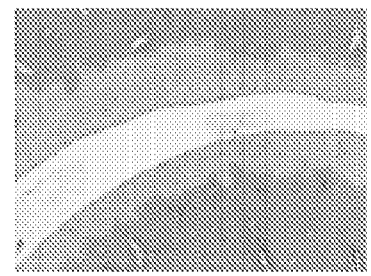
Figure 5:
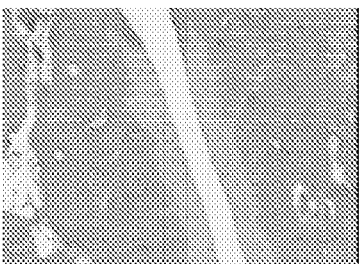
Figure 5:
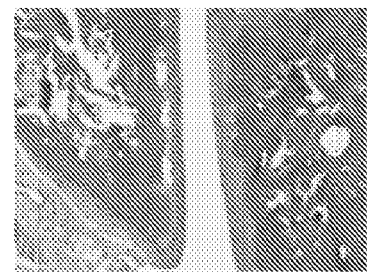
Figure 6A:
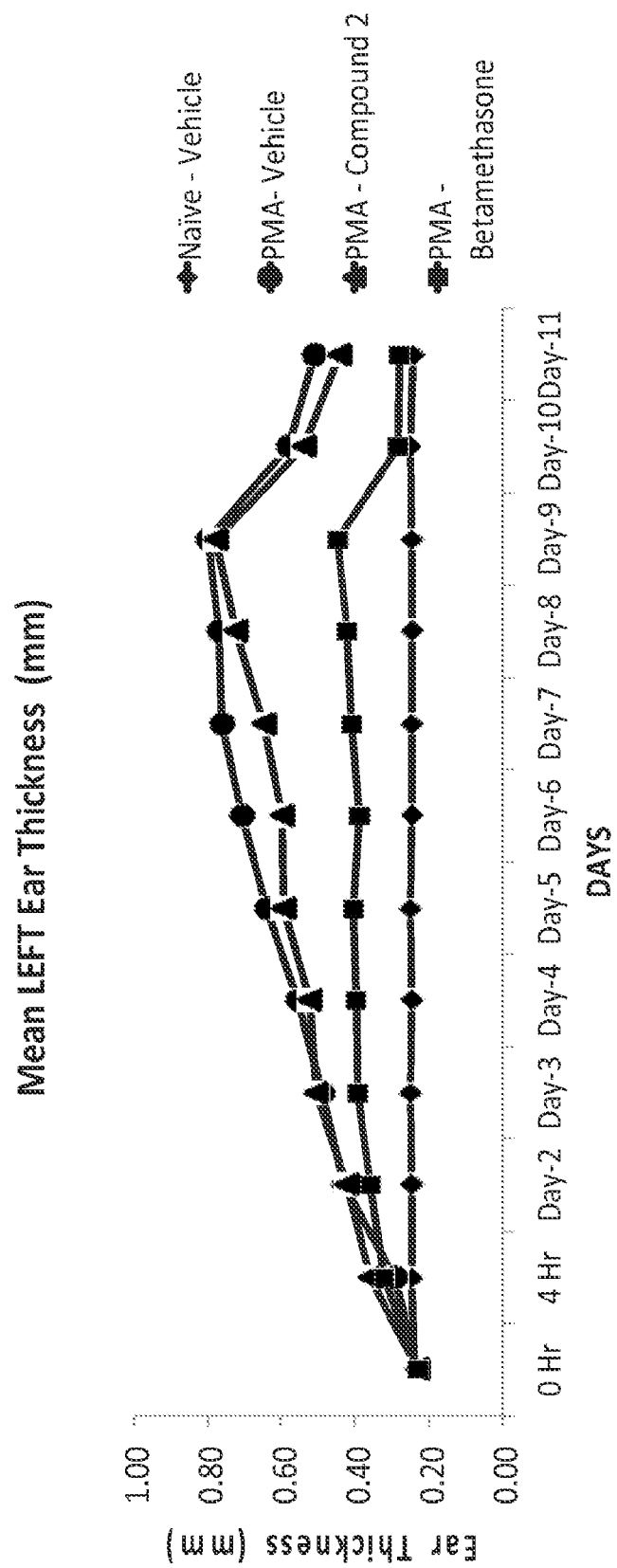
FIG. 6A is a graph of ear thickness versus time, and shows the group mean left ear thickness of female BALB/c mice treated with vehicle, PMA and vehicle, PMA and Compound 2 or PMA and betamethasone.
Figure 6B:
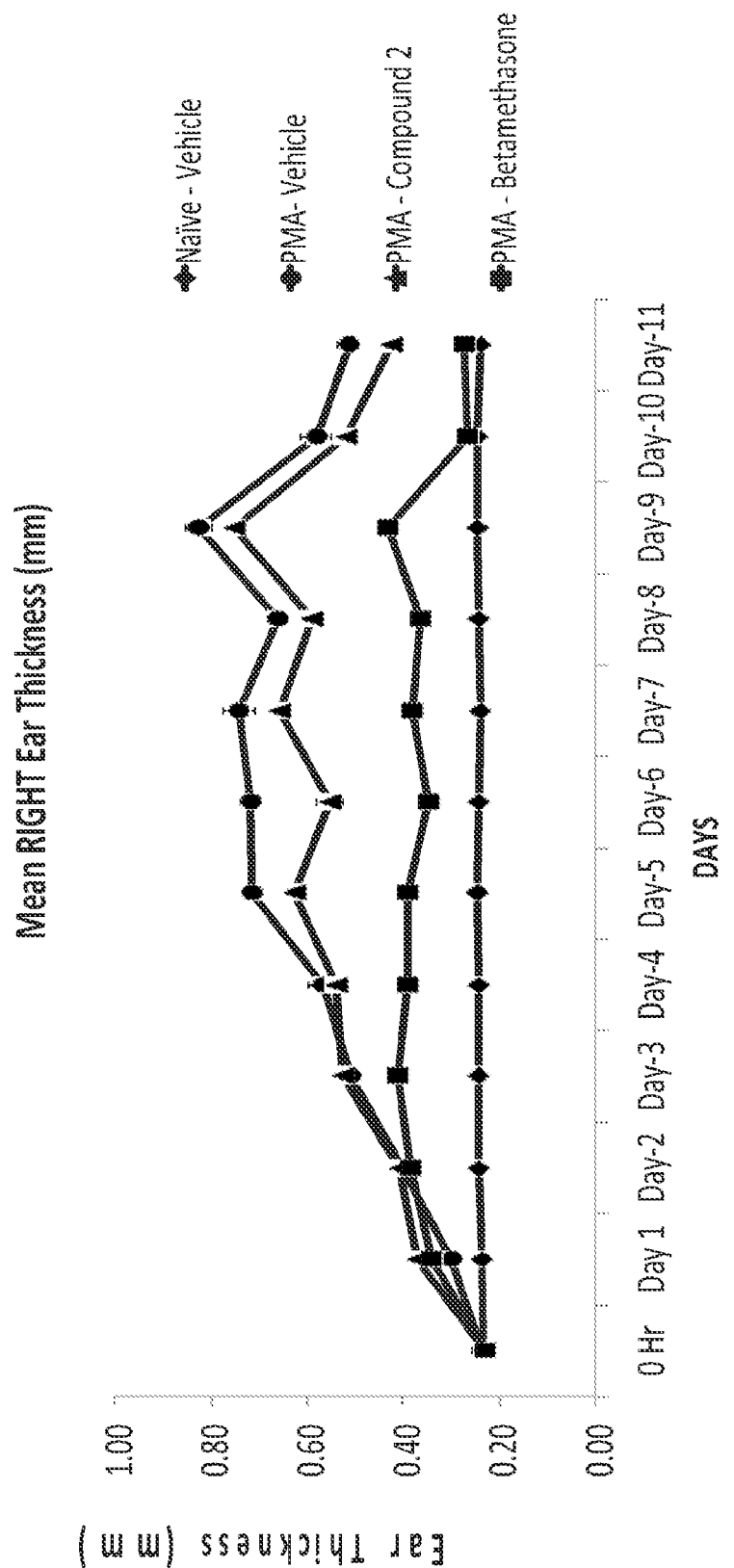
FIG. 6B is a graph of ear thickness versus time, and shows the group mean right ear thickness of female BALB/c mice treated with vehicle, PMA and vehicle, PMA and Compound 2 or PMA and betamethasone.
Figure 6C:
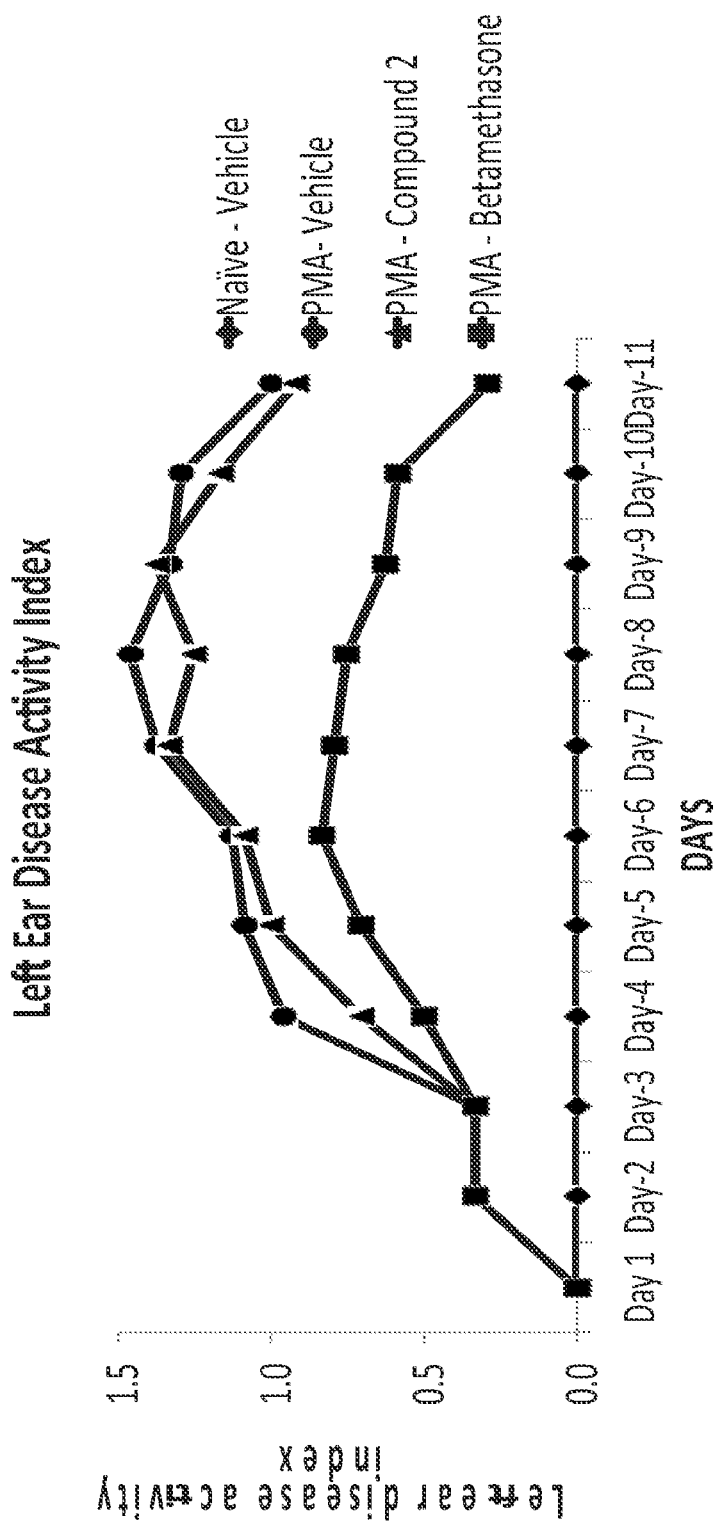
FIG. 6C is a graph of disease activity versus time, and shows the group mean left ear disease activity of female BALB/c mice treated with vehicle, PMA and vehicle, PMA and Compound 2 or PMA and betamethasone.
Figure 6D:
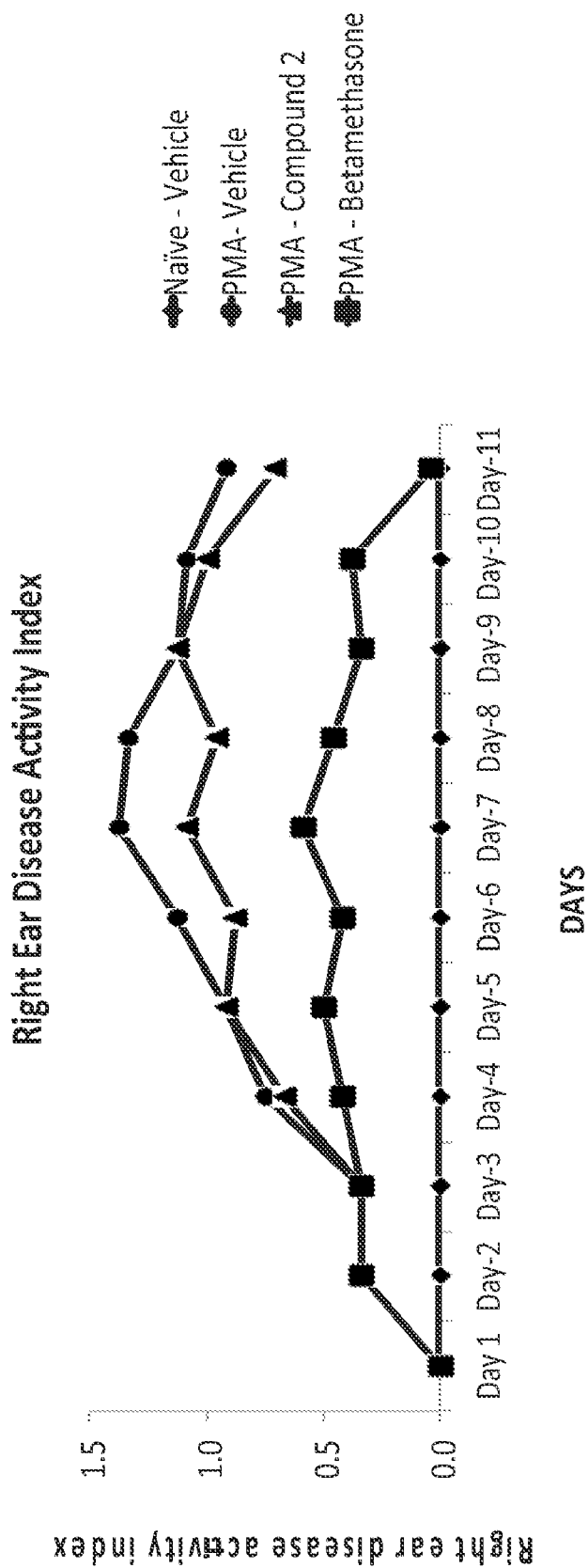
FIG. 6D is a graph of disease activity versus time, and shows the group mean right ear disease activity of female BALB/c mice treated with vehicle, PMA and vehicle, PMA and Compound 2 or PMA and betamethasone.

Histopathological analysis of the control animals showed cartilage erosion and pannus formation in line with course of the disease. However, in the Compound 2 treated rats, relatively intact cartilage was found on the joint surface and pannus formation was minimal. The results of the histological analysis are shown in FIG. 5.

The Clinical Score, Joint Swelling and histological examination data showed correlations. The results also showed the therapeutic efficacy of Compound 2 at 4 mg/kg (MPK), as shown by its effects on Clinical Scores, Joint Swelling and histological examination. The results of the CIA model in Lewis rats are depicted in FIGS. 4A and 4B, and FIG. 5.

Anti-Psoriasis Activity of Compound 2 in Phorbol-12-Myristate-13-Acetate (PMA)-Induced Psoriasis in Female BALB/C Mice Twenty-four (24) female BALB/c mice, aged 6 to 8 weeks with a body weight between 22 and 30 g were used. The mice were randomized into four (4) groups of eight (8) mice each. The grouping of animals was as follows: Group I (Naïve; ethanol), Group II (PMA; ethanol), Group III (PMA; Compound 2 10 µM) and Group IV (PMA; betamethasone). Twenty (20)µL of PMA (4 µg/20 µL of acetone) was applied topically on the upper surface of pinna of ear of all animals in Group II to Group IV. PMA was applied daily on left ear and on alternate days (M-W-F) on right ear from Day 1 to Day 9. Thirty (30) minutes after application of PMA, vehicle or standard compound (betamethasone) or Compound 2 was applied topically to the ears of animals from different groups. Of note, vehicle, standard compound, and Compound 2 were applied daily to both ears of different animals from Day 1 to Day 12.

Animals were observed daily for a period of 12 days for any treatment related symptoms. Basal ear thickness was recorded in all animals (before application of PMA) using digital screw gauge at time TO (Day 1). For the entire duration of the study, 4 hours after application of vehicle, standard compound, or Compound 2, the thickness of the ears was measured daily using digital screw gauge and scores of erythema, scaling and folding were recorded. Severity of damage to the pinna of ear was assessed by the scoring systems shown in Table 8.

TABLE 8

Psoriasis scores

| Parameter/Score | 0 | 1 | 2 | 3 |
| --- | --- | --- | --- | --- |
| Erythema | Normal | Mild | Moderate | Severe |
| Scaling | | | | |
| Folding | | | | |

The animals were supplied with nutritionally balanced autoclaved pelleted feed (Nutrivet Life Sciences, Pune (India)) ad libitum and had access to normal drinking water throughout the experimental periods.

Commercially available 100% DMSO (LR Grade) and ethanol (LR Grade) were used to prepare the formulations. PMA was prepared by dissolving 10 mg of PMA in 50.0 mL of acetone. Compound 2 was prepared by dissolving 1.47 mg of Compound 2 in 300 µL of 100% DMSO.

The experimental results are expressed in FIGS. 6A-6D as mean±SEM. There was no significant difference between all treatment groups in body weight, food and water consumption. PMA application showed, (i) the thickness of left as well as right ear increased (Group II vs. Naïve) and (ii) the disease activity index (DAI) of left as well as right ear increased (Group II vs. Naïve). Importantly, topical application of Compound 2 led to a prominent reduction in PMA-induced increases in (i) left and right ear thickness, and (ii) left and right ear DAI. This effect was prominent on Days 6-8 of the study when more animals treated with Compound 2 had reduced left/right ear thickness (compared to animals from Group II), and DAI (compared to animals from Group II). Of note, Compound 2-mediated reduction in PMA-induced increases in left/right ear thickness and DAI diminished as the study progressed (Day 10 and beyond).

In a PMA induced psoriasis model in mice, Compound 2 displayed statistically significant anti-psoriatic activity.

Anti-Psoriasis Activity of Compound 2 in the Imiquimod (IMQ)-Induced Dermal Inflammation/Psoriasis Model (STUDY 1)

Forty (40) male BALB/c mice aged 6 to 8 weeks were used with a pretreatment body weight of 22 to 30 g. The BALB/c mice were randomized into four (4) groups of 10 mice per group. A small area (about 2×2 cm$^2$) of skin on the dorsum of all the animals was neatly shaved. Group-I animals served as Naïve animals. Psoriasis was induced in Groups II to IV [Group II (IMQ; vehicle), Group III (IMQ; Compound 2 (1 µM)) and Group IV (IMQ; cyclophosphamide (10 mg/kg)] by topical application of 31.25 mg of IMQ cream daily on the dorsum of the animals from Day 1 to Day 13. Four hours after application of IMQ, vehicle or standard compound (cyclophosphamide) or Compound 2 was administered (topically—30 µL; orally—according to body weight) to the appropriate group from Day 1 to Day 13 daily. Two hours after administration of vehicle or standard compound or Compound 2, erythema, scaling, folding and thickening of skin were recorded to determine the disease activity index (DAI).

Animals were observed daily for a period of 13 days for any treatment-related symptoms. The daily observations included body weight, feed intake, skin thickening, scaling, folding, erythema, nasal discharge, movement, respiration, hair, distended abdomen, skin condition, fur, mucous membrane, presence or absence of secretions, eye condition, tail elevation, motor activity, posture and gait. Severity of damage to the dorsal portion of the skin was assessed by assigning erythema, scaling, folding and skin thickening scores based on external observations of skin, according to rubric in Table 9.

TABLE 9

Psoriasis scores

| Parameter/Score | 0 | 1 | 2 | 3 |
|---|---|---|---|---|
| Erythema<br>Scaling<br>Folding<br>Skin thickening | Normal | Mild | Moderate | Severe |

Commercially available 100% DMSO (LR Grade), ethanol (LR Grade), cyclophosphamide (CMC), PVP and Pluronic were used to prepare the formulations. Compound 2 was prepared by dissolving 1.47 mg of Compound 2 in 300 µL of 100% DMSO. Cyclophosphamide was prepared by dissolving 500 mg of CMC in 100 mL distilled water.

Figure 7A:
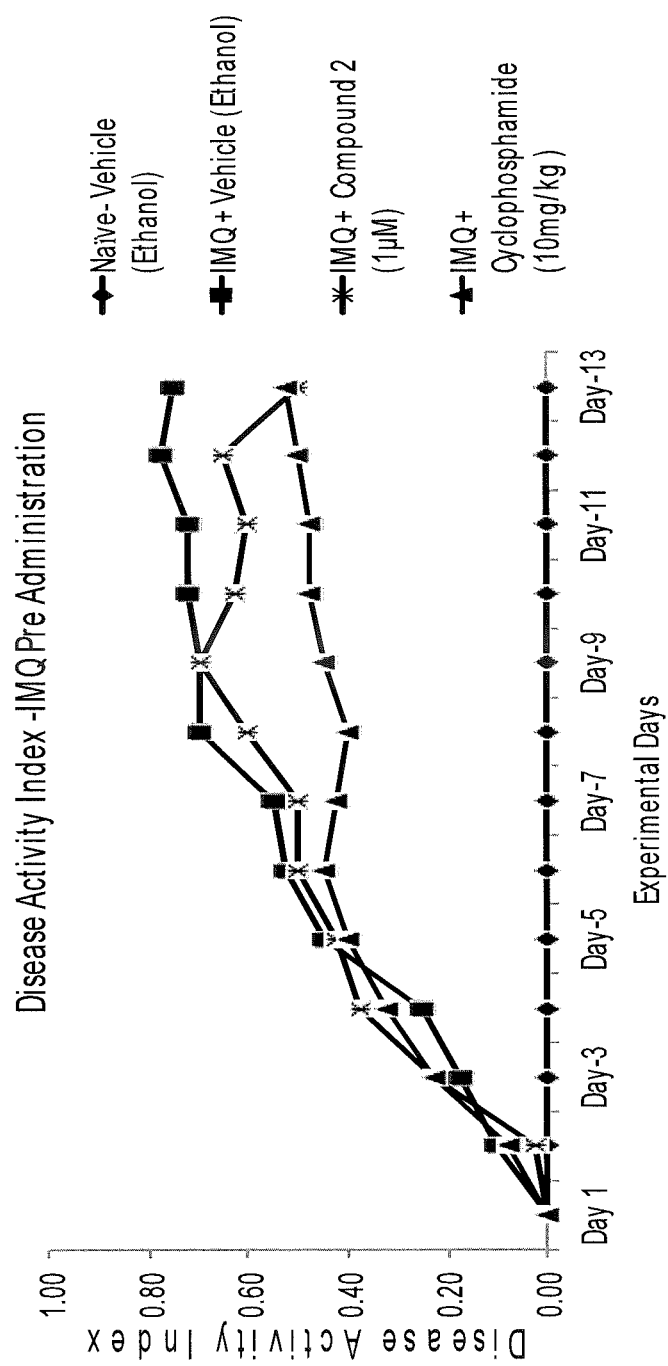
FIG. 7A is a graph of disease activity index versus time, and shows the disease activity of male BALB/c mice treated with vehicle, IMQ and vehicle, IMQ and 1 μM Compound 2, or IMQ and 10 mg/kg cyclophosphamide before IMQ administration.
Figure 7B:
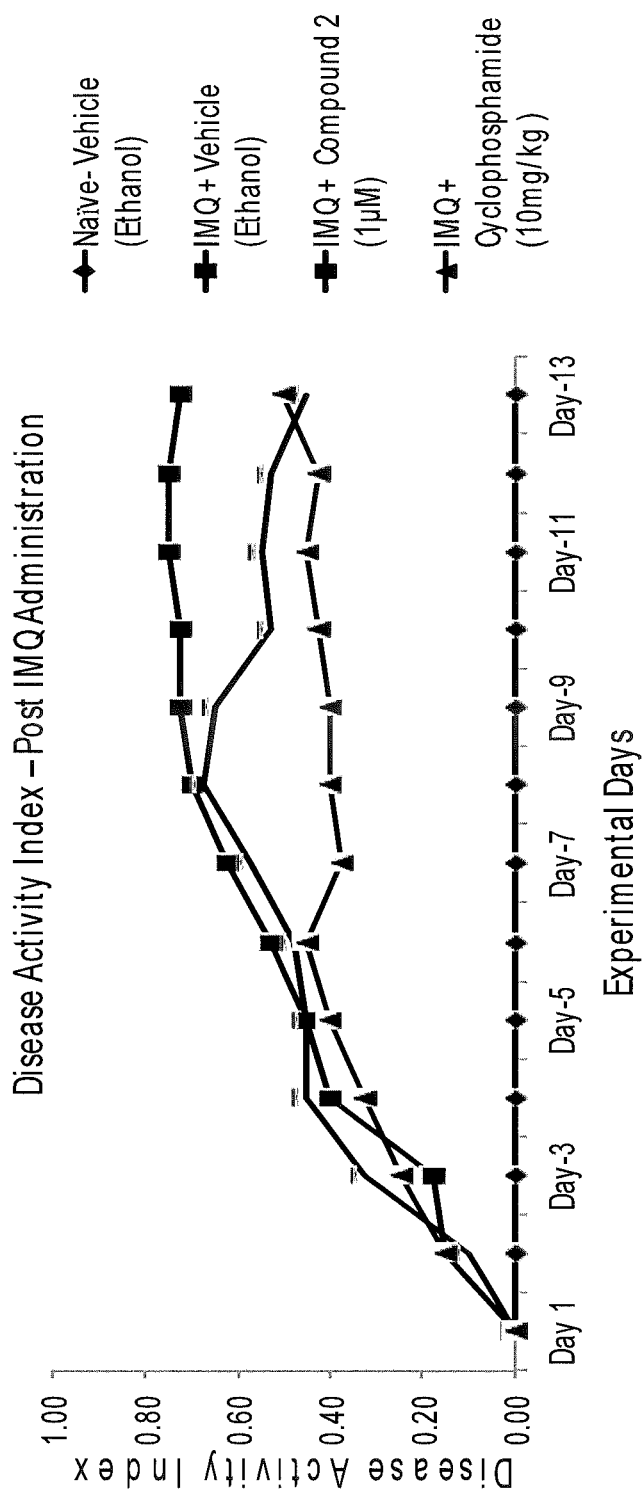
FIG. 7B is a graph of disease activity index versus time, and shows the disease activity of male BALB/c mice treated with vehicle, IMQ and vehicle, IMQ and 1 μM Compound 2, or IMQ and 10 mg/kg cyclophosphamide after IMQ administration.

The experimental results shown in FIGS. 7A and 7B are expressed as mean±SEM.

There was no significant difference in the body weight, food consumption and water intake in the treatment group when compared to the control group during the duration of the study. Compound 2 diminished IMQ-induced disease manifestation.

Compound 2 shows anti-psoriatic activity, as evidenced by the reduction in disease activity index in comparison to the vehicle treated group. Further, Compound 2 caused this effect without adversely affecting body weight, food and water intake.

Anti-Psoriasis Activity of Compound 2 in the Imiquimod (IMQ)-Induced Dermal Inflammation/Psoriasis Model (STUDY 2)

Forty (40) male BALB/c mice (Biological E Limited, Hyderabad (CPCSEA registration number: 36/99/CPCSEA)) were divided into four (4) groups consisting of ten (10) mice each. Animals were randomized based on their body weight. The groups were designated as Group-I (Naïve), Group-II (IMQ; vehicle (PEG 400 and HPBCD)), Group-III (IMQ; Compound 2 (2.5 mg/kg)) and Group-IX (IMQ; cyclophosphamide (10 mg/kg)).

A small area on the dorsum of each mouse was shaved, ensuring that these areas were of equal size/area. Psoriasis was induced in Groups II to IV by topical application of 50 mg of IMQ cream daily from Day 1 to Day 6 on the dorsum of the animals. On Day 1 and Day 2 of the study, four hours after topical application of IMQ, Compound 2 or positive control (cyclophosphamide) or vehicle were administered to animals in pertinent groups. Of note, animals in Group II and Group III were subjected to subcutaneous injections, whereas animals in Group IV received oral administration. The Compound 2, vehicle and cyclophosphamide treatment was terminated on Day 2. These groups of animals were maintained on daily IMQ treatments until Day 6. On Day 7, the psoriasis-induced animals were re-randomized into 3 groups consisting of 10 animals each based on Cumulative Disease Activity Index (CDAI). From Day 7 to Day 9, animals received vehicle or positive control or Compound 2. Of note, on these days animals were not treated with IMQ. From Day 10 to Day 14, the animals were treated alternatively with IMQ (Days 10, 12 and 14), or vehicle, positive control or Compound 2 (Days 11, 13).

All animals were observed daily for a period of 16 days for gross observations, body weight and feed and water intake. On Days 1 and 2, scorings of erythema, scaling, folding and thickening of skin were recorded 2 hours after administration of vehicle/positive control/test compounds, and on Days 3 to 14 scorings were recorded 4 hours after IMQ application, or administration of positive control, vehicle or Compound 2. The severity of induction on the dorsum of animal was assessed and scored as shown in Table 10.

Vehicle was prepared by dissolving 40 mg of HPBCD in 70.0 mL of distilled water. Compound 2 was prepared by dissolving 3.59 mg in 0.5% PVP and 0.5% Pluronic. Cyclophosphamide was prepared by dissolving 500 mg of CMC in 100 mL distilled water.

The experimental results shown in Table 10 are expressed as mean±SEM. Data was assessed using one-way ANOVA, and post hoc analysis was performed using Dunnett's test.

TABLE 10

Rate of reduction of Disease Activity Index (DAI)

Rate of reduction of DAI

Pre-IMQ/drug administration readings

% change from 1st dose administration (i.e., from pre-IMQ/drug administration readings on Day 7)

| | Day 7 | Day 8 | Day 9 | Day 10 | Day 11 | Day 12 | Day 13 | Day 14 | Day 15 |
|---|---|---|---|---|---|---|---|---|---|
| Naïve, Vehicle | 0.0 | 0.0 | 0.0 | 0.0 | 0.0 | 0.0 | 0.0 | 0.0 | 0.0 |
| IMQ, Vehicle | 0.0 | 4.2 | −33.3 | −66.7 | −60.4 | −54.2 | −45.8 | −43.8 | −43.8 |
| IMQ, Compound 2 | 0.0 | −33.8 | −58.8 | −88.2 | −73.5 | −80.9 | −61.8 | −66.2 | −64.7 |
| IMQ, cyclophosphamide | 0.0 | 16.3 | −39.5 | −79.1 | −25.6 | −39.5 | −25.6 | −34.9 | −41.9 |

TABLE 10-continued

Rate of reduction of Disease Activity Index (DAI)
Rate of reduction of DAI

|  | 4 hr. post-IMQ/drug administration readings % change from 1st dose administration (i.e., from pre-IMQ/drug administration readings on Day 7) | | | | | | | |
| --- | --- | --- | --- | --- | --- | --- | --- | --- |
|  | Day 7 | Day 8 | Day 3 | Day 10 | Day 11 | Day 12 | Day 13 | Day 14 |
| Naïve, Vehicle | 0.0 | 0.0 | 0.0 | 0.0 | 0.0 | 0.0 | 0.0 | 0.0 |
| IMQ, Vehicle | 4.2 | 8.3 | −35.4 | −70.8 | −58.3 | −52.1 | −39.6 | −41.7 |
| IMQ, Compound 2 | −30.9 | −35.3 | −63.2 | −88.2 | −70.6 | −73.5 | −60.3 | −63.2 |
| IMQ, cyclophosphamide | 23.3 | 20.9 | −41.9 | −86.0 | −25.6 | −34.9 | −32.6 | −32.6 |

It was observed that the rate of reduction of disease activity index in animals treated with Compound 2 was significantly greater than that observed in animals treated with vehicle. There was no significant difference in the body weight, food consumption and water intake in the treatment group when compared to the control group during the duration of the study.

The results obtained indicate that treatment with Compound 2 diminished IMQ-induced disease manifestation without greatly impacting the consumption of food or water, and thereby not showing any effect on the body weight of animals in the treated groups.

The Effect of Compound 2 in Zucker Rats

Twenty-one (21) male Zucker rats aged 7 months were allocated into 3 groups of N=7 based on equivalent body weights and food intakes. An additional group of N=7 age matched Zucker lean controls were included as a control. Body weights and food and water intakes were measured at approximately the same time each day (14:30-15:30 h). On treatment days, dosing was at 14:30-15:30 h (approximately 2 hours before lights off).

The Zucker obese and lean controls were orally treated with vehicle (10 mL/kg dose volume; 0.5% Pluronic F68 and 0.5% PVP K29/32 in water) on each weekday. Both Compound 2 (1.5 mg/kg and 3 mg/kg) groups were orally treated on each weekday (10 mL/kg dose volume; 0.5% Pluronic F68 and 0.5% PVP K29/32 in water). Prior to the treatment phase, 4 days baseline data were collected. The treatment phase was for 16 days and a washout phase of 6 days was also included.

Figure 8A:
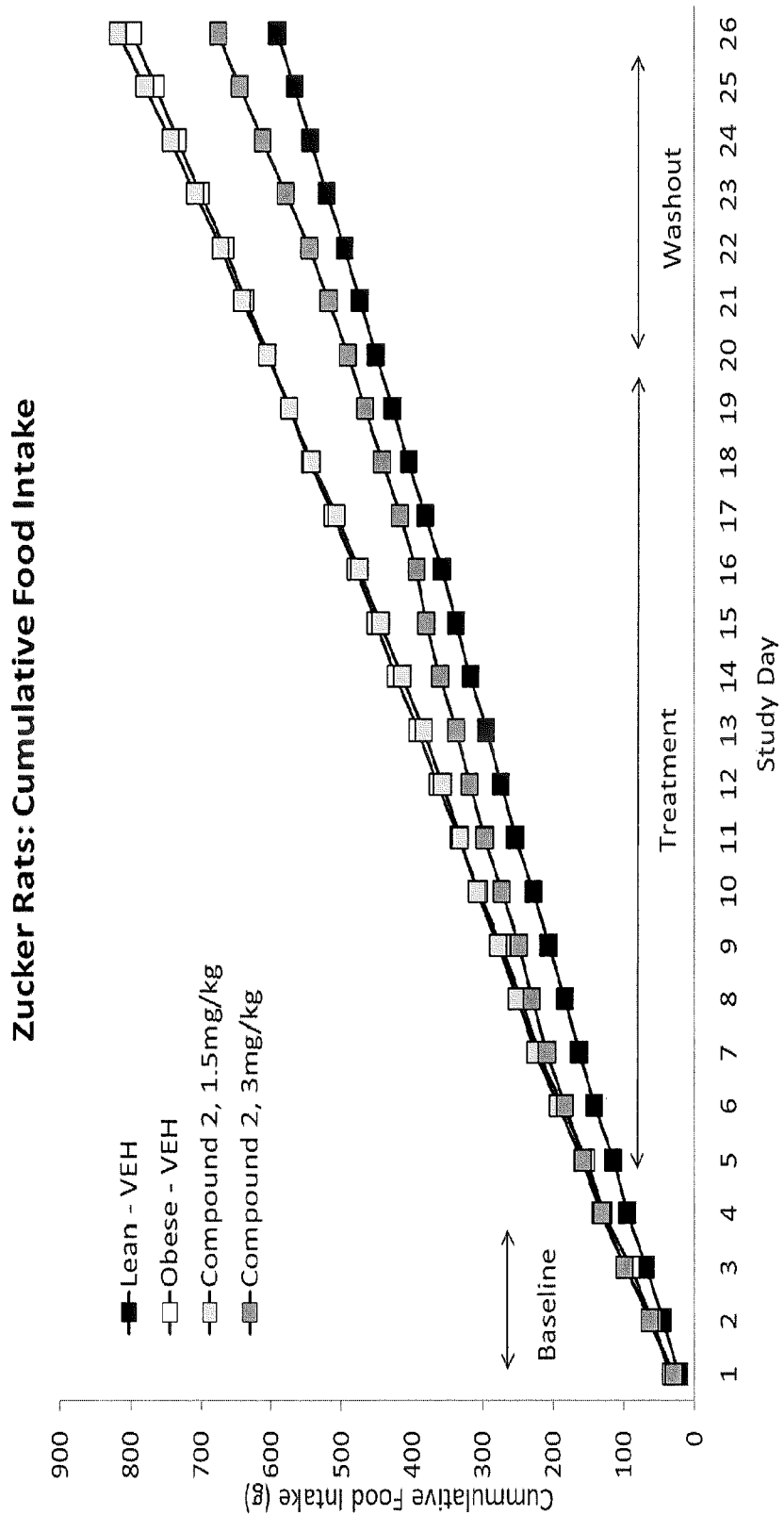
FIG. 8A is a graph of cumulative food intake versus time, and shows the cumulative food intake of lean Zucker rats and obese Zucker rats treated with vehicle (VEH), 1.5 mg/kg Compound or 3.0 mg/kg Compound 2.
Figure 8B:
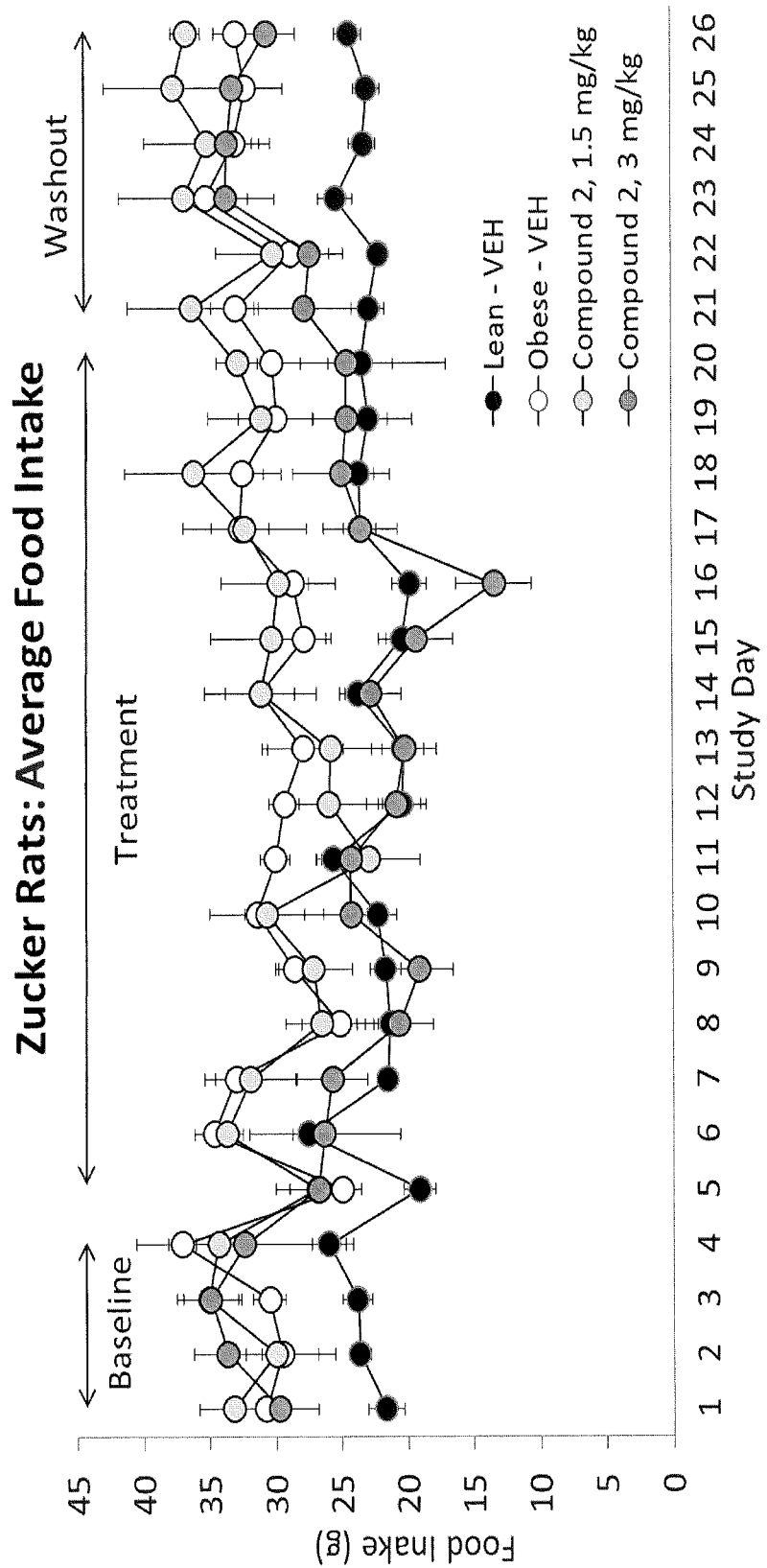
FIG. 8B is a graph of average food intake versus time, and shows the average food intake of lean Zucker rats and obese Zucker rats treated with vehicle (VEH), 1.5 mg/kg Compound or 3.0 mg/kg Compound 2.
Figure 9:
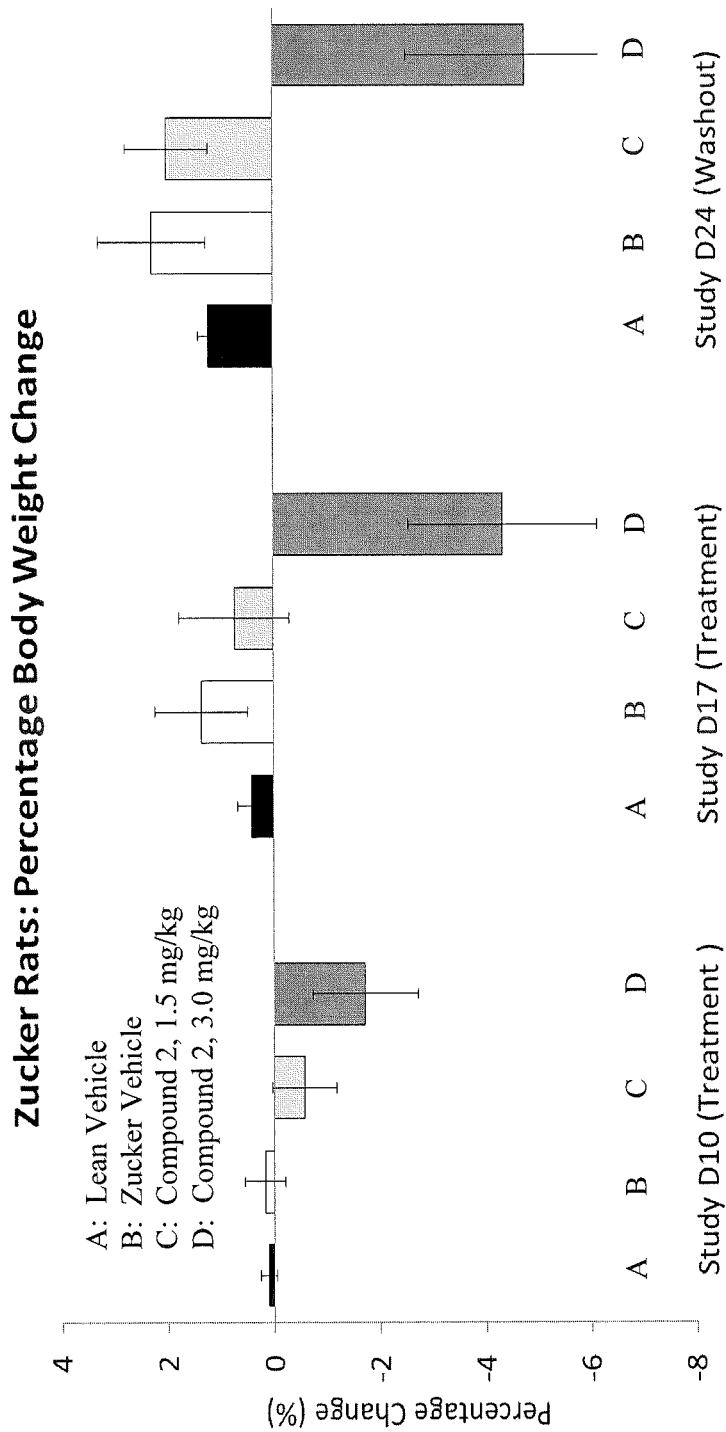
FIG. 9 is a bar graph of percentage body weight change versus time, and shows the percentage body weight change of lean Zucker rats and obese Zucker rats treated with vehicle (VEH), 1.5 mg/kg Compound or 3.0 mg/kg Compound 2 during the treatment period (Study Days 10 and 17) and during the washout period (Study Day 24) of the experiment.

FIGS. 8A and 8B and FIG. 9 show the effects of Compound 2 on Zucker rats. At baseline, there was no significant difference in body weight and daily food intake between the 3 Zucker obese groups. However, all groups were significantly different from the Zucker lean group.

Compound 2 (1.5-3 mg/kg oral) produced a dose-related decrease in daily food intake and body weight over the 16 day treatment period compared to the Zucker control group. Compound 2 treatment also significantly increased water intake measured over the same period. There was a significant difference in body weight gain between the 3 mg/kg Compound 2 group and the Zucker vehicle group. There was no significant difference in weight gain between the 1.5 mg/kg Compound 2-treated group and the Zucker vehicle group.

Compound 2 showed a dose dependent decrease in daily food effect with the higher dose (3 mg/kg) being more effective than the 1.5 mg/kg dose. Further, the Compound 2 group at 3 mg/kg showed lower weight gain in comparison to the Zucker control group.

Effect of Compound 2 in Diet-Induced Obesity Model

Male Sprague-Dawley rats of age 2 months were placed on a high fat diet (Research Diets Inc., product code D12492, 60% kcal % fat) for 3 months. A group of age-matched rats were fed normal lab chow (LabDiet 5001, ~13% kcal % fat), these animals served as controls for DIG group.

At age 4 months, and 2 months into placement of high fat diet, all rats were allocated into 3 groups of N=7 based on equivalent body weights and food intakes. Body weights and food and water intakes were measured at approximately the same time each day. On treatment days, dosing was at approximately 2 hours before lights off.

The DIO control group was treated with vehicle (oral, 10 mL/kg dose volume; 0.5% Pluronic F68 and 0.5% PVP K29/32 in water) on each weekday. The Compound 2 1.5 mg/kg group was orally treated on each weekday throughout the treatment phase (dose 10 mL/kg dose volume; 0.5% Pluronic F68 and 0.5% PVP K29/32 in water). The Compound 2 3 mg/kg group (10 mL/kg dose volume; 0.5% Pluronic F68 and 0.5% PVP K29/32 in water) was orally treated initially once daily on each weekday for week 1, then twice weekly (Monday, Wednesday) for week 2. During treatment weeks 3 and 4, Compound 2 3 mg/kg treatment continued twice weekly, except dosing was on Monday and Thursday.

Prior to the treatment phase, 3 days baseline data were collected. The treatment phase was for 4 weeks. A washout phase of 10 days was also included.

Compound 2 was supplied in powder form. The test compound had an active percentage of 65.89%. Active percentage was adjusted using BEW of 1.437 and prepared by dissolving into 0.5% w/v Pluronic F-68 and 0.5% w/v PVP K-29-32 vehicle solution. The vehicle solution was prepared on a weekly basis while Compound 2 was prepared fresh every 2 days and stored at +4° C. Animals were dosed at a volume of 10 mL/kg. Individual doses were calculated based on the most recent body weights to provide the proper mg/kg/day dosage.

Figure 10A:
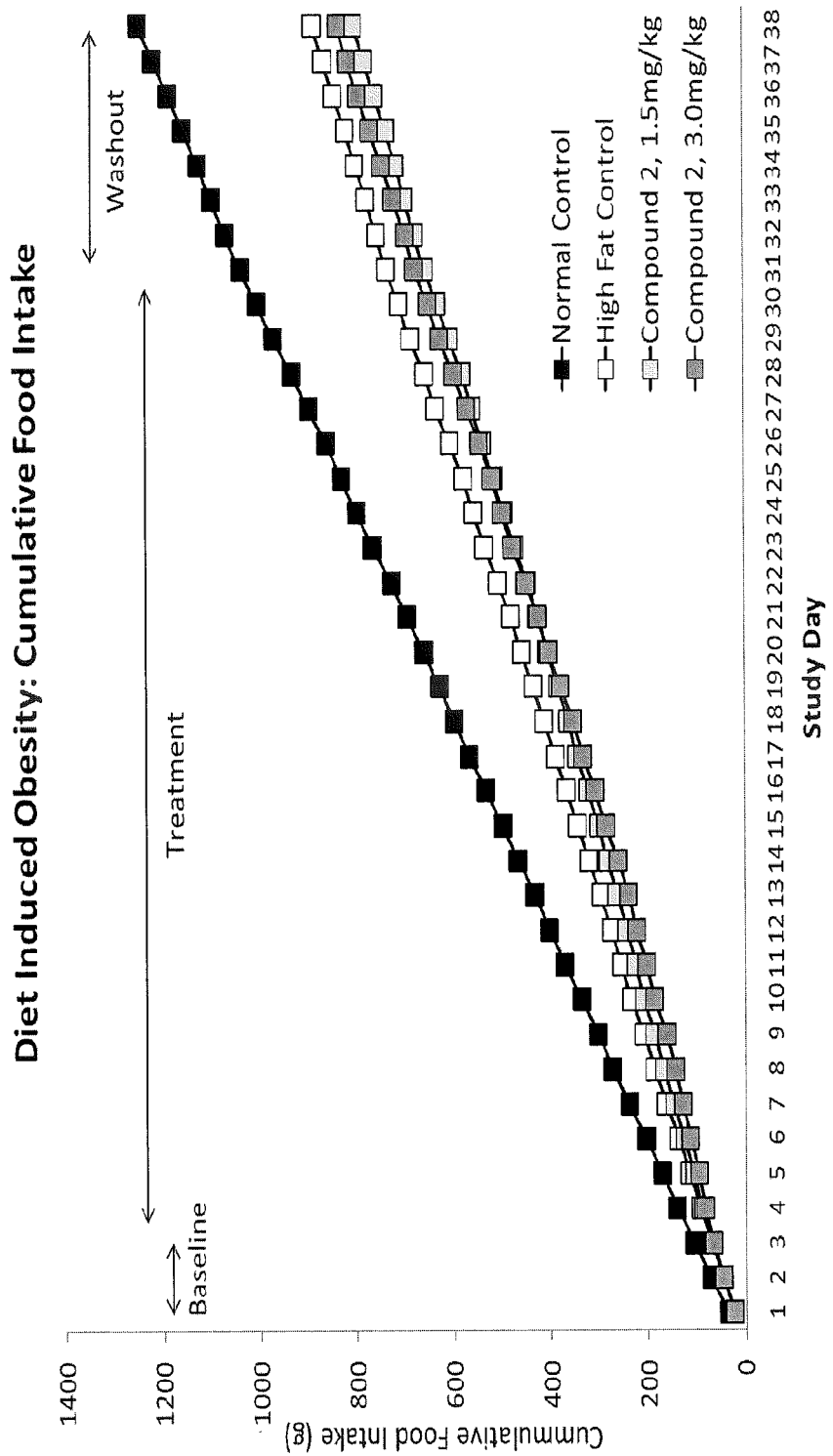
FIG. 10A is a graph of cumulative food intake versus time, and shows the cumulative food intake of rats fed normal chow and rats fed a high-fat diet and treated with vehicle, 1.5 mg/kg Compound or 3.0 mg/kg Compound 2 during the baseline, treatment and washout phases of the study.
Figure 10B:
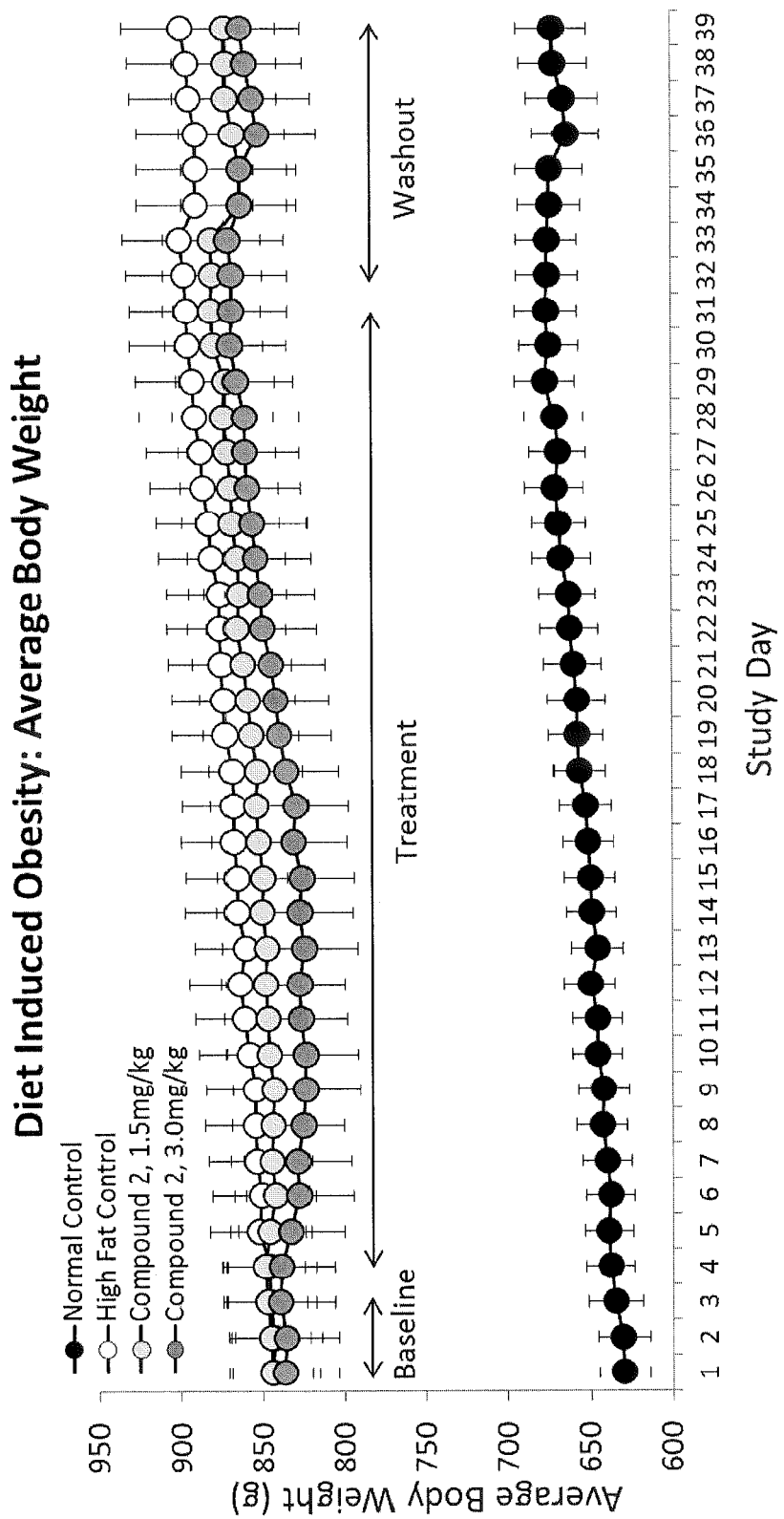
FIG. 10B is a graph of average body weight versus time, and shows the average body weight of rats fed normal chow and rats fed a high-fat diet and treated with vehicle, 1.5 mg/kg Compound or 3.0 mg/kg Compound 2 during the baseline, treatment and washout phases of the study.
Figure 11:
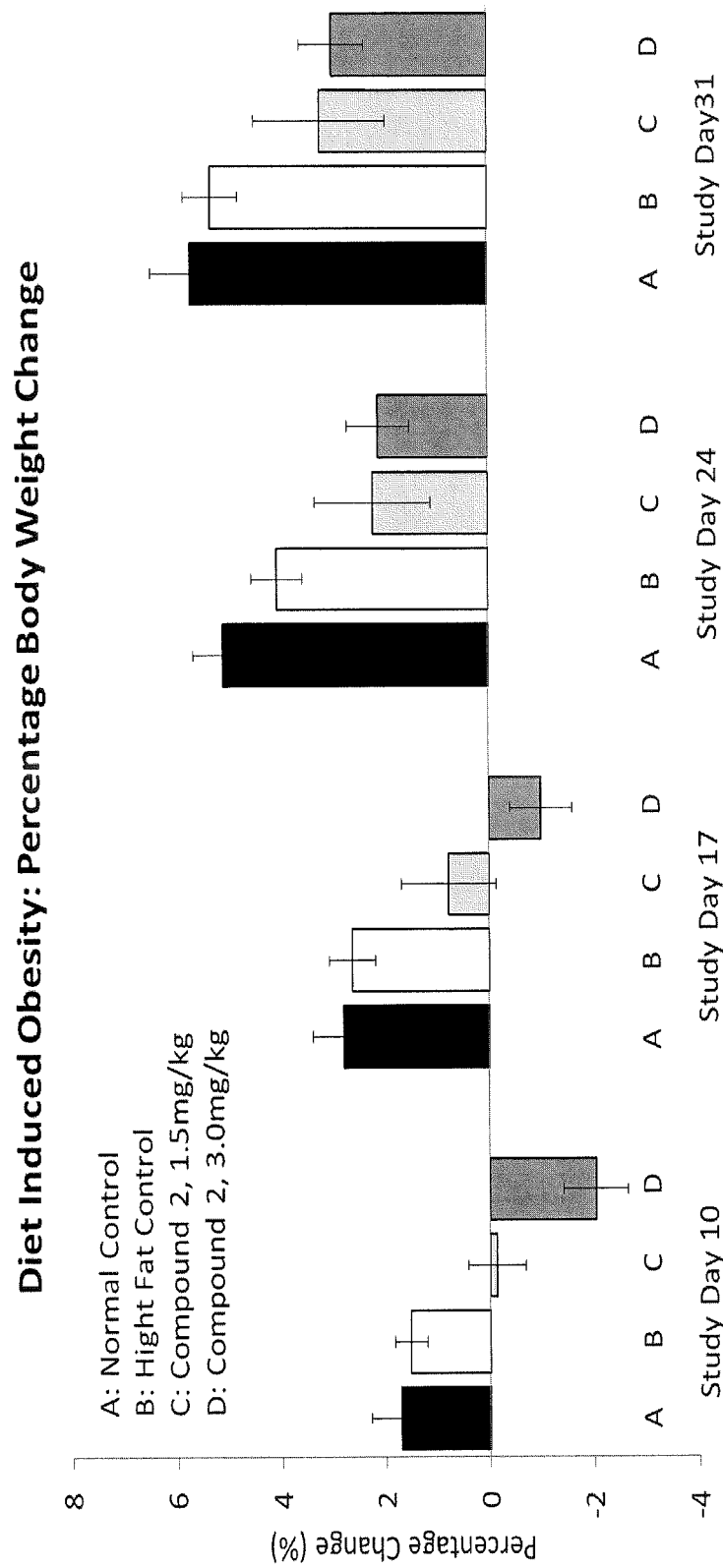
FIG. 11 is a bar graph of percentage body weight change versus time, and shows the percentage body weight change of rats fed normal chow and rats fed a high-fat diet and treated with vehicle, 1.5 mg/kg Compound or 3.0 mg/kg Compound 2.

FIGS. 10A and 10B and FIG. 11 shows the effects of Compound 2 in the diet-induced obesity model. At baseline, there was no significant difference in body weight and daily food and water intake between the 3 DIO groups. However, all DIO groups were significantly different from the regular diet group. Specifically, the animals fed under the regular diet were of significantly lower body weight relative to rats fed the high fat diet. Conversely, rats fed the high fat diet consumed significantly less daily food and water relative to the rats fed the regular diet.

Compound 2 (1.5-3 mg/kg oral) produced a dose-related decrease in daily food intake and body weight over the 28 day treatment period compared to the DIO control group.

Compound 2 treatment also significantly increased water intake measured over the same period (F3,27=11.2, P<0.01).

In terms of treatment effect on body weight gain, this was formally measured as percentage of body weight change from study day 3. There was a significant reduction in weight gain in both Compound 2 groups compared to DIO controls at treatment days 7 (study day 10) and 14 (study day 17).

Body weight, food/water intakes were measured daily over the washout phase. Food intake in the Compound 2 groups was similar to DIG controls. Body weight in the Compound 2 groups remained lower than DIG controls.

Compound 2 decreases daily food intake in a dose dependent manner. Compound 2 also affects body weight gain at both 1.5 and 3 mg/kg doses.

Compound 1 Induction of the Nrf2 Anti-Inflammatory Pathway

THP-1 (human acute monocytic leukemia cells) cells were used to evaluate the effects of Compound 1 on the Nrf2 pathway in an inflammation environment. Nuclear factor (erythroid-derived 2)-like 2 (Nrf2) is an anti-inflammatory transcription factor. Under normal conditions, Nrf2 is kept in the cytoplasm by Kelch like-ECH associated protein 1 (KEAP1), which degrades Nrf2 by ubiquitination. Nrf2 can also move into the nucleus and back into the cytoplasm as a CRM1 cargo. In the current study, Nrf2 was protected from degradation by knocking down KEAP1 with siRNA. Then, KEAP1-depleted cells were treated with TNFα to induce inflammation, and the ability of Compound 1 to reverse inflammation by up-regulation of the Nrf2 pathway was tested. To demonstrate activation of the Nrf2 pathway, the expression of two of its downstream genes NAD(P)H dehydrogenase [quinone]1 (NQO1) and epoxide hydrolase 1 (EPHX1) were quantified by quantitative PCR.

THP-1 (acute monocytic leukemia) cells were plated in two 10 cm culture dishes ($6*10^6$ cells/dish) with RPMI-1640 medium (Lonza) supplemented with 10% heat-inactivated fetal bovine serum (Invitrogen) and 2-mercaptoethanol to a final concentration of 0.05 mM. Cells in one dish were transfected with 50 nM of KEAP1 siRNA (Life Technologies, Silencer Select, siRNA ID #s18982) using Lipofectamine RNAiMax (Invitrogen), whereas the cells in the other dish were transfected with 50 nM of control siRNA, Block-iT (Invitrogen). Transfected cells were left for 72 h and the KEAP1 knockdown efficiency was calculated with quantitative PCR using a probe against KEAP1.

Next, the cells from each of the dishes were divided equally into 4 wells in different 6-well plates. One of the wells from each of the plates was pre-treated with 1 μM of Compound 1 for 1 h, followed by 20 ng/mL TNFα for 24 h. The other wells were treated with either 1 μM Compound 1 or 20 ng/mL TNFα or neither for 24 h. Following the treatment, RNA was extracted from the cells using an RNA extraction kit (Qiagen). RNA samples from each treatment group were reverse transcribed and real-time PCR was performed on the corresponding cDNA sequences using probes against Nrf2 and two of its downstream genes, NQO1 and EPHX1. THP-1 cells were transfected with KEAP1 siRNA. 40% knockdown efficiency was achieved. The KEAP1 knockdown cells were treated with either 1 μM of Compound 1 or 20 ng/mL of TNFα or both together for 24 h.

Figure 12A:
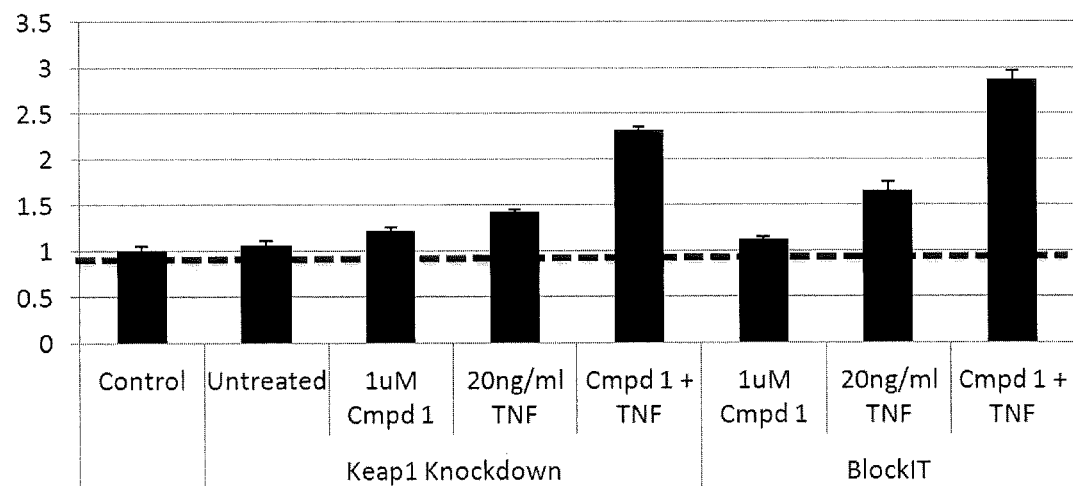
FIG. 12A is a graph of Nrf2 expression under a variety of conditions, including knock-down conditions.

FIG. 12A shows a 2.5-fold increase in Nrf2 expression in cells treated with a combination of TNFα and Compound 1 when compared to the untreated cells. But, a similar (up to a 3-fold) increase in Nrf2 mRNA levels was also found in cells treated with Compound 1 and TNFα without the KEAP1 knockdown. Compound 1 or TNFα alone did not have any significant effect on Nrf2 expression with or without KEAP1 knockdown.

Figure 12B:
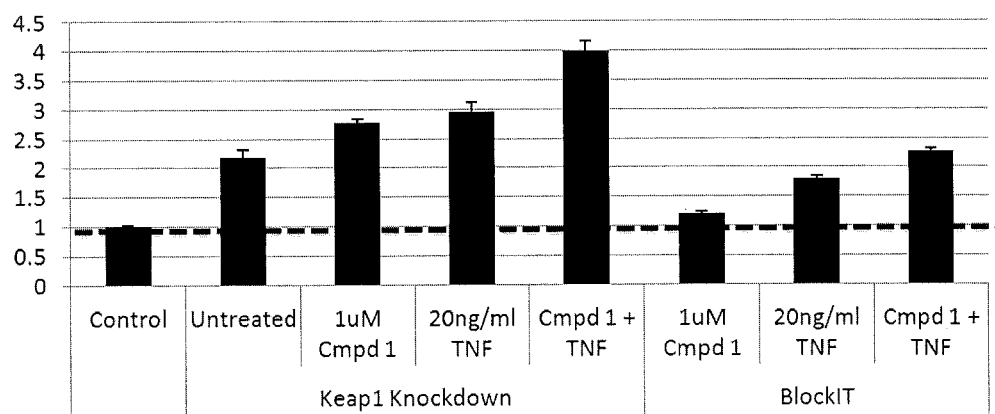
FIG. 12B is a graph of NQO1 expression under a variety of conditions, including knock-down conditions.

FIG. 12B shows the expression of NAD(P)H dehydrogenase [quinone]1 or NQO1 in cells with or without KEAP1 knockdown. FIG. 12B shows that KEAP1 knockdown had an effect on NQO1 expression. Even the sample without any treatment showed a 2-fold increase in its mRNA levels upon KEAP1 knockdown. The combination of Compound 1 and TNFα resulted in a 4-fold increase in NQO1 expression for the KEAP1 knockdown sample compared to a 2-fold increase, seen with the same combination in cells without KEAP1 knockdown.

Figure 12C:
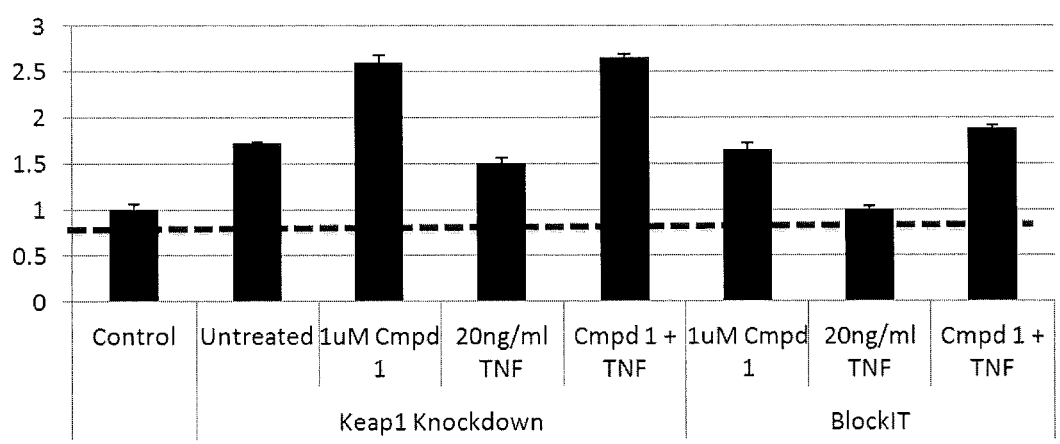
FIG. 12C is a graph of EPHX1 expression under a variety of conditions, including knock-down conditions.

FIG. 12C shows the mRNA levels of epoxide hydrolase 1 or EPHX1 in cells with or without KEAP1 knockdown after treatment with Compound 1 and/or TNFα. FIG. 12C shows that Compound 1 up-regulated the expression of EPHX1 in the presence or absence of TNFα. KEAP1 knockdown added to the effect of Compound 1, as induction up to 2.5-fold was observed in the samples with Compound 1 and KEAP1 knockdown.

Treatment with 1 μM Compound 1 for 24 hrs in the presence of 20 ng/mL TNFα up-regulated Nrf2 signaling. KEAP1 knockdown enhanced this effect, as seen by larger fold induction of NQO1 (4-versus 2-fold) and EPHX1 (2.5-versus 1.5-fold) relative to their levels of expression without KEAP1 knockdown. The results show that CRM1 inhibition can activate Nrf2 pathway during inflammation, and suggests that treatment of Compound 1 in combination with KEAP1 inhibitors could be more effective than treatment with Compound 1 alone.

Effects of Compounds 1, 2, and 12 on NF-κB Transcriptional Activity

TNFα can induce the transcription activity of NF-1B. This transcription activity is initiated when IκB, which binds to NFκB and inhibits its activity, is degraded. Then, a member of the class II family of NF-κB protein, RelA or p65, that forms a heterodimer with a member of the class I family, p50, moves into the nucleus. The p65 subunit has a transactivation domain in its C terminus, which activates transcription of inflammation related genes. Like NF-κB, IκB can also move into the cell nucleus. Nuclear accumulation of IκB protects the protein from degradation, as degradation occurs mainly in the cytoplasm. CRM1 is responsible for the nuclear export of IκB. Therefore, blocking nuclear export of IκB through inhibition of CRM1 minimizes NF-κB activity, as nuclear IκB binds NF-κB and prevents NF-κB from binding to DNA sequences.

The compounds were tested on HeLa (adenocarcinoma) cells to quantify their ability to inhibit NF-κB transcriptional activity. NF-κB activity was induced in HeLa cells by TNFα, and then the compounds were added to inhibit the induced NF-κB activity. Half maximal inhibitory concentrations ($IC_{50}$) of several compounds, namely Compound 1, Compound 2 and Compound 12, were determined by dose response studies.

HeLa cells were plated in a 12-well plate (200,000 cells/well) and cultured in Eagle's Minimal Essential medium (EMEM) from Lonza supplemented with 10% heat-inactivated fetal bovine serum (Invitrogen) and 50 μg/mL penicillin/streptomycin (Invitrogen), and were left overnight to attach. Cells were pre-treated with serial diluted (started at 30 μM; 1:3 dilution) compounds for 1 h and then exposed to 20 ng/mL TNFα (Peprotech) for 4 h in serum free media. After the treatment, the cells were washed with PBS (Invitrogen), and lysed with RIPA buffer (Thermo Scientific) . The transcription activity of NF-κB in the cells was measured by Chemiluminescent Transcription Factor Assay kit (Thermo Scientific Catalog #89859), according to the manufacturer's instruction. Briefly, 1.5 mg/mL of RIPA lysed whole cell extract from each treatment were incubated in a 96-well plate bound with NF-κB biotinylated-consensus sequence. The active NF-κB transcription factor bound to the consensus sequence was incubated with NF-κB p65 primary antibody and then with a secondary HRP-conjugated antibody. A chemiluminescent substrate was added to the wells and the resulting signal was detected using a luminometer. Three separate experiments were analyzed for each concentration of the $IC_{50}$ curves. XLFit model 205 was used to calculate $IC_{50}$ curves.

Inhibition of NF-κB transcriptional activity was measured by serial dilutions of Compound 1, Compound 2 and Compound 12 after 1 h of compound pre-treatment followed by 4 h of 20 ng/mL TNFα exposure. Three independent experiments were scored for each concentration, with the average being presented here. Compound 1 had an $1C_{50}$ value of 1.59 μM, Compound 2 an $IC_{50}$ value of 1.22 μM, and Compound 12 an $1C_{50}$ value of 1.46 μM.

Evaluation of the Effects of Compound 1 on the Expression of the Pro-Inflammatory Protein, COX-2, in HeLa Cells Grown In Vitro HeLa cells were plated in a 6-well culture dish ($2.5 \times 10^5$ cells/well) with EMEM medium (Lonza) supplemented with 10% heat-inactivated fetal bovine serum (Invitrogen). Two of the wells of the plate were pre-treated with 10 μM Compound 1 for 30 minutes, at which time one one of the wells was exposed to 20 ng/ml TNFα (Preprotech) for 1 hour. The other wells were treated with either 20 ng/ml TNFα or nothing for 1 hour. Following the treatment, RNA was extracted from the cells using RNA extraction kit (Qiagen). RNA samples from each treatment group were reverse transcribed and quantitative real time (qRT) PCR was performed on the corresponding cDNA sequences using probes against COX-2 (Life Technologies).

HeLa cells were plated in a 6-well culture dish ($5 \times 10^5$ cells/well) with EMEM medium (Lonza) supplemented with 10% heat-inactivated fetal bovine serum (Invitrogen). Two of the wells of the plate were pre-treated with 1 μM of Compound 1 for 30 minutes, at which time one of the wells was exposed to 20 ng/ml TNFα (Preprotech) for 24 hours. The other wells were treated with either 20 ng/ml TNFα or nothing for 24 hours. Following the treatment, whole-cell lysates were generated from the cells by lysis with RIPA buffer supplemented with protease and phosphatase inhibitors (Roche). Immunoblot detection of COX-2 protein was performed using an anti-COX-2 antibody (Cayman). Signal intensity for the COX-2 protein was normalized to that of beta-actin (Santa Cruz) for each sample and plotted graphically as arbitrary intensity units.

Figure 13A:
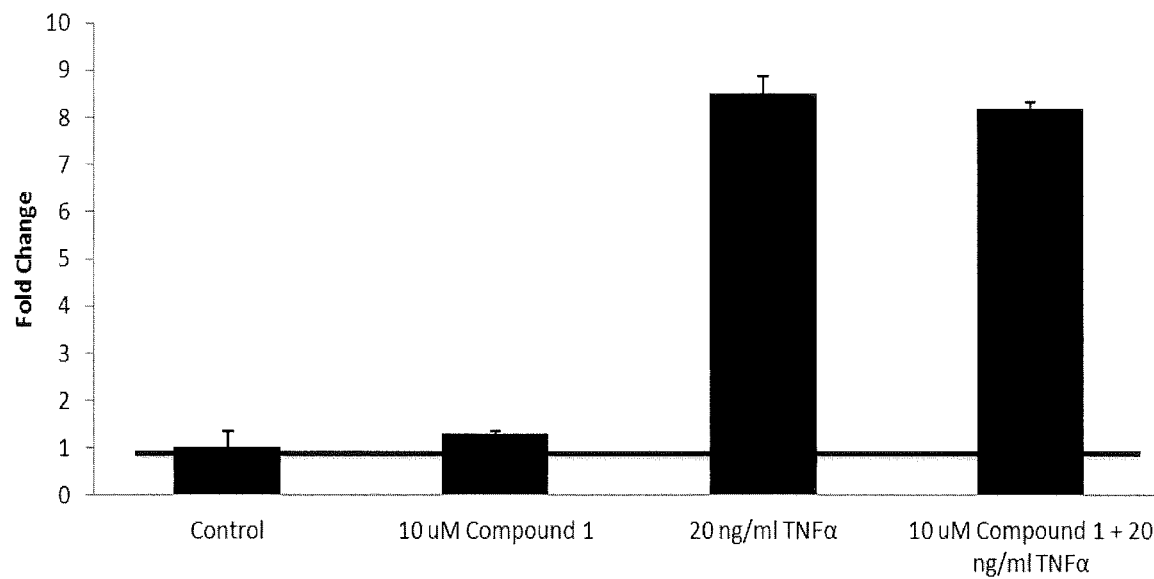
FIG. 13A is a bar graph of fold change of COX-2 mRNA expression, and shows that Compound 1 does not affect COX-2 transcription. COX-2 mRNA expression analysis by qRT-PCR of untreated HeLa cells (control) was compared to HeLa cells treated with 10 μM Compound 1, 20 ng/ml TNFα, or 10 μM Compound 1+20 ng/ml TNFα.

Data from the mRNA analysis by qRT-PCR is shown in FIG. 13A. After 1 hour of treatment, TNFα induced an approximately 8-fold increase in the expression of COX-2 mRNA compared to the control, whereas Compound 1 alone had no effect on the level of COX-2 expression. Compound 1 was not the cause of the increase in COX-2 mRNA expression.

Figure 13B:
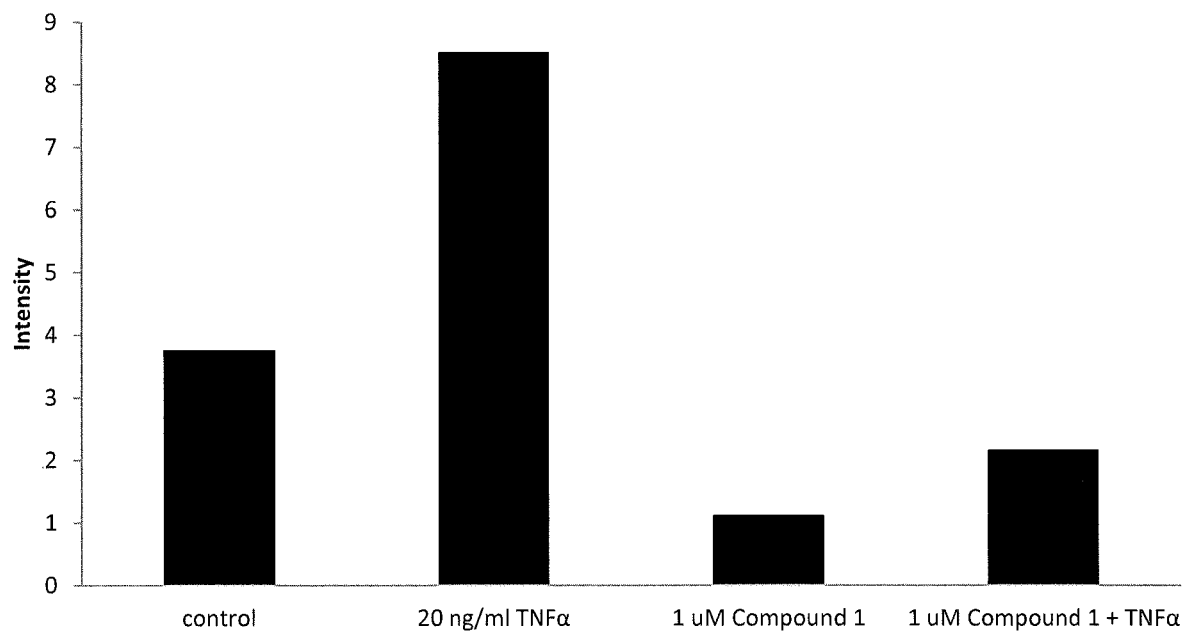
FIG. 13B is a graph of intensity of COX-2 protein expression, and shows that Compound 1 inhibits TNFα-induced COX-2 protein expression.

Data from the protein analysis by immunoblot is shown in FIG. 13B. HeLa cells were left untreated, treated with either 20 ng/ml TNFα or 1 μM Compound 1, or with 20 ng/ml TNFα and 1 μM Compound 1 for 24 hours, then evaluated for the amount of COX-2 protein present by immunoblot detection. COX-2 protein increased by 24 hours in TNFα-stimulated cells compared to untreated control and to Compound 1 treated cells, while Compound 1 decreased the amount of COX-2 protein in the presence of TNFα. The intensity of the immunoblot signals for COX-2 protein were normalized to that of j-actin for each sample and represented graphically.

Compound 1 does not affect the TNFα induced expression of COX-2, but does reduce the amount of TNFα induced expression of COX-2 protein.

Compound 1 Localizes Inflammation-Related CRM1 Cargos to the Nucleus

HeLa and THP-1 (human acute monocytic leukemia) cells were treated with inflammation inducing factor, TNFα, alone or in combination with 1-10 μM of Compound 1 for 4-24 h, and then were analyzed by immunofluorescence (IF) for the nuclear localization of inflammation-related CRM1 cargo proteins: IκB, Nrf2, HMGB1, FoxP3, FOXO1a, RxRα, PPARγ and NFκB (p65 subunit).

For the detection of IκB, Nrf2, RxRα and PPARγ localization, cells were pre-incubated with 10 μM Compound 1 for 30 minutes, followed by incubation with 20 ng/mL TNFα for 4 hrs in serum free media. For detection of HMGB1, FoxP3 and Foxo1A, cells were pre-incubated with 1 μM of Compound 1 for 2 h, followed by incubation with 20 ng/mL TNFα for 24 hours. For detection of NFκB, cells were pre-incubated with 1 μM Compound 1 for 2 h, followed by incubation with 20 ng/mL TNFα for 24 hours. Cells were either fixed with 100% ice-cold methanol (MeOH) and permeabilized/blocked with 0.1% Tween 20, 0.3 M glycine, and 1% BSA in PBS, or fixed with PFA (3% paraformaldehyde and 2% sucrose in PBS) and permeabilized/blocked with 0.1% Triton-X100 and 1% BSA in PBS. IκB was detected by the primary rabbit monoclonal (E130) antibody from Abcam (ab32518); Nrf2 was detected by the primary rabbit polyclonal antibody from Santa Cruz (sc722); RxR alpha was detected by the primary rabbit polyclonal antibody from Santa Cruz (sc553); PPAR gamma was detected by the primary rabbit monoclonal [E130] antibody from Cell Signaling (#2443); Foxo1A was detected by the primary rabbit monoclonal [C29H4] antibody from Cell Signaling (#2880); HMGB1 was detected by the primary rabbit polyoclonal antibody from Abcam (ab18256); FoxP3 was detected by the primary rabbit polyclonal antibody from Abcam (ab10563); NFκB-p65 was detected by the primary rabbit monoclonal [C22B4] antibody from Cell Signaling (#4764). The rabbit secondary antibody, Alexa Fluor 488 (Invitrogen, A11008) was used for all the staining. Images were taken at 20× magnification.

Locking inflammation-related CRM1 cargos in the nucleus has adverse effects on inflammation and, therefore, IF assays can serve as biomarkers for anti-inflammatory effects of CRMI inhibitors.

IκB is the inhibitor of NFκB that induces the expression of pro-inflammatory pathways. Because most IκB degradation occurs in the cytoplasm, its nuclear localization protects IκB from degradation and enables it to bind to nuclear NFκB, blocking the pro-inflammation activity of NFκB. Nrf2 is a leucine zipper transcription factor that induces in the nucleus the expression of anti-inflammatory activity. HMGB1 is the high-mobility-group box 1 factor, and is usually bound tightly to chromatin. Upon active secretion or passive release from damaged cells, HMGB1 functions as a cytokine and induces the pro-inflammatory response. Locking HMGB1 in the nucleus prevents its pro-inflammatory effects. FoxP3, forkhead box P3, functions as a master transcription factor in the development and function of regulatory T cells that possess immunosuppressive activity. FOXO1a is a transcription factor capable of inducing anti-inflammatory genes, such as angiopoietin-2. Therefore, nuclear localization protects FOXO1a from phosphorylation, nuclear exclusion and subsequent degradation. RxRα is a retinoid nuclear receptor that regulates the expression of chemokines such as Ccl6 and Ccl9 in macrophages. RxRα is essential for the recruitment of leukocytes to sites of inflammation. Nuclear entrapment of RxRα results in the recruitment and the depletion of transcription co-activators that otherwise serve to bind pro-inflammatory transcription factors such as NFκB. PPARγ is a ligand-activated transcription factor belonging to the nuclear receptor superfamily, and regulates the expression of anti-inflammation genes.

Figure 14A:
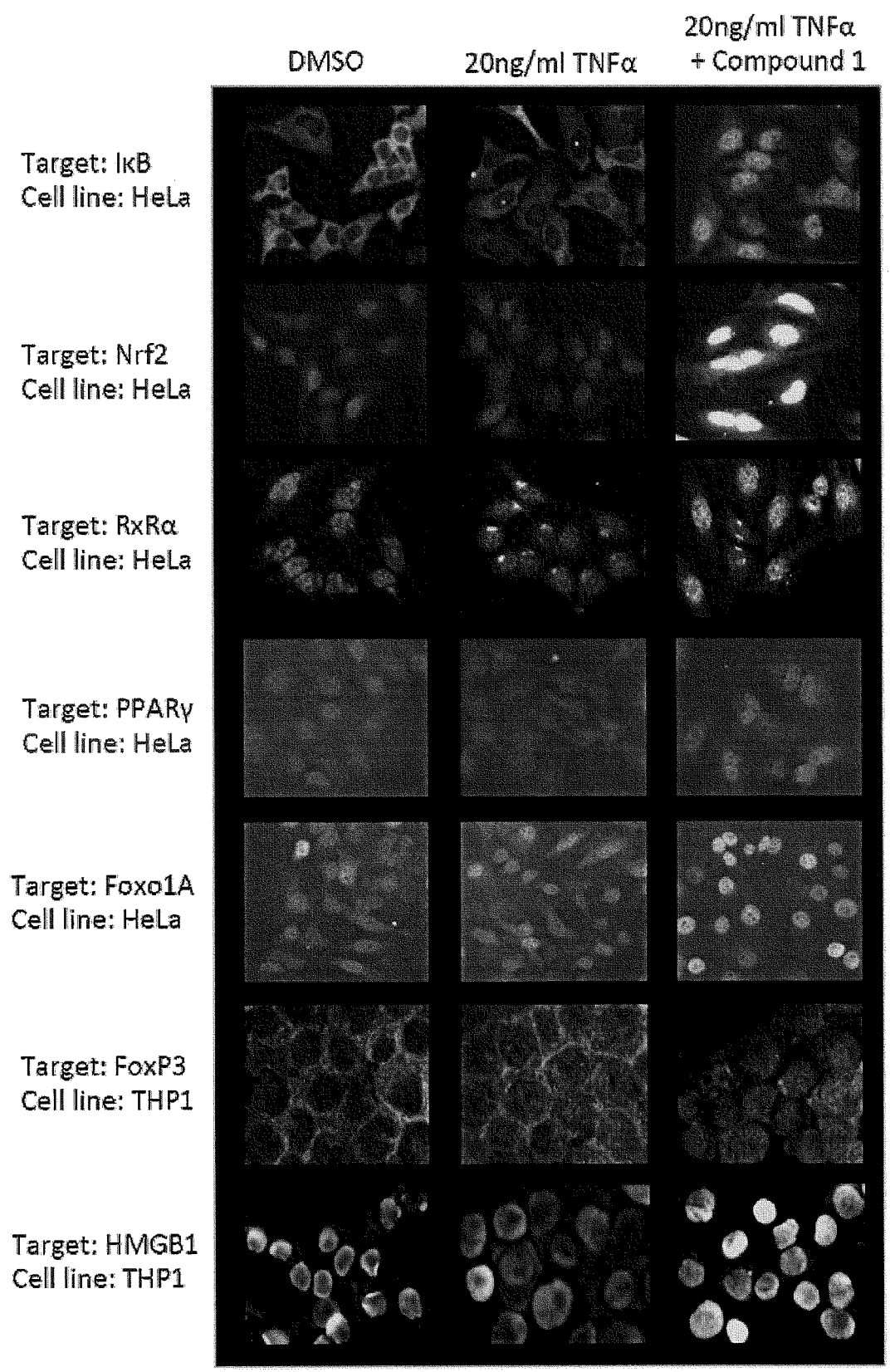
FIG. 14A is an image of cells treated with DMSO, 20 ng/mL TNFα, or Compound 1+20 ng/mL TNFα, and shows the localization of a variety of inflammation-related CRM1 cargo proteins.
Figure 14B:
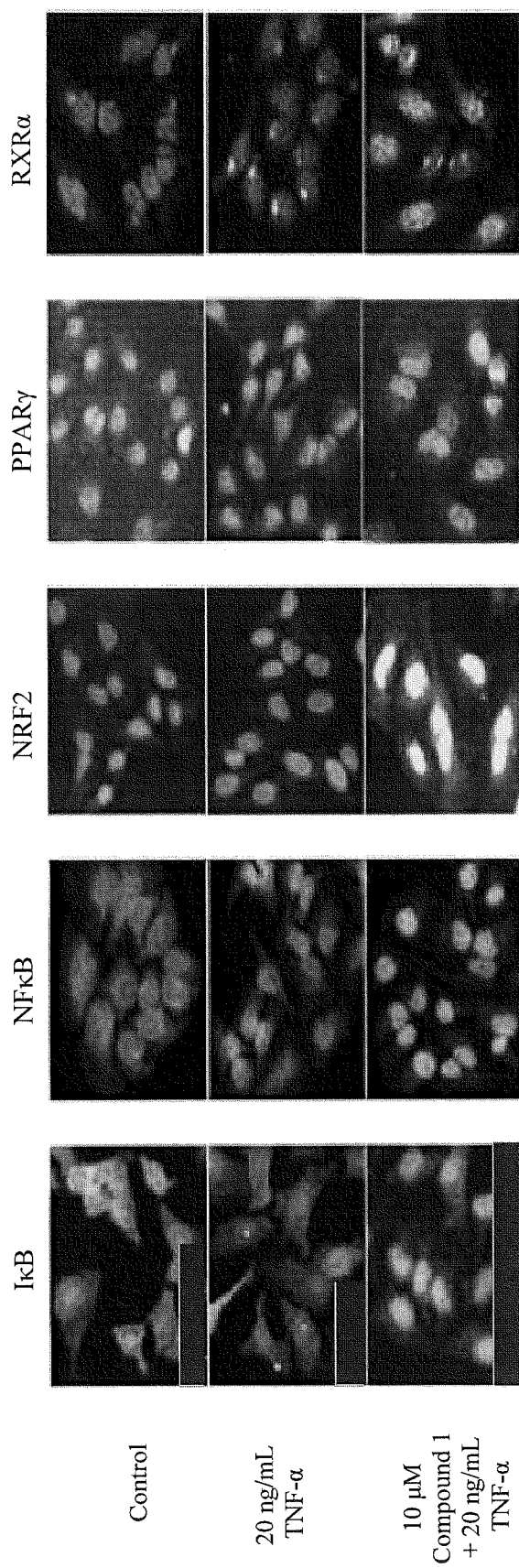
FIG. 14B is an image of cells treated with DMSO, 20 ng/mL TNFα, or Compound 1+20 ng/mL TNFα, and shows the localization of IκB, NFκB, NRF2, PPARγ and RXRα.

The results, shown in FIGS. 14A and 14B, demonstrate nuclear localization of the above cargos, even in the presence of TNFα, which is known to induce inflammation. The results indicate the ability of Compound 1 to induce anti-inflammation pathways to overcome inflammation.

Evaluation of the Effect of Compound 1 on Cognitive Deficits after BCCI Injury in Rats Bilateral controlled cortical impact (BCCI) injury to the medial frontal cortex (MFC) of male Sprague Dawley rats was induced by a cortical contusion device. After CCI any cortical surface hemorrhaging was controlled, and the fascia and scalp were sutured. Sham-operated rats were anesthetized, mounted in the stereotaxic apparatus, and a craniotomy was performed.

Progesterone 16 mg/mL was dissolved in 22.5% 2-hydroxypropyl-β-cyclodextrin and the initial injection (16 mg/kg) was given i.p. 1 h after injury. The remaining injections (all 16 mg/kg) were given subcutaneously at 6 h post-injury and continued for 5 days after injury. Progesterone injections were made at a concentration of 1 mL/kg. Progesterone was used as a control.

Compound 1 0.2, 0.4, and 0.6 mg/mL was suspended in vehicle (0.6% w/v Pluronic® F-68 and 0.6% w/v PVP K-29/32 in water) and administered p.o at a concentration of 10 mL/kg, 16 h before injury and 2 h after injury, and administrations were continued for 4 days. Control rats received equivalent injections of the vehicle for Compound 1, at the same time points. Treatment groups are summarized in Table 11.

TABLE 11

Treatment Groups

| Group | Number of animals | Test Article | Dose | Route of Administration | Schedule |
|---|---|---|---|---|---|
| 1 | 8 | Vehicle + Sham | N/A | PO | 16 h before injury, 2 h after injury and continued for 4 days. |
| 2 | 8 | Vehicle + BCCI | N/A | PO | 16 h before injury, 2 h after injury and continued for 4 days. |
| 3 | 8 | Progesterone | 16 mg/kg | IP + SC | 1 h after injury, [IP] 6 h post-injury and continued for 5 days after injury [SC] |
| 4 | 8 | Compound 1 | 2 mg/kg | PO | 16 h before injury, 2 h after injury and continued for 4 days. |
| 5 | 8 | Compound 1 | 4 mg/kg | PO | 16 h before injury, 2 h after injury and continued for 4 days. |
| 6 | 8 | Compound 1 | 6 mg/kg | PO | 16 h before injury, 2 h after injury and continued for 4 days. |

The Morris Water Maze (MWM) test is a spatial navigation task that measures learning and memory in rodents using visual cues. Subjects learn over the course of days to find a hidden platform. A MWM test was conducted two weeks after injury. Male Sprague Dawley rats were allowed to swim in the pool until they reached the platform located in the southwest quadrant of a tank, or until 90 seconds had elapsed. Behavior was tracked by a video camera hanging from above the pool and recorded and analyzed using video track software (ANY-maze).

Figure 15A:
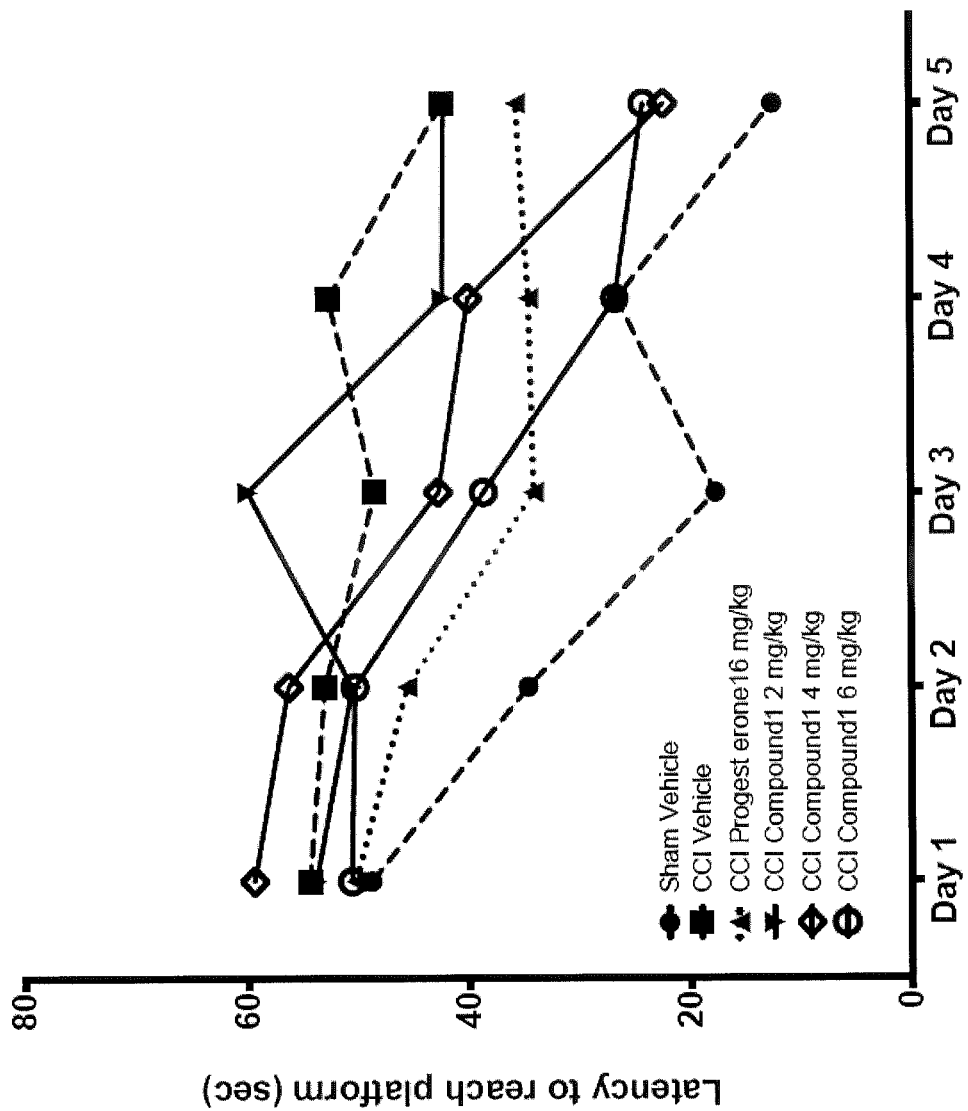
FIG. 15A is a graph of latency to reach platform in the MWM test as a function of time, and shows the effect of sham treatment, control treatment, progesterone treatment and varying doses of Compound 1 on the latency of mice to reach the platform during the acquisition phase of the MWM test (data represent mean±SEM).

The effects of Compound 1 and progesterone on acquisition of the MWM test are shown in FIG. 15A. Two way repeated measures ANOVA found a significant treatment effect. Compared to sham injury rats, BCCI-injured rats showed a significant spatial learning deficit, as indicated by a significant increase in the latency to find the hidden platform during the 5-day acquisition phase (FIG. 15A). Compared to vehicle-treated BCCI-injured rats, Compound 1 (2, 4 and 6 mg/kg) showed a dose dependent decrease in the latency to find the hidden platform, with significant effects on days 17 and 18 after injury with 6 mg/kg and on day 18 with 4 mg/kg. The data suggest that Compound 1 has a neuroprotective effect.

Figure 15B:
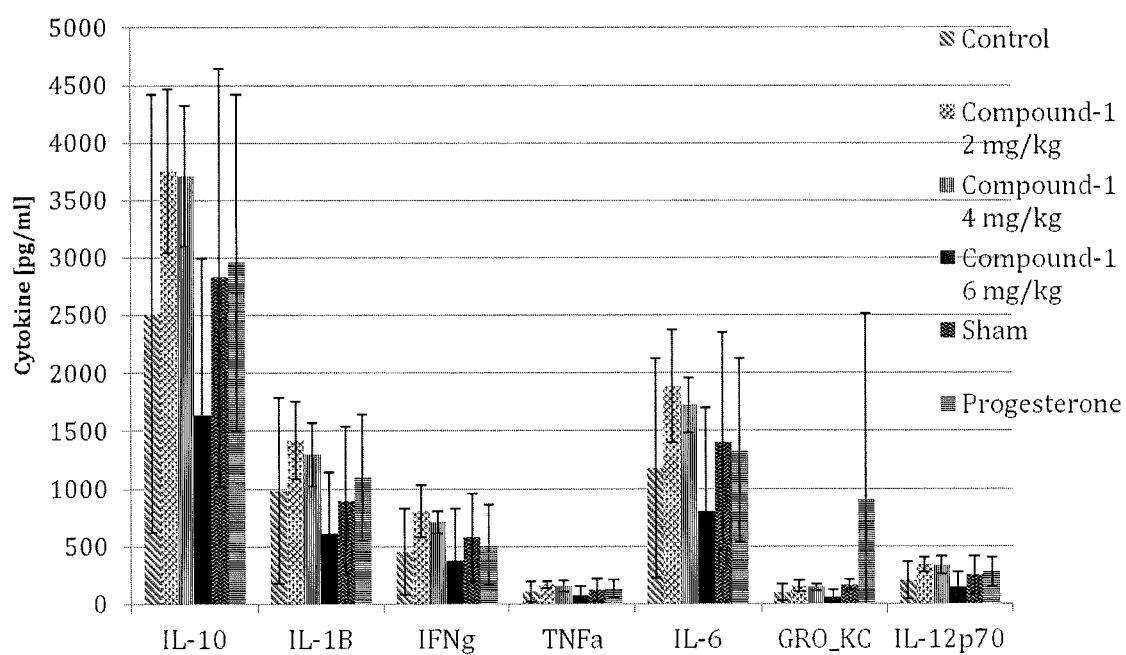
FIG. 15B is a graph of cytokine concentration, and shows the concentration of several cytokines in rat plasma.
Figure 15C:
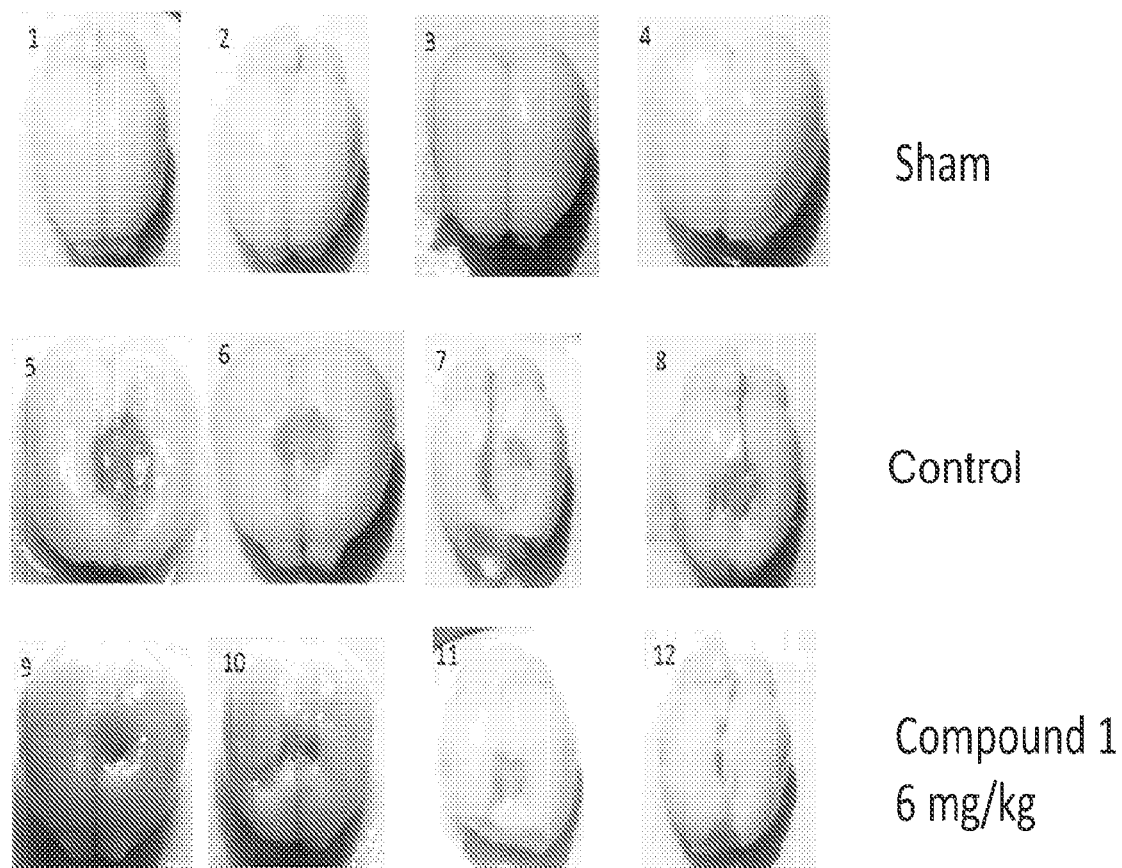
FIG. 15C is photographs of whole brains of animals receiving sham lesions (Sham), CCI+vehicle (Control), or CCI+Compound 1 (6 mg/kg), and shows the results of a qualitative visual inspection of whole brains prior to vibratome sectioning. The inspection indicated that none (0 of 4) of the Sham animals exhibited damage to dorsal-medial cortical tissue. In stark contrast, all four of the CCI controls exhibited severe bilateral injury restricted to this region of the cortex. CCI animals which received Compound 1 showed damage ranging from moderate to minimal. Notably, the brain demonstrating the most severe injury in the Compound 1 group was less dramatic than all brains in the CCI control group.

FIG. 15C is photographs of whole brains of animals receiving sham lesions (Sham), CCI+vehicle (Control), or CCI+Compound 1 (6 mg/kg), and shows the results of a qualitative visual inspection of whole brains prior to vibratome sectioning. The inspection indicated that none (0 of 4) of the Sham animals exhibited damage to dorsal-medial cortical tissue. In stark contrast, all four of the CCI controls exhibited severe bilateral injury restricted to this region of the cortex. CCI animals which received Compound 1 showed damage ranging from moderate to minimal. Notably, the brain demonstrating the most severe injury in the Compound 1 group was less dramatic than all brains in the CCI control group.

The expression level of several cytokines in plasma harvested from rats in each treatment group was measured. The samples were received frozen and stored at −80° C. On the day of the experiment, the samples were thawed, diluted four-fold, and analyzed for cytokine expression on a Luminex platform. The samples were analyzed for the cytokines GRO/KC, IFNy, IL-1B, IL-6, IL-10, IL-12p70 and TNFa, using a multipliex kit manufactured by Millipore. As shown in FIG. 15B, the same patterns were observed in expression levels between samples. The biggest change was in IL-10. Compound 1 at 6 mg/kg reduced IL-10 compared to vehicle-treated control group.

In many cases, traumatic injury elicits a secondary injury response. In most cases, the result will be inflammation. The inflammatory response is driven by cytokines and chemokines and is partially propagated by damaged tissue derived products (Damage associated Molecular Patterns).

Multiple Organ Dysfunction Syndrome (MODS), a poorly understood syndrome of sequential and gradual loss of organ function, is the most frequent cause of late deaths post-injury, accounting for substantial morbidity and mortality. MODS is considered to be due, in part, to excessive or maladaptive activation of inflammatory pathways.

Figure 15D:
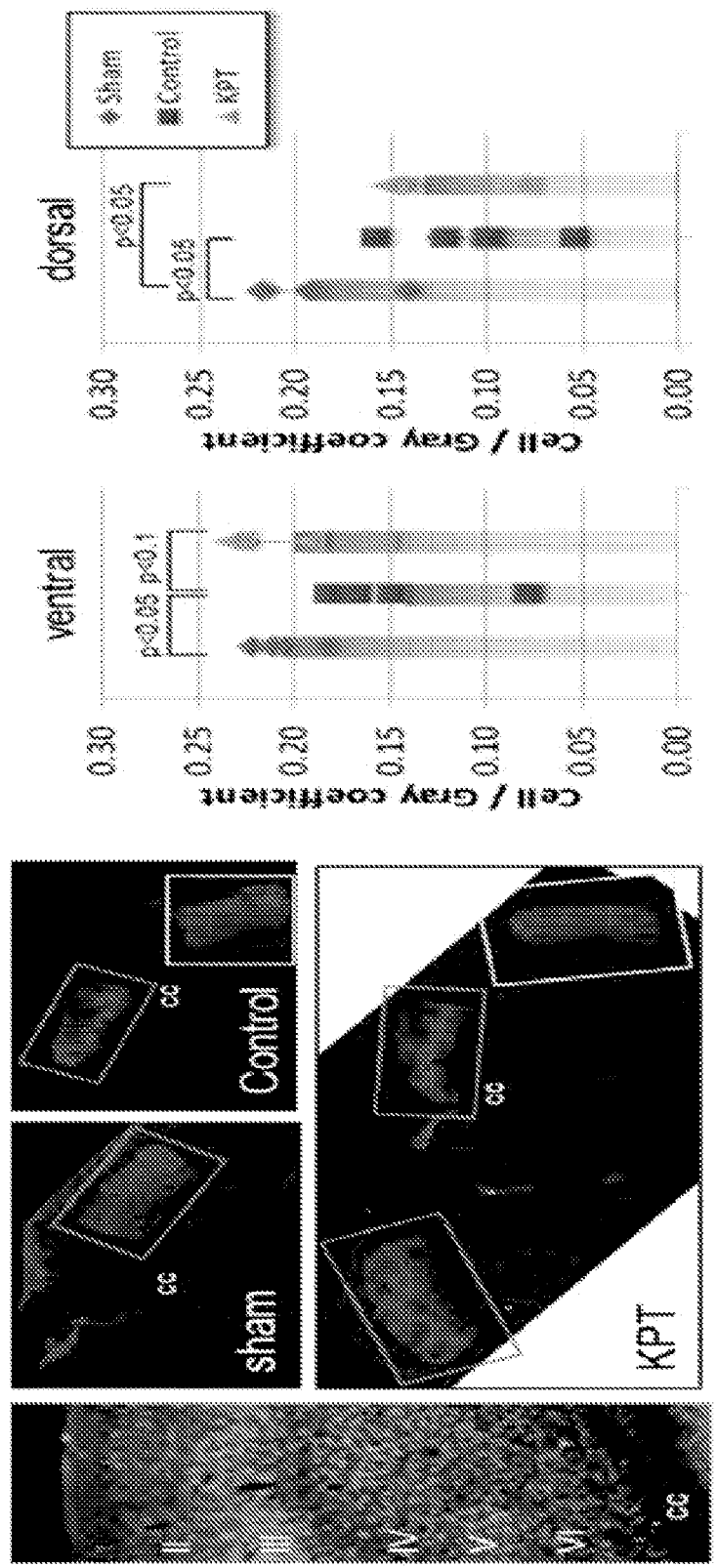
FIG. 15D is a low-power micrograph of NeuN labeling of the dorsal cortical zone and the ventral cortical zone of sham-treated (Sham), CCI+vehicle-treated (Control), and CCI+Compound 1-treated (KPT) animals.

Quantitative measures of cell density were collected from anti-NeuN immunolabeled subsections from approximately 2-3 mm anterior to bregma. Regions of interest (ROIs) were drawn (blind to experimental condition) around Layers IV-VI in the cortical region adjacent to the injury site in CCI-treated animals or in the equivalent zone (dorsal cortex) in sham animals. An ROI of similar area was also evaluated in a ventral cortical region of the same section. Cell identification was performed using the cell counting module of Keyence BZ-II Analyzer software. Cell-to-gray matter (CG) area coefficients were determined for each ROI. Sham animals exhibited uniform dense labeling within both dorsal and ventral regions. As expected, CCI control animals showed reduced CG coefficients in both dorsal (−45% compared to sham) and ventral (−30% compared to sham) cortical zones versus sham animals (FIG. 15D). The CCI-induced reduction in CG coefficient was mitigated by treatment with Compound 1 in the ventral cortex (−3% compared to sham; p=0.09). Although the effect of Compound 1 versus vehicle treatment in the ventral cortex is not statistically significant, it is anticipated that this effect would breach statistical significance in a larger study. No effect of Compound 1 was detected in the dorsal cortical region (−32% compared to sham) immediately adjacent to the injury site. The difference in the observed effect of Compound 1 on the ventral region versus the dorsal region may be a threshold effect related to the degree of injury, which was inversely related to the distance from the injury site. Thus, the damage to the dorsal cortical region could be too severe to be rescued by Compound 1 under these conditions.

Immunofluorescence was performed to evaluate the impact of TBI on several pathways of immune response, and to determine if Compound 1 might be mediating its neuroprotective effects via one or more of those pathways. Semi-quantitative measures of secondary injury responses were examined using immunofluorescent labeling for anti-Rat IgG (an indicator of blood-brain barrier (BBB) permeability), and TNFα (an indicator of neural inflammation). All markers were imaged at 20× magnification in the areas of the cortex surrounding the injury site in adjacent subsections within 300 m to those used for the NeuN labeling assessments. For each label, a target ROI was outlined within Layers IV-VI adjacent to the injury site (or an equivalent region of dorsal cortex for sham animals), and a reference ROI was collected from the same laminae in ventral cortex. Normalized fluorescence intensity was assessed in each of the two ROIs. For all labels, the ventral cortex reference site was determined not to be different between groups (p>0.5); therefore, the percent target to reference value (IF) was determined.

Figure 15E:
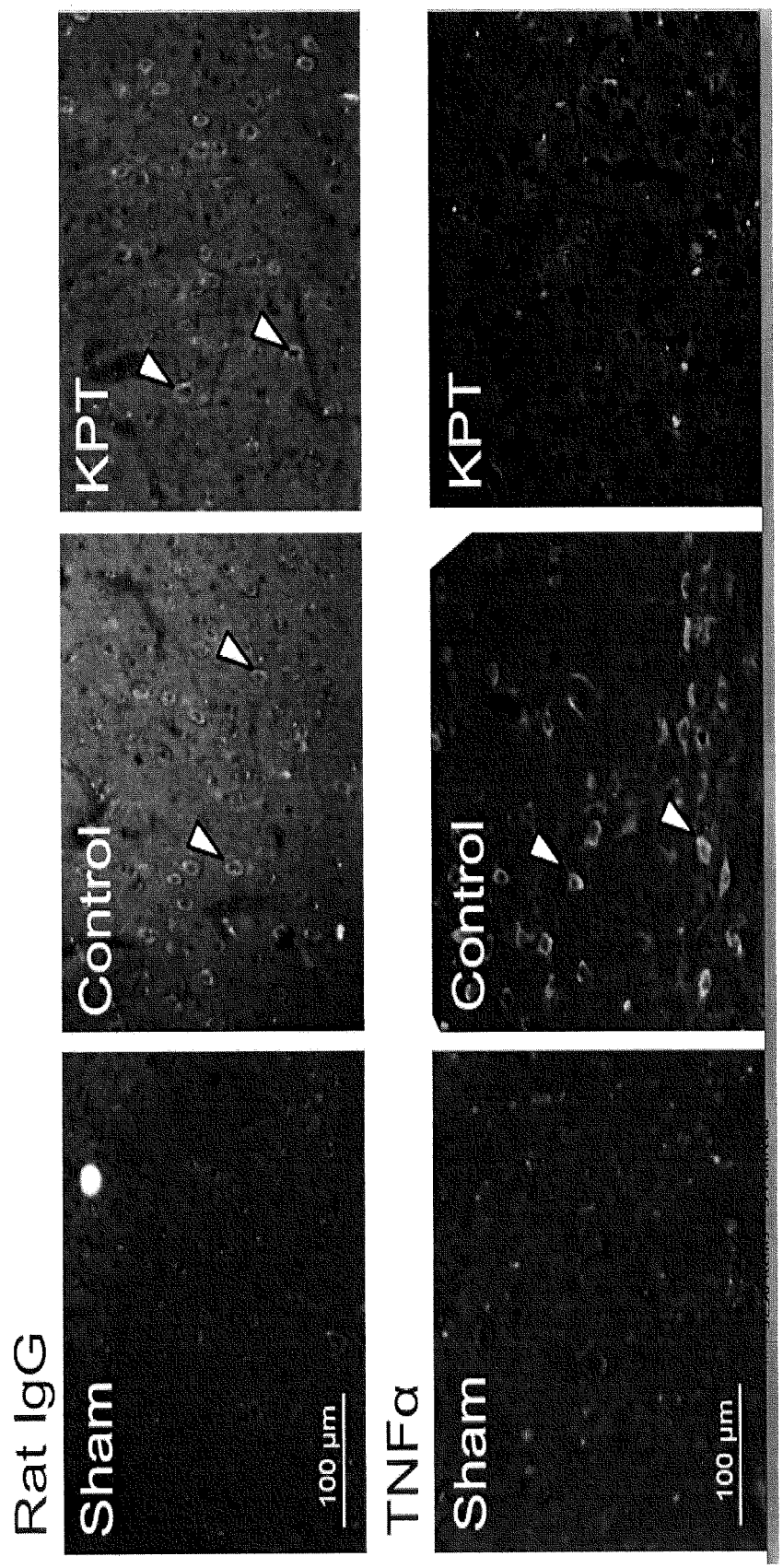
FIG. 15E is photomicrographs of immunofluorescent labeling of Rat IgG and TNFα in sham-treated (Sham), CCI+vehicle-treated (Control), and CCI+Compound 1-treated (KPT) animals.

Anti-Rat IgG was expressed in neurons (indicated by the arrowhead in FIG. 15E) in injured tissue. FIG. 15E shows that the anti-rat IgG was distributed within the neurophil of damaged areas of cortical tissue. Anti-rat IgG was not present in sham tissue. TNFα immunopositive cells (indicated by the arrowhead in FIG. 15E) were clearly visible in damaged tissue surrounding the injury site in control animals. These elements were largely absent in Compound 1-treated and sham animals. FIG. 15E shows that Compound 1 reduces secondary injury responses in rats exposed to brain injury.

Collagen-Induced Arthritis (CIA) Study No. 2

To further investigate the effect of the compounds described herein on inflammation biomarkers, a second CIA model was initiated. In this model, the groups were designated as group A (naïve), group B (model; vehicle-treated), group C (Compound 2 at 5 mg/kg QoD). The rats in groups B and C were immunized intradermally with bovine Type II collagen in IFA on day 0, and a booster injection was given on day 7. Compound 2 was orally administered to rats with CIA after the onset of arthritis (Day 11). CIA development was evaluated via macroscopic scoring and measurements of paw swelling. This was assessed every day for the first 5 days after sensitization (day 7), and then twice per week (Monday and Thursday) until Day 28 using the clinical scoring system described in Table 7 above. In addition, ELISAs for CD45, CRP, CCL2/MCP-1, TNF-α, IL1-β, IL-6, IL-17, and measurements for cathepsin K and elastase were performed 4 days (Day 15 of the study) and 10 days (Day 21 of the study—peak for the disease) after compound treatment and at the very end of the study (Day 28) on all group animals. Additionally, on the last day of the study (Day 28), a few representative animals from each group were subjected to three-dimensional micro-tomodensitometry of calcaneus, and bone erosion in the paws was quantified.

Figure 16A:
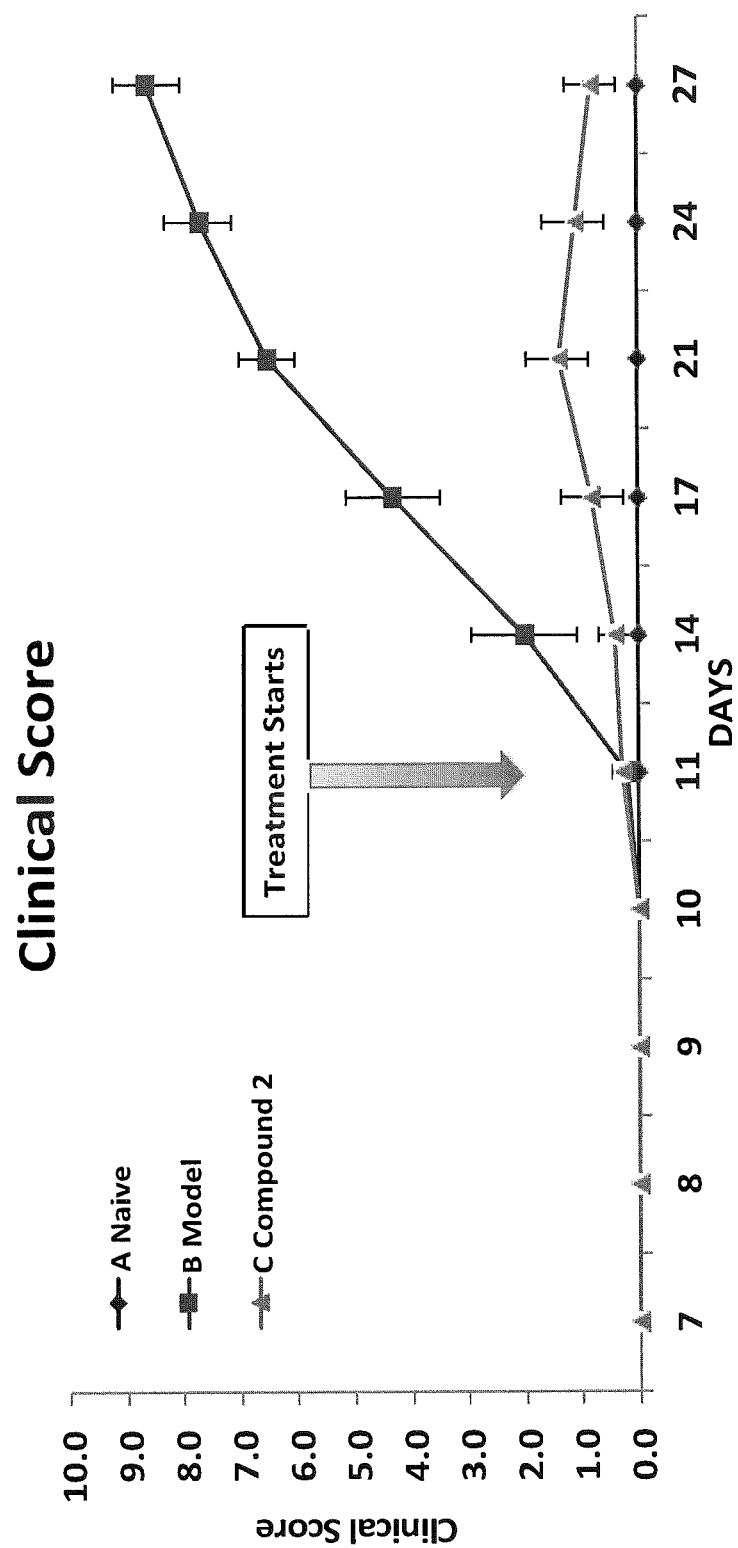
FIG. 16A is a graph of clinical score as a function of time, and shows the clinical arthritis scores of naïve female Lewis rats, control female arthritic Lewis rats, or female arthritic Lewis rats treated with Compound 2.
Figure 16B:
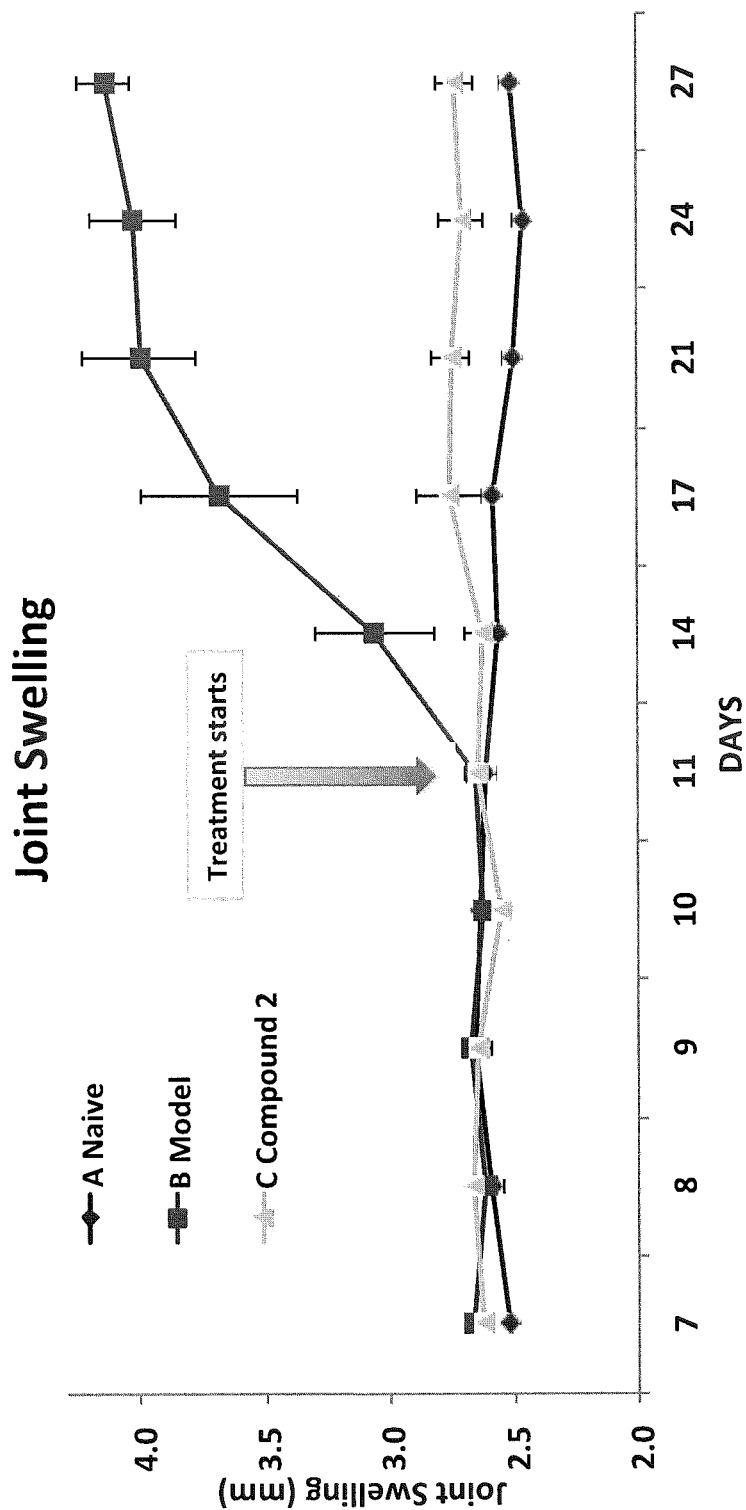
FIG. 16B is a graph of joint swelling as a function of time, and shows the joint swelling measured on a scale of 0-4 in naïve female Lewis rats, control female arthritic Lewis rats, or female arthritic Lewis rats treated with Compound 2.

FIGS. 16A and 16B show that rats treated with Compound 2 at 5 mg/kg had significantly reduced joint swelling (FIG. 16B) and clinical scores (FIG. 16A) compared to vehicle-treated rats.

Figure 17A:
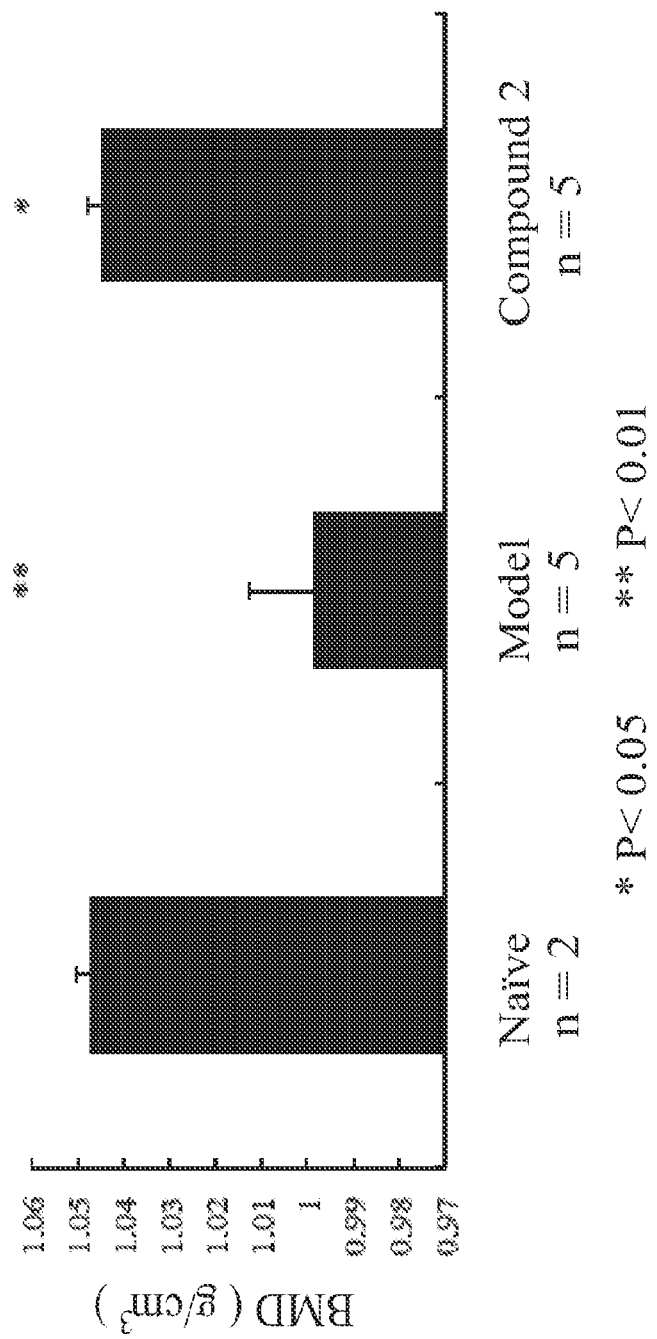
FIG. 17A is a graph of bone mineral density (BMD) of tarsal bones of naïve female Lewis rats, control female arthritic Lewis rats, and female arthritic Lewis rats treated with Compound 2.
Figure 17B:
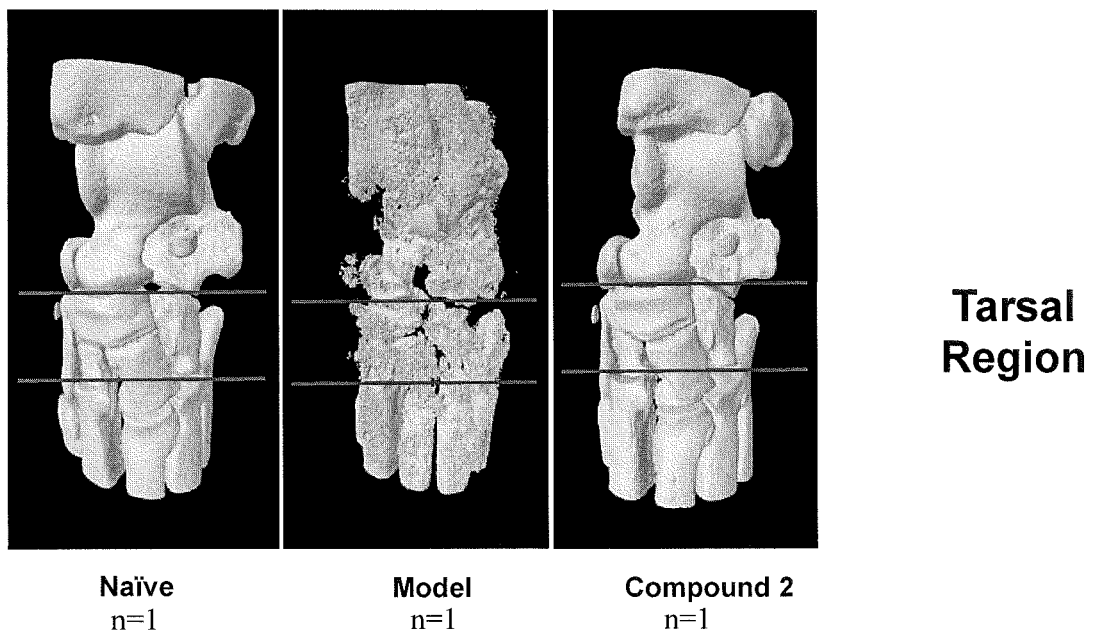
FIG. 17B is a visualization by three-dimensional micro CT imaging of hind paws of naïve female Lewis rats, control female arthritic Lewis rats, and female arthritic Lewis rats treated with Compound 2.
Figure 17D:
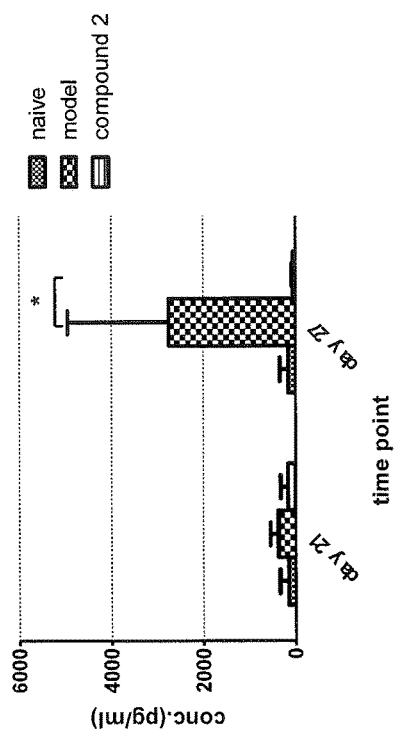
FIG. 17D is a graph of concentration of IL-6 in synovial fluid as a function of time, and shows the concentration of IL-6 in synovial fluid collected from rats in Group A (naïve), Group B (model) and Group C (Compound 2 at 5 mg/kg QoD) at Days 21 and 27 of CIA Study No. 2.
Figure 17F:
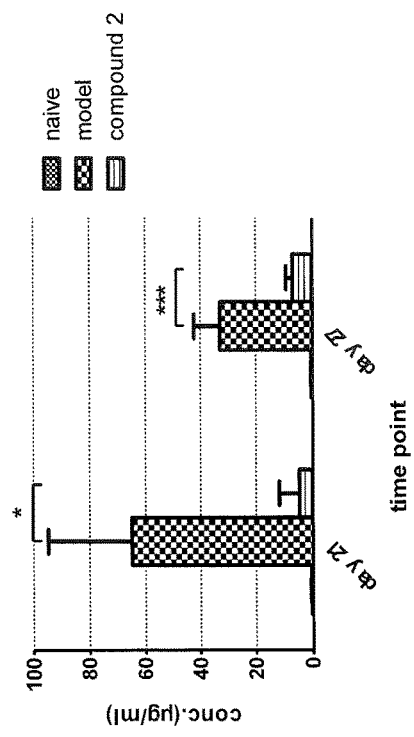
FIG. 17F is a graph of concentration of CRP in synovial fluid as a function of time, and shows the concentration of CRP in synovial fluid collected from rats in Group A (naïve), Group B (model) and Group C (Compound 2 at 5 mg/kg QoD) at Days 21 and 27 of CIA Study No. 2.
Figure 17C:
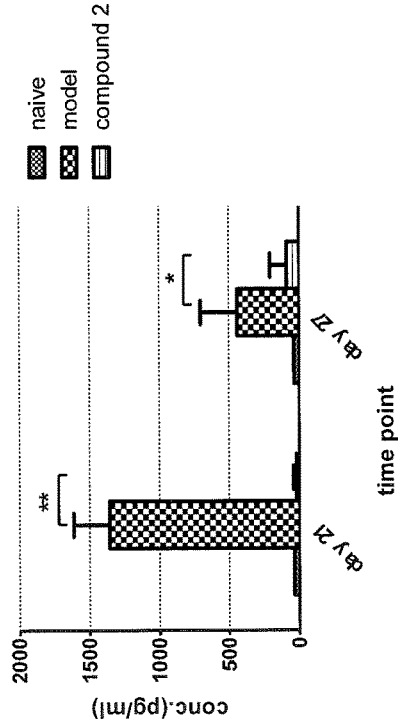
FIG. 17C is a graph of concentration of IL-1β in synovial fluid as a function of time, and shows the concentration of IL-1β in synovial fluid collected from rats in Group A (naïve), Group B (model) and Group C (Compound 2 at 5 mg/kg QoD) at Days 21 and 27 of CIA Study No. 2.
Figure 17E:
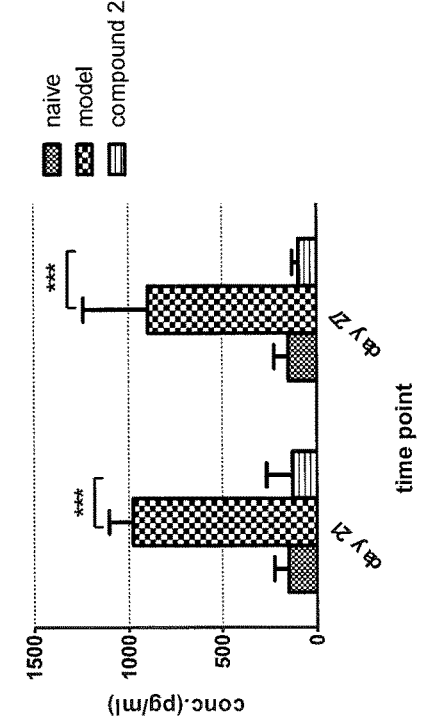
FIG. 17E is a graph of concentration of MCP-1 in synovial fluid as a function of time, and shows the concentration of MCP-1 in synovial fluid collected from rats in Group A (naïve), Group B (model) and Group C (Compound 2 at 5 mg/kg QoD) at Days 21 and 27 of CIA Study No. 2.

FIGS. 17A and 17B show that rats treated with Compound 2 at 5 mg/kg had significantly reduced bone erosion in the rear paws compared to vehicle-treated rats. Joint condition in animals treated with Compound 2 was comparable to that of naïve animals. In contrast, vehicle-treated animals displayed statistically significant increased bone erosion in their rear paws.

A LUMINEX® assay and ELISA were used to measure the effects of Compound 2 on the levels of pro-inflammatory cytokines and inflammation markers. Synovial fluid was collected on Day 21, after the first immunization, from 2 rats in the model group and 2 rats in the Compound 2-treated group, and at the end of the study from 2 rats in the naïve group, 3 rats in the model group and 3 rats in the Compound 2-treated group.

FIGS. 17C-17F show that, compared to the model group, Compound 2 showed inhibitory effects on the production of pro-inflammatory cytokines and an inflammation marker in synovial fluid samples. The reduced cytokines include IL-1β, IL-6 and MCP-1, and the inflammation marker is C-reactive protein (CRP).

A LUMINEX® assay was also used to measure the levels of pro-inflammatory cytokines in serum. Serum samples (1 mL of blood per rat) were collected 4 days after compound treatment (Day 15), 10 days after compound treatment (usually at the disease peak—Day 21) and at the end of the study (Day 27).

Figure 17G:
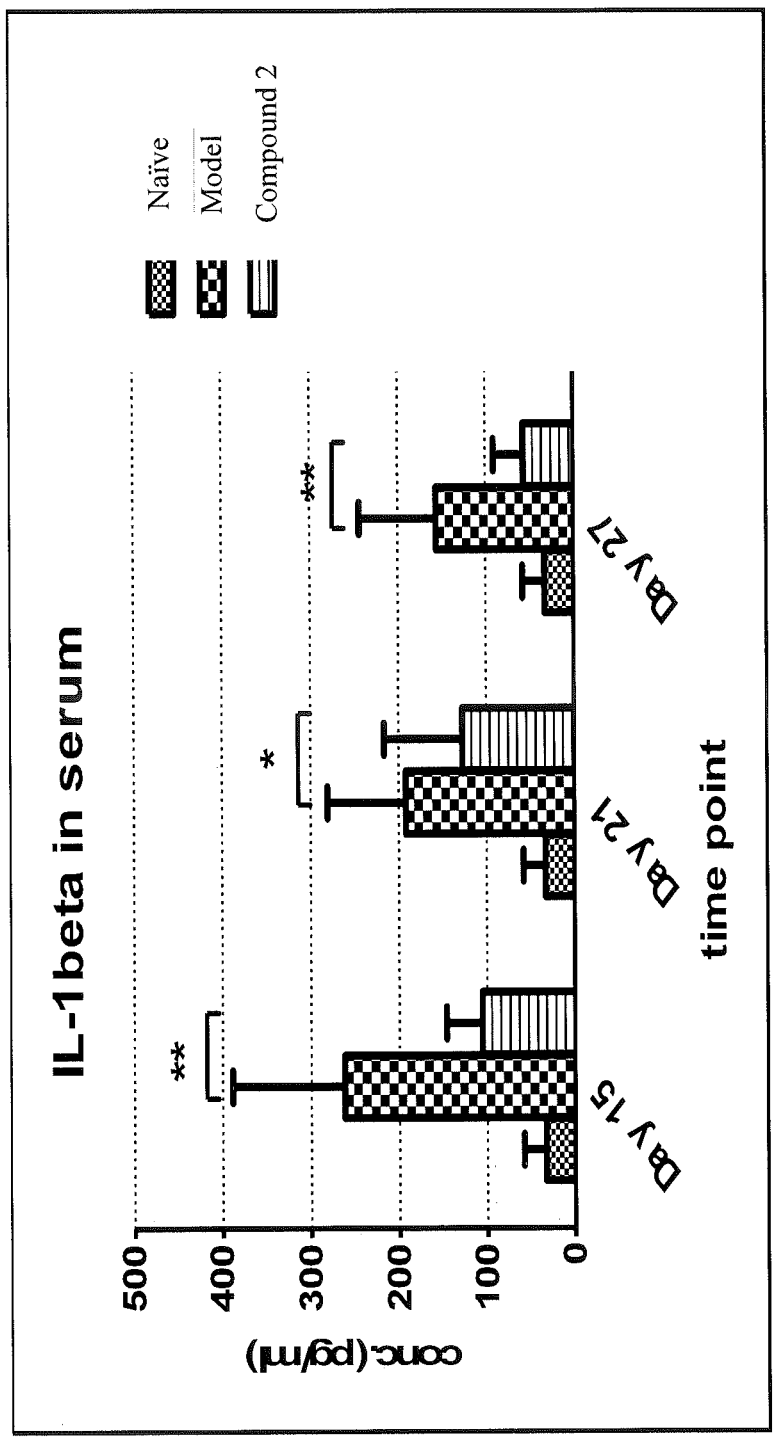
FIG. 17G is a graph of concentration of IL-13 in serum as a function of time, and shows the concentration of IL-1β in rat serum samples collected from rats in Group A (naïve), Group B (model) and Group C (Compound 2 at 5 mg/kg QoD) at Days 15, 21 and 27 of CIA Study No. 2.

FIG. 17G shows that, compared to the model group, Compound 2 showed an inhibitory effect on IL-1β production in serum samples.

Experimental Autoimmune Encephalomyelitis (EAE) Model

Figure 18A:
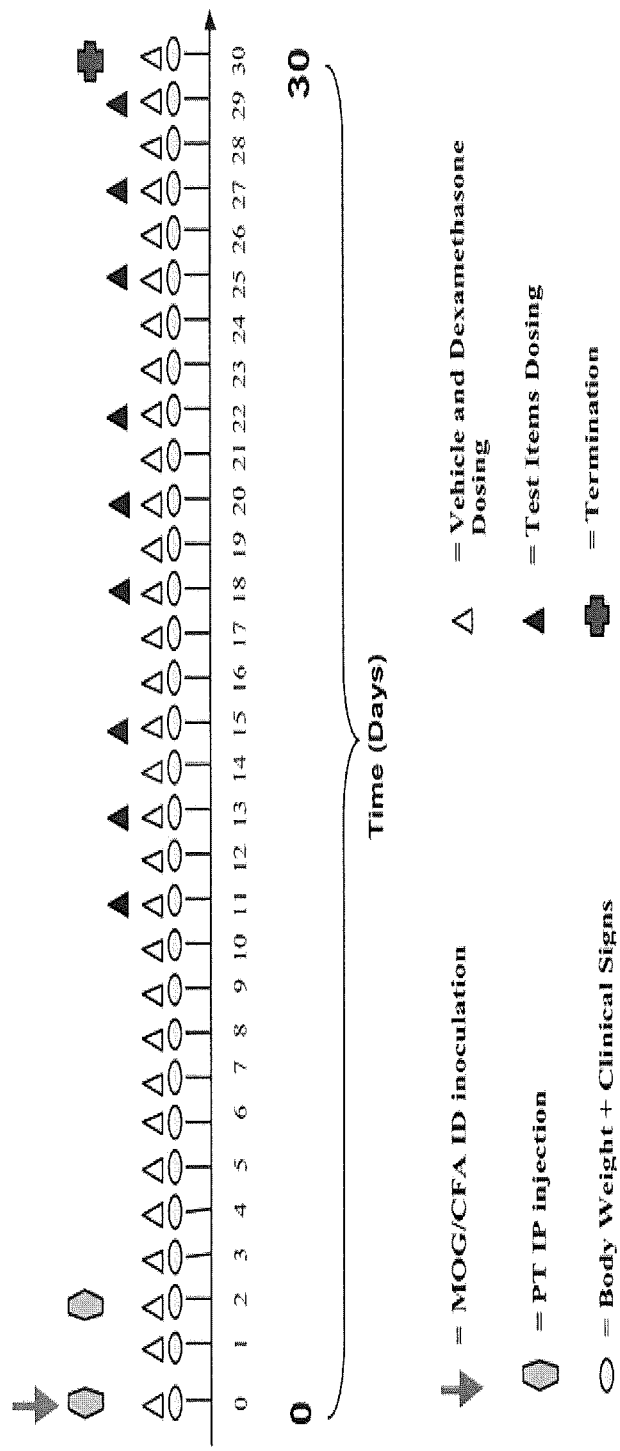
FIG. 18A is a schematic of the MOG-induced EAE murine model in female mice described herein.

The EAE Model is an accepted model for the study of human CNS demyelinating diseases such as multiple sclerosis. The effects of Compound 1 were investigated in MOG-induced in an EAE murine model in female C57Bl/6J mice. The animals were divided into 3 groups designated as Group I (vehicle control), Group II (dexamethasone-positive control) and Group III (Compound 1 at 7.5 mg/kg). Saline, dexamethasone and Compound 1 were administered according to the schedule shown in FIG. 18A. Saline and dexamethasone were administered intraperitonally every day starting from day 0. Compound 1 at 7.5 mg/kg was administered orally starting from day 11 (disease onset) on Monday, Wednesday and Friday for 3 consecutive weeks. The disease was induced by the single intradermal injection of MOG emulsified in Complete Freund's Adjuvant (CFA) on study day 0, followed by intraperitoneal supplemental immunostimulation with pertussis toxin (PT) carried out on study day 0, and again 48 hours later on study day 2.

Figure 18B:
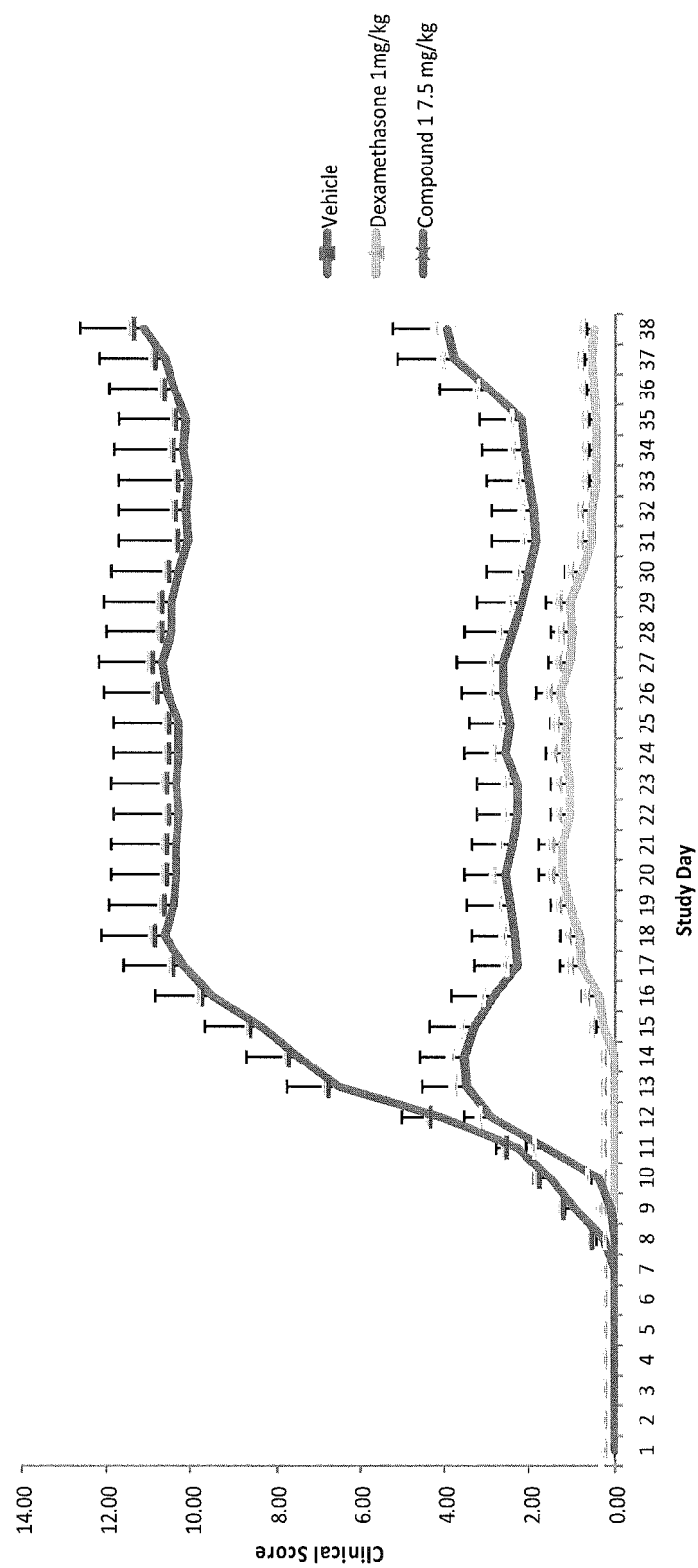
FIG. 18B is a graph of clinical score as a function of study day, and shows the effects of vehicle treatment, dexamethasone treatment and Compound 1 treatment on the clinical score of female mice in the MOG-induced EAE murine model described herein.

As shown in FIG. 18B, the first signs of the disease were noticed 7-9 days following MOG immunization and the disease peak developed on study day 17. Treatment with dexamethasone starting from day 0 at a dose of 1 mg/kg IP significantly reduced the clinical scores on study days 8-37 (Group II) when compared to the vehicle control (Group I). Treatment with Compound 1 starting from Day 11 at a dose of 7.5 mg/kg (Group III) significantly decreased disease score and severity. These results are shown in FIG. 18B.

In view of the findings obtained under the conditions of this study, treatment with Compound 1 at a dose of 7.5 mg/kg p.o. starting on study day 11 resulted in a decrease in disease score and severity.

Example 18. Wound Healing Models

Materials

Mice—C57BL/6J mice, males, aged 6-8 weeks, SPF, obtained from Harlan Laboratories LTD. Mice were kept in sterile individual ventilated cages (IVC) with food and water available ad libitum, 12 h/12 h cycles of darkness and light, controlled temperature of 19-21° C., controlled humidity of 40-60%, positive air pressure inside animal's room, and health report control every 3 months, which was performed on selected sentinels.

Pigs—Sus scrofa domestica, Domestic swine (mainly Landrace X large White), female, approximately 60 Kg, 4-5 months old, Lahav Institute of Animal Research, Kibbutz Lahav, Israel. Pigs kept in clean non-SPF environment, tap water ad libitum directly from public source, food according to recommendation of standard growth tables under supervision of veterinarian.

ISOFLURANE 99.9% for inhalation, lot 6027962, Abbot Laboratories Ltd, England

Water—water for injection, batch 11481012, B. Braun Melsungen AG, Germany

Saline—0.9% sodium chloride for injection, batch 12224012, B. Braun Melsungen AG, Germany DMSO—dimethyl sulfoxide, D2650, Sigma-Aldrich Inc., U.S.

PLURONIC® F-68

PVP K-29/32

Evaluation of the Effects of Systemic Administration and Topical Application of Compound 1 on C57BL Mice Skin Wounds The effects of Compound 1 on skin wound healing were studied in a mouse longitudinal full thickness skin incision wound model. Upon arrival, animals were identified by ear tags, weighed and left to acclimate for several days before initiation of the experiment. On the day of wounding, mice were weighed and divided into 6 experimental groups with 6 animals per group, in accordance to weight differences stratified randomization. Prior to the surgical procedure, mice were anesthetized with isoflurane and the back of the animals was trimmed. Full thickness longitudinal incisions of 20 mm were performed using a standard scalpel blade on the backs of the animals (parallel to the backbone). Three hours after wounding, due to skin elasticity and activity of the animals, the incisions took on elliptical shapes. At this stage, the widest area of the wound was measured to establish a baseline wound width. Wound healing evaluation was made by measuring the widest area of the wound. Treatment groups consisted of oral gavage or topical groups. During the experiment, wounds were photo-documented and morphological analysis was performed. At the end of the experiment, 8 days post wounding, mice were sacrificed, wound widths were measured and biopsies of the wound area were collected and subjected to analysis.

TABLE 12

Initial Study Groups

| Group | Number of mice | Test Article | Dose | Route of Administration | Schedule |
|---|---|---|---|---|---|
| 1 | 6 | Control aqueous 0.6% w/v Pluronic® F-68 and 0.6% w/v PVP K-29/32 solution | 0.2 mL | PO | every other day |
| 2 | 6 | Compound 1 in PVP/Pluronic® F-68 | 4 mg/kg | PO | every other day |
| 3 | 6 | Compound 1 in PVP/Pluronic® F-68 | 7.5 mg/kg | PO | every other day |
| 4 | 3 | Vehicle, water for injection | 0.2 mL | Topical | Daily |
| 5 | 6 | Compound 1 in water | 2.5 µM | Topical | Daily |
| 6 | 6 | Compound 1 in water | 1 µM | Topical | Daily |

Dosing solutions were prepared fresh on each day of dosing. Compound 1 for oral gavage was supplied as a lyophilized powder and reconstituted in aqueous 0.6% w/v Pluronic® F-68 and 0.6% w/v PVP K-29/32 solution to make a 0.75 mg/mL stock suspension, which was subsequently diluted with aqueous 0.6% w/v Pluronic® F-68 and 0.6% w/v PVP K-29/32 for preparation of working solutions of 7.5 mg/kg and 4 mg/kg. Compound 1 for topical application was supplied as a lyophilized powder and suspended in water to a concentration of 10 mM, which was further diluted with water to achieve a final working concentration for topical application.

Figure 19:
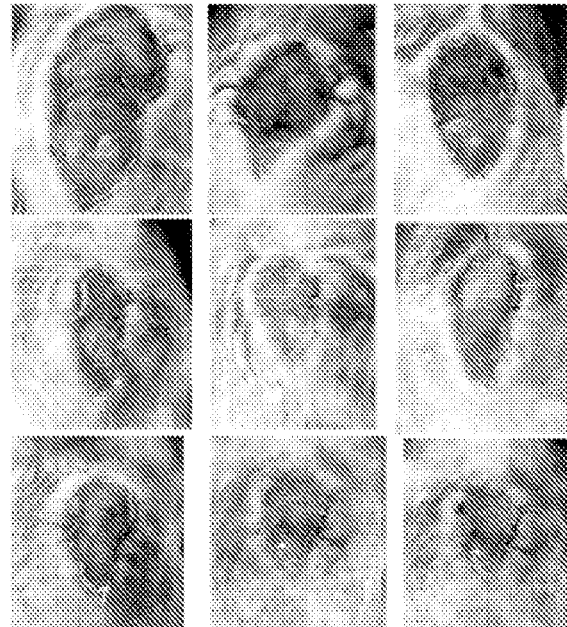
FIG. 19 is photographs of wounds treated topically or systemically with Compound 1 or its appropriate vehicle, and shows the results of a wound morphology assessment conducted on Day 5 post-wounding.

As a part of a daily morphological assessment, photo-documentation was performed using a digital camera FinePix S700. FIG. 19 is photographs of representative wounds from each experimental group on Day 5 post-wounding. The black scale bar represents 1 cm. A total of 33 wounds were made in 33 mice. The morphological assessment demonstrated the positive effect of treatment with Compound 1, either orally or topically. All treatments induced superior wound healing than controls. Treated wounds were smaller in size and the scabs were lighter, thinner and homogenous without cracks, indicating a later stage of wound healing. When evaluated on the same day as treatment groups, control group wounds appeared larger in size and were covered with thick cracked scabs that exposed a non-healed wound area (observed as reddish and pink areas) both at the edges and in the middle of the wounds.

Morphological analysis is the primary parameter utilized in wound healing assessment in preclinical studies on animals and in clinical treatments of human wounds. Based on morphological analysis, Compound 1 displayed efficacy, and had a positive impact on wound healing. Of note, both topical application and systemic administration of Compound 1 resulted in better wound healing, as measured by wound size reduction and better scabbing properties.

Evaluation of the Effects of Topical Application of a Test Compound on Pig Skin Wounds The effects of a test compound on skin wound healing can be studied in a pig longitudinal full thickness skin incision wound model. Upon arrival, animals are identified by ear tags, weighed and left to acclimate for several days before initiation of the experiment. Three days prior to the surgery, pigs are transferred to the hospitalization facility for acclimation. Twelve hours prior to the procedure, food is withheld. On the day of surgery, the pig is anesthetized using ketamine, xylazin, diazepam and isoflurane. The hair on the dorsum thorax and abdomen is carefully cut using an Oster® clipper machine (blade size 30) and 20 individual regions of 4 cm$^2$ each are marked in two rows (10 regions per row). Ten pairs of 2.5 cm full thickness longitudinal skin incisions are made using #11 scalpel blade, 4 cm from either side of the dorsum midline.

Following the surgical procedure, wounds are divided into experimental groups and treated daily by topical application on the wound area and on wound edges. Treatment area consists of a surface of skin up to a distance of 2 cm from the wound center. Dosing solutions are applied gradually on each wound using a pipette, until the entire treatment volume (for example, 1 mL of saline or test compound) is absorbed by tissue.

Several hours after wounding, due to skin elasticity and activity of the animals, the incisions take on elliptical shapes. At this stage, the widest area of the wound is measured to establish a baseline wound width. Wound healing evaluation is made by measuring the widest area of the wound. During the experiment, wounds are photo-documented and morphological analysis is performed.

At the end of the experiment (for example, 12 days after wounding), pigs are sacrificed by administration of anesthetic and KCl. Wound morphology is assessed, wound width is measured and biopsies of wound area are harvested and fixed using 4% paraformaldehyde for further analysis. Following fixation, wound biopsies are photo-documented using high resolution digital camera, for example, a FinePix S700, and biopsies of the wound area are subjected to histopathological analysis. Assessment of wound healing is performed in a paired manner in which each wound treated with test compound is directly compared to the control wound at the same anatomical location on the other side of the dorsum midline. This paired assessment of healing is crucial in terms of objective assessment and objective comparison of treated wounds to non-treated because of variability associated with a degree of vascularization and blood circulation in the skin at different areas of the pig's back. Wounds located in the front area near the neck display far better healing properties than wounds located on the rear back.

TABLE 13

Initial Study Groups

| Group | Number of wounds | Test Article | Dose | Route of Administration | Schedule |
|---|---|---|---|---|---|
| 1 | 5 front wounds on the right side | Control saline | 1 mL | Topical | Daily |
| 2 | 5 rear wounds on the right side 5 | Control saline | 1 mL | Topical | Daily |
| 3 | 5 front wounds on the left side | Test compound | 3 µM | Topical | Daily |
| 4 | 5 rear wounds on the left side 5 | Test compound | 1 µM | Topical | Daily |

Dosing solutions are prepared fresh on each day of dosing. Test compound is supplied as a lyophilized powder and further reconstituted in injectable 0.9% sodium chloride to make a 3 mg/mL stock suspension. The stock suspension is further diluted with injectable 0.9% sodium chloride to final concentrations of 3 µM and 1 µM for topical application.

Homogenous, thin and uniformly organized scab surfaces without incidents of oozing, bleeding or secretion from the wound are indicative of wound healing. Highly heterogeneous, cracked and dark colored scabs indicate numerous incidents of exudation, oozing and bleeding during the course of the wound healing process.

Evaluation of the Effects of Topical Application of a Test Compound on Early Wound Healing Processes in Pigs The effects of a test compound on early wound healing can be studied in a wound model of longitudinal full thickness skin incision in pigs. Five pairs of 2.5 cm longitudinal full thickness incisions are performed on the frontal section of the back of anaesthetized pigs using #11 scalpel blades, 4 cm from either side of the dorsum midline. Within several hours post-procedure, the longitudinal incision becomes an elliptical wound.

Wounds are divided into experimental groups and treated daily by topical application on the wound area (including edges and on skin area near the wound). Treatment phase starts 24 hours following wounding. Dosing solutions are applied gradually on each wound using a pipette, until the entire treatment volume is absorbed by tissue (for example, 1 mL of saline or a test compound).

On day 5, the state of wound healing and morphology is assessed according to the following parameters: bleeding, oozing, swelling, inflammation, pus secretion and scab formation. Assessment is performed in a paired manner in which each wound treated with the test compound is directly compared to the control wound at the same anatomical location on the other side of the dorsum midline.

TABLE 14

Initial Study Groups

| Group | Number of wounds | Test Article | Dose | Route of Administration | Schedule |
|---|---|---|---|---|---|
| 1 | 5 | Control saline | 1 mL | Topical | Daily |
| 2 | 5 | Test compound | 3 µM | Topical | Daily |

Dosing solutions are prepared fresh on each day of dosing. Test compound is supplied as a lyophilized powder and reconstituted in 0.9% sodium chloride to a 3 mg/mL stock suspension. This stock suspension is further diluted with 0.9% sodium chloride for the preparation of the final 3 µM topical solution.

A morphological wound healing assessment is conducted on Day 5 of treatment. Swelling is examined, scored according to the severity in each wound and documented as mild, moderate or severe. Wounds that exhibit moderate and severe swelling are presented as a percentage of total wounds in experimental group. Secretion is examined and scored in a binary mode: a wound that exhibited minimal secretion was considered positive and, a wound without any detectable secretion is considered negative for this parameter. Wounds that exhibit secretions (positive for this parameter) are presented as a percentage of total wounds in experimental group. A scab is considered completely formed when a continuous layer of a hard, dry, reddish, dark yellow or brown formation covered the entire wound area and is strongly attached to the wound bed and, therefore, provided a continuous and strong barrier between the external environment and the wounded tissues. Scab formation is examined and scored in a binary mode: wounds which exhibited a completely formed scab which was dry and strong are considered as positive and wounds without a scab or with scabs at an earlier stage are considered as negative for this parameter. Wounds with a completely formed scab are presented as a percentage of total wounds per group.

Swelling, secretion and scab formation are also evaluated. Swelling and secretion are part of an excessive inflammatory response that might delay tissue repair and induce unaesthetic scarring.

Evaluation of the Effects of Topical Application of a Test Compound on Early Wound Healing on Pig Skin and on Irritations and Scratching Associated with Damaged or Wounded Skin The effect of a test compound on skin wound healing can be studied in a longitudinal full thickness skin incision wound model in pigs. Three days prior to surgery, pigs are transferred to the hospitalization facility for acclimation. Twelve hours prior to the surgical procedure, food is withheld. On the day of surgery, the pigs are anesthetized using ketamine, xylazin, diazepam and isoflurane. The hair on the dorsum thorax and abdomen is cut using Oster® clipper machine (blade size 30). Ten pairs of 4 cm² each sections are marked, and 2.5 cm full thickness longitudinal skin incisions are made using #11 scalpel blade, on either side of the dorsum midline.

Following surgical procedure, wounds are divided into experimental groups and are treated daily by topical application on the wound area (including edges and on skin area near the wound up to a distance of 2 cm from the wound in all directions). Dosing solutions are applied gradually on each wound using a pipette, until the entire treatment volume is absorbed by tissue (for example, 1 mL of vehicle or test compound).

Within several hours post-procedure, the longitudinal incision becomes an elliptical wound due to skin elasticity and activity of the animals. During the experiment, wounds are photo-documented and morphological analysis is performed. Assessment of wound healing is performed in a paired manner in which each wound treated with test compound is directly compared to the control wound at the same anatomical location on the other side of the dorsum midline. During the first 5 days following wounding, wound morphology and animal behavior are recorded.

TABLE 15

Initial Study Groups

| Group | Number of wounds | Test Article | Dose | Route of Administration | Schedule |
|---|---|---|---|---|---|
| 1 | 5 front wounds on the right side | 0.02% DMSO in water | 1 mL | Topical | Daily |
| 2 | 5 rear wounds on the right side | 0.067% DMSO in water | 1 mL | Topical | Daily |
| 3 | 5 front wounds on the left side | Test compound in 0.02% DMSO | 3 µM | Topical | Daily |
| 4 | 5 rear wounds on the left side | Test compound in 0.067% DMSO | 1 µM | Topical | Daily |

Dosing solutions are prepared fresh on each day of dosing. Test compound is supplied as a lyophilized powder and dissolved in 100% DMSO to a stock concentration of 15 mM. Further dilutions in injectable water are performed to achieve a final concentration of 3 µM and 1 µM for topical application.

As part of the daily morphological assessment, photo-documentation of the wounds is performed using, for example, a digital high resolution camera FinePix S700. In addition to the wound status, areas of irritated and scratched skin are observed. Usually, the scratching does not cause damage to the wounds or interfere with the wound healing process because the wound is inflicted on the back near the dorsum midline, such that it is hard and almost impossible for the animal to reach the wounds.

Evaluation of the Effects of Compound 1 in in PVP/Pluronic® F-68 and Compound 1 in Water on Scratching Associated with Skin Healing in Mice In the skin wound studies described herein in mice, the behavior of the animals was also observed, and attempts to remove scars, signs of discomfort, and scratching of the wound area were quantified. Abnormal behavior and abnormal displays of scratching and signs of pain from all the studies performed in mice were analyzed. In these studies, treatment was performed using Compound 1 in PVP/Pluronic® F-68 and Compound 1 in water, and the respective vehicle controls.

During all wound healing experiments in mice, monitoring of healing parameters associated with wound healing, signs of skin irritations and other skin conditions at the area near the wound and the treated skin area, was performed. Additionally, during the treatment phase of all skin healing models, special attention was paid to the behavior of the animals, such as signs of discomfort and pain; and signs of scratching and tampering with wounds and skin. Soothing and calming effects of the treatment compounds were highly obvious in comparison to control animals, which were predisposed to tamper with their wounds.

In mice, treatment with Compound 1 in PVP/Pluronic® F-68 or Compound 1 in water reduced the incidence of tampering with wounds in comparison to the vehicle treated mice (DMSO in water, saline, PVP/pluronic or water).

In mice, tampering with wounds usually resulted in the removal of the scab and bleeding or damage to the newly formed tissue on the wound bed that was strongly attached to the scab. The vast majority of such incidents happened in vehicle treated groups (about 20-30% in all experiments).

According to the summary of skin conditions and animal behavior, it can be concluded that treatment of wounds with Compound 1 in PVP/Pluronic® F-68 or Compound 1 in water prevented tampering with wounds in mice, possibly, due to some soothing and calming effects of the treatment compounds on wounded and irritated skin.

Dose Response of a Test Compound on Skin Wound Healing in Mice

The effects of a test compound on skin wound healing can be studied in mice longitudinal full thickness skin incision wound model. Upon arrival, animals are identified by ear tags, weighed and left to acclimate for several days before initiation of the experiment. On the day of wounding, mice are weighed and divided into 7 experimental groups (N=6 or N=7), in accordance to weight differences stratified randomization. The vehicle group receives 0.1% DMSO in water while the positive control group is treated with an aqueous 0.6% w/v Pluronic® F-68 and 0.6% w/v PVP K-29/32. Prior to the surgical procedure, mice are anesthetized with isoflurane and the hair on the back of the animals is trimmed. Full thickness longitudinal incisions of 20 mm are performed using a standard scalpel blade on the backs of the animals (parallel to the backbone). Three hours after wounding, due to skin elasticity and activity of the animals, the incisions take on elliptical shapes. At this stage, the widest area of the wound is measured to establish a baseline wound width. Wound healing evaluation is made by measuring the widest area of the wound. Treatment of wounds is performed by topical application (daily) of dosing solutions (for example, 0.2 mL) directly on wounds.

TABLE 16

Initial Study Groups

| Group | Number of mice | Test Article | Dose | Route of Administration | Schedule |
|---|---|---|---|---|---|
| 1 | 7 | 0.1% DMSO in water | 0.2 mL | Topical | Daily |
| 2 | 6 | Test compound in 0.1% DMSO | 9 µM | Topical | Daily |
| 3 | 6 | Test compound in 0.1% DMSO | 3 µM | Topical | Daily |
| 4 | 6 | Test compound in 0.1% DMSO | 1 µM | Topical | Daily |
| 5 | 6 | Test compound in 0.1% DMSO | 0.3 µM | Topical | Daily |
| 6 | 7 | Control aqueous 0.6% w/v Pluronic ® F-68 and 0.6% w/v PVP K-29/32 | 0.2 mL | Topical | Daily |

Dosing solutions are prepared fresh on each day of dosing. Test compound is supplied as lyophilized powder and reconstituted in 0.1% DMSO in water to a 3 mg/mL stock suspension. The stock suspension is further diluted with 0.1% DMSO in water to prepare the final topical solution. Wounds in control groups are topically treated with 0.1% DMSO in water, or aqueous 0.6% w/v Pluronic® F-68 and 0.6% w/v PVP K-29/32 solution.

At the end of the experiment, 8 days post wounding, mice are sacrificed by inhalation of $CO_2$, wound widths are measured and biopsies of the wound area are collected and subjected to histological analysis. The biopsies are fixed using 4% paraformaldehyde. Following fixation of the entire wound area, a dissection of 5 mm of the widest area of the wound is performed and these specimens are subjected to paraffin embedding. Paraffin blocks are prepared utilizing standard procedures of graduate dehydration and paraffin embedding of tissues. Thereafter, histological sections are prepared and tissues are stained with hematoxylin and eosin (H&E) stain. H&E stained slides are examined and assessment of wound healing efficacy is performed.

Advanced dermal closure is assessed on Day 8 by the examination of eosin stained healthy dermis and the newly formed dermis edges at the wound gap. Wounds with both dermal edges observed in 100× magnification field of the microscope (BX41 Olympus or Axiovert 25, Zeiss) are considered positive for the advanced dermal closure healing parameter. The number of wounds with advanced dermal closure is presented as a percent of total wounds in experimental groups.

Advanced epidermal closure is assessed on Day 8 using H&E staining by analyzing histological section at the widest area of the wound. Wounds that exhibit the presence of a continuous layer of epidermis covering the entire wound gap and wounds with the most advanced migration of the epidermal edges observed in the microscope field at 400× magnification are considered positive to advanced epidermal closure parameter. The results are presented as a percent of total per experimental group.

Epidermal migration is assessed on Day 8 using H&E staining by analyzing condensed hematoxylin stained newly formed epidermis at both wound edges. The epidermal edge is considered migratory when newly formed epidermal edge covered about 20-30% of the wound gap. Migratory epidermal edges in the groups are counted and presented as a percent of total number of epidermal edges (twice the number of wounds in the group). Both epidermal edges are considered migratory in wounds that exhibited complete or advanced epidermal closure. A total of 62 wounds are made in 62 mice.

Treatment of Wounds with a Test Compound Prevents Wound Healing Complications, Such as Hyperplasia of the Epidermis and Adhesions The effects of a test compound on skin wound healing can be studied in a mice longitudinal full thickness skin incision wound model. Prior to the surgical procedure, mice are anesthetized with isoflurane, and the back of the animals is shaved. Full thickness longitudinal incisions of 20 mm are performed using a scalpel blade on the backs (parallel to backbone) of the animals. Three hours after wounding, due to skin elasticity and activity of the animals, the incisions take on elliptical shapes. Wound healing evaluation is made by measuring the widest area of the wound. Treatment of wounds is performed by topical daily application of, for example, 0.2 mL of test compound directly on the wounds. Wound care process is partially in a moist environment—after each daily treatment, wounds are wet for some time. At the end of the experiment, 8 days post wounding, mice are sacrificed, wound widths are measured and biopsies of the wound area are collected and subjected to histological analysis.

TABLE 17

Initial Study Groups

| Group | Number of mice | Test Article | Dose | Route of Administration | Schedule |
|---|---|---|---|---|---|
| 1 | 7 | 0.1% DMSO in water | 0.2 mL | Topical | Daily |
| 2 | 6 | Test compound in 0.1% DMSO | 3 µM | Topical | Daily |
| 3 | 6 | Test compound in 0.1% DMSO | 1 µM | Topical | Daily |
| 4 | 7 | Control aqueous 0.6% w/v Pluronic® F-68 and 0.6% w/vPVP K-29/32 | 0.2 mL | Topical | Daily |

Dosing solutions are prepared fresh on each dosing day. Test compound is supplied as a lyophilized powder and reconstituted in 0.1% DMSO in water to a 3 mg/mL stock suspension, which is subsequently diluted with 0.1% DMSO in water to achieve a working concentration for topical application. Wounds in control groups are topically treated with 0.1% DMSO in water or aqueous 0.6% w/v Pluronic® F-68 and 0.6% w/v PVP K-29/32.

At the end of treatment phase, on day 8 post-wounding, mice are sacrificed by inhalation of $CO_2$ and biopsies of the wound area are harvested. Fixation of wound tissues is performed using 4% paraformaldehyde. Following fixation of the entire wound area, a dissection of 5 mm of the widest area of the wound is performed and subjected to paraffin embedding. Paraffin blocks are prepared using standard procedures of graduate dehydration. Thereafter, histological sections are prepared and tissues are stained with hematoxylin and eosin (H&E). Wound healing parameters are assessed and graphed.

Hyperplasia of the epidermis is assessed on Day 8. Non-migratory and hyperplastic epidermal edges in the group are counted, and are presented as a percent of total number of epidermal edges (twice the number of wounds in the group). Hyperplastic epidermal edges are assessed using H&E staining by analyzing condensed hematoxylin stained areas of the epidermis. When the epidermal edge appears thicker than normal epidermis in a healthy skin area and when such an epidermal edge does not exhibit migration toward sealing the wound gap, it is considered to be hyperplastic and non-migratory.

Adhesions at the wound gap are assessed on Day 8. Adhesions are assessed by analyzing cellular and tissue structures at the wound gap. The wound adhesions are scored on a mild, moderate or severe scale. A negative score is considered when there is a clot at the wound gap or normal granulation tissue is replaced by other tissue, such as skeletal muscles or extensive lymphoid tissues. Several adhesions or abnormal granulation occupying more than 40% of the wound gap area are considered as severe. Adhesion is considered mild when it is non-significant and does not interfere with normal skin tissue renewal. Wounds with severe adhesions are calculated as a percent of total wounds per experimental group and graphed as shown. A total of 32 wounds (64 epidermal edges) are made in 32 mice.

One of the most important wound healing complications is hyperplasia of the epidermis. As a response to the stress signals associated with wounding, proliferation of cells in the basal layer of the epidermis occurs to compensate for skin loss. Normally, in uneventful wound healing, epidermal cells initiate migration toward sealing the wound gap soon after proliferation. When migration does not occur or is slowed down, for example, in skin complications caused by hyperglycemia in diabetic wounds, epidermal hyperplasia becomes prominent, and may cause even more complications in wound healing. In acute open wounds, as in the model employed in this experiment, or in acute sutured wounds, such as post-surgical wounds, a decline in epidermal healing associated with hyperplasia of epidermal edges increases risk for contamination and other wound healing complications such as wound dehiscence, fluid draining from the wound, or tissue protruding from the wound.

In an effective wound healing process, the primary blood clot undergoes gradual changes in order to form granulation tissue at the wound gap, which, following remodeling, eventually becomes newly formed skin tissue with fully restored functions. When adhesion of non-skin related tissues occurs in the wound gap, granulation tissue does not form properly and, as a result, final tissue remodeling is limited. This may cause further limitations in the functions of healed skin.

Treatment of Wounds with a Test Compound in a Saline-Based Formulation Improves Wound Healing and Prevents Severe Adhesions The effects of a test compound on skin wound healing were studied in a mouse longitudinal full thickness skin incision wound model. Surgical procedures are performed on 7-8 weeks old C57BL male mice anesthetized with isoflurane. Prior to surgical procedure, mice are anesthetized with isoflurane and the fur is cut. Full thickness longitudinal incisions of 20 mm are performed using a standard scalpel blade. Three hours after wounding, due to skin elasticity and activity of the animals, the incisions take on elliptical shapes. At this stage, the widest area of the wound is measured to establish a baseline wound width. Wound healing evaluation is made by measuring the widest area of the wound. Treatment of wounds is performed by a daily application of a topical 0.2 mL solution directly on the wound. The wound care process is conducted partially in a moist environment because after each daily treatment, wounds are wet for some time (3-5 hours). At the end of the experiment, 8 days post wounding, mice are sacrificed, wound widths are measured and biopsies of the wound area are collected and subjected to histological analysis.

TABLE 18

Initial Study Groups

| Group | Number of mice | Test Article | Dose | Route of Administration | Schedule |
|---|---|---|---|---|---|
| 1 | 5 | Saline | 0.2 mL | Topical | Daily |
| 2 | 7 | Test compound in saline | 3 uM | Topical | Daily |

Dosing solutions are prepared fresh on each dosing day. Test compound is supplied as a lyophilized powder and reconstituted in saline to make a 3 mg/mL stock suspension, which is subsequently diluted with saline to achieve a working concentration of 3 µM for topical application. Wounds in control groups are topically treated with saline.

At the end of the treatment phase, 8 days post-wounding, mice are sacrificed by inhalation of $CO_2$ and biopsies of wound area are harvested. Fixation of wound tissues is performed using 4% paraformaldehyde. Following fixation of the entire wound area, a dissection of 5 mm of the widest area of the wound is performed and the dissected area is subjected to paraffin embedding. Paraffin blocks are prepared using standard procedures of graduate dehydration. Thereafter, histological sections are prepared and tissues are stained with hematoxylin and eosin (H&E). Wound healing parameters are assessed and graphed.

Epidermal closure is assessed using H&E staining by analyzing histological sections at the widest area of the wound. Wounds which exhibit the presence of a continuous layer of epidermis covering the entire wound gap, and wounds with the most advanced migration of the epidermal edges when both edges were observed in the microscope field at 400× magnification are considered positive for the advanced epidermal closure parameter. The results are presented as a percent of total per experimental group.

Dermal healing is assessed by the examination of eosin stained healthy dermis and the newly formed dermis edges at the wound gap. Wounds with both dermal edges observed in 100× magnification field of the microscope (BX41 Olympus or Axiovert 25, Zeiss) are considered positive for the advanced dermal closure healing parameter. The number of wounds with advanced dermal closures is presented as a percent of total wounds in experimental groups.

Granulation tissue is assessed utilizing H&E staining. When the primary fibrin clot is replaced by fibrous connective tissue containing adipocytes, new capillaries and an infiltrate containing lymphoid cells, macrophages, and plasma cells the granulation tissue is considered early. Early granulation tissue replaced by tissue with a high abundance of fibroblasts and collagen fibers is considered advanced. Overall, areas of advanced granulation tissue at the wound gap are documented as percent of the total wound gap area. A wound gap displaying advanced granulation tissue formation covering 40% of the wound gap is considered positive for this parameter. Results are calculated as a percent of total wounds per group.

Adhesions are assessed by analyzing cellular and tissue structures at the wound gap. The wound adhesions are scored on a mild, moderate or severe scale. A negative score is considered when there is a clot at the wound gap or normal granulation tissue is replaced by other tissue, such as skeletal muscles or extensive lymphoid tissues. Several adhesions or abnormal granulation occupying more than 40% of the wound gap area are considered as severe. Adhesion is considered mild when it is non-significant and does not interfere with normal skin tissue renewal. Wounds with severe adhesions are calculated as a percent of total wounds per experimental group. Nineteen wounds (38 epidermal edges) were made in 19 mice.

Evaluation of the Effects of Topical Application of a Test Compound on Healing Process and Scarring in the Late Stages of Wound Healing on Pig Skin The effects of a test compound on late stages of skin wound healing are studied in a pig wound model of longitudinal full thickness incision. On the day of surgery, the pig is anesthetized using ketamine, xylazin, diazepam and isoflurane. The hair on the dorsum thorax and abdomen is cut and 10 pairs of 2.5 cm full thickness longitudinal skin incisions are performed using a #11 scalpel blade, 4 cm from either side of the dorsum midline. Following the surgical procedure, wounds are divided into experimental groups and treated daily by topical application on the wound area and on wound edges including treatment of skin near the wound area up to a distance of 2 cm from the wound in all directions. Dosing solutions are applied gradually on each wound using a pipette, until the entire treatment volume (for example, 1 mL of vehicle or test compound) is absorbed by the tissue. The skin near the wound is treated with gauze soaked in test compound or vehicle solution.

During the experiment, wounds are photo-documented and morphological analysis is performed. At the end of the treatment phase (day 19 post-wounding), pigs are sacrificed by dosing of anesthetic and KCl. Morphology of the wounds is examined, wounds are photo-documented and biopsies of wound area are harvested for fixation and further morphological and histological analysis.

TABLE 19

Initial Study Groups

| Group | Number of wounds | Test Article | Dose | Route of Administration | Schedule |
|---|---|---|---|---|---|
| 1 | 5 front wounds on the right side | 0.02% DMSO in water | 1 mL | Topical | Daily |
| 2 | 5 rear wounds on the right side | 0.067% DMSO in water | 1 mL | Topical | Daily |
| 3 | 5 front wounds on the left side | Test compound in 0.02% DMSO | 3 µM | Topical | Daily |
| 4 | 5 rear wounds on the left side | Test compound in 0.067% DMSO | 1 µM | Topical | Daily |

Dosing solutions are prepared fresh on each day of dosing. Test compound is supplied as a lyophilized powder and dissolved in 100% DMSO to prepare a stock solution of 15 mM. Subsequently, dilutions in injectable water are performed to achieve final concentrations of 3 M and 1 µM for topical application.

At the end of the treatment phase (day 19 post-wounding), the assessment of wound healing is performed. Fully healed wounds are reported as a percent of total wounds per group. The average width of scars in the wounds that healed completely and exhibited full scab detachment is also reported. Scars were measured (mm) and the average width of scars and standard deviation are calculated. A total of 20 wounds was performed.

At the end of the treatment phase (day 19 post-wounding), pigs are sacrificed by an overdose of anesthetic and KCl and biopsies of wound area are harvested. Fixation of wound biopsies is performed using 4% paraformaldehyde. Following fixation, wound biopsies are photo-documented using, for example, a digital camera FinePix 5700 at the highest resolution.

BIBLIOGRAPHY

Cronshaw J M and Matunis M J. 2004. The nuclear pore complex: disease associations and functional correlations TRENDS Endocrin Metab. 15:34-39

Falini B et al. 2006. Both carboxy-terminus NES motif and mutated tryptophan(s) are crucial for aberrant nuclear export of nucleophosmin leukemic mutants in NPMc+ AML Blood. 107:4514-4523.

Cai X and Liu X. 2008. Inhibition of Thr-55 phosphorylation restores p53 nuclear localization and sensitizes cancer cells to DNA damage. PNAS. 105:16958-16963.

Daelemans D, Afonina E, Nilsson J 2002 A synthetic HIV-1 Rev inhibitor interfering with the CRM1-mediated nuclear export. Proc Natl Acad Sci USA 99(22):14440-5.98052-2517.

Davis J R et al. 2007. Controlling protein compartmentalization to overcome disease Pharmaceut Res. 24:17-27.

Freundt E, Yu L, Park E, et al 2009 Molecular determinants for subcellular localization of the severe acute respiratory syndrome coronavirus open reading frame 3b protein. J Virol 83(13):6631-40.

Ghildyal R, Ho A, Dias M, et al 2009 The respiratory syncytial virus matrix protein possesses a Crm1-mediated nuclear export mechanism. J Virol 83(11):5353-62.

Ghosh C C et al 2008 Analysis of nucleocytoplasmic shuttling of NF kappa B proteins in human leukocytes. Methods Mol Biol. 457:279-92.

Gupta N et al 2008 Retinal tau pathology in human glaucomas. Can J Ophthalmol. 2008 February; 43(1):53-60.

Hoshino L et al. 2008. Combined effects of p53 gene therapy and leptomycin B in human esophageal squamous cell carcinoma. Oncology. 75:113-119.

Lain S et al. 1999a An inhibitor of nuclear export activates the p53 response and induces the localization of HDM2 and p53 to U1A-positive nuclear bodies associated with the PODs Exp Cell Res. 248:457-472.

Lain S et al. 1999b. Accumulating active p53 in the nucleus by inhibition of nuclear export: a novel strategy to promote the p53 tumor suppressor function Exp Cell Res. 253:315.

Muller P A et al. 2009 Nuclear-cytosolic transport of COMMD1 regulates NF-kappaB and HIF-1 activity. Traffic 10(5):514-27.

Mutka S 2007 Nuclear Export Inhibitors (NEIs) as novel cancer therapies AACR Annual Meeting. Poster 5609.

Mutka S, Yang W, Dong S, et al. 2009. Identification of nuclear export inhibitors with potent anticancer activity in vivo. Cancer Res. 69: 510-7.

Nakahara J et al. 2009. Abnormal expression of TIP30 and arrested nucleocytoplasmic transport within oligodendrocyte precursor cells in multiple sclerosis J Clin Invest. 119:169-181.

Noske A et al. 2008. Expression of the nuclear export protein chromosomal region maintenance/exportin 1/Xpo1 is a prognostic factor in human ovarian cancer. Cancer. 112: 1733-1743.

Pollard V & Malim M. 1998 The HIV-1 Rev protein Annu Rev Microbiol 52:491-532.

Rawlinson S, Pryor M, Wright P, Jans D 2009 CRM1-mediated nuclear export of dengue virus RNA polymerase NS5 modulates interleukin-8 induction and virus production. J Biol Chem 284(23):15589-97.

Sanchez V, Mahr J, Orazio N, et al 2007 Nuclear export of the human cytomegalovirus tegument protein pp65 requires cyclin-dependent kinase activity and the Crm1 exporter. J Virol 81(21):11730-6.

Sorokin A V et al. 2007. Nucleocytoplasmic transport of proteins. Biochemistry 72:1439-1457.

Terry L J et al. 2007. Crossing the nuclear envelope: hierarchical regulation of nucleocytoplasmic transport. Science 318:1412-1416.

Van der Watt P J et al. 2008. The Karyopherin proteins, Crm1 and Karyopherin beta1, are overexpressed in cervical cancer and are critical for cancer cell survival and proliferation. Int J Canc. 124:1829-1840.

Walsh M D et al. 2008 Exportin 1 inhibition attenuates nuclear factor-kappaB-dependent gene expression. Shock 29:160-166.

Williams P, Verhagen J, Elliott G 2008 Characterization of a CRM1-dependent nuclear export signal in the C terminus of herpes simplex virus type 1 tegument protein UL47. J Virol 82(21):10946-52.

Yang W 2007 Anti-tumor activity of novel nuclear export inhibitors (NEIs) in multiple murine leukemia models. AACR Annual Meeting. Poster 5597.

Yao Y et al. 2009. The expression of CRM1 is associated with prognosis in human osteosarcoma. Oncol Rep. 21:229-35.

Zimmerman T L et al 2006 Nuclear export of retinoid X receptor alpha in response to interleukin-1beta-mediated cell signaling: roles for JNK and SER260. J Biol Chem 281:15434-15440.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

We claim:

1. A method of synthesizing (Z)-3-(3-(3,5-bis(trifluoromethyl)phenyl)-1H-1,2,4-triazol-1-yl)-N'-pivaloylacrylohydrazide comprising reacting (Z)-3-(3-(3,5-bis(trifluoromethyl)phenyl)-1H-1,2,4-triazol-1-yl)acrylic acid with pivalohydrazide having a formula of 2. The method of claim 1, wherein the (Z)-3-(3-(3,5-bis(trifluoromethyl)phenyl)-1H-1,2,4-triazol-1-yl)acrylic acid is formed by reacting (Z)-isopropyl 3-(3-(3,5-bis(trifluoromethyl)phenyl)-1H-1,2,4-triazol-1-yl)acrylate with LiOH.

3. The method of claim 2, wherein the (Z)-isopropyl 3-(3-(3,5-bis(trifluoromethyl)phenyl)-1H-1,2,4-triazol-1-yl)acrylate is formed by reacting 3-(3,5-bis(trifluoromethyl)phenyl)-1H-1,2,4-triazole with (Z)-isopropyl 3-iodoacrylate.

4. The method of claim 3, wherein the 3-(3,5-bis(trifluoromethyl)phenyl)-1H-1,2,4-triazole is formed by reacting 3,5-bis(trifluoromethyl)benzothioamide with hydrazine hydrate.

5. The method of claim 4, wherein the 3,5-bis(trifluoromethyl)benzothioamide is formed by reacting 3,5-bis(trifluoromethyl)benzonitrile with sodium sulfhydrate.

6. A method of synthesizing (Z)-3-(3-(3,5-bis(trifluoromethyl)phenyl)-1H-1,2,4-triazol-1-yl)acrylic acid comprising reacting (Z)-isopropyl 3-(3-(3,5-bis(trifluoromethyl)phenyl)-1H-1,2,4-triazol-1-yl)acrylate with LiOH.

* * * * *